US012576037B2

(12) United States Patent
Wang et al.

(10) Patent No.: US 12,576,037 B2
(45) **Date of Patent: *Mar. 17, 2026**

(54) POLYMER-ENCAPSULATED DRUG PARTICLES

(71) Applicant: Tonic Medical, Inc., Brooklyn Park, MN (US)

(72) Inventors: Lixiao Wang, Henderson, NV (US); Peter Barnett, Shakopee, MN (US)

(73) Assignee: Tonic Medical, Inc., Brooklyn Park, MN (US)

( * ) Notice: Subject to any disclaimer, the term of this patent is extended or adjusted under 35 U.S.C. 154(b) by 796 days.

This patent is subject to a terminal disclaimer.

(21) Appl. No.: 17/180,338

(22) Filed: Feb. 19, 2021

(65) Prior Publication Data

US 2021/0259976 A1 Aug. 26, 2021

Related U.S. Application Data

(60) Provisional application No. 63/104,965, filed on Oct. 23, 2020, provisional application No. 62/979,980, filed on Feb. 21, 2020.

(51) Int. Cl.

| | |
|---|---|
| ***A61K 9/48*** | (2006.01) |
| ***A61K 31/337*** | (2006.01) |
| ***A61K 31/436*** | (2006.01) |
| ***A61M 25/10*** | (2013.01) |
| ***A61P 1/00*** | (2006.01) |

(52) U.S. Cl.

CPC .......... *A61K 9/4816* (2013.01); *A61K 9/4833* (2013.01); *A61K 31/337* (2013.01); *A61K 31/436* (2013.01); *A61M 25/10* (2013.01); *A61M 25/1029* (2013.01); *A61P 1/00* (2018.01); *A61M 2025/1031* (2013.01); *A61M 2025/105* (2013.01); *A61M 2210/105* (2013.01)

(58) Field of Classification Search

CPC .. A61K 9/4816; A61K 9/4833; A61K 31/337; A61K 31/436; A61P 1/00; A61M 25/10; A61M 25/1029; A61M 2025/105; A61M 2210/105

See application file for complete search history.

(56) References Cited

U.S. PATENT DOCUMENTS

| | | | |
|---|---|---|---|
| 5,171,299 | A | 12/1992 | Heitzmann et al. |
| 5,263,931 | A | 11/1993 | Miller |
| 5,312,430 | A | 5/1994 | Rosenbluth et al. |
| 5,314,443 | A | 5/1994 | Rudnick |
| 5,419,763 | A | 5/1995 | Hildebrand |
| 5,423,755 | A | 6/1995 | Kesten et al. |
| 5,718,684 | A | 2/1998 | Gupta |
| 5,752,522 | A | 5/1998 | Murphy |
| 5,904,648 | A | 5/1999 | Arndt et al. |
| 6,059,713 | A | 5/2000 | Urick et al. |
| 6,268,390 | B1 | 7/2001 | Kunz |
| 6,306,421 | B1 | 10/2001 | Kunz et al. |
| 6,403,635 | B1 | 6/2002 | Kinsella et al. |
| 6,495,579 | B1 | 12/2002 | Hunter |
| 6,515,009 | B1 | 2/2003 | Kunz et al. |
| 6,530,948 | B1 | 3/2003 | Vrba |
| 6,663,881 | B2 | 12/2003 | Kunz et al. |
| 6,730,064 | B2 | 5/2004 | Ragheb et al. |
| 7,803,149 | B2 | 9/2010 | Bates et al. |
| 7,811,622 | B2 | 10/2010 | Bates et al. |
| 7,882,841 | B2 | 2/2011 | Aljuri et al. |
| 8,052,668 | B2 | 11/2011 | Sih |
| 8,092,864 | B2 | 1/2012 | Isch et al. |
| 8,241,249 | B2 | 8/2012 | Wang |
| 8,244,344 | B2 | 8/2012 | Wang |
| 8,257,305 | B2 | 9/2012 | Speck et al. |
| 8,366,660 | B2 | 2/2013 | Wang |
| 8,366,662 | B2 | 2/2013 | Wang |
| 8,403,910 | B2 | 3/2013 | Wang |
| 8,404,300 | B2 | 3/2013 | Wang |

(Continued)

FOREIGN PATENT DOCUMENTS

| | | |
|---|---|---|
| CN | 101610798 | 12/2009 |
| CN | 104936629 | 9/2015 |

(Continued)

OTHER PUBLICATIONS

F.S.T. Mirakabad, et al. "PLGA-Based Nanoparticles as Cancer Drug Delivery Systems," Asian Pac J Cancer Prev, 15 (2), 2014 517-535. (Year: 2014).*

"U.S. Appl. No. 14/438,327, Preliminary Amendment filed Jul. 28, 2015", 9 pgs.

"U.S. Appl. No. 14/438,327, Restriction Requirement mailed Jul. 12, 2016", 9 pgs.

"U.S. Appl. No. 14/438,327, Response filed Aug. 24, 2016 to Restriction Requirement mailed Jul. 12, 2016", 9 pgs.

"U.S. Appl. No. 14/438,327, Non Final Office Action mailed Oct. 6, 2016", 10 pgs.

"U.S. Appl. No. 14/438,327, Response filed Dec. 28, 2016 to Non Final Office Action mailed Oct. 6, 2016", 13 pgs.

(Continued)

*Primary Examiner* — Michael P Cohen

(74) *Attorney, Agent, or Firm* — Schwegman, Lundberg & Woessner, P.A.

(57) ABSTRACT

Various embodiments disclosed relate to polymer-encapsulated drug particles and a drug-releasing coating including the same, as well as drug-coated balloon catheters for treating, preventing, or reducing the recurrence of strictures in body lumens and methods of using the same. A drug-coated balloon catheter for delivering a therapeutic agent to a target site of a body lumen stricture includes an elongated balloon. The balloon catheter includes a coating layer overlying an exterior surface of the balloon. The coating layer includes the polymer-encapsulated drug particles; or a drug-releasing coating including the polymer-encapsulated drug particles; or a therapeutic agent and a first and/or second additive; or a combination thereof.

31 Claims, 11 Drawing Sheets

(56) References Cited

U.S. PATENT DOCUMENTS

| | | | |
|---|---|---|---|
| 8,414,525 | B2 | 4/2013 | Wang |
| 8,414,526 | B2 | 4/2013 | Wang |
| 8,414,909 | B2 | 4/2013 | Wang |
| 8,414,910 | B2 | 4/2013 | Wang |
| 8,425,459 | B2 | 4/2013 | Wang |
| 8,430,055 | B2 | 4/2013 | Wang et al. |
| 8,439,868 | B2 | 5/2013 | Speck et al. |
| 8,557,272 | B2 | 10/2013 | Zhao |
| 8,586,125 | B2 | 11/2013 | Hossainy et al. |
| 8,617,611 | B2 * | 12/2013 | Burgermeister ........ A61L 27/34 424/497 |
| 8,673,387 | B2 | 3/2014 | Bates et al. |
| 8,722,132 | B2 | 5/2014 | Labrecque et al. |
| 9,066,990 | B2 | 6/2015 | Speck et al. |
| 9,180,281 | B2 | 11/2015 | Gerrans et al. |
| 9,242,081 | B2 | 1/2016 | Drasler et al. |
| 9,375,481 | B2 * | 6/2016 | Troiano .................. A61P 13/08 |
| 9,492,594 | B2 * | 11/2016 | Ahlering ................... A61P 9/14 |
| 9,728,840 | B2 | 8/2017 | Shi et al. |
| 9,750,818 | B2 | 9/2017 | Alargova et al. |
| 10,098,987 | B2 | 10/2018 | Ahlering et al. |
| 10,117,972 | B2 | 11/2018 | Mcclain et al. |
| 10,188,772 | B2 | 1/2019 | Mcclain et al. |
| 10,245,419 | B2 | 4/2019 | Drasler et al. |
| 10,668,188 | B2 | 6/2020 | Wang |
| 10,675,386 | B2 | 6/2020 | Wang |
| 10,806,830 | B2 | 10/2020 | Wang et al. |
| 10,850,076 | B2 | 12/2020 | Wang et al. |
| 10,881,839 | B2 | 1/2021 | Wang et al. |
| 10,888,640 | B2 | 1/2021 | Wang et al. |
| 10,898,700 | B2 | 1/2021 | Wang et al. |
| 2003/0203991 | A1 | 10/2003 | Schottman et al. |
| 2004/0098019 | A1 | 5/2004 | Tomaschko et al. |
| 2004/0144387 | A1 | 7/2004 | Amar |
| 2004/0267355 | A1 | 12/2004 | Scott et al. |
| 2005/0054978 | A1 | 3/2005 | Segal et al. |
| 2005/0196518 | A1 | 9/2005 | Stenzel |
| 2005/0249770 | A1 | 11/2005 | Hunter |
| 2006/0002852 | A1 | 1/2006 | Saltzman et al. |
| 2006/0083768 | A1 | 4/2006 | Labrecque et al. |
| 2007/0005094 | A1 | 1/2007 | Eaton et al. |
| 2007/0009692 | A1 | 1/2007 | Wang et al. |
| 2007/0027523 | A1 | 2/2007 | Toner et al. |
| 2007/0031371 | A1 | 2/2007 | Kozlowski |
| 2007/0088255 | A1 | 4/2007 | Toner et al. |
| 2008/0025952 | A1 | 1/2008 | Scheule et al. |
| 2008/0113035 | A1 | 5/2008 | Hunter |
| 2008/0118544 | A1 | 5/2008 | Wang |
| 2008/0175887 | A1 | 7/2008 | Wang |
| 2008/0245375 | A1 | 10/2008 | Trudel |
| 2008/0255508 | A1 | 10/2008 | Wang |
| 2008/0255509 | A1 | 10/2008 | Wang |
| 2008/0255510 | A1 | 10/2008 | Wang |
| 2008/0276935 | A1 | 11/2008 | Wang |
| 2008/0286372 | A1 | 11/2008 | Pacetti et al. |
| 2009/0018565 | A1 | 1/2009 | To et al. |
| 2009/0028920 | A1 | 1/2009 | Hodges |
| 2009/0171241 | A1 | 7/2009 | Garcia et al. |
| 2009/0283206 | A1 | 11/2009 | Eskaros et al. |
| 2010/0015200 | A1 | 1/2010 | McClain et al. |
| 2010/0030183 | A1 | 2/2010 | Toner et al. |
| 2010/0049182 | A1 | 2/2010 | Ryan et al. |
| 2010/0055294 | A1 | 3/2010 | Wang et al. |
| 2010/0076402 | A1 | 3/2010 | Mazzone et al. |
| 2010/0198150 | A1 | 8/2010 | Michal et al. |
| 2010/0209472 | A1 | 8/2010 | Wang |
| 2010/0233228 | A1 | 9/2010 | Speck |
| 2010/0285085 | A1 | 11/2010 | Stankus et al. |
| 2011/0008260 | A1 | 1/2011 | Flanagan |
| 2011/0015664 | A1 | 1/2011 | Kangas et al. |
| 2011/0022027 | A1 | 1/2011 | Morishita et al. |
| 2011/0098683 | A1 | 4/2011 | Wiita et al. |
| 2011/0144578 | A1 | 6/2011 | Pacetti et al. |
| 2011/0159169 | A1 | 6/2011 | Wang |
| 2011/0160575 | A1 | 6/2011 | Beyar et al. |
| 2011/0160658 | A1 | 6/2011 | Wang |
| 2011/0160660 | A1 | 6/2011 | Wang |
| 2011/0166548 | A1 | 7/2011 | Wang |
| 2011/0196340 | A1 | 8/2011 | Barry et al. |
| 2011/0295200 | A1 | 12/2011 | Speck et al. |
| 2011/0300221 | A1 | 12/2011 | Kunz et al. |
| 2012/0029426 | A1 | 2/2012 | Wang |
| 2012/0035530 | A1 | 2/2012 | Wang |
| 2012/0109105 | A1 | 5/2012 | Cambronne |
| 2012/0172796 | A1 | 7/2012 | Chappa |
| 2012/0231037 | A1 | 9/2012 | Levi et al. |
| 2012/0239001 | A1 | 9/2012 | Barry et al. |
| 2012/0296274 | A1 | 11/2012 | Slager |
| 2012/0302954 | A1 | 11/2012 | Zhao |
| 2012/0316633 | A1 | 12/2012 | Flanagan et al. |
| 2013/0190689 | A1 | 7/2013 | Slager |
| 2013/0197434 | A1 | 8/2013 | Wang |
| 2013/0231638 | A1 | 9/2013 | Speck et al. |
| 2013/0245058 | A1 | 9/2013 | Hoffmann et al. |
| 2013/0253466 | A1 | 9/2013 | Campbell et al. |
| 2013/0253475 | A1 | 9/2013 | Wang |
| 2013/0261603 | A1 | 10/2013 | Wang |
| 2013/0304029 | A1 | 11/2013 | Barry et al. |
| 2014/0005541 | A1 | 1/2014 | Bates et al. |
| 2014/0228751 | A1 | 8/2014 | Speck et al. |
| 2014/0228752 | A1 | 8/2014 | Speck et al. |
| 2014/0371717 | A1 | 12/2014 | Mcclain et al. |
| 2014/0378896 | A1 | 12/2014 | Venturelli |
| 2015/0231375 | A1 | 8/2015 | Kubo et al. |
| 2015/0273117 | A1 | 10/2015 | Wang |
| 2016/0038648 | A1 | 2/2016 | Gemborys |
| 2016/0082159 | A1 | 3/2016 | Orlowski |
| 2016/0250388 | A1 | 9/2016 | Wang |
| 2016/0324782 | A1 | 11/2016 | Vail et al. |
| 2016/0338793 | A1 | 11/2016 | Shohat et al. |
| 2017/0028105 | A1 | 2/2017 | Ahlering et al. |
| 2017/0086929 | A1 | 3/2017 | Moll et al. |
| 2017/0151339 | A1 * | 6/2017 | White ..................... A61P 35/00 |
| 2018/0104383 | A1 | 4/2018 | Wang et al. |
| 2019/0009063 | A1 | 1/2019 | Cottone et al. |
| 2019/0015639 | A1 | 1/2019 | Wang et al. |
| 2019/0015640 | A1 | 1/2019 | Wang et al. |
| 2019/0046693 | A1 | 2/2019 | Ahlering et al. |
| 2019/0111187 | A1 * | 4/2019 | Steele ............... A61M 25/0045 |
| 2019/0167854 | A1 | 6/2019 | Wang |
| 2019/0344053 | A1 | 11/2019 | Wang et al. |
| 2019/0374685 | A1 | 12/2019 | Wang et al. |
| 2020/0254148 | A1 | 8/2020 | Wang |
| 2020/0360571 | A1 | 11/2020 | Wang et al. |
| 2022/0193310 | A1 | 6/2022 | Labhasetwar |
| 2025/0082582 | A1 | 3/2025 | Wang et al. |
| 2025/0213491 | A1 | 7/2025 | Wang et al. |

FOREIGN PATENT DOCUMENTS

| | | | |
|---|---|---|---|
| CN | 107405424 | | 11/2017 |
| CN | 107635593 | | 1/2018 |
| CN | 109414528 | | 3/2019 |
| CN | 111166942 | | 5/2020 |
| CN | 115461096 | | 12/2022 |
| CN | 119236187 | A | 1/2025 |
| EP | 0474906 | | 3/1992 |
| EP | 1135165 | | 9/2001 |
| EP | 1143968 | | 8/2003 |
| EP | 1539266 | | 4/2008 |
| EP | 2292225 | | 5/2012 |
| EP | 2098230 | | 6/2012 |
| EP | 2262547 | | 1/2013 |
| EP | 2324866 | | 6/2014 |
| EP | 2324867 | | 6/2014 |
| EP | 2531229 | | 12/2014 |
| EP | 2451496 | | 7/2015 |
| EP | 2911711 | | 9/2015 |
| EP | 3442612 | | 8/2020 |
| JP | 2010523595 | A | 7/2010 |
| JP | 2010540159 | | 12/2010 |
| JP | 2012502690 | | 2/2012 |
| JP | 2013523209 | | 6/2013 |
| JP | 2014523790 | | 9/2014 |

(56) References Cited

FOREIGN PATENT DOCUMENTS

| | | | |
|---|---|---|---|
| JP | 2015536709 | 12/2015 | |
| JP | 2016503330 | 2/2016 | |
| JP | 2016036730 | 3/2016 | |
| JP | 2016518200 | 6/2016 | |
| JP | 2017507741 | 3/2017 | |
| JP | 2017524467 A | 8/2017 | |
| JP | 2018517454 | 7/2018 | |
| JP | 2019523032 | 8/2019 | |
| JP | 2019218354 | 12/2019 | |
| JP | 2020049269 | 4/2020 | |
| JP | 2020075155 | 5/2020 | |
| JP | 2023514737 | 4/2023 | |
| WO | 9728840 | 8/1997 | |
| WO | 0025848 | 5/2000 | |
| WO | 0032238 | 6/2000 | |
| WO | 2011147407 | 12/2001 | |
| WO | 03072080 | 9/2003 | |
| WO | 2009051614 | 4/2009 | |
| WO | 2010136604 | 12/2010 | |
| WO | 2011008393 | 1/2011 | |
| WO | 2011119159 | 9/2011 | |
| WO | 2012122023 | 9/2012 | |
| WO | 2013015941 | 1/2013 | |
| WO | 2013059509 | 4/2013 | |
| WO | WO-2013059509 A1 * | 4/2013 | ....... A61B 17/12136 |
| WO | 2014066085 | 5/2014 | |
| WO | 2014087395 | 6/2014 | |
| WO | 2014177678 | 11/2014 | |
| WO | 2015103447 | 7/2015 | |
| WO | 2015136106 | 9/2015 | |
| WO | 2016073294 | 5/2016 | |
| WO | 2016118923 | 7/2016 | |
| WO | 2016172343 | 10/2016 | |
| WO | WO-2017049245 A2 * | 3/2017 | ......... A61K 31/7105 |
| WO | 2018204782 | 11/2018 | |
| WO | WO-2019009809 A1 | 1/2019 | |
| WO | 2019152811 | 8/2019 | |
| WO | 2020172560 | 8/2020 | |
| WO | 2021168284 | 8/2021 | |

OTHER PUBLICATIONS

"U.S. Appl. No. 14/438,327, Final Office Action mailed May 3, 2017", 10 pgs.
"U.S. Appl. No. 14/438,327, Response filed Jul. 27, 2017 to Final Office Action mailed May 3, 2017", 13 pgs.
"U.S. Appl. No. 14/438,327, Non Final Office Action mailed Sep. 29, 2017", 11 pgs.
"U.S. Appl. No. 14/438,327, Response filed Dec. 15, 2017 to Non Final Office Action mailed Sep. 29, 2017", 16 pgs.
"U.S. Appl. No. 14/438,327, Final Office Action mailed Apr. 2, 2018", 14 pgs.
"U.S. Appl. No. 14/438,327, Response filed Jun. 1, 2018 to Final Office Action mailed Apr. 2, 2018", 16 pgs.
"U.S. Appl. No. 14/438,327, Advisory Action mailed Jul. 18, 2018", 6 pgs.
"U.S. Appl. No. 14/438,327, Response filed Aug. 1, 2018 to Advisory Action mailed Jul. 18, 2018 and Final Office Action mailed Apr. 2, 2018", 17 pgs.
"U.S. Appl. No. 16/135,436, Restriction Requirement mailed Nov. 2, 2018", 7 pgs.
"U.S. Appl. No. 16/135,436, Response filed Nov. 14, 2018 to Restriction Requirement mailed Nov. 2, 2018", 10 pgs.
"U.S. Appl. No. 14/438,327, Non Final Office Action mailed Jan. 28, 2019", 14 pgs.
"U.S. Appl. No. 15/568,614, Restriction Requirement mailed Feb. 8, 2019", 9 pgs.
"U.S. Appl. No. 16/135,436, Notice of Non-Responsive Amendment mailed Mar. 8, 2019", 2 pgs.
"U.S. Appl. No. 15/568,614, Response filed Mar. 20, 2019 to Restriction Requirement mailed Feb. 8, 2019", 8 pgs.
"U.S. Appl. No. 16/135,436, Response filed Mar. 28, 2019 to Notice of Non-Responsive Amendment mailed Mar. 8, 2019", 10 pgs.
"U.S. Appl. No. 14/438,327, Response filed Apr. 16, 2019 to Non Final Office Action mailed Jan. 28, 2019", 29 pgs.
"U.S. Appl. No. 15/568,614, Notice of Non-Responsive Amendment mailed Jul. 1, 2019", 2 pgs.
"U.S. Appl. No. 15/568,614, Response filed Jul. 9, 2019 to Non-Responsive Amendment mailed Jul. 1, 2019 and Restriction Requirement mailed Feb. 8, 2019", 8 pgs.
"U.S. Appl. No. 16/135,436, Non Final Office Action mailed Jul. 29, 2019", 38 pgs.
"U.S. Appl. No. 14/438,327, Final Office Action mailed Aug. 9, 2019", 20 pgs.
"U.S. Appl. No. 16/135,436, Response filed Aug. 21, 2019 to Non Final Office Action mailed Jul. 29, 2019", 18 pgs.
"U.S. Appl. No. 15/568,614, Non Final Office Action mailed Nov. 18, 2019", 22 pgs.
"U.S. Appl. No. 16/135,436, Final Office Action mailed Nov. 29, 2019", 41 pgs.
"U.S. Appl. No. 16/135,472, Final Office Action mailed Nov. 29, 2019", 43 pgs.
"U.S. Appl. No. 14/438,327, Response filed Dec. 3, 2019 to Final Office Action mailed Aug. 9, 2019", 32 pgs.
"U.S. Appl. No. 14/438,327, Non Final Office Action mailed Jan. 7, 2020", 11 pgs.
"U.S. Appl. No. 16/135,436, Response filed Jan. 13, 2020 to Final Office Action mailed Nov. 29, 2019", 22 pgs.
"U.S. Appl. No. 14/438,327, Response filed Feb. 7, 2020 to Non Final Office Action mailed Jan. 7, 2020", 13 pgs.
"U.S. Appl. No. 15/568,614, Response filed Feb. 10, 2020 to Non Final Office Action mailed Nov. 18, 2019", 17 pgs.
"U.S. Appl. No. 14/438,327, Examiner Interview Summary mailed Feb. 12, 2020", 3 pgs.
"U.S. Appl. No. 16/135,436, Non Final Office Action mailed Mar. 5, 2020", 48 pgs.
"U.S. Appl. No. 16/135,436, Response filed Apr. 6, 2020 to Non Final Office Action mailed Mar. 5, 2020", 21 pgs.
"U.S. Appl. No. 16/135,436, Examiner Interview Summary mailed Apr. 8, 2020", 3 pgs.
"U.S. Appl. No. 14/438,327, Notice of Allowance mailed Apr. 22, 2020", 10 pgs.
"U.S. Appl. No. 14/438,327, Corrected Notice of Allowability mailed May 5, 2020", 3 pgs.
"U.S. Appl. No. 15/568,614, Final Office Action mailed May 15, 2020", 25 pgs.
"U.S. Appl. No. 16/135,472, Examiner Interview Summary mailed May 19, 2020", 4 pgs.
"U.S. Appl. No. 16/135,436, Notice of Allowance mailed Jul. 10, 2020", 10 pgs.
"U.S. Appl. No. 15/568,614, Response filed Jul. 14, 2020 to Final Office Action mailed May 15, 2020", 23 pgs.
"U.S. Appl. No. 16/135,472, Final Office Action mailed Aug. 21, 2020", 6 pgs.
"U.S. Appl. No. 16/135,436, Corrected Notice of Allowability mailed Sep. 11, 2020", 7 pgs.
"U.S. Appl. No. 15/568,614, Notice of Allowance mailed Sep. 30, 2020", 10 pgs.
"U.S. Appl. No. 15/568,614, Corrected Notice of Allowability mailed Nov. 30, 2020", 8 pgs.
"U.S. Appl. No. 16/135,472, Corrected Notice of Allowability mailed Nov. 30, 2020", 8 pgs.
"37 C.F.R. section 1.132 Declaration for U.S. Appl. No. 16/135,436, filed Jan. 13, 2020", (2020), 5 pgs.
"International Application Serial No. PCT US2013 064842, International Search Report mailed Jan. 17, 2014", 3 pgs.
"European Application Serial No. 13848400.1, Extended European Search Report mailed Apr. 28, 2016", 8 pgs.
"International Application Serial No. PCT US2013 064842, Written Opinion mailed Jan. 17, 2014", 10 pgs.
"International Application Serial No. PCT US2013 064842, International Preliminary Report on Patentability mailed May 7, 2015", 12 pgs.

(56) References Cited

OTHER PUBLICATIONS

"International Application Serial No. PCT US2016 028652, International Search Report mailed Jul. 26, 2016", 2 pgs.
"International Application Serial No. PCT US2016 028652, Written Opinion mailed Jul. 26, 2016", 8 pgs.
"Chinese Application Serial No. 201380055869.X, Response filed Sep. 9, 2016 to Office Action mailed May 26, 2016", (With English Translation), 18 pgs.
"European Application Serial No. 13848400.1, Response filed Oct. 19, 2015 to Communication pursuant to Rules 161(1) and 162 EPC mailed Jun. 2, 2015", 17 pgs.
"European Application Serial No. 13848400.1, Response filed Oct. 14, 2016 to Extended European Search Report mailed Apr. 28, 2016", 17 pgs.
"Chinese Application Serial No. 201380055869.X, Response filed Feb. 28, 2017 to Office Action mailed Dec. 15, 2016", w English Claims, 21 pgs.
"Japanese Application Serial No. 2015-539651, Office Action mailed Jul. 11, 2017", w English Translation, 10 pgs.
"Chinese Application Serial No. 201380055869.X, Response filed Sep. 4, 2017 to Office Action mailed Jun. 19, 2017", w English Claims, 17 pgs.
"Japanese Application Serial No. 2015-539651, Response filed Sep. 6, 2017 to Office Action mailed Jul. 11, 2017", w English claims, 15 pgs.
"International Application Serial No. PCT US2016 028652, International Preliminary Report on Patentability mailed Nov. 2, 2017", 10 pgs.
"Japanese Application Serial No. 2015-539651, Examiners Decision of Final Refusal mailed Nov. 21, 2017", w English Translation, 13 pgs.
"Japanese Application Serial No. 2015-539651, Response filed Mar. 20, 2018 to Examiners Decision of Final Refusal mailed Nov. 21, 2017", w English Claims, 34 pgs.
"Chinese Application Serial No. 201380055869.X, Respone filed Apr. 12, 2018 to Office Action mailed Nov. 27, 2017", w English Claims, 17 pgs.
"Japanese Application Serial No. 2015-539651, Office Action mailed May 15, 2018", w English Translation, 15 pgs.
"European Application Serial No. 13848400.1, Communication Pursuant to Article 94(3) EPC mailed Apr. 9, 2018", 7 pgs.
"European Application Serial No. 16783856.4, Response filed Jun. 22, 2018 to Communication pursuant to Rules 161(2) and 162 EPC mailed Dec. 13, 2017", 11 pgs.
"International Application Serial No. PCT US2018 031083, International Search Report mailed Jul. 27, 2018", 4 pgs.
"International Application Serial No. PCT US2018 031083, Written Opinion mailed Jul. 27, 2018", 33 pgs.
"European Application Serial No. 13848400.1, Response filed Sep. 14, 2018 to Communication Pursuant to Article 94(3) EPC mailed Apr. 9, 2018", 42 pgs.
"Japanese Application Serial No. 2017-555548, Office Action mailed Aug. 21, 2018", w English translation, 8 pgs.
"Japanese Application Serial No. 2017-555548, Examiners Decision of Final Refusal mailed Mar. 26, 2019", w English translation, 5 pgs.
"European Application Serial No. 16783856.4, Extended European Search Report mailed Nov. 9, 2018", 7 pgs.
"European Application Serial No. 18794752.8, Communication Pursuant to Article 94(3) EPC mailed Apr. 10, 2019", 8 pgs.
"European Application Serial No. 16783856.4, Response filed May 28, 2019 to Extended European Search Report mailed Nov. 9, 2018", 16 pgs.
"European Application Serial No. 18794752.8, Extended European Search Report mailed Mar. 29, 2019", 5 pgs.
"European Application Serial No. 13848400.1, Communication Pursuant to Article 94(3) EPC mailed Jun. 4, 2019", 9 pgs.
"Japanese Application Serial No. 2017-555548, Respone filed Jul. 26, 2019 to Examiners Decision of Final Refusal mailed Mar. 26, 2019", w English Claims, 19 pgs.
"European Application Serial No. 18794752.8, Response filed Aug. 5, 2019 to Communication Pursuant to Article 94(3) EPC mailed Apr. 10, 2019", 55 pgs.
"International Application Serial No. PCT US2018 031083, International Preliminary Report on Patentability mailed Nov. 14, 2019", 35 pgs.
"European Application Serial No. 13848400.1, Response filed Dec. 16, 2019 to Communication Pursuant to Article 94(3) EPC mailed Jun. 4, 2019", 30 pgs.
"Drug Coated Balloon Catheters for Nonvascular Strictures".
"Chinese Application Serial No. 201680029925.6, Office Action mailed Feb. 21, 2020", w English translation, 15 pgs.
"European Application Serial No. 13848400.1, Communication Pursuant to Article 94(3) EPC mailed Apr. 24, 2020", 8 pgs.
"Chinese Application Serial No. 201680029925.6, Response filed Jul. 6, 2020 to Office Action mailed Feb. 21, 2020", w English Claims, 36 pgs.
"International Application Serial No. PCT US2020 019274, International Search Report mailed Jun. 26, 2020", 6 pgs.
"International Application Serial No. PCT US2020 019274, Written Opinion mailed Jun. 26, 2020", 7 pgs.
"Chinese Application Serial No. 201680029925.6, Office Action mailed Jul. 16, 2020", w English Translation, 22 pgs.
"Japanese Application Serial No. 2017-555548, Office Action mailed Aug. 25, 2020", w English translation, 22 pgs.
"European Application Serial No. 13848400.1, Response filed Oct. 19, 2020 to Communication Pursuant to Article 94(3) EPC mailed Apr. 24, 2020", 13 pgs.
"Chinese Application Serial No. 201680029925.6, Office Action mailed Oct. 22, 2020", w English translation, 25 pgs.
"Chinese Application Serial No. 201680029925.6, Response filed Jan. 5, 2021 to Office Action mailed Oct. 22, 2020", w o English Claims, 6 pgs.
Guha, Madhumita, "Effects of acyl chain length, unsaturation, and pH on thermal stability of model discoidal HDLs", Journal of Lipid Research vol. 49, (2008), 10 pgs.
Huang, Weigua, "Effect of transurethral split of the prostate using a double-columnar balloon catheter for benign prostatic hyperplasia", Medicine 95:40, (Mar. 1, 2016), 4 pgs.
Jaidishan, Shishir, "Effect of hydrophobic mismatch and interdigitation on sterol sphingomyelin interaction in ternary bilayer membranes", Biochimica et Biophysica Acta 1808, (2011), 1940-1945.
Kalaji, Nader, "Colloidal and physicochemical characterization of protein-containing PLGA microspheres before and after drying", e-Polymers 2009, No. 010, (Jan. 2009), 13 pgs.
Shiel Jr, William C, "Definition of stricture", [Online] Retrieved from the internet:https: www.medicinenet.com scriptmain art.asp? articlekey= 166621, (2019), 1 pg.
"European Application Serial No. 21712307.4, Response to Communication Pursuant to Rules 161 and 162 filed Apr. 5, 2023", 30 pgs.
Tian, Juanhua, "Rectifying disorder of extracellularmatrix to suppress urethral stricture by protein nanofilm-controlled drug delivery from urinary catheter", nature communications, (May 17, 2023), 17 pgs.
"European Application Serial No. 21712307.4, Communication Pursuant to Article 94(3) EPC mailed Feb. 29, 2024", 7 pgs.
"Japanese application Serial No. 2022-550683, Voluntary Amendment Filed Feb. 16, 2024", w/ English Claims, 11 pgs.
"Chinese Application Serial No. 202180029802.3, Office Action mailed Nov. 7, 2023", w English Translation, 28 pgs.
"International Application Serial No. PCT US2021 018823, Invitation to Pay Additional Fees mailed Jun. 7, 2021", 14 pgs.
"International Application Serial No. PCT US2021 018823, International Search Report mailed Aug. 10, 2021", 8 pgs.
"International Application Serial No. PCT US2021 018823, Written Opinion mailed Aug. 10, 2021", 12 pgs.
Bose, Rajendran JC, "Lipid polymer hybrid nanospheres encapsulating antiproliferative agents for stent applications", Journal of Industrial and Engineering Chemistry, the Korean Society of Industrial and Engineering Chemistry, Korea, vol. 36, (Feb. 24, 2016), 284-292.

(56) References Cited

OTHER PUBLICATIONS

"Chinese Application Serial No. 201380055869.X, Office Action mailed May 26, 2016", w English Translation, 6 pgs.
"Chinese Application Serial No. 201380055869.X, Office Action mailed Dec. 15, 2016", with English Translation, 20 pgs.
"Chinese Application Serial No. 201380055869.X, Office Action mailed Jun. 19, 2017", With English Translation, 13 pgs.
"Chinese Application Serial No. 201380055869.X, Office Action mailed Nov. 27, 2017", W English Translation, 13 pgs.
"U.S. Appl. No. 16/135,472, Restriction Requirement mailed Nov. 2, 2018", 5 pgs.
"U.S. Appl. No. 16/135,472, Response filed Nov. 14, 2018 to Restriction Requirement mailed Nov. 2, 2018", 10 pgs.
"U.S. Appl. No. 16/135,472, Notice of Non Responsive Amendment mailed Mar. 8, 2019", 2 pgs.
"U.S. Appl. No. 16/267,434, Non Final Office Action mailed Mar. 22, 2019", 11 pgs.
"U.S. Appl. No. 16/135,472, Response filed Mar. 28, 2019 to Notice of Non Responsive Amendment mailed Mar. 8, 2019", 10 pgs.
"U.S. Appl. No. 16/267,434, Response Filed Apr. 24, 2019 to Non-Final Office Action Mailed Mar. 22, 2019", 11 pgs.
"U.S. Appl. No. 16/267,434, Final Office Action mailed Jun. 14, 2019", 15 pgs.
"U.S. Appl. No. 16/135,472, Non Final Office Action mailed Jul. 30, 2019", 40 pgs.
"U.S. Appl. No. 16/135,472, Response filed Aug. 21, 2019 to Non Final Office Action mailed Jul. 30, 2019", 23 pgs.
"U.S. Appl. No. 16/267,434, Response filed Sep. 11, 2019 to Final Office Action mailed Jun. 14, 2019", 17 pgs.
"U.S. Appl. No. 16/519,720, Restriction Requirement mailed Oct. 18, 2019", 5 pgs.
"U.S. Appl. No. 16/519,720, Response filed Oct. 31, 2019 to Restriction Requirement mailed Oct. 18, 2019", 10 pgs.
"U.S. Appl. No. 16/267,434, Non Final Office Action mailed Nov. 18, 2019", 19 pgs.
"Chinese Application Serial No. 201380055869.X, Notice of Reexamination mailed Nov. 21, 2019", w English Translation, 8 pgs.
"U.S. Appl. No. 16/519,677, Restriction Requirement mailed Nov. 20, 2019", 5 pgs.
"U.S. Appl. No. 16/519,677, Response filed Dec. 13, 2019 to Restriction Requirement mailed Nov. 20, 2019", 10 pgs.
"U.S. Appl. No. 16/135,472, Response filed Jan. 13, 2020 to Final Office Action mailed Nov. 29, 2019", 27 pgs.
"U.S. Appl. No. 16/519,720, Non Final Office Action mailed Feb. 6, 2020", 23 pgs.
"U.S. Appl. No. 16/267,434, Response filed Feb. 13, 2020 to Non Final Office Action mailed Nov. 18, 2019", 17 pgs.
"U.S. Appl. No. 16/135,472, Non Final Office Action mailed Mar. 19, 2020", 56 pgs.
"U.S. Appl. No. 16/519,677, Non Final Office Action mailed Mar. 19, 2020", 31 pgs.
"U.S. Appl. No. 16/267,434, Final Office Action mailed Mar. 30, 2020", 18 pgs.
"U.S. Appl. No. 16/267,434, Response filed Mar. 31, 2020 to Final Office Action mailed Mar. 30, 2020", 8 pgs.
"U.S. Appl. No. 16/267,434, Notice of Allowance mailed Apr. 22, 2020", 10 pgs.
"U.S. Appl. No. 16/519,720, Response filed May 6, 2020 to Non Final Office Action mailed Feb. 6, 2020", 19 pgs.
"U.S. Appl. No. 16/267,434, Corrected Notice of Allowability mailed May 13, 2020", 3 pgs.
"U.S. Appl. No. 16/135,472, Response filed May 15, 2020 to Non Final Office Action mailed Mar. 19, 2020", 29 pgs.
"U.S. Appl. No. 16/519,677, Response filed Jun. 19, 2020 to Non Final Office Action mailed Mar. 19, 2020", 19 pgs.
"U.S. Appl. No. 16/519,720, Final Office Action mailed Aug. 21, 2020", 23 pgs.
"U.S. Appl. No. 16/135,472, Response filed Sep. 4, 2020 to Final Office Action mailed Aug. 21, 2020", 12 pgs.
"U.S. Appl. No. 16/519,720, Response filed Sep. 4, 2020 to Final Office Action mailed Aug. 21, 2020", 12 pgs.
"U.S. Appl. No. 16/519,677, Notice of Allowance mailed Sep. 21, 2020", 10 pgs.
"U.S. Appl. No. 16/135,472, Notice of Allowance mailed Oct. 7, 2020", 9 pgs.
"U.S. Appl. No. 16/519,720, Notice of Allowance mailed Oct. 21, 2020", 8 pgs.
"U.S. Appl. No. 16/986,683, Non Final Office Action mailed Oct. 29, 2020", 14 pgs.
"U.S. Appl. No. 16/864,373, Restriction Requirement mailed Nov. 17, 2020", 5 pgs.
"U.S. Appl. No. 16/519,677, Corrected Notice of Allowability mailed Nov. 30, 2020", 7 pgs.
"U.S. Appl. No. 16/986,683, Response filed Dec. 4, 2020 to Non Final Office Action mailed Oct. 29, 2020", 9 pgs.
"U.S. Appl. No. 16/864,373, Response filed Dec. 10, 2020 to Restriction Requirement mailed Nov. 17, 2020", 7 pgs.
"U.S. Appl. No. 17/133,088, Preliminary Amendment filed Dec. 29, 2020", 8 pgs.
"U.S. Appl. No. 16/986,683, Notice of Allowance mailed Jan. 4, 2021", 9 pgs.
Daughtry, "Balloon Dilation of the Ureter: A Means to Facilitate Passage of Ureteral and Renal Calculi", The Journal of Urology, vol. 136, (1986), 1063-1065.
Daughtry, "Balloon dilation of urethral strictures", Urology, vol. 31, (1988), 231-233.
Goldenberg, S L, "Balloon Dilatation of the Prostate", Alternate Methods in the Treatment of Benign Prostatic Hyperplasia, (1993), 97-119.
Vale, Ja, "Balloon dilatation of the prostate-should it have a place in the urologist's armamentarium?", Journal of the Royal Society of Medicine vol. 86, (Feb. 1993), pp. 83-86.
"Japanese Application Serial No. 2017-555548, Response filed Nov. 20, 2018 to Office Action mailed Aug. 21, 2018", w English Claims, 11 pgs.
"Japanese Application Serial No. 2018-052874, Office Action mailed Jan. 29, 2019", w English translation, 15 pgs.
"Japanese Application Serial No. 2018-563611, Notification of Reasons for Refusal mailed Apr. 23, 2019", w English translation, 7 pgs.
"Japanese Application Serial No. 2018-052874, Response filed May 14, 2019 to Office Action mailed Jan. 29, 2019", w English Claims, 24 pgs.
"PMA P130024: FDA Summary of Safety and Effectiveness Data (SSED)", Retrieved from the Internet:URL:https: www.accessdata.fda.gov cdrh_docs pdf13 P130024b.pdf, 44 pgs.
"Stricture", definition accessed online on Jun. 10, 2019, [Online] Retrieved from the internet:www.merriam-webster.com dictionary stricture, (2019), 1 pg.
"Japanese Application Serial No. 2018-563611, Response filed Jul. 22, 2019 to Notification of Reasons for Refusal mailed Apr. 23, 2019", w English Claims, 14 pgs.
"Japanese Application Serial No. 2018-563611, Notification of Reasons for Refusal mailed Aug. 20, 2019", w English translation, 7 pgs.
"Japanese Application Serial No. 2018-052874, Office Action mailed Oct. 1, 2019", w English translation, 6 pgs.
"Japanese Application Serial No. 2019-137680, Notification of Reasons for Rejection mailed Jul. 21, 2020", W English Translation, 5 pgs.
"Japanese Application Serial No. 2019-137680, Response filed Oct. 6, 2020 to Notification of Reasons for Rejection mailed Jul. 21, 2020", w English Translation, 5 pgs.
Aaron, Latayia, "Review of Prostate Anatomy and Embryology and the Etiology of BPH", Urol Clin North Am 43(3), (Aug. 2016), pp. 279-288.
Donatucci, Craig F, "Randomized Clinical Trial Comparing Balloon Dilatation to Transurethral Resection of Prostate for Benign Prostatic Hyperplasia", Adult Urology vol. 4 2, No. 1, (Jul. 1993), 42-49.
Lukacs, B, "One-year follow-up of 2829 patients with moderate to severe lower urinary tract symptoms treated with alt uzosin in

(56) References Cited

OTHER PUBLICATIONS general practice according to IPSS and a health-related quality-of-life questionnaire", BPM Group in General Practice, Urology; 55(4), (2000), 7 pgs.
Milonas, Daimantas, "The effect of complete transurethral resection of the prostate on symptoms, quality of life, and voiding function improvement", Central European Journal of Urology, (2015), pp. 169-174.
Oesterling, Joseph E, "The Origin and Development of Benign Prostatic Hyperplasia an Age-Dependent Process", Journal of Andrology, vol. 12, No. 6,, (1991), 8 pgs.
Pekker, M, "The surface charge of a cell lipid membrane", J Phys Chem Biophys 5, (2015), 15 pgs.
Roehrborn, C G, "Pathology of benign prostatic hyperplasia", International Journal of Impotence Research 20, (2008), S11-S18.
Shin, "Tissue Hyperplasia: Influence of a Paclitaxel-eluting Covered Stent-Preliminary Study in a Canine Urethral Model", Radiology, (2005), 438-444.
Szule, Joseph A, "The Effects of Acyl Chain Length and Saturation of Diacylglycerols and Phosphatidylcholines on Membrane Monolayer Curvature", Biophysical Journal vol. 83, (Aug. 2002), 977-984.
Van Loenhout, Rhiannon, "Prostate Cancer—PI-RADS v2", https: radiologyassistant.nl abdomen prostate-cancer-pi-rads-v2 Accessed on May 14, 2020, (Aug. 1, 2018), 19 pgs.
Yazdani, Saami K, "Vascular, Downstream, and Pharmacokinetic Responses to Treatment with a Low Dose Drug-Coated Balloon in a Swine Femoral Artery Model", Catheterization and Cardiovascular Interventions 83: 132-140, (2014), 132-140.
"Chinese Application Serial No. 202180029802.3, Office Action mailed Apr. 27, 2024", W/English Translation, 7 pgs.
"Chinese Application Serial No. 202180029802.3, Response filed Mar. 22, 2024 to Office Action mailed Nov. 7, 2023", w/ current English claims, 21 pgs.
"European Application Serial No. 21712307.4, Response filed Jun. 5, 2024 to Communication Pursuant to Article 94(3) EPC mailed Feb. 29, 2024", 14 pgs.
"Chinese Application Serial No. 202180029802.3, Response filed Jun. 13, 2024 to Office Action mailed Apr. 27, 2024", W English Claims, 15 pgs.
"Japanese Application Serial No. 2022-550683, Notification of Reasons for Refusal mailed Jan. 28, 2025", w/ English translation, 12 pgs.
"Japanese Application Serial No. 2022-550683, Response filed Apr. 28, 2025 to Notification of Reasons for Refusal mailed Jan. 28, 2025", W English Claims, 28 pgs.
"Japanese Application Serial No. 2022-550683, Notification of Reasons for Refusal mailed Jul. 15, 2025", w English Translation, 15 pgs.
"U.S. Appl. No. 18/631,293, Non Final Office Action mailed Oct. 22, 2025", 14 pgs.
"European Application Serial No. 21712307.4, Response Filed Sep. 2, 2025 to Communication under Rule 71(3) mailed May 21, 2025", 367 pgs.
Gross, Seth A., "Use of a Through-the-Scope Balloon System for Deep Enteroscopy", Gastroenterology & Hepatology, vol. 12, Issue 6, Jun. 2016, 386-387., (Year: 2016).
Mangiavillano, Benedetto, et al., "Biliary and pancreatic stenting: Devices and insertion techniques in therapeutic endoscopic retrograde U cholangiopancreatography and endoscopic ultrasonography", World J Gastrointest Endoso, Feb. 10, 2016; 8(3): 143-156., (Year: 2016).
"U.S. Appl. No. 18/672,320, Non Final Action with Restriction Requirements mailed Nov. 5, 2025", 18 pgs.
"U.S. Appl. No. 18/631,293, Response filed Dec. 10, 2025 to Non Final Office Action mailed Oct. 22, 2025", 15 pgs.

* cited by examiner

502
DISTAL FIXED WIRE BAND
506
INFLATED BALLOON LENGTH
504
503
510
511
505

501
509
PROXIMAL FIXED WIRE BAND
508
507

502
506
DEFLATED BALLOON LENGTH
504
503

510
511
505
501
509
508
507

505
501

510
505
503

POLYMER-ENCAPSULATED DRUG PARTICLES

CROSS-REFERENCE TO RELATED APPLICATIONS

This application claims the benefit of priority to U.S. Provisional Patent Application Ser. No. 62/979,980 filed Feb. 21, 2020, and U.S. Provisional Patent Application Ser. No. 63/104,965 filed Oct. 23, 2020, the disclosures of which are incorporated herein in their entirety by reference.

The disclosure of each of the following applications are incorporated herein by reference in their entirety. U.S. patent application Ser. No. 16/135,436, which is a continuation-in-part of international Application No. PCT/US2018/03108 filed May 4, 2018, which claims the benefit of priority to U.S. Provisional Patent Application Ser. No. 62/502,212 filed May 5, 2017. U.S. patent application Ser. No. 16/135,436 is also a continuation-in-part of U.S. patent application Ser. No. 15/568,614 filed Oct. 23, 2017, which is a U.S. National Stage Filing under 35 U.S.C. 371 from International Application No. PCT/US2016/028652 filed Apr. 21, 2016, which claims the benefit of priority to U.S. Provisional Patent Application Ser. No. 62/152,559 filed Apr. 24, 2015. U.S. patent application Ser. No. 16/135,436 is also a continuation-in-part of U.S. patent application Ser. No. 14/438,327 filed Apr. 24, 2015, which is a U.S. National Stage Filing under 35 U.S.C. 371 from International Application No. PCT/US2013/064842 filed Oct. 14, 2013, which claims the benefit of priority to U.S. Provisional Patent Application Ser. No. 61/795,790 filed Oct. 26, 2012. U.S. patent application Ser. No. 16/135,472, which is a continuation-in-part of international Application No. PCT/US2018/03108 filed May 4, 2018, which claims the benefit of priority to U.S. Provisional Patent Application Ser. No. 62/502,212 filed May 5, 2017. U.S. patent application Ser. No. 16/135,472 is also a continuation-in-part of U.S. patent application Ser. No. 15/568,614 filed Oct. 23, 2017, which is a U.S. National Stage Filing under 35 U.S.C. 371 from International Application No. PCT/US2016/028652 filed Apr. 21, 2016, which claims the benefit of priority to U.S. Provisional Patent Application Ser. No. 62/152,559 filed Apr. 24, 2015. U.S. patent application Ser. No. 16/135,472 is also a continuation-in-part of U.S. patent application Ser. No. 14/438,327 filed Apr. 24, 2015, which is a U.S. National Stage Filing under 35 U.S.C. 371 from International Application No. PCT/US2013/064842 filed Oct. 14, 2013, which claims the benefit of priority to U.S. Provisional Patent Application Ser. No. 61/795,790 filed Oct. 26, 2012.

BACKGROUND

Benign prostatic hyperplasia is a non-cancerous enlargement of the prostate gland, affecting more than 50% percent of men over the age of 60. The prostate early in life is the size and shape of a walnut and weighs about 20 grams. Prostate enlargement appears to be a normal process. With age, the prostate gradually increases in size to twice or more its normal size. As the prostate grows, it presses against and narrows the urethra, causing prostatic urethra compression and urinary obstruction that makes voiding difficult or impossible.

Male urethral stricture disease occurs at a rate as high as 0.6% in some populations. Urethral stricture diseases appear to be more common in the elderly population. Patients with urethral strictures experience moderate to severe complications, such as lower urinary tract voiding symptoms or urinary retention, recurrent urinary tract infection and the need for repeat urethral procedures such as dilation, urethrotomy, or urethroplasty.

Ureteral strictures of the upper urinary tract are either congenital or acquired. Congenital ureteral strictures are most commonly located at the ureteropelvic junction. Most ureteral strictures are acquired and usually are iatrogenic. The most common etiology of the ureteral strictures is injury during endoscopic, open, or laparoscopic surgical procedures.

Bladder neck strictures (e.g., stenosis or contracture) and urethral strictures are recognized complications of all treatments for prostate cancer. Recalcitrant bladder neck strictures are relatively rare overall; however, these are associated with significant morbidity, often requiring multiple interventions with associated complications and impact upon quality of life. Bladder neck strictures and urethral strictures are complications following treatment for prostate cancer such as radical prostatectomy (RP), radiotherapy, cryotherapy, and high intensity focused ultrasound (HIFU).

Strictures in the digestive body lumen or the gastrointestinal tracts include esophageal strictures, achalasia strictures, biliary strictures, stomach strictures, small intestine strictures, duodenum strictures, jejunum strictures, ileum strictures, colon strictures, rectum strictures, and large intestine strictures. The type of disease classifies a stricture into benign or malignant.

A biliary stricture, also referred to as a bile duct stricture, occurs when the bile duct gets smaller or narrower. The bile duct is the tube that takes bile from the liver to the small intestine. When the bile duct becomes narrow, it makes it difficult for food to digest. Biliary strictures can be caused by any injuries to the bile duct, swelling, pancreatitis, intestinal injuries, and cancers in the bile duct or pancreas. The symptoms of the biliary stricture include pain, chills and fever, itching, and nausea or vomiting.

Esophageal strictures are a problem commonly encountered in gastroenterological medicine and can be caused by malignant or benign lesions. Dysphagia is the symptom experienced by all patients. Most of these patients require palliative treatment to relieve the dysphagia.

Barrett's disease, also called Barrett's esophagus, is a condition in which there is an abnormal (metaplastic) change in the mucosal cells lining the lower portion of the esophagus, from normal stratified squamous epithelium to simple columnar epithelium with interspersed goblet cells that are normally present only in the colon. This change is considered to be a premalignant condition because it is associated with a high incidence of further transition to esophageal adenocarcinoma, an often-deadly cancer.

Eosinophilic esophagitis (EoE) is a chronic inflammatory disease. The symptoms of the disease include dysphagia and food impaction, and are often a consequence of esophageal strictures. Repeated endoscopic dilation of the esophageal fibrostenotic strictures of eosinophilic esophagitis using bougie and balloon catheter is used for treatment of such strictures.

Lower gastrointestinal tract strictures are a narrowing of a section of the intestine that causes problems by slowing or blocking the movement of food through the area. The strictures are caused by recurrent inflammations, cancer, Crohn's disease, and ulcerative colitis. The strictures include esophageal strictures, achalasia strictures, strictures in stents, biliary strictures, stomach strictures, small intestine strictures, duodenum strictures, jejunum strictures, ileum strictures, colon strictures, rectum strictures, and large intestine strictures.

Inflammatory bowel disease (IBD) includes Crohn's disease (CD) and ulcerative colitis (UC). Chrohn's disease- and ulcerative colitis-induced strictures are a common complication of inflammatory bowel disease and surgeries for the treatment thereof. Stricture rates for those suffering from inflammatory bowel disease range from 34% to 70% over time. Some of the strictures are refractory or reoccurring, which require repeated endoscopic dilation for treatment.

An anastomosis is a connection or opening between two body structures that carry fluid. A surgical anastomosis is the joining of two fluid-carrying body lumen structures via a surgical technique. An anastomotic stricture is a narrowing of an anastomosis. Anastomotic strictures are a common complication of surgical anastomoses and of various other surgical procedures such as radical prostatectomies, bowel resections, and gastric bypass surgery. Anastomotic strictures are usually fibrotic and can be difficult to manage and treat. An anastomotic stricture can include a stricture in an anastomosis between two portions of the same body structure, or between two different body structures, wherein the body structure can be an esophagus, biliary tract, stomach, small intestine, duodenum, jejunum, ileum, colon, rectum, large intestine, colon, rectum, urethra, ureter, or bladder neck. An anastomotic stricture can be a colorectal stricture, a stricture after gastric bypass, an ileocolonic stricture, a gastrointestinal stricture, a J-pouch stricture, or a bladder neck stricture (e.g., stenosis). While balloon dilation has been shown to be a safe and effective nonsurgical method of managing anastomotic strictures, problems still remain, such as a need for repeated balloon dilations due to refractory or reoccurring anastomotic strictures.

Vaginal stenosis is an abnormal condition in which the vagina becomes narrower and shorter due to the formation of fibrous tissue. Vaginal stenosis can have a negative impact on sexual dysfunction, dyspareunia and make pelvic exams difficult and painful. The lining of the vagina may also be thinner and drier and contain scar tissue. This condition can result in pain during sexual intercourse or a pelvic exam. Vaginal stenosis is often caused by an episiotomy, radiation therapy to the pelvis, or various types of surgery.

Chronic obstructive pulmonary disease (COPD) is a term used to classify two major airflow obstruction disorders: chronic bronchitis and emphysema. Approximately 16 million Americans have COPD, 80-90% of them were smokers throughout much of their lives. COPD is a leading cause of death in the U.S. Chronic bronchitis is inflammation of the bronchial airways. The bronchial airways connect the trachea with the lungs. When inflamed, the bronchial tubes secrete mucus, causing a chronic cough. Emphysema is an over-inflation of the alveoli, or air sacs in the lungs. This condition causes shortness of breath.

Asthma is a chronic respiratory disease characterized by inflammation of the airways, excess mucus production and airway hyper-responsiveness, and a condition in which airways narrow excessively or too easily respond to a stimulus. Asthma episodes or attacks cause narrowing of the airways, which make breathing difficult. Asthma attacks can have a significant impact on a patient's life, limiting participation in many activities. In severe cases, asthma attacks can be life threatening. Presently, there is no known cure for asthma.

Chronic sinusitis is an inflammation of the membrane lining of one or more paranasal sinuses. Chronic sinusitis lasts longer than three weeks and often continues for months. In cases of chronic sinusitis, there is usually tissue damage. According to the Center for Disease Control (CDC), thirty-seven million cases of chronic sinusitis are reported annually.

Radiation (e.g., radiotherapy) is used as one of mode of treatment for localized cancers. Localized cancer is the most commonly diagnosed cancer. The majority of patients are diagnosed in potentially curable early stages. Standard local treatment options include active surveillance, radical prostatectomy (RP) for prostate cancer, and, generally for all cancer treatments, radiotherapy (RT). Radiotherapy can be delivered via external beam (EBRT) or brachytherapy (BT). The side effects associated with each treatment can vary significantly. Localized cancers include prostate cancers, urethral cancers, ureteral cancers, esophageal cancers, biliary cancers, stomach cancers, small intestine cancers, duodenum cancers, jejunum cancers, ileum cancers, colon cancers, rectum cancers, large intestine cancers, and pulmonary cancers. The radiation treatment can create injury in adjacent health tissue, such as strictures. Radiation treatment-induced strictures can include urethral strictures, ureteral strictures, esophageal strictures, biliary tract strictures, stomach strictures, small intestine strictures, duodenum strictures, jejunum strictures, ileum strictures, colon strictures, rectum strictures, and large intestine strictures. Treatment of radiation-induced strictures can be complex and difficult. Due to the high survival rates, the number of prostate cancer survivors in the United States annually increased by 220,000 men up to almost 2.8 million in 2015, leaving a large number of men at risk for short- or long-term side effects of radiation therapy for prostate cancer treatment. The development of urethral strictures as a side effect of radiation therapy for prostate cancer treatment is particularly problematic.

Various minimally invasive methods used to treat various cancers, large colon polyps, and Barrett's esophagus are worldwide practice. The various minimally invasive methods are gaining favor over surgical procedures when the patients prefer to avoid a surgical operation. Several randomized controlled trials and meta-analyses have proven the clinical and oncological safety and effectiveness of the laparoscopic gastrectomy, robot-assisted gastrectomy, EMR (endoscopic mucosal resection) and ESD (endoscopic submucosal dissection) in treatment of cancers and Barrett's esophagus of various stages. EMR (endoscopic mucosal resection) and ESD (endoscopic sub-mucosal dissection) are safe and effective for treatment of superficial cancers during the early stages, such as esophageal cancers, biliary cancers, stomach cancers, small intestine cancers, duodenum cancers, jejunum cancers, ileum cancers, colon cancers, rectum cancers, colorectal cancers, ileocolonic cancers, and gastrointestinal cancers. EMR and ESD are safe and effective for treatment of high-graded Barrett's esophagus. Laparoscopic gastrectomy, robot-assisted gastrectomy, EMR, and ESD are feasible procedures in terms of clinical and oncological safety; however, the recurrences of malignancy and refractory stricture were noted in some of patients. The local reoccurrence rate of cancers after minimally invasive treatments is in the range of 2-20%, depending on the type and stage of the cancer and on follow-up times. The occurrence rate of strictures or stenoses after minimally invasive procedures is about 26%-70%. Repeated endoscopic balloon dilations are needed to treat refractory or reoccurring strictures or stenoses.

Cardiovascular disease or atherosclerosis is characterized by hardening and narrowing of the arteries due to deposition of fatty plaques on the arterial lumens. Over time the plaque build-up can become severe enough to block the flow of oxygen rich blood to downstream tissue. Atherosclerosis can occur in any arteries in the body. The blockage, or stenosis, of critical arteries such as the carotid artery and coronary arteries can lead to sudden death. Stenosed peripheral arteries such as the iliac, superficial femoral, popliteal, tibial, and peroneal arteries can lead to the need for amputation. Chronic kidney disease can occur if the renal arteries are blocked. Currently drug-coated balloons and drug eluting stents are being used to treat the stenosis. Long term mortality rates, thrombosis rates, and efficacy of these drug coated devices is still not good enough. Better devices are needed to improve the safety and efficacy for cardiovascular disease stenosis.

Kidney failure is a disease that leads to the build-up of waste products in the blood. To prevent waste product build-up patients have a medical procedure called chronic hemodialysis. During hemodialysis the blood is sent through a dialyzer to remove waste products. The access point for the blood is typically in a limb at a special vascular junction created called an arteriovenous fistula (AVF) or arteriovenous grafts (AVG). AVFs are a special type of anastomosis in which the artery is sutured directly to a vein. AVGs are a different type of anastomosis in which the connection between the artery and vein is facilitated by a synthetic or autologous tube. AVFs and AVGs frequently become stenosed and cause blood flow obstruction. When this happens they must either be dilated open or abandoned for the creation of a new AVF or AVG in order to complete the dialysis treatments. Drug-coated balloons are used to dilate stenosed AVFs and AVGs but better devices are needed to improve safety and efficacy.

Heart valve disease is common disease afflicting the aging population. It is diagnosed by listening to the heartbeat with a stethoscope during a physical exam. An abnormal sound the heart makes is called a murmur and different murmurs can be indicative of a specific type of heart valve disease. Types of heart valve disease include stenosis, regurgitation, prolapse, and atresia. Heart valve stenosis is a narrowing or stiffening of the heart valve that results in the valve not opening or closing properly. The flaps of the valve may thicken, stiffen, or fuse together. As a result, the valve cannot fully open and the heart then has to work harder to pump blood through the valve. The result of this could be hypoxia or reduced oxygen supply affecting the whole body, local tissue, or a region of the body. Heart valve stenosis can be treated by a procedure called balloon valvuloplasty or BAV. BAV involves tracking an inflatable balloon through the vasculature to the heart valve and dilating the heart valve anulus. Recently the number of BAV procedures performed has increased because BAV is utilized before, after, and/or during transcatheter aortic valve replacement (TAVR) procedures. Restenosis rates following BAV have been noted in the 40-80% range at 5-9 months indicating the need for improvement in devices and technique.

SUMMARY OF THE INVENTION

In various embodiments, the present invention provides polymer-encapsulated drug particles that include a therapeutic agent and one or more polymers. Optionally, the polymer-encapsulated drug particles include a first ionic or zwitterionic additive. The first ionic or zwitterionic additive, when present, is in the polymer-encapsulated drug particles, coated on a surface of the polymer-encapsulated drug particles, or a combination thereof.

In various embodiments, the present invention provides a drug-releasing coating that includes polymer-encapsulated drug particles that include a therapeutic agent and one or more polymers. Optionally, the polymer-encapsulated drug particles include a first ionic or zwitterionic additive. The first ionic or zwitterionic additive, when present, is in the polymer-encapsulated drug particles, coated on a surface of the polymer-encapsulated drug particles, or a combination thereof. The coating also includes a release matrix including an ionic or zwitterionic additive. The coating can be located in any suitable location, such as on a balloon catheter, a drug-coated catheter, a drug-eluting stent, a drug-eluting stent on a balloon, a drug-eluting stent on a drug-coated balloon, a stent on a drug-coated balloon, or a combination thereof.

In various embodiments, the present invention provides a drug-releasing coating that includes polymer-encapsulated drug particles that include a therapeutic agent and one or more polymers that encapsulate the therapeutic agent. The polymer-encapsulated drug particles also include an ionic or zwitterionic additive. The polymer-encapsulated drug particles can be charged polymer-encapsulated drug particles.

Various embodiments provide a method for treating or preventing a nonvascular or vascular stricture or stenosis. The method includes inserting a catheter into the body lumen, wherein the catheter includes a balloon or stent including the drug coating that includes the polymer-encapsulated drug particles. The method includes expanding the balloon or stent to contact the coating layer with the stricture, stenosis, or area wherein the stricture or stenosis is to be prevented. When a balloon is used, the method can include deflating the balloon. When a balloon is used, the method can also include removing the balloon or stent from the body lumen.

Various embodiments provide a method of making polymer-encapsulated drug particles. The method includes forming a suspension including a therapeutic agent and a polymer. The method includes processing the suspension to reduce particle size of the suspension. The method also includes adding an aqueous premix to the suspension to form polymer-encapsulated drug particles in the suspension. The polymer-encapsulated drug particles include the therapeutic agent and the polymer.

Various embodiments provide a method of making polymer-encapsulated drug particles. The method includes forming an organic premix including an organic solvent, one or more polymers, a therapeutic agent, and optionally a first ionic or zwitterionic additive. The method includes forming an aqueous premix including water and a water-soluble polymer or surfactant. The method includes adding an organic solvent to the aqueous premix. The method includes combining the aqueous premix and the organic premix together. The method also includes agitating the combined aqueous premix and organic premix to form an emulsion including the polymer-encapsulated drug particles.

In various embodiments, the present invention provides a method for preparing polymer-encapsulated drug particles that comprise a therapeutic agent, one or more polymers, and optionally a first ionic or zwitterionic additive. The method comprises making an organic premix by solubilizing and mixing one or more polymers, therapeutic agent, and optionally a first ionic or zwitterionic additive to form a premix in organic solvent. The organic solvent can be is at least partially miscible with aqueous solutions (e.g., a polar organic solvent). The method includes making a second aqueous premix comprising a water-soluble polymer and adding the organic solvent used in the first premix. The method comprises mixing the organic premix into the aqueous premix such that an organic solvent in water coacervate is created. The method comprises further adding water to the coacervate solution to drive the organic solvent out of the coacervate to harden it into the polymer-encapsulated drug particles.

Various embodiments provide a method of making a balloon catheter. The method includes applying the polymer-encapsulated drug particles or the drug-releasing coating including the same to an exterior of a balloon of a balloon catheter.

Various embodiments provide a balloon catheter. The balloon catheter includes an elongated balloon. The balloon catheter also includes a coating layer overlying an exterior surface of the balloon. The coating layer includes the polymer-encapsulated drug particles; or the drug-releasing coating including the same; or a composition including a therapeutic agent, a first additive, and a second additive; or a combination thereof. The therapeutic agent in the composition is chosen from paclitaxel, docetaxel, taxol, an mTOR inhibitor, rapamycin, sirolimus, zotarolimus, everolimus, tacrolimus, umirolimus, an analogue thereof, and combinations thereof, and the therapeutic agent has a particle size of 0.2 micron to 10 microns. The first additive includes a water-insoluble or partially water-insoluble additive including at least one alkyl fatty group or cholesteryl group and with the first additive having a molecular weight of 50 to 750. The second additive is more hydrophilic or more water-soluble than the first additive and includes a polyethylene glycol (—$(CH_2CH_2O)$—) or a polyglycerol (—$(CH_2$—CHOH—$CH_2O)$—) unit. The second additive has a molecular weight in the range of 750 to 100,000.

In various embodiments, the present invention provides a balloon catheter for delivering a therapeutic agent to a target site of a body lumen. The balloon catheter includes an elongated balloon, and a coating layer overlying an exterior surface of the balloon. The coating layer includes the polymer-encapsulated drug particles; or the drug-releasing coating including the polymer-encapsulated drug particles; or a composition including two or more additives and an initial drug load of a therapeutic agent. The therapeutic agent in the composition is chosen from an mTOR inhibitor, paclitaxel, docetaxel, taxol, an mTOR inhibitor, rapamycin, sirolimus, zotarolimus, everolimus, tacrolimus, umirolimus, an analogue thereof, and combinations thereof. The therapeutic agent in the composition is crystalline, partially crystalline, amorphous, partially amorphous, or a combination thereof. The first additive includes a water-insoluble or partially water-insoluble additive including at least one alkyl fatty group or cholesteryl group with a molecular weight of 50 to 750 (e.g., 50 or more, or less than, equal to, or greater than 100, 150, 200, 250, 300, 350, 400, 450, 500, 550, 600, 650, 700, or 750 or less). The second additive is more hydrophilic or more water-soluble than the first additive and includes a polyethylene glycol (—$(CH_2CH_2O)$—) or a polyglycerol (—$(CH_2$—CHOH—$CH_2O)$—) unit. The second additive has a molecular weight in the range of 750 to 100,000 (e.g., 750 or more, or less than, equal to, or less than 1,000, 2,000, 4,000, 6,000, 8,000, 10,000, 20,000, 40,000, 60,000, 80,000, 90,000, or 100,000 or less). The particle size of the therapeutic agent particles in the coating is in the range of 0.2 micron to 10 micron (e.g., 0.2 microns or more, or less than, equal to, or greater than 0.3 microns, 0.4, 0.5, 0.6, 0.7, 0.8, 0.9, 1, 1.2, 1.4, 1.6, 1.8, 2, 2.2, 2.4, 2.6, 2.8, 3, 3.2, 3.4, 3.6, 3.8, 4, 4.5, 5, 5.5, 6, 6.5, 7, 7.5, 8, 8.5, 9, 9.5, or 10 microns or less).

In various embodiments, the present invention provides a balloon catheter for delivering a therapeutic agent to a target site of a body lumen stricture or stenosis. The balloon catheter includes an elongated balloon, and a coating layer overlying an exterior surface of the balloon. The coating layer includes the polymer-encapsulated drug particles; or the drug-releasing coating including the polymer-encapsulated drug particles; or a composition including two or more additives and an initial drug load of a therapeutic agent. The balloon includes a polyester, a polyamide, a nylon 12, a nylon 11, a polyamide 12, a block copolymer of a polyether and a polyamide, a polyether block amide, a polyurethane, a block copolymer of a polyether and a polyester, or a combination thereof. The therapeutic agent in the composition is chosen from paclitaxel, docetaxel, taxol, their analogues, an mTOR inhibitor, rapamycin, sirolimus, zotarolimus, everolimus, tacrolimus, umirolimus, an analogue thereof, and combinations thereof. The therapeutic agent in the composition is crystalline, partially crystalline, amorphous, partially amorphous, or a combination thereof. The particle size of the therapeutic agent in the composition is in the range of 0.2 micron to 5 micron (e.g., 0.2 microns or more, or less than equal to, or greater than 0.3 microns, 0.4, 0.5, 0.6, 0.7, 0.8, 0.9, 1, 1.2, 1.4, 1.6, 1.8, 2, 2.2, 2.4, 2.6, 2.8, 3, 3.2, 3.4, 3.6, 3.8, 4, 4.2, 4.4, 4.6, 4.8, or 5 microns or less). In embodiments including the composition, the first additive, the second additive, or a combination thereof encapsulates the therapeutic agent, the additive-encapsulated therapeutic agent has a larger particle size than the therapeutic agent itself, and the particle size of the additive-encapsulated therapeutic agent in the coating is in the range of 0.3 micron to 10 micron (e.g., 0.3 microns or more, or less than, equal to, or greater than 0.4 microns, 0.5, 0.6, 0.7, 0.8, 0.9, 1, 1.2, 1.4, 1.6, 1.8, 2, 2.2, 2.4, 2.6, 2.8, 3, 3.2, 3.4, 3.6, 3.8, 4, 4.5, 5, 5.5, 6, 6.5, 7, 7.5, 8, 8.5, 9, 9.5, or 10 microns or less). In embodiments including the composition, the additive-encapsulated therapeutic agent is encapsulated partially or fully, such that the therapeutic agent is partially or completely surrounded by additive (e.g., as discrete particles, or as a partially or fully continuous coating) that contacts the therapeutic agent. For example, 25%-100% of the surface area of the additive-encapsulated therapeutic agent can be in contact with the first additive, the second additive, or a combination thereof, or 50-100%, 75-100%, or 1% or more, or less than, equal to, or greater than 25%, 30, 35, 40, 45, 50, 55, 60, 65, 70, 75, 80, 85, 90, 91, 92, 93, 94, 95, 96, 97, 98, 99%, or 100% or less. The first additive includes a water-insoluble or slightly or partially water-insoluble additive including at least one alkyl fatty group or cholesteryl group and the first additive can have a molecular weight of 50 to 750. In embodiments including the composition, the first additive in the coating has a lower melting temperature than that of the first additive in its pure form, and the first additive in the coating has a lower crystallinity than that of the first additive in its pure form. The second additive is more hydrophilic or more water-soluble than the first additive and that includes a polyethylene glycol (—$(CH_2CH_2O)$—) or a polyglycerol (—$(CH_2$—CHOH—$CH_2O)$—) unit. The second additive has a molecular weight in the range of 750 to 100,000, or 750 to 50,000, or 750 to 10,000. The body lumen stricture or stenosis is chosen from urethral stricture, prostatic urethral stricture, ureteral stricture, esophageal stricture, sinus stricture, stomach stricture, small intestine stricture, colon stricture, rectum stricture, large intestine stricture, bladder neck stricture, a biliary tract stricture, vaginal stricture, in-stent restenosis, coronary artery stenosis, superficial femoral artery stenosis, popliteal artery stenosis, anterior tibial artery stenosis, posterior tibial artery stenosis, and peroneal artery stenosis. The first additive with cholesteryl group is chosen from cholesterol, cholesteryl acetate, cholesteryl phenylacetate, cholesteryl laurate, cholesteryl palmitate, cholesteryl stearate, cholesteryl n-valerate, cholesteryl benzoate, cholesteryl heptylate, cholesteryl decylate, cholesteryl caproate, cholesteryl oleate, cholesteryl oleyl carbonate, cholesteryl linoleate, cholesteryl pelargonate, cholesteryl erucate, cholesteryl caprylate, 5α-cholestane, 5α-cholestan-3-one, and combinations thereof. The water-insoluble or slightly or partial water-insoluble first additive with alkyl fatty group is chosen from alkyl glyceryl ethers, monoglycerides of C8-C12 fatty acids, alkyl alcohol, alkyl ether, alkyl ester, caprylic acid, monocaprilin, capric acid, monocaprin, lauric acid, dodecyl glycerol, butanoic acid, hexanoic acid, octanoic acid, decanoic acid, dodecanoic acid, tetradecanoic acid, hexadecanoic acid, octadecanoic acid, octadecatrienoic acid, eicosanoic acid, eicosenoic acid, eicosatetraenoic acid, eicosapentaenoic acid, docosahexaenoic acid, tocotrienol, butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, natural or synthetic phospholipids, mono-, di-, or triacylglycerols, cardiolipin, phosphatidylglycerol, phosphatidic acid, phosphatidylcholine, alpha tocoferol, phosphatidylethanolamine, sphingomyelin, phosphatidylserine, phosphatidylinositol, dimyristoylphosphatidylcholine, dioleoylphosphatidylcholine, dipalmitoylphosphatidylcholine, distearoylphosphatidylcholine, phosphatidylethanolamines phosphatidylglycerols, sphingolipids, prostaglandins, gangliosides, neobee, niosomes, derivatives thereof, and combinations thereof. The water-soluble second additive is chosen from cholesteryl-polyethylene glycol 600 sebacate, polyoxyethanyl α-tocopheryl sebacate, methylated polyethylene glycol cholesterol (mPEG cholesterol), polyethylene glycol cholesterol (PEG cholesterol), polyethylene glycol ester cholesterol (PEG cholesterol), polyethylene glycol ether cholesterol (PEG cholesterol), methylated polyethylene glycol-amide-cholesterol (mPEG cholesterol), polyethylene glycol-amide-cholesterol (PEG cholesterol), polyethylene glycol (PEG)-cholesteryl sebacate, polyethylene glycol cholesterol, PEG amide ester cholesterol, PEG amide ether cholesterol, mPEG amide ester cholesterol, DSPE-PEG-cholesterol, PEGylated phospholipid, methylated PEGylated phospholipid, PEG caprylic/capric diglycerides, PEG8 caprylic/capric glycerides, PEG caprylate, PEG caprate, PEG caproate, PEG-20 sorbitan monolaurate (Tween-20), PEG-20 sorbitan monopalmitate (Tween-40), PEG-20 sorbitan monostearate (Tween-60), PEG-20 sorbitan monooleate (Tween-80), PEG laurate, PEG oleate, PEG stearate, PEG glyceryl laurate, PEG-30 glyceryl oleate, polyglyceryl fatty acid esters, polyglyceryl oleate (Plurol Oleique), polyglyceryl-2 dioleate (Nikkol DGDO), polyglyceryl-10 trioleate, polyglyceryl stearate, polyglyceryl laurate, polyglyceryl myristate, polyglyceryl palmitate, polyglyceryl linoleate, polyglyceryl-10 laurate (Nikkol Decaglyn 1-L), polyglyceryl-10 oleate (Nikkol Decaglyn 1-0), polyglyceryl-10 mono/dioleate (Caprol™ PEG 860), polyglyceryl-10 stearate, polyglyceryl-10 laurate, polyglyceryl-10 myristate, polyglyceryl-10 palmitate, polyglyceryl-10 linoleate, polyglyceryl-6 stearate, polyglyceryl-6 laurate, polyglyceryl-6 myristate, polyglyceryl-6 palmitate, polyglyceryl-6 linoleate, and combinations thereof.

In various embodiments, the present invention provides a method for prevention or treatment of strictures in the digestive body lumen or the gastrointestinal tract. The method includes inserting a balloon catheter into a target site in a body lumen including the non-vascular stricture. The balloon catheter including an elongated balloon, and a coating layer overlying an exterior surface of the balloon. The coating layer includes the polymer-encapsulated drug particles; or the drug-releasing coating including the polymer-encapsulated drug particles; or a composition including two or more additives and an initial drug load of a therapeutic agent. The composition includes a first additive comprising a water-insoluble or partially water-insoluble additive, a second additive that is more hydrophilic or more water-soluble than the first additive, and an initial drug load of a therapeutic agent chosen from paclitaxel, docetaxel, taxol, an mTOR inhibitor, rapamycin, sirolimus, zotarolimus, everolimus, tacrolimus, umirolimus, an analogue thereof, and combinations thereof. In embodiments including the composition, the first additive, the second additive, or a combination thereof encapsulates the therapeutic agent, the additive-encapsulated therapeutic agent has a larger particle size than the therapeutic agent itself, and the particle size of the additive-encapsulated therapeutic agent in the coating is in the range of 0.3 micron to 10 micron. The method includes inflating the balloon at the target site to contact the coating layer with walls of the body lumen at the location of the non-vascular stricture until the balloon achieves an inflated balloon diameter for an inflation period. The method includes deflating the balloon after the inflation period. The method includes withdrawing the balloon catheter from the body lumen. The strictures in the digestive body lumen or the gastrointestinal tracts include esophageal strictures, achalasia strictures, biliary strictures, stomach strictures, small intestine strictures, duodenum strictures, jejunum strictures, ileum strictures, colon strictures, rectum strictures, ileoanal J-pouch strictures, and large intestine strictures. The strictures in the digestive body lumen or the gastrointestinal tracts include esophageal stricture of eosinophilic esophagitis, radiation induced strictures, Crohn's disease induced strictures, ulcerative colitis induced strictures, chronic inflammatory bowel disease (IBD) induced strictures, anastomotic strictures of surgical procedures, or combinations thereof.

In various embodiments, the present invention provides a method for prevention or treatment of stenosis or stricture in a vascular body lumen. The method includes inserting a balloon catheter into a target site in a body lumen including the vascular stenosis or stricture. The balloon catheter includes an elongated balloon, and a coating layer overlying an exterior surface of the balloon. The coating layer includes the polymer-encapsulated drug particles; or the drug-releasing coating including the polymer-encapsulated drug particles; or a composition including two or more additives and an initial drug load of a therapeutic agent. The composition includes a first additive, a second additive, and an initial drug load of a therapeutic agent chosen from paclitaxel, docetaxel, taxol, an mTOR inhibitor, rapamycin, sirolimus, zotarolimus, everolimus, tacrolimus, umirolimus, an analogue thereof, and combinations thereof. In the composition, the therapeutic agent is crystalline, partially crystalline, amorphous, partially amorphous, or a combination thereof. In the composition, the particle size of the therapeutic agent is in the range of 0.2 micron to 5 micron. In embodiments including the composition, the first additive, the second additive, or a combination thereof encapsulates the therapeutic agent, the additive-encapsulated therapeutic agent has a larger particle size than the therapeutic agent itself, and the particle size of the additive-encapsulated therapeutic agent in the coating is in the range of 0.3 micron to 10 micron. The first additive comprises a water-insoluble or slightly or partially water-insoluble additive comprising at least one alkyl fatty group or cholesteryl group can the first additive can have a molecular weight of 50 to 750. In embodiments including the composition, the first additive in the coating has a lower melting temperature than that of the first additive in its pure form, and the first additive in the coating has a lower crystallinity than that of the first additive in its pure form. The second additive is more hydrophilic or more water-soluble than the first additive and that comprises polyethylene glycol (—($CH_2CH_2O$)—) or a polyglycerol (—($CH_2$—CHOH—$CH_2O$)—) unit. The molecular weight of the second additive is in the range of 750 to 100,000. The method includes inflating the balloon at the target site to contact the coating layer with walls of the body lumen at the location of the stenosis or stricture until the balloon achieves an inflated balloon diameter for an inflation period. The method includes deflating the balloon after the inflation period. The method includes withdrawing the balloon catheter from the body lumen.

In various embodiments, the present invention provides a method for preparing a coated balloon catheter. The method includes providing a crystalline therapeutic agent, wherein the therapeutic agent is chosen from paclitaxel, docetaxel, taxol, an mTOR inhibitor, rapamycin, sirolimus, zotarolimus, everolimus, tacrolimus, umirolimus, an analogue thereof, and combinations thereof. The method includes processing the therapeutic agent so that a majority of the therapeutic agent crystals have a particle size of 0.2 microns to 5.0 microns. The method includes providing a fluid in which the therapeutic agent is substantially insoluble. The method includes mixing the fluid with the therapeutic agent, a first water-insoluble additive, and a second water-soluble additive wherein the first additive encapsulates the therapeutic agent crystals and the first additive has a particle size of 0.3 microns to 10 microns. The method includes applying the mixture to the external surface of a balloon catheter. The first additive, the second additive, or a combination thereof encapsulates the therapeutic agent, the additive-encapsulated therapeutic agent has a larger particle size than the therapeutic agent itself, and the particle size of the additive-encapsulated therapeutic agent in the coating is in the range of 0.3 micron to 10 microns.

In various embodiments, the present invention provides a method for preparing a drug coating solution. The method includes mixing water, water-miscible solvent, therapeutic agent, and a water-soluble additive to form a premix. The method includes processing the premix to reduce the particle size of the therapeutic agent. The method includes mixing insoluble water additive, the water-soluble additive, water, and water-miscible solvent to form a second premix. The method includes mixing the second premix with the first processed premix to form a coating solution. The therapeutic agent is chosen from paclitaxel, docetaxel, taxol, an mTOR inhibitor, rapamycin, sirolimus, zotarolimus, everolimus, tacrolimus, umirolimus, an analogue thereof, and combinations thereof. The therapeutic agent is crystalline, partially crystalline, amorphous, partially amorphous, or a combination thereof. The coating solution is an aqueous suspension of the therapeutic agent. The particle size of the therapeutic agent is in the range of 0.2 micron to 5 micron. The first additive, the second additive, or a combination thereof encapsulates the therapeutic agent, the additive-encapsulated therapeutic agent has a larger particle size than the therapeutic agent itself, and the particle size of the additive-encapsulated therapeutic agent in the coating is in the range of 0.3 micron to 10 micron. The processing is one of microfluidization, homogenization, rotator-stator milling, high or low energy bead milling, or high-power ultrasonic probe homogenization. The first additive includes a water-insoluble or slightly or partially water-insoluble additive including at least one alkyl fatty group or cholesteryl group and the first additive can have a molecular weight of 50 to 750. The first additive in the coating has a lower melting temperature than that of the first additive in its pure form (e.g., as determined by DSC of the coating versus DSC of the pure additive). The first additive in the coating has a lower crystallinity than that of the first additive in its pure form (e.g., as determined by DSC of the coating versus DSC of the pure additive). The second additive is more hydrophilic or more water-soluble than the first additive and that includes a polyethylene glycol (—($CH_2CH_2O$)—) or a polyglycerol (—($CH_2$—CHOH—$CH_2O$)—) unit. The second additive has a molecular weight in the range of 750 to 100,000, or 750 to 50,000, or 750 to 10,000.

In various embodiments, the present invention provides a method for coating a balloon catheter. The method includes preparing an aqueous suspension coating solution. Preparing the aqueous suspension includes mixing water, water-miscible solvent, therapeutic agent, and a water-soluble additive to form a premix. Preparing the suspension includes processing the premix to reduce the particle size of the therapeutic agent. Preparing the suspension includes mixing insoluble water additive, the water-soluble additive, water, and water-miscible solvent to form a second premix. Preparing the suspension includes mixing the second premix with the first processed premix to form a coating solution. The therapeutic agent can be an mTOR inhibitor (e.g., rapamycin, sirolimus, zotarolimus, everolimus, tacrolimus, umirolimus, or a combination thereof) or an analogue or derivative thereof. The therapeutic agent is crystalline, partial crystalline, amorphous, partially amorphous, or a combination thereof. The coating solution is an aqueous suspension of the therapeutic agent. The particle size of the therapeutic agent is in the range of 0.2 micron to 5 micron. The first additive, the second additive, or a combination thereof encapsulates the therapeutic agent, the additive-encapsulated therapeutic agent has a larger particle size than the therapeutic agent itself, and the particle size of the additive-encapsulated therapeutic agent in the coating is in the range of 0.3 micron to 10 micron. The first additive includes a water-insoluble or slightly or partially water-insoluble additive including at least one alkyl fatty group or cholesteryl group and the first additive can have a molecular weight of 50 to 750. The first additive in the coating has a lower melting temperature than that of the first additive in its pure form. The first additive in the coating has a lower crystallinity than that of the first additive in its pure form. The second additive is more hydrophilic or more water-soluble than the first additive and that includes a polyethylene glycol (—($CH_2CH_2O$)—) or a polyglycerol (—($CH_2$—CHOH—$CH_2O$)—) unit. The second additive has a molecular weight in the range of 750 to 100,000, or 750 to 50,000, or 750 to 10,000. The method includes preparing a balloon catheter. Preparing the balloon catheter includes inflating the balloon catheter. Preparing the balloon catheter includes cleaning the surface of the balloon, such as with an ethanol wipe. Preparing the balloon catheter includes fixturing the balloon so it can be mounted inside a coating machine horizontally and rotated at a fixed speed. The method includes dispensing the coating solution onto the surface of the balloon while the nozzle is translating laterally across the balloon. The method includes continuing to rotate the balloon to evaporate the solvent at room temperature or higher than room temperature. The method includes pleating and folding the balloon catheter. The method includes sterilizing the coated balloon catheter.

In various embodiments, the present invention provides a minimally invasive method for treatment or prevention of nonvascular or vascular strictures or stenosis. The method includes inserting a catheter with an expandable body through the body lumen that contains the stricture or stenosis such that the expandable body is inside the stricture or stenosis. The catheter with an expandable body includes balloon catheters, drug coated catheters, drug eluting stents, drug eluting stents crimped on a drug-coated balloon. The catheter includes an expandable body with a coating layer overlying the exterior surface of the expandable body of the catheter. The coating layer includes the polymer-encapsulated drug particles; or the drug-releasing coating including the polymer-encapsulated drug particles; or a composition including two or more additives and an initial drug load of a therapeutic agent. The one or more additives are chosen from water-insoluble additives, slightly or partially soluble water additives, water-soluble additives, or a combination thereof. The method includes expanding the body to contact the coating layer with the stricture or stenosed body lumen to a certain diameter for a period of time. The method includes contracting the expanded body after the time period and withdrawing from the stricture or stenosed body lumen. In some embodiments, the method further includes performing a surgical procedure to dilate, cut, or remove tissue prior to the insertion of the balloon catheter into the target site.

Embodiments of the present invention provide a medical device coating formulation including a therapeutic agent or drug for treatment of the strictures in nonvascular and vascular body lumens, and additives that enhance absorption of the drug into tissue of body lumens. Some embodiments provide a coating that overlays the expandable portion of the catheter that has a single layer or multiple layers that contain a single or multiple therapeutic agent. In some embodiments the layer in contact with the expandable portion of the catheter has no therapeutic agent and is formulated with ingredients that allow the entire or a substantial portion of the coating to transfer to the stricture or stenosis upon expansion of the catheter. Causes of body lumen strictures, and related diseases, can include infections and inflammations by pathogens such as bacteria and viruses. In some embodiments the coating has additives that have antibacterial and antiviral properties. In some embodiments the layer of coating that contains the therapeutic agent has drug that is crystalline, amorphous, or a combination thereof. In some embodiments that layer of coating that contains the therapeutic agent has at least one hydrophilic ingredient and at least one hydrophobic ingredient. In some embodiments the coatings layers contain ingredients that enhance the adhesion of the coating with the luminal surface of the dilated stricture or stenosis. In some embodiments the coating is formulated such that upon expansion of the catheter the coating transfers to the stricture or stenosis as particulate, agglomerated particulate, dissolved matter, or a combination thereof. In some embodiments the size of the particulate or agglomerated particulate transferred is small and less than 10 μm, or more preferably less than 5 μm. In some embodiments the coating layer includes the polymer-encapsulated drug particles or a drug-releasing coating including the same.

In various embodiments, the present invention provides a catheter including an expandable portion of an elongated body that is used to dilate nonvascular and vascular strictures or stenosis. In some embodiments the elongated body is a balloon with a cylindrical shape. In some embodiments the elongated body is a balloon that has a shape or longitudinal profile that prevents migration of the balloon in the body lumen it is expanded in.

In various embodiments, the present invention provides a method for applying a coating solution to an expandable portion of a catheter, evaporating the liquid in the coating solution to leave the dried coating on the catheter.

BRIEF DESCRIPTION OF THE FIGURES

The drawings illustrate generally, by way of example, but not by way of limitation, various embodiments of the present invention.

FIGS. 8A-C illustrate diagrams of exemplary powder x-ray diffraction graphs obtained from: FIG. 8A crystalline sirolimus, FIG. 8B dodecyl glycerol, and FIG. 8C sterilized sirolimus drug coating on balloon.

FIGS. 9A-C illustrate diagrams of DSC scans of: FIG. 9A crystalline sirolimus, FIG. 9B dodecyl glycerol, and FIG. 9C sirolimus drug-coated balloon, in accordance with various embodiments.

DETAILED DESCRIPTION OF THE INVENTION

Figure 1:
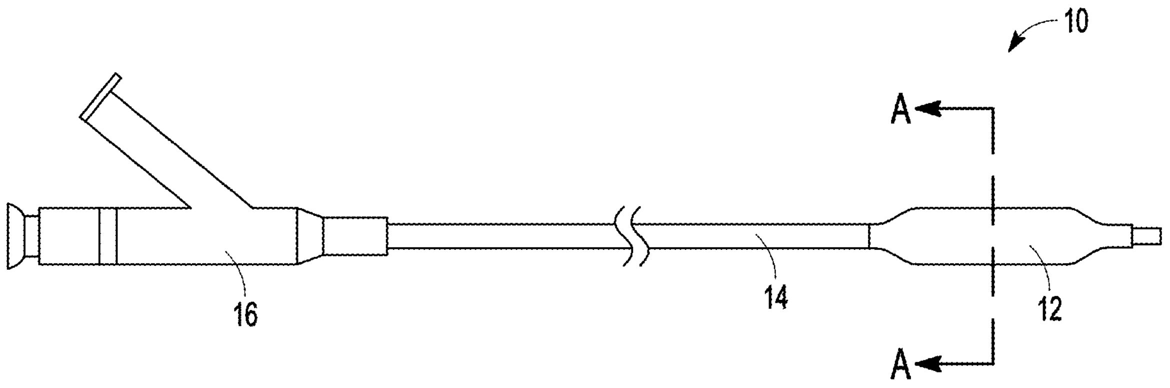
FIG. 1 is a perspective view of an embodiment of a balloon catheter according to the present invention (the balloon catheter includes a fixed wire, over the wire, and rapid exchanged balloon catheters details not shown in FIG. 1), in accordance with various embodiments.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

Polymer-Encapsulated Drug Particles.

Various embodiments provide polymer-encapsulated drug particles. The polymer-encapsulated drug particles include a therapeutic agent and one or more polymers that encapsulate the therapeutic agent. Optionally, the polymer-encapsulated drug particles include a first ionic or zwitterionic additive. The first ionic or zwitterionic additive, when present, is in the polymer-encapsulated drug particles (e.g., encapsulated by the encapsulating polymer), coated on a surface of the polymer-encapsulated drug particles (e.g., on an outer surface of the encapsulating polymer), or a combination thereof. In some embodiments, the polymer-encapsulated drug particles include the first ionic or zwitterionic additive. In other embodiments, the polymer-encapsulated drug particles are free of the first ionic or zwitterionic additive.

The therapeutic agent can be any suitable therapeutic agent. The therapeutic agent can be chosen from paclitaxel, docetaxel, taxol, an mTOR inhibitor, rapamycin, sirolimus, zotarolimus, everolimus, tacrolimus, umirolimus, an analogue thereof, and combinations thereof. The therapeutic agent can be crystalline, partially crystalline, amorphous, partially amorphous, or a combination thereof. The therapeutic agent can be crystalline and/or partially crystalline. The therapeutic agent can have any suitable largest dimension (e.g., diameter), such as a largest dimension of 0.1 to 29.9 microns, or 0.5 to 15 microns, or 1 to 10 microns, or less than or equal to 29.9 microns and greater than or equal to 0.1 micron, 0.5, 1, 2, 3, 4, 5, 6, 7, 8, 9, 10, 12, 14, 16, 18, 20, 22, 24, 26, 28, or 29 microns. The therapeutic agent can form any suitable proportion of the polymer-encapsulated drug particle, such as 5-45 wt %, or 25-35 wt %, or less than or equal to 45 wt % and equal to or greater than 5, 10, 15, 20, 25, 26, 27, 28, 29, 30, 31, 32, 33, 34, 35, or 40 wt %.

The polymer that encapsulates the therapeutic agent in the polymer-encapsulated drug particles can be any suitable one or more polymers. The polymer can be at least one chosen from polylactic acid, (PL), polyglycolic acid (GA), a polylactic acid/polyglycolic acid copolymer (PLGA), polydioxanone, polycaprolactone, polyphosphazene, collagen, gelatin, chitosan, glycosoaminoglycans, and copolymers thereof. The PLGA copolymer can be ester-capped or can have carboxylic acid end groups. The PLGA copolymer can have a weight ratio of lactic acid to glycolic acid of 50:50, 65:35, 75:25, or 85:15. The molecular weight of the PLGA copolymer can range from 20,000 g/mol to 300,000 g/mol. The one or more polymers can form any suitable proportion of the polymer-encapsulated drug particle, such as 30-80 wt %, or 50-75 wt %, or less than or equal to 80 wt % and equal to or greater than 30, 35, 40, 45, 50, 55, 56, 57, 58, 59, 60, 61, 62, 63, 64, 65, 66, 67, 68, 69, 70, or 75 wt %. The polymer can be a neutral polymer. The polymer can be an anionic, cationic, or zwitterionic polymer, such as any polymer described herein as suitable for use as the first ionic or zwitterionic additive of the second ionic or zwitterionic additive.

In the polymer-encapsulated drug particles, the polymer encapsulates the therapeutic agent. The polymer-encapsulated drug particles have a larger diameter than the therapeutic agent particles that are encapsulated. As used herein, "encapsulate" can refer to 50-100% surface area coverage of the encapsulated material (i.e., therapeutic agent and optional first ionic or zwitterionic additive) by the encapsulant (e.g., polymer, first ionic or zwitterionic additive, and/or first and second additive as described herein), or 60-100%, 75-100%, 90-100%, or equal to or greater than 50%, 55, 60, 65, 70, 75, 80, 85, 90, 92, 94, 96, 98, 99, 99.5, or 99.9% or more.

The polymer-encapsulated drug particles can include a first ionic or zwitterionic additive. The first ionic or zwitterionic additive can be in the polymer-encapsulated drug particles, coated on a surface of the polymer-encapsulated drug particles, or a combination thereof. The first ionic or zwitterionic additive can be homogeneously distributed within the particle (e.g., with the therapeutic agent within the encapsulating polymer), outside of the particle (e.g., on the encapsulating polymer), or a combination thereof. The first ionic or zwitterionic additive can be coated on a surface of the polymer-encapsulated particle. The coating of the first ionic or zwitterionic additive can be part of the polymer-encapsulated drug particle, such that the coating of the first ionic or zwitterionic additive can be considered in the dimensions of the particle when determining the largest dimension of the polymer-encapsulated drug particles. The polymer-encapsulated drug particle can include 1, 2, 3, or 4 or more first ionic or zwitterionic additives, such as 1 or 2 first ionic or zwitterionic additives, such as 1 first ionic or zwitterionic additive. The one or more first ionic or zwitterionic additives can form any suitable proportion of the polymer-encapsulated drug particles, such as 0.5-20 wt %, 1-10 wt %, or less than or equal to 20 wt % and greater than or equal to 0.5, 1, 2, 3, 4, 5, 6, 7, 8, 9, 10, 11, 12, 14, 16, or 18 wt %.

The first ionic or zwitterionic additive can include a cationic molecule, an anionic additive, or a zwitterionic additive. The first ionic or zwitterionic additive can increase the zeta potential of the polymer-encapsulated drug particles (i.e. make the zeta potential more positive). A positive zeta potential of the polymer-encapsulated drug particles can provide better adhesion to the tissue and/or better drug transfer to the tissue. For example, a positive zeta potential of the polymer-encapsulated drug particles can attract amino groups in peptides or proteins, and/or negatively-charged lipids of lipid bilayers in cell membranes (e.g., negative ions on the surface of cell membranes), causing better adhesion. Increased adhesion can prolong the stay of the polymer-encapsulated drug particles on the wall of the body lumen, leading to higher drug dose to the tissue and/or greater rate of drug delivery to the tissue. The first ionic or zwitterionic additive can include a charged polymer, a charged lipid, a phospholipid, a phosphocholine, a phosphatidylcholine, a phosphatidylethanolamine, a phosphatidylserine, a phosphatidylinositol, and combinations thereof.

Two acyl groups of the charged lipid or two acyl groups of the charged phospholipid (e.g., of the esters bonded to the triglyceride backbone) include mis-matched acyl groups that differ in one or more properties or characteristics. The mis-matched acyl groups can differ by length, degree of saturation, substituents thereon, substitution patterns thereon, or a combination thereof. For example, both acyl groups can be saturated, or one can be saturated and one can be unsaturated, or both can be unsaturated. For example, 1,2-dioleoyl-sn-glycero-3-phosphocholine (DOPC) has two unsaturated acyl chains and 1-palmitoyl-2-oleoyl-glycero-3-phosphocholine has acyl groups where one is saturated and one is unsaturated. In embodiments with two unsaturated acyl groups, the unsaturated acyl groups can have a double bond at the same or different carbon locations or can have multiple double bonds along the carbon chain in the same or different locations. The mis-matched or matched acyl groups with different length, degree of saturation, substituents thereon, and substitution patterns can have a different phase transition or softening temperature. The phase transition or softening temperature of the charged lipid can affect the properties of the coating, such as coating integrity, dry durability, the rate of drug release from the coating, rate and/or degree drug uptake into the tissue, or a combination thereof. Lipids and phospholipids that have a high phase transition temperature can lead to brittle coatings that crack and flake leading to inconsistent drug dosing. Lipids and phospholipids that have a low phase transition temperature can be hard to handle because they can be wet and sticky which leads to inconsistent drug dosing. The phase transition temperatures of charged lipids and phospholipids can range from −70° C. to 80° C. The preferable range of phase transition temperatures is −30° C. to 50° C. The most preferable range of phase transition temperatures is −20° C. to 40° C. In some embodiments coatings can have a mixture of lipids and/or phospholipids that allow the phase transition temperature of the coating to be in the desirable range with desirable mechanical properties (dry and pliable, and not sticky or brittle).

The mis-matched acyl groups of the charged lipid or charged phospholipid can have lengths of C6-C34, such as C6, 7, 8, 9, 10, 11, 12, 13, 14, 15, 16, 17, 18, 19, 20, 21, 22, 23, 24, 25, 26, 27, 28, 29, 30, 31, 32, 33, or 34. In some embodiments, the same or different lengths of the acyl groups having chain lengths of C6-C34 can create perturbations, unevenness, and/or curvature in the lipid bilayer of the cell membrane to enhance the drug permeation to the tissue. In embodiments with charged lipids or phospholipids having mis-matched acyl groups that differ in length, the length of the two acyl groups can differ by a length of C1-C28, or C1-C10, or C1-C8, or greater than or equal to C1, 2, 3, 4, 5, 6, 7, 8, 9, 10, 11, 12, 13, 14, 15, 16, 17, 18, 19, 20, 21, 22, 23, 24, 25, 26, 27, or C28. For example, the two acyl groups that differ in length can have lengths of C12/C14, C12/C16, C12/C18, C12/C20, C12/C22, C12/C24, C12/C26, C14/C16, C14/C18, C14/C20, C14/C22, C14/C24, C14/C26, C16/C18, C16/C20, C16/C22, C16/C24, C16/C26, C18/C20, C18/C22, C18/C24, C18/C26, C20/C22, C20/C24, C20/C26, C22/C24, C22/C26, or C24/C26.

The charged polymer can be chosen from polycation-containing cyclodextrin, amino cyclodextrin or a derivative thereof, amino dextran, a histone, a protamine, cationized human serum albumin, an aminopolysaccharide, chitosan, a peptide, poly-L-lysine, poly-L-ornithine, poly(4-hydroxy-L-proline ester), a polyethylenimine, a polyallylamine, a polypropylenimine, a polyamidoamine dendrimer, a cationic polyoxazoline, a poly(beta-aminoester), a PEG-PEI copolymer, a PLGA-PEI copolymer, a positively charged gelatin (e.g., base-treated gelatin), hydroxy-terminated poly(2-methyl-2-oxazoline), poly(2-ethyl-2-oxazoline), stearic acid-modified branched polyethylenimine, branched PEI-g-PEG, poly(1-vinylpyrrolidone-co-2-dimethylaminoethyl methacrylate), poly(1-vinylpyrrolidone)-graft-(1-triacontene), polylysine, polyarginine, poly(N,N-dimethylaminoethyl methacrylate), a cationic copolymer of dimethylaminoethyl methacrylate/butyl methacrylate/methyl methacrylate (e.g., Eudragit E), an anionic copolymer of methacrylic acid/methyl methacrylate (e.g., Eudragit L and/or Eudragit S), a copolymer of ethyl acrylate/methyl methacrylate/methacrylic acid ester with quaternary ammonium groups (e.g., Eudragit RS and/or SR), and combinations thereof. An example of a methacrylic acid ester with quaternary ammonium groups is trimethylammonioethyl methacrylate chloride.

The charged lipid can be chosen from 1,2-dipalmitoyl-sn-glycero-3-ethylphosphocholine (chloride salt), 1,2-distearoyl-sn-glycero-3-ethylphosphocholine (chloride salt), cholic acid, deoxycholic acid, chenodeoxycholic acid, lithocholic acid, 1,2-dilauroyl-sn-glycero-3-phosphoglycerol, sodium salt, 1,2-dihexanoyl-sn-glycero-3-phosphocholine, 1,2-diheptanoyl-sn-glycero-3-phosphocholine, 1,2-dioctanoyl-sn-glycero-3-phosphocholine, 1,2-dinonanoyl-sn-glycero-3-phosphocholine, 1,2-decanoyl-sn-glycero-3-phosphocholine, 1,2-diundecanoyl-sn-glycero-3-phosphocholine, 1,2-dilauroyl-sn-glycero-3-phosphocholine, 1,2-dimyristoyl-sn-glycero-3-phosphocholine, 1,2-dipalmitoyl-sn-glycero-3-phosphocholine, 1,2-distearoyl-sn-glycero-3-phosphocholine, 1-palmitoyl-2-stearoyl-sn-glycero-3-phosphocholine, 1-stearoyl-2-palmitoyl-sn-glycero-3-phosphocholine, 1-palmitoyl-2-lauroyl-sn-glycero-3-phosphocholine, 1,2-dioleoyl-sn-glycero-3-phosphocholine (DOPC), 1-palmitoyl-2-oleoyl-glycero-3-phosphocholine (POPC), 1-stearoyl-2-hydroxy-sn-glycero-3-phosphocholine, 1-lauroyl-2-hydroxy-sn-glycero-3-phosphocholine, 1-myristoyl-2-hydroxy-sn-glycero-3-phosphocholine, 1-palmitoyl-2-hydroxy-sn-glycero-3-phosphocholine, dieicosenoyl phosphatidylcholine (1,2-dieicosenoyl-sn-glycero-3-phosphocholine, C20:1 PC), diarachidonoyl phosphatidylcholine (1,2-diarachidoyl-sn-glycero-3-phosphocholine, C20:0 PC), dierucoyl phosphatidylcholine (1,2-dierucoyl-sn-glycero-3-phosphocholine, C22:1 PC), didocosahexaenoyl phosphatidylcholine (1,2-didocosahexaenoyl-sn-glycero-3-phosphocholine, C22:6 PC), heneicosenoyl phosphatidylcholine (1,2-heneicosenoyl-sn-glycero-3-phosphocholine, C21:1 PC), and dinervonyl phosphatidylcholine (1,2-dinervonoyl-sn-glycero-3-phosphocholine, C24:1 PC), and combinations thereof.

The first ionic or zwitterionic additive can be chosen from 1,2-dipalmitoyl-sn-glycero-3-ethylphosphocholine (chloride salt), 1,2-distearoyl-sn-glycero-3-ethylphosphocholine (chloride salt), cholic acid, deoxycholic acid, chenodeoxycholic acid, lithocholic acid, 1,2-dilauroyl-sn-glycero-3-phosphoglycerol, sodium salt, 1,2-dihexanoyl-sn-glycero-3-phosphocholine, 1,2-diheptanoyl-sn-glycero-3-phosphocholine, 1,2-dioctanoyl-sn-glycero-3-phosphocholine, 1,2-dinonanoyl-sn-glycero-3-phosphocholine, 1,2-decanoyl-sn-glycero-3-phosphocholine, 1,2-diundecanoyl-sn-glycero-3-phosphocholine, 1,2-dilauroyl-sn-glycero-3-phosphocholine, 1,2-dimyristoyl-sn-glycero-3-phosphocholine, 1,2-dipalmitoyl-sn-glycero-3-phosphocholine, 1,2-distearoyl-sn-glycero-3-phosphocholine, 1-palmitoyl-2-stearoyl-sn-glycero-3-phosphocholine, 1-stearoyl-2-palmitoyl-sn-glycero-3-phosphocholine, 1-palmitoyl-2-lauroyl-sn-glycero-3-phosphocholine, 1,2-dioleoyl-sn-glycero-3-phosphocholine (DOPC), 1-palmitoyl-2-oleoyl-glycero-3-phosphocholine (POPC), 1-stearoyl-2-hydroxy-sn-glycero-3-phosphocholine, 1-lauroyl-2-hydroxy-sn-glycero-3-phosphocholine, 1-myristoyl-2-hydroxy-sn-glycero-3-phosphocholine, 1-palmitoyl-2-hydroxy-sn-glycero-3-phosphocholine, and a combination thereof.

The first ionic or zwitterionic additive can include or be a water-insoluble or slightly or partial water-insoluble additive including at least one acyl group. The first ionic or zwitterionic additive can have a molecular weight of 50 to 750, 750 to 100,000, or 750 to 50,000, or 750 to 10,000. The first ionic or zwitterionic additive can have a lower melting temperature than that of the additive in its pure form. The first ionic or zwitterionic additive can have a lower crystallinity than that of the additive in its pure form.

The polymer-encapsulated drug particle can have any suitable zeta potential, such as a negative zeta potential, or a positive zeta potential. The zeta potential is the electrical potential at the slipping plane (i.e., the at the interface which separates mobile fluid from fluid that remains attached to the surface of the particle). The zeta potential of the polymer-encapsulated drug particle can be measured in any suitable way, such as using electrophoretic light scattering (ELS) or electroacoustic determination. The polymer-encapsulated drug particle can have a positive zeta potential, such as a zeta potential of greater than zero, or 1-50, or 2-40, or less than or equal to 50 and greater than or equal to 0.5, 1, 2, 3, 4, 5, 6, 8, 10, 12, 14, 16, 18, 20, 25, 30, 35, 40, or 45. The polymer-encapsulated drug particle can have a negative zeta potential, such as a zeta potential or less than zero, or −1 to −50, or −2 to −40, or more positive than or equal to −50 and more positive or equal to −45. −40, −35, −30, −25, −20, −18, −16, −14, −12, −10, −8, −6, −5, −4, −3, −2, −1, or −0.5. A positive zeta potential of the polymer-encapsulated drug particle can provide better adhesion to the tissue and/or better drug transfer to the tissue. For example, a positive zeta potential of the polymer-encapsulated drug particles can attract amino groups in peptides or proteins, and/or negatively-charged lipids of lipid bilayers in cell membranes (e.g., negative ions on the surface of cell membranes), causing better adhesion. Increased adhesion can prolong the stay of the polymer-encapsulated drug particles on the wall of the body lumen, leading to higher drug dose to the tissue and/or greater rate of drug delivery to the tissue. In embodiments of the polymer-encapsulated drug particle that include the first ionic or zwitterionic additive thereon or therein, the zeta potential of the polymer-encapsulated drug particles can be higher than (i.e., more positive than) that of a corresponding polymer-encapsulated drug particle that is free of the first ionic or zwitterionic additive. A polymer-encapsulated drug particle that is a CPDEP is a polymer-encapsulated drug particle that has a zeta potential that is not zero (e.g., is less than or greater than zero), such as due to the presence of a first ionic or zwitterionic addition inside the particle, on the surface of the particle, or a combination thereof, and/or the use of one or more charged polymers as the encapsulating polymer. The ionic or zwitterionic additives in the CPDEP particles can migrate to the surface of the CPDEP and/or be applied to the surface of the CPDEP particles. The charged head of the ionic or zwitterionic additive can be oriented away from the particle, with the hydrophobic tail oriented toward the particle, such that the zeta potential of the polymer-encapsulated drug particle is higher.

The polymer-encapsulated drug particles can have any suitable dimensions. The first ionic or zwitterionic additive, if present, in combination with the polymer, can be used in the determination of particle size. The polymer-encapsulated drug particles can have a largest dimension of 0.2 micron to 30 microns, or 0.5 micron to 5 microns, or 0.8 micron to 3 microns, or less than or equal to 30 microns and greater than or equal to 0.2 micron, 0.5, 0.6, 0.8, 1, 1.2, 1.4, 1.6, 1.8, 2, 2.5, 3, 4, 5, 6, 7, 8, 9, 10, 12, 14, 16, 18, 20, 22, 24, 26, or 28 microns.

The polymer-encapsulated drug particles can be polymer encapsulated drug particles (PEDP), charged polymer encapsulated drug particles (CPEDP), or a combination thereof. A positive charge density or zeta potential of the CPEDP can be higher than (i.e., more positive than) that of the PEDP. A positive charge density or zeta potential of the CPEDP can be higher than that of the therapeutic agent in the absence of the polymer encapsulant. For polymer-encapsulated drug particles that are CPEDPs that include the first ionic or zwitterionic additive, the positive charge density or zeta potential of the CPEDP can be higher than that of the therapeutic agent in the absence of the first ionic or zwitterionic additive.

The polymer-encapsulated drug particles can include one or more antioxidants, such as BHT. The one or more antioxidants can be mixed with the therapeutic agent during formation of the particles. The one or more antioxidants can be any suitable proportion of the polymer-encapsulated drug particles, such as 0.5-20 wt %, or 1-10 wt %, or less than 20 wt % and greater than or equal to 1, 2, 3, 4, 5, 6, 7, 8, 9, or 10 wt %.

The polymer-encapsulated drug particles can be on any suitable surface intended for drug delivery to a target location, such as on a medical device, such as on a balloon catheter, a drug-coated catheter, a drug-eluting stent, a drug-eluting stent on a balloon, a drug-eluting stent on a drug-coated balloon, a stent on a drug-coated balloon, or a combination thereof. The polymer-encapsulated drug particles can be part of a coating on a medical device, wherein the coating is a drug-releasing coating.

Drug-releasing coating including the polymer-encapsulated drug particles.

Various embodiments of the present invention provide a drug-releasing coating. The drug-releasing coating includes the polymer-encapsulated drug particles that include the therapeutic agent and the one or more polymers that encapsulate the therapeutic agent. Optionally, the polymer-encapsulated drug particles include a first ionic or zwitterionic additive. The first ionic or zwitterionic additive, when present, is in the polymer-encapsulated drug particles, coated on a surface of the polymer-encapsulated drug particles, or a combination thereof. In some embodiments, the polymer-encapsulated drug particles include the first ionic or zwitterionic additive. In other embodiments, the polymer-encapsulated drug particles are free of the first ionic or zwitterionic additive. The drug-releasing coating also includes a release matrix including a second ionic or zwitterionic additive. Any coating including a drug referred to herein (e.g., a drug coating or a drug coating layer) can be or include the drug-releasing coating including the polymer-encapsulated drug particles.

The polymer-encapsulated drug particles can be homogeneously dispersed in the release matrix. The polymer-encapsulated drug particles can form any suitable proportion of the drug-releasing coating, such as 10 wt % to 90 wt %, 10 wt % to 80 wt %, 25 wt % to 70 wt %, 40 wt % to 60 wt %, or less than or equal to 90 wt % and greater than or equal to 10 wt %, 15, 20, 25, 30, 35, 40, 45, 50, 55, 60, 65, 70, 75, 80, or 85 wt %.

The release matrix can include particles of the therapeutic agent that are free of encapsulation by the polymer (i.e. the polymer of the polymer-encapsulated drug particles), such as crystalline particles of the therapeutic agent. In other embodiments, the release matrix can be substantially free of particles of the therapeutic agent that are free of encapsulation by the polymer. Particles of the therapeutic agent that are free of encapsulation by the polymer can form any suitable proportion of the drug-releasing coating, such as 0.001 wt % to 50 wt %, or 1 wt % to 20 wt %, or 1 wt % to 10 wt %, or less than or equal to 50 wt % and greater than or equal to 0.001 wt %, 0.005, 0.01, 0.05, 0.1, 0.5, 1, 1.5, 2, 2.5, 3, 4, 5, 6, 7, 8, 9, 10, 12, 14, 16, 18, 20, 25, 30, 35, 40, or 45 wt %. The particles of the therapeutic agent that are free of encapsulation by the polymer can be homogeneously distributed in the release matrix.

The second ionic or zwitterionic additive can have the same molecular structure as the first ionic or zwitterionic additive, or the second ionic or zwitterionic additive can have a different molecular structure as the first ionic or zwitterionic additive. The drug-releasing coating can include 1, 2, 3, or 4 or more second ionic or zwitterionic additives, such as 1 or 2 second ionic or zwitterionic additives, such as 2 second ionic or zwitterionic additives. The one or more second ionic or zwitterionic additives can form any suitable proportion of the drug-releasing coating, such as 10-80 wt %, or 40-60 wt %, or less than or equal to 80 wt % and greater than or equal to 10, 15, 20, 25, 30, 35, 40, 45, 50, 55, 60, 65, 70, or 75 wt %.

The second ionic or zwitterionic additive can include a cationic molecule, an anionic additive, or a zwitterionic additive. The second ionic or zwitterionic additive can increase (i.e., make more positive) the zeta potential of the drug-releasing coating, which can increase adhesion of the drug-releasing coating to the tissue and/or increase the rate of drug transfer from the coating to the tissue. For example, a positive zeta potential of the drug-releasing coating can attract amino groups in peptides or proteins, and/or negatively-charged lipids of lipid bilayers in cell membranes (e.g., negative ions on the surface of cell membranes), causing better adhesion. Increased adhesion can prolong the stay of the drug-releasing coating on the wall of the body lumen, leading to higher drug dose to the tissue and/or greater rate of drug delivery to the tissue. The second ionic or zwitterionic additive can include a charged polymer, a charged lipid, a phospholipid, a phosphocholine, a phosphatidylcholine, a phosphatidylethanolamine, a phosphatidylserine, a phosphatidylinositol, and combinations thereof. The second ionic or zwitterionic additives can migrate to the surface of the drug-releasing coating. The charged head of the ionic or zwitterionic additive can be oriented away from the coating, with the hydrophobic tail oriented toward the coating, such that the zeta potential of the coating is higher.

Two acyl groups of the charged lipid or two acyl groups of the charged phospholipid (e.g., of the esters bonded to the triglyceride backbone) include mis-matched acyl groups that differ in one or more properties or characteristics. The mis-matched acyl groups can differ by length, degree of saturation, substituents thereon, substitution patterns thereon, or a combination thereof. For example, both acyl groups can be saturated, or one can be saturated and one can be unsaturated, or both can be unsaturated. For example, 1,2-dioleoyl-sn-glycero-3-phosphocholine (DOPC) has two unsaturated acyl chains and 1-palmitoyl-2-oleoyl-glycero-3-phosphocholine has acyl groups where one is saturated and one is unsaturated. In embodiments with two unsaturated acyl groups, the unsaturated acyl groups can have a double bond at the same or different carbon locations or can have multiple double bonds along the carbon chain in the same or different locations. The mis-matched or matched acyl groups with different length, degree of saturation, substituents thereon, and substitution patterns can have a different phase transition or softening temperature. The phase transition or softening temperature of the charged lipid can affect the properties of the coating, such as coating integrity, dry durability, the rate of drug release from the coating, rate and/or degree drug uptake into the tissue, or a combination thereof. Lipids and phospholipids that have a high phase transition temperature can lead to brittle coatings that crack and flake leading to inconsistent drug dosing. Lipids and phospholipids that have a low phase transition temperature can be hard to handle because they can be wet and sticky which leads to inconsistent drug dosing. The phase transition temperatures of charged lipids and phospholipids can range from −70° C. to 80° C. The preferable range of phase transition temperatures is −30° C. to 50° C. The most preferable range of phase transition temperatures is −20° C. to 40° C. In some embodiments coatings can have a mixture of lipids and/or phospholipids that allow the phase transition temperature of the coating to be in the desirable range with desirable mechanical properties (dry and pliable, and not sticky or brittle).

The mis-matched acyl groups of the charged lipid or charged phospholipid can have lengths of C6-C34, such as C6, 7, 8, 9, 10, 11, 12, 13, 14, 15, 16, 17, 18, 19, 20, 21, 22, 23, 24, 25, 26, 27, 28, 29, 30, 31, 32, 33, or 34. In some embodiments, the same or different lengths of the acyl groups having chain lengths of C6-C34 can create perturbations, unevenness, and/or curvature in the lipid bilayer of the cell membrane to enhance the drug permeation to the tissue. In embodiments with charged lipids or phospholipids having mis-matched acyl groups that differ in length, the length of the two acyl groups can differ by a length of C1-C28, or C1-C10, or C1-C8, or greater than or equal to C1, 2, 3, 4, 5, 6, 7, 8, 9, 10, 11, 12, 13, 14, 15, 16, 17, 18, 19, 20, 21, 22, 23, 24, 25, 26, 27, or C28. For example, the two acyl groups that differ in length can have lengths of C12/C14, C12/C16, C12/C18, C12/C20, C12/C22, C12/C24, C12/C26, C14/C16, C14/C18, C14/C20, C14/C22, C14/C24, C14/C26, C16/C18, C16/C20, C16/C22, C16/C24, C16/C26, C18/C20, C18/C22, C18/C24, C18/C26, C20/C22, C20/C24, C20/C26, C22/C24, C22/C26, or C24/C26.

The charged polymer can be chosen from polycation-containing cyclodextrin, amino cyclodextrin or a derivative thereof, amino dextran, a histone, a protamine, cationized human serum albumin, an aminopolysaccharide, chitosan, a peptide, poly-L-lysine, poly-L-ornithine, poly(4-hydroxy-L-proline ester), a polyethylenimine, a polyallylamine, a polypropylenimine, a polyamidoamine dendrimer, a cationic polyoxazoline, a poly(beta-aminoester), a PEG-PEI copolymer, a PLGA-PEI copolymer, a positively charged gelatin (e.g., base-treated gelatin), hydroxy-terminated poly(2-methyl-2-oxazoline), poly(2-ethyl-2-oxazoline), stearic acid-modified branched polyethylenimine, branched PEI-g-PEG, poly(1-vinylpyrrolidone-co-2-dimethylaminoethyl methacrylate), poly(1-vinylpyrrolidone)-graft-(1-triacontene), polylysine, polyarginine, poly(N,N-dimethylaminoethyl methacrylate), a cationic copolymer of dimethylaminoethyl methacrylate/butyl methacrylate/methyl methacrylate (e.g., Eudragit E), an anionic copolymer of methacrylic acid/methyl methacrylate (e.g., Eudragit L and/or Eudragit S), a copolymer of ethyl acrylate/methyl methacrylate/methacrylic acid ester with quaternary ammonium groups (e.g., Eudragit RS and/or SR), and combinations thereof. An example of a methacrylic acid ester with quaternary ammonium groups is trimethylammonioethyl methacrylate chloride.

The charged lipid can be chosen from 1,2-dipalmitoyl-sn-glycero-3-ethylphosphocholine (chloride salt), 1,2-distearoyl-sn-glycero-3-ethylphosphocholine (chloride salt), cholic acid, deoxycholic acid, chenodeoxycholic acid, lithocholic acid, 1,2-dilauroyl-sn-glycero-3-phosphoglycerol, sodium salt, 1,2-dihexanoyl-sn-glycero-3-phosphocholine, 1,2-diheptanoyl-sn-glycero-3-phosphocholine, 1,2-dioctanoyl-sn-glycero-3-phosphocholine, 1,2-dinonanoyl-sn-glycero-3-phosphocholine, 1,2-decanoyl-sn-glycero-3-phosphocholine, 1,2-diundecanoyl-sn-glycero-3-phosphocholine, 1,2-dilauroyl-sn-glycero-3-phosphocholine, 1,2-dimyristoyl-sn-glycero-3-phosphocholine, 1,2-dipalmitoyl-sn-glycero-3-phosphocholine, 1,2-distearoyl-sn-glycero-3-phosphocholine, 1-palmitoyl-2-stearoyl-sn-glycero-3-phosphocholine, 1-stearoyl-2-palmitoyl-sn-glycero-3-phosphocholine, 1-palmitoyl-2-lauroyl-sn-glycero-3-phosphocholine, 1,2-dioleoyl-sn-glycero-3-phosphocholine (DOPC), 1-palmitoyl-2-oleoyl-glycero-3-phosphocholine (POPC), 1-stearoyl-2-hydroxy-sn-glycero-3-phosphocholine, 1-lauroyl-2-hydroxy-sn-glycero-3-phosphocholine, 1-myristoyl-2-hydroxy-sn-glycero-3-phosphocholine, 1-palmitoyl-2-hydroxy-sn-glycero-3-phosphocholine, dieicosenoyl phosphatidylcholine (1,2-dieicosenoyl-sn-glycero-3-phosphocholine, C20:1 PC), diarachidonoyl phosphatidylcholine (1,2-diarachidoyl-sn-glycero-3-phosphocholine, C20:0 PC), dierucoyl phosphatidylcholine (1,2-dierucoyl-sn-glycero-3-phosphocholine, C22:1 PC), didocosahexaenoyl phosphatidylcholine (1,2-didocosahexaenoyl-sn-glycero-3-phosphocholine, C22:6 PC), heneicosenoyl phosphatidylcholine (1,2-heneicosenoyl-sn-glycero-3-phosphocholine, C21:1 PC), and dinervonyl phosphatidylcholine (1,2-dinervonoyl-sn-glycero-3-phosphocholine, C24:1 PC), and combinations thereof.

The second ionic or zwitterionic additive can be chosen from 1,2-dipalmitoyl-sn-glycero-3-ethylphosphocholine (chloride salt), 1,2-distearoyl-sn-glycero-3-ethylphosphocholine (chloride salt), cholic acid, deoxycholic acid, chenodeoxycholic acid, lithocholic acid, 1,2-dilauroyl-sn-glycero-3-phosphoglycerol, sodium salt, 1,2-dihexanoyl-sn-glycero-3-phosphocholine, 1,2-diheptanoyl-sn-glycero-3-phosphocholine, 1,2-dioctanoyl-sn-glycero-3-phosphocholine, 1,2-dinonanoyl-sn-glycero-3-phosphocholine, 1,2-decanoyl-sn-glycero-3-phosphocholine, 1,2-diundecanoyl-sn-glycero-3-phosphocholine, 1,2-dilauroyl-sn-glycero-3-phosphocholine, 1,2-dimyristoyl-sn-glycero-3-phosphocholine, 1,2-dipalmitoyl-sn-glycero-3-phosphocholine, 1,2-distearoyl-sn-glycero-3-phosphocholine, 1-palmitoyl-2-stearoyl-sn-glycero-3-phosphocholine, 1-stearoyl-2-palmitoyl-sn-glycero-3-phosphocholine, 1-palmitoyl-2-lauroyl-sn-glycero-3-phosphocholine, 1,2-dioleoyl-sn-glycero-3-phosphocholine (DOPC), 1-palmitoyl-2-oleoyl-glycero-3-phosphocholine (POPC), 1-stearoyl-2-hydroxy-sn-glycero-3-phosphocholine, 1-lauroyl-2-hydroxy-sn-glycero-3-phosphocholine, 1-myristoyl-2-hydroxy-sn-glycero-3-phosphocholine, 1-palmitoyl-2-hydroxy-sn-glycero-3-phosphocholine, and a combination thereof.

The second ionic or zwitterionic additive can include or be a water-insoluble or slightly or partial water-insoluble additive including at least one acyl group. The second ionic or zwitterionic additive can have a molecular weight of 50 to 750, 750 to 100,000, or 750 to 50,000, or 750 to 10,000. The second ionic or zwitterionic additive can have a lower melting temperature than that of the additive in its pure form. The second ionic or zwitterionic additive can have a lower crystallinity than that of the additive in its pure form.

The drug-releasing coating can be located on any suitable surface intended for drug delivery to a target location, such as on a medical device, such as on a balloon catheter, a drug-coated catheter, a drug-eluting stent, a drug-eluting stent on a balloon, a drug-eluting stent on a drug-coated balloon, a stent on a drug-coated balloon, or a combination thereof. Method for treating or preventing a nonvascular or vascular stricture or stenosis including using a medical device that includes polymer-encapsulated drug particles.

Various embodiments provide a method for treating or preventing a nonvascular or vascular stricture or stenosis. The method including inserting a catheter including a balloon or stent into the body lumen, wherein the balloon or stent includes the polymer-encapsulated drug particles that include the therapeutic agent and the one or more polymers that encapsulated the therapeutic agent, or the drug-releasing coating that includes the polymer-encapsulated drug particles. The method can include expanding the balloon or stent to contact the coating layer with the stricture, stenosis, or area wherein the stricture or stenosis is to be prevented. When a balloon is used, the method can include deflating the balloon or stent. When a balloon is used, the method can also include removing the balloon from the body lumen. When a stent is used, it can be either a self-expanding or balloon-expandable stent.

Method of Making Polymer-Encapsulated Drug Particles and/or Drug-Releasing Coating.

Various embodiments provide a method of making the polymer-encapsulated drug particles that include the therapeutic agent and the one or more polymers that encapsulate the therapeutic agent. The method includes forming a suspension including the therapeutic agent and the polymer. The suspension can include undissolved solid therapeutic agent particles. The method includes processing the suspension to reduce particle size of the suspension. The method also includes adding an aqueous premix to the suspension to form polymer-encapsulated drug particles in the suspension.

The polymer-encapsulated drug particles can be a final product or can be an intermediate with additional steps to be performed to achieve a particular embodiment of the polymer-encapsulated drug particles of the present invention.

The processing can be any suitable processing that reduces particle size of the suspension. The processing can include sonicating. The method can further include adding the first ionic or zwitterionic additive to the suspension or to the formed polymer-encapsulated drug particles to coat the particles therewith. The method can further include forming a suspension including the therapeutic agent, the polymer, and the first ionic or zwitterionic additive, such that the formed polymer-encapsulated drug particles include the first ionic or zwitterionic additive therein, thereon, or a combination thereof.

The method can be a method of forming the drug releasing coating including the polymer-encapsulated drug particles and the release matrix. The method can further include adding the second ionic or zwitterionic additive to the suspension, optionally agitating the suspension to homogeneously distribute the polymer-encapsulated drug particles, and drying the suspension, to form the drug-releasing coating.

A method of making the polymer-encapsulated drug particles can include forming an organic premix comprising an organic solvent, the one or more polymers, the therapeutic agent, and optionally the first ionic or zwitterionic additive. The method can include forming an aqueous premix comprising water and a water-soluble polymer or surfactant. The method can include adding an organic solvent to the aqueous premix. In some embodiments, the organic solvent of the organic premix and the organic solvent added to the aqueous premix are the same organic solvent. The organic solvent of the organic premix and the organic solvent added to the aqueous premix can be a polar organic solvent. The method can include combining the aqueous premix and the organic premix together. The method can include agitating the combined aqueous premix and organic premix to form an emulsion comprising the polymer-encapsulated drug particles. The method can include adding water to the emulsion comprising the polymer-encapsulated particles, such as to harden the formed polymer-encapsulated drug particles. The method can include separating the polymer-encapsulated drug particles from the combined aqueous premix and organic premix. The method can include washing the polymer-encapsulated drug particles with an aqueous liquid, drying the polymer-encapsulated drug particles, or a combination thereof. The aqueous liquid used for the washing can optionally include one or more water-soluble additives, such as any water-soluble additive or ionic or zwitterionic additive described herein, which can coat the polymer-encapsulated drug particles during the washing. The coating of the polymer-encapsulated drug particles during the washing can modify the zeta potential of the polymer-encapsulated drug particles.

The organic solvent of the organic premix and the organic solvent added to the aqueous premix can independently be (a) alkanes such as hexane, octane, cyclohexane, and heptane, (c) aromatic solvents such as benzene, toluene, and xylene, (d) alcohols such as ethanol, propanol, and isopropanol, diethylamide, ethylene glycol monoethyl ether, Trascutol, and benzyl alcohol (e) ethers such as dioxane, dimethyl ether and tetrahydrofuran, (f) esters/acetates such as ethyl acetate and isobutyl acetate, (g) ketones such as acetone, acetonitrile, diethyl ketone, and methyl ethyl ketone, and (h) chlorinated solvents such as chloroform or methylene chloride.

The water-soluble polymer or surfactant of the aqueous premix can be any suitable water-soluble polymer or surfactant, such as any water soluble polymer or surfactant disclosed herein, such as polyvinyl alcohol, polyethylene glycol, a phosphatidylcholine, or a combination thereof. The water-soluble polymer or surfactant can be N1-[2-((1S)-1-[(3-aminopropyl)amino]-4-[di(3-amino-propyl)amino]butylcarboxamido)ethyl]-3,4-di[oleyloxy]-benzamide, 1,2-di-O-octadecenyl-3-trimethylammonium propane (chloride salt), 1,2-distearoyl-3-dimethylammonium-propane, 1,2-dioleoyl-3-trimethylammonium-propane (chloride salt), $N^4$-cholesteryl-spermine HCl salt, 1,2-dioleyloxy-3-dimethylaminopropane, calcifediol, cholecalciferol, 1α,25-dihydroxyvitamin $D_3$, poly(1-vinylpyrrolidone)-graft-(1-triacontene), poly(1-vinylpyrrolidone-co-2-dimethylaminoethyl methacrylate), poly 2-dimethylaminoethyl methacrylate, branched PEI-g-PEG, stearic acid-modified branched polyethylenimine, poly(2-ethyl-2-oxazoline), hydroxy terminated poly(2-methyl-2-oxazoline), 1-stearoyl-sn-glycero-3-phosphocholine, poly(2-(dimethylamino)ethyl methacrylate), acetylcholine iodide, acetylcholine chloride, or a combination thereof.

The emulsion formed from the combination of the organic premix and the aqueous premix can be a coacervate of the organic solvent and water, with the dispersed phase being the organic solvent. Adding water to the coacervate solution can harden the polymer-encapsulated drug particles, and can drive organic solvent out of the continuous water phase. The mixing used to form the emulsion can be any suitable agitation, such as ultrasonic bath or probe, rotor-stator, flow through a packed bed, stir-bar, eductor funnel, mill type, homogenizer, or overhead impeller type. The collection of the polymer-encapsulated drug particles can include any suitable collection method, such as filtration or centrifugation. During collection the particles can be washed with an aqueous liquid. The aqueous wash liquid can optionally include one or more water-soluble additives, such as any water-soluble additive or ionic or zwitterionic additive described herein, which can coat the polymer-encapsulated drug particles during the washing. The coating of the polymer-encapsulated drug particles during the washing can modify the zeta potential of the polymer-encapsulated drug particles. The drying of the particles can include spray drying, vacuum drying, sublimation, or evaporation. The formed polymer-encapsulated drug particles can optionally be used to prepare a drug coating solution for forming the drug-releasing coating.

A method of forming the drug-releasing coating can include forming a first mixture comprising the polymer-encapsulated drug particles and an organic solvent. The first mixture can be a dispersion of the polymer-encapsulated drug particles in the organic solvent, such as made via a suitable mixing method, such as via sonic probe mixing, stir bar, vortexer, overhead stirrer, or rotor stator. The method can include forming a second mixture comprising the second ionic or zwitterionic additive and an organic solvent. The method can include combining the first mixture and second mixture. In some embodiments, the organic solvent of the first mixture and the second mixture is a nonpolar organic solvent, such as hexane, cyclohexane, heptane or pentane. In some embodiments, the organic solvent of the first mixture and the second mixture is the same organic solvent. The method can include drying the combined first mixture and second mixture, to form the drug-releasing coating. The method can include agitating the combined first mixture and second mixture prior to the drying to homogeneously disperse the polymer-encapsulated drug particles therein.

The second ionic or zwitterionic additive used to form the drug-releasing coating can be any suitable material described herein, such as a phospholipid, such as 1,2-dipalmitoyl-sn-glycero-3-ethylphosphocholine (chloride salt), 1,2-distearoyl-sn-glycero-3-ethylphosphocholine (chloride salt), cholic acid, deoxycholic acid, chenodeoxycholic acid, lithocholic acid, 1,2-dilauroyl-sn-glycero-3-phosphoglycerol (sodium salt), 1,2-dihexanoyl-sn-glycero-3-phosphocholine, 1,2-diheptanoyl-sn-glycero-3-phosphocholine, 1,2-dioctanoyl-sn-glycero-3-phosphocholine, 1,2-dinonanoyl-sn-glycero-3-phosphocholine, 1,2-decanoyl-sn-glycero-3-phosphocholine, 1,2-diundecanoyl-sn-glycero-3-phosphocholine, 1,2-dilauroyl-sn-glycero-3-phosphocholine, 1,2-dimyristoyl-sn-glycero-3-phosphocholine, 1,2-dipalmitoyl-sn-glycero-3-phosphocholine, 1,2-distearoyl-sn-glycero-3-phosphocholine, 1-palmitoyl-2-stearoyl-sn-glycero-3-phosphocholine, 1-stearoyl-2-palmitoyl-sn-glycero-3-phosphocholine, 1-palmitoyl-2-lauroyl-sn-glycero-3-phosphocholine, 1,2-dioleoyl-sn-glycero-3-phosphocholine (DOPC), 1-palmitoyl-2-oleoyl-glycero-3-phosphocholine (POPC), 1-stearoyl-2-hydroxy-sn-glycero-3-phosphocholine, 1-lauroyl-2-hydroxy-sn-glycero-3-phosphocholine, 1-myristoyl-2-hydroxy-sn-glycero-3-phosphocholine, 1-palmitoyl-2-hydroxy-sn-glycero-3-phosphocholine, and a combination thereof in a nonpolar solvent such as hexane, cyclohexane, heptane or pentane. The second premix may be heated to ensure the phospholipids dissolve fully. The second premix can then be allowed to cool if it was heated, and then it can be added to the first premix. The final mixture of the two premixes can be fully mixed by any suitable mixing method such as sonic probe mixing, stir bar, vortexer, overhead stirrer, or rotor stator.

Method of Making a Balloon Catheter that Includes the Polymer-Encapsulated Drug Particles.

Various embodiments of the present invention provide a method of making a balloon catheter. The method includes applying the polymer-encapsulated drug particles including the therapeutic agent and the one or more polymers that encapsulate the therapeutic agent or the drug-releasing coating including the same to an exterior of a balloon of a balloon catheter.

Drug-Coated Balloon Catheter.

The balloon catheters described throughout this application can include a coating layer that includes the polymer-encapsulated drug particles that include the therapeutic agent and the one or more polymers that encapsulate the therapeutic agent; or the drug-releasing coating including the polymer-encapsulated drug particles; or a composition; or a combination thereof. The composition can include a therapeutic agent; or a first additive; or a second additive; or a combination thereof. The therapeutic agent can be chosen from paclitaxel, docetaxel, taxol, an mTOR inhibitor, rapamycin, sirolimus, zotarolimus, everolimus, tacrolimus, umirolimus, an analogue thereof, and combinations thereof. The therapeutic agent can have a particle size of 0.2 micron to 10 microns. The first additive can include a water-insoluble or partially water-insoluble additive including at least one alkyl fatty group or cholesteryl group. The first additive can have a molecular weight of 50 to 750. The second additive can be more hydrophilic or more water-soluble than the first additive and can include a polyethylene glycol (—$(CH_2CH_2O)$—) or a polyglycerol (—$(CH_2$—$CHOH$—$CH_2O)$—) unit. The second additive can have a molecular weight in the range of 750 to 100,000.

The balloon catheter can be any suitable balloon catheter described herein. The balloon of the balloon catheter can include a polyester, a polyamide, a nylon 12, a nylon 11, a polyamide 12, a block copolymer of a polyether and a polyamide, a polyether block amide, a polyurethane, a block copolymer of a polyether and a polyester, or a combination thereof.

The balloon catheter can be used for delivering the therapeutic agent to a body lumen stricture or stenosis, wherein the body lumen stricture or stenosis is chosen from urethral stricture, prostatic urethral stricture, ureteral stricture, esophageal stricture, sinus stricture, stomach stricture, small intestine stricture, colon stricture, rectum stricture, large intestine stricture, bladder neck stricture, a biliary tract stricture, vaginal stricture, in-stent restenosis, coronary artery stenosis, superficial femoral artery stenosis, popliteal artery stenosis, anterior tibial artery stenosis, posterior tibial artery stenosis, and peroneal artery stenosis.

The balloon catheter can be used for delivering the therapeutic agent to a target site of a body lumen, wherein the target site of the body lumen is chosen from urethral stricture, prostatic urethral stricture, ureteral stricture, esophageal stricture, sinus stricture, stomach stricture, small intestine stricture, colon stricture, rectum stricture, large intestine stricture, bladder neck stricture, a biliary tract stricture, vaginal stricture, in-stent restenosis, coronary artery stenosis, superficial femoral artery stenosis, popliteal artery stenosis, anterior tibial artery stenosis, posterior tibial artery stenosis, and peroneal artery stenosis.

In one embodiment, the present invention relates to a balloon catheter for delivering a therapeutic agent to a target site of a body lumen stricture or stenosis, the balloon includes a polyester, a polyamide, a nylon 12, a nylon 11, a polyamide 12, a block copolymer of a polyether and a polyamide, a polyether block amide, a polyurethane, a block copolymer of a polyether and a polyester, or a combination thereof. In one embodiment, the present invention relates to a balloon catheter for delivering a therapeutic agent to a target site of a body lumen stricture, the balloon catheter includes a drug coating overlying an exterior surface of a balloon The coating can include the polymer-encapsulated drug particles that include the therapeutic agent and the one or more polymers that encapsulate the therapeutic agent; or the drug-releasing coating including the polymer-encapsulated drug particles; or a composition including a therapeutic agent and one or more additives; or a combination thereof. The composition can include an initial drug load of a therapeutic agent, and one or more water-insoluble or slightly or partially water-insoluble additive and one more water-soluble additive. The therapeutic agent can be chosen from paclitaxel, docetaxel, taxol, an mTOR inhibitor, rapamycin, sirolimus, zotarolimus, everolimus, tacrolimus, umirolimus, an analogue thereof, and combinations thereof. The therapeutic agent can be crystalline, partially crystalline, amorphous, partially amorphous, or a combination thereof. The particle size of the therapeutic agent can be in the range of 0.2-10 μm or preferably 0.2-5 μm. The first additive, the second additive, or a combination thereof can encapsulate the therapeutic agent, the additive-encapsulated therapeutic agent can have a larger particle size than the therapeutic agent itself, and the particle size of the additive-encapsulated therapeutic agent in the coating can be in the range of 0.3 micron to 10 micron. The first additive can include a water-insoluble or slightly or partially water-insoluble additive including at least one alkyl fatty group or cholesteryl group. The first additive can have a molecular weight of 50 to 750. The water-insoluble additive in the coating can have a lower melting temperature than its pure form. The water-insoluble additive in the coating can have a lower crystallinity than that of its pure form. The water-soluble additive can be more hydrophilic or more water-soluble than the water-insoluble or slightly or partially water-insoluble additive. The water-soluble additive can include a polyethylene glycol ($—(CH_2CH_2O)—$) or a polyglycerol ($—(CH_2—CHOH—CH_2O)—$) unit. The second additive can have a molecular weight in the range of 750 to 100,000, or 750 to 50,000, or 750 to 10,000;

The water-insoluble or slightly or partially water-insoluble additive can be chosen from cholesteryl acetate, cholesteryl phenylacetate, cholesteryl laurate, cholesteryl palmitate, cholesteryl stearate, cholesteryl n-valerate, cholesteryl benzoate, cholesteryl heptylate, cholesteryl decylate, cholesteryl caproate, cholesteryl oleate, cholesteryl oleyl carbonate, cholesteryl linoleate, cholesteryl pelargonate, cholesteryl erucate, cholesteryl caprylate, 5α-cholestane, 5α-cholestan-3-one. The water-insoluble or slightly or partial water-insoluble first additive with alkyl fatty group can be chosen from alkyl glyceryl ethers, monoglycerides of C8-C12 fatty acids, alkyl alcohol, alkyl ether, alkyl ester, caprylic acid, monocaprilin, capric acid, monocaprin, lauric acid, dodecyl glycerol, butanoic acid, hexanoic acid, octanoic acid, decanoic acid, dodecanoic acid, tetradecanoic acid, hexadecanoic acid, octadecanoic acid, octadecatrienoic acid, eicosanoic acid, eicosenoic acid, eicosatetraenoic acid, eicosapentaenoic acid, docosahexaenoic acid, tocotrienol, butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, natural or synthetic phospholipids, mono-, di-, or triacylglycerols, cardiolipin, phosphatidylglycerol, phosphatidic acid, phosphatidylcholine, alpha tocoferol, phosphatidylethanolamine, sphingomyelin, phosphatidylserine, phosphatidylinositol, dimyristoylphosphatidylcholine, dioleoylphosphatidylcholine, dipalmitoylphosphatidylcholine, distearoylphosphatidylcholine, phosphatidylethanolamines phosphatidylglycerols, sphingolipids, prostaglandins, gangliosides, neobee and derivatives, and combinations thereof.

The water-soluble second additive can include polyoxyethanyl α-tocopheryl sebacate, methylated polyethylene glycol cholesterol (mPEG cholesterol), PEG amide ether cholesterol, PEG amide ester cholesterol, mPEG amide ether cholesterol, mPEG amide ester cholesterol, DSPE-PEG-cholesterol, PEGylated phospholipid, methylated PEGylated phospholipid, PEG caprylic/capric diglycerides, PEG8 caprylic/capric glycerides, PEG caprylate, PEG caprate, PEG caproate, PEG-20 sorbitan monolaurate (Tween-20), PEG-20 sorbitan monopalmitate (Tween-40), PEG-20 sorbitan monostearate (Tween-60), PEG-20 sorbitan monooleate (Tween-80), PEG laurate, PEG oleate, PEG stearate, PEG glyceryl laurate, PEG-30 glyceryl oleate, polyglyceryl fatty acid esters, polyglyceryl oleate (Plurol Oleique), polyglyceryl-2 dioleate (Nikkol DGDO), polyglyceryl-10 trioleate, polyglyceryl stearate, polyglyceryl laurate, polyglyceryl myristate, polyglyceryl palmitate, polyglyceryl linoleate, polyglyceryl-10 laurate (Nikkol Decaglyn 1-L), polyglyceryl-10 oleate (Nikkol Decaglyn 1-0), polyglyceryl-10 mono/dioleate (Caprol™ PEG 860), polyglyceryl-10 stearate, polyglyceryl-10 laurate, polyglyceryl-10 myristate, polyglyceryl-10 palmitate, polyglyceryl-10 linoleate, polyglyceryl-6 stearate, polyglyceryl-6 laurate, polyglyceryl-6 myristate, polyglyceryl-6 palmitate, polyglyceryl-6 linoleate, polyethylene glycol (PEG)-cholesteryl sebacate (disebacate diester linkages, cholesterol, water-soluble, CAS 69068-97-9):

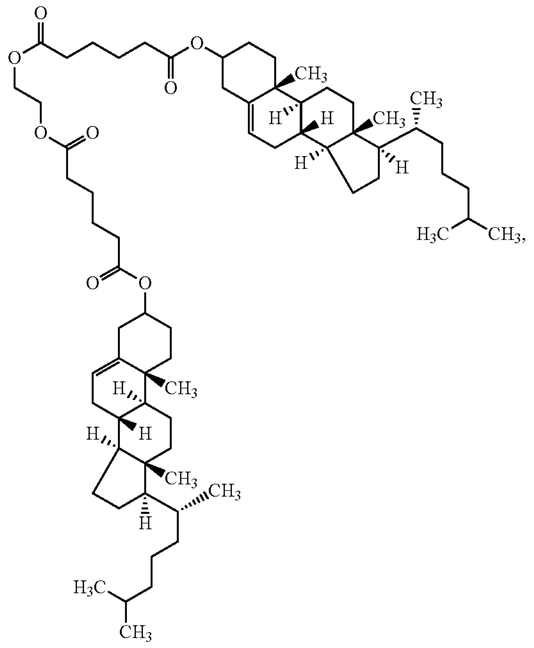

polyethylene glycol cholesterol (ether linkage, cholesterol-(polyethylene glycol-600)):

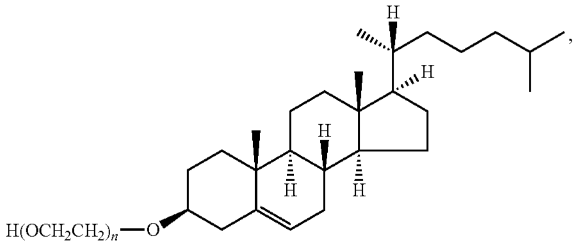

PEG amide ester cholesterol (ester amide linkage, hydroxyl terminated PEG cholesterol, various molecular weights):

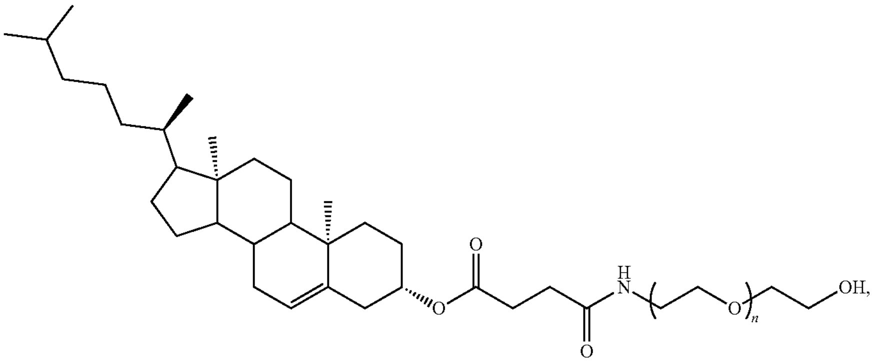
PEG amide ether cholesterol (methyl terminated, amide ether linkage, MW=550, 1K, 2K, 5K, 10K, 20K, 30K, 40K):
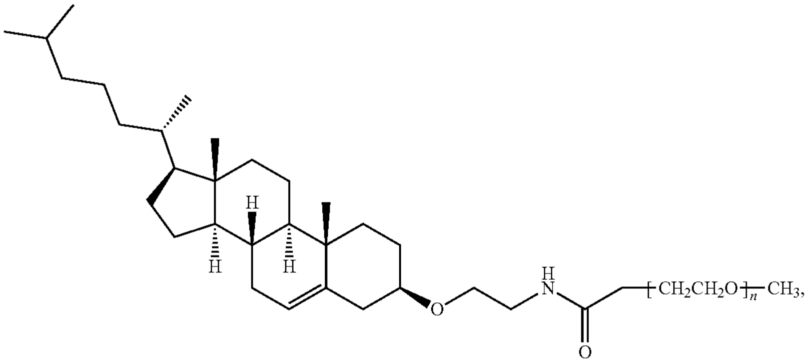
mPEG amide ester cholesterol (methyl terminated, amide ester linkage, MW=550, 1K, 2K, 5K, 10K, 20K, 30K, 40K):
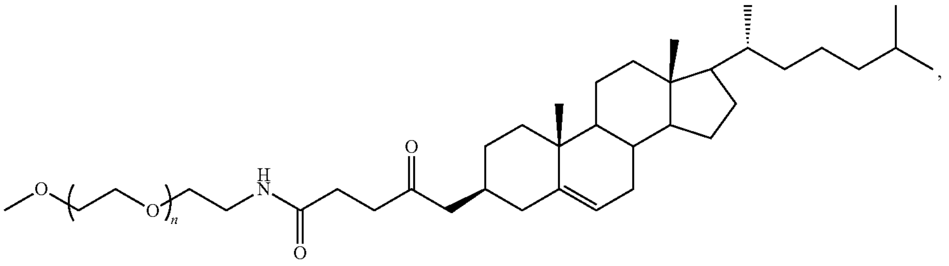

DSPE-PEG-cholesterol:

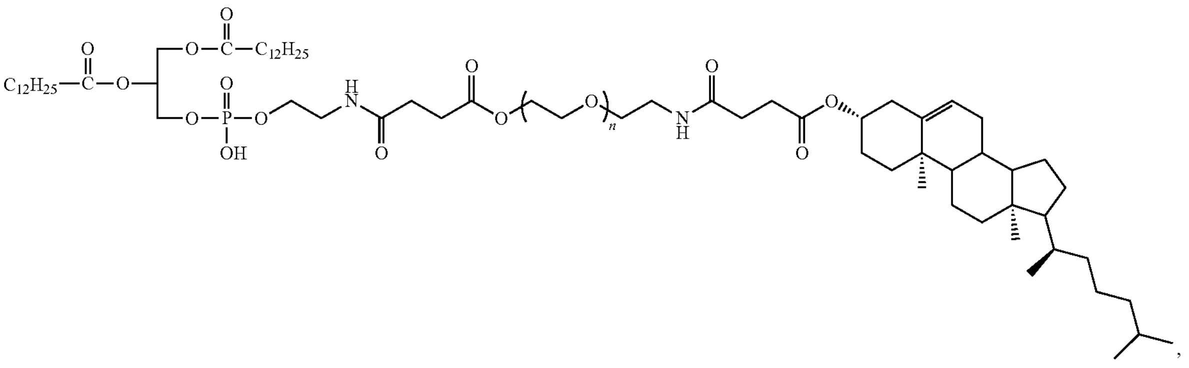

or a combination thereof.

In one embodiment, the concentration density of the at least one therapeutic agent applied to the surface of the medical device is from about 1 to 20 μg/mm$^2$, or from about 2 to 6 μg/mm$^2$, or about 0.5 microgram/mm$^2$ or less, or less than, equal to, or greater than about 1, 2, 3, 4, 5, 6, 7, 8, 9, 10, 12, 14, 16, 18, or about 20 micrograms/mm$^2$ or more. If the medical device is a balloon, these measurements are calculated at nominal diameter. The ratio of additives to drug by weight in the coating layer in embodiments of the present invention can be about 20 to 0.05, about 10 to 0.1, or about 6 to 0.15.

The ratio by weight of the therapeutic agent in the coating layer to the total weight of the one or more additives in the coating layer can be about 0.05 to about 20, about 0.1 to about 10, about 0.1 to about 5, about 0.5 to about 8, about 0.5 to about 3, about 2 to about 6, or about 0.05 or less, or less than, equal to, or greater than about 1, 2, 3, 4, 5, 6, 7, 8, 9, 10, 11, 12, 13, 14, 15, 16, 17, 18, 19, or about 20 or more.

The present invention provides novel drug-coated balloon catheters and there uses. The new methods open the lumen and prevents, reduces, or minimizes re-narrowing and recurrent nonvascular or vascular strictures. Vascular lumens include arteries, veins, or any lumens with blood. Nonvascular lumens include those lumens without blood. The methods involve using a medical device in the lumen that includes a drug coating. The coating can include the polymer-encapsulated drug particles that include the therapeutic agent and the one or more polymers that encapsulate the therapeutic agent; or the drug-releasing coating including the polymer-encapsulated drug particles; or a composition including a therapeutic agent and one or more additives; or a combination thereof. The drug coating can have more than one layer and can include an effective amount of therapeutic agents such as anti-inflammatory and antiproliferative drugs (e.g., paclitaxel, taxol, docetaxel, rapamycin, sirolimus, zotarolimus, tacrolimus, everolimus, umirolimus, mTOR inhibitors, or their analogues), one or more water-soluble additives, and one or more water-insoluble or partially water-soluble additives for delivery to a stricture or stenosis of a body lumen. The treatment is intended for a variety of animals, such as premature neonates to adult humans.

The stretch ratio is defined herein, unless otherwise indicated, as the ratio of the nominal diameter of the balloon to the diameter of the body lumen in the area being treated by the balloon catheter. The nominal diameter of the balloon is the diameter the balloon achieves in an unrestricted environment at the nominal pressure. The lumen diameter is the average of the diameters of the stricture or stenosis or lesion of the lumen. For the urinary tract, for example, in the urethra and prostatic urethra, the body lumen diameter will be the average diameter of the voiding urethra of the obstructed body lumen. The inflated balloon diameter can be the actual diameter of the balloon following inflation, which in some embodiments can equal to, less than, or greater than the nominal diameter of the balloon. In various embodiments, the stretch ratio of the balloon catheter of the present invention makes it more effective for treating non-vascular lumens than other catheters. During performance of a method of the present invention, the stretch ratio can be selected to be any suitable ratio that achieves the desired ratio of actual inflated balloon diameter to lumen diameter at the range of pressures used during the method. In various embodiments, the stretch ratio of the balloon can be about 1.0 to 40, 1.1 to 40, 1.2 to 40, 1.3 to 40, or 1.4 to 40 (e.g., 1, or greater than, less than, or equal to 1.1, 1.2, 1.3, 1.4, 1.5, 1.6, 1.7, 1.8, 1.9, 2, 2.2, 2.4, 2.6, 2.8, 3, 3.5, 4, 4.5, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 or less, or any value therebetween); such a stretch ratio can result in a desired ratio of inflated balloon diameter to lumen diameter at the pressures used during the inflation period that can be the same, similar to, or different than the stretch ratio, such as about 1.0 to 40, 1.1 to 40, 1.2 to 40, 1.3 to 40, or 1.4 to 40 (e.g., 1, or greater than, less than, or equal to 1.1, 1.2, 1.3, 1.4, 1.5, 1.6, 1.7, 1.8, 1.9, 2, 2.2, 2.4, 2.6, 2.8, 3, 3.5, 4, 4.5, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 or less, or any value therebetween).

Various embodiments of the present invention relate to a coated medical device The device includes one of a balloon catheter, a fixed wire balloon catheter, over the wire balloon catheter, rapid exchange balloon catheter, a perfusion balloon catheter, a spaced double balloon, a cutting balloon catheter, a scoring balloon catheter, or an infusion catheter (e.g., a distal perforated drug infusion tube, a perforated balloon, spaced double balloon, porous balloon, or a weeping balloon). As shown in FIG. 1, in one embodiment, the medical device is a balloon catheter. The balloon catheter can be any suitable catheter for the desired use, including conventional cylindrical balloon catheters known to one of ordinary skill in the art. For example, balloon catheter 10 can include an expandable, inflatable balloon 12 at a distal end of the catheter 10, a handle assembly 16 at a proximal end of the catheter 10, and an elongate flexible member 14 extending between the proximal and distal ends. Handle assembly 16 can connect to and/or receive one or more suitable medical devices, such as a source of inflation media (e.g., air, saline, or contrast media). Flexible member 14 can be a tube made of suitable biocompatible material and having one or more lumens therein. At least one of the lumens is configured to receive inflation media and pass such media to balloon 12 for its expansion. The balloon catheter can be a rapid exchange or over-the-wire catheter and made of any suitable biocompatible material. The material of balloon 12 can include one or more of polyesters, polyamides, nylon 12, nylon 11, polyamide 12, block copolymers of polyether and polyamide, PEBAX®, polyurethanes, and block copolymers of polyether and polyester. The balloon catheters shafts can be constructed of polyether-amide block copolymers, polyamides, nylons, polyesters, polyethylene terephthalate, or any other semi-compliant to non-compliant polymer including their blends. The balloon catheter shaft can also be constructed using a rigid material such as stainless steel, polycarbonate, titanium, PEEK (polyether ether ketone), or any other rigid biocompatible material.

Figure 3A:
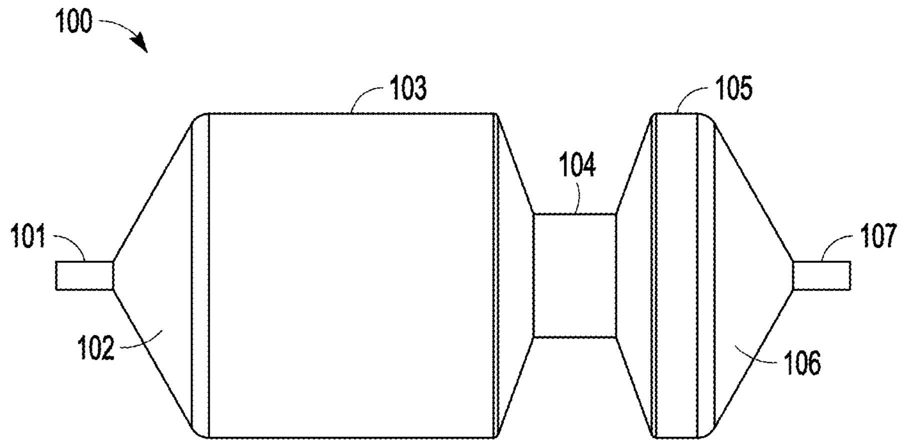
FIG. 3A illustrates a balloon catheter having one neck section, in accordance with various embodiments.

In some embodiments, the balloon can include one neck section and is free of other neck sections, such that the balloon includes two main sections separated by one neck section. The one neck section can have any suitable position on the balloon, such as approximately centered with respect to the balloon length, or off-center with respect to the balloon length. The one neck section can be off-center with respect to the length of the balloon and can be at a distal end of the balloon. An embodiment of the balloon including one neck section that is off-center with respect to the length of the balloon is illustrated in FIG. 3A.

Figure 3B:
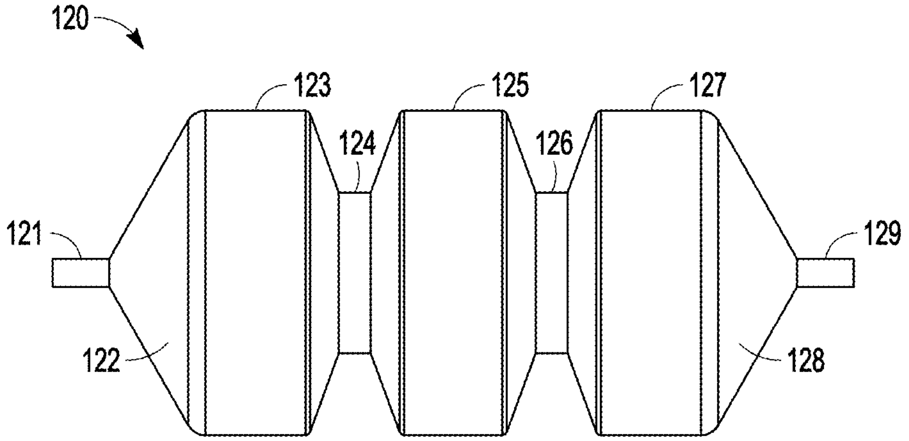
FIG. 3B illustrates a balloon catheter having two neck sections, in accordance with various embodiments.

In some embodiments, the balloon can include two neck sections and is free of other neck sections, such that the balloon includes three lobes separated by two neck sections. The two neck sections can have about the same diameter, or one of the neck sections can have a smaller diameter than the other neck sections. The two neck sections can be symmetrically or asymmetrically located with respect to the center of the balloon length. The three main sections can have approximately equal length or can have different lengths. FIG. 3B illustrates an embodiment of a balloon catheter having two neck sections with three main sections, wherein the neck sections are symmetrically located about the center of the length of the balloon, and wherein the three main sections of the balloon have about the same length. During use, the distal neck section (e.g., the neck section on the distal end of the balloon catheter which is inserted into the body first) can anchor and locate the balloon at the bladder neck, while the proximal neck section can be positioned in the prostatic urethra. In some embodiments, the distal main section of the balloon catheter can be free of the therapeutic agent.

Figure 3C:
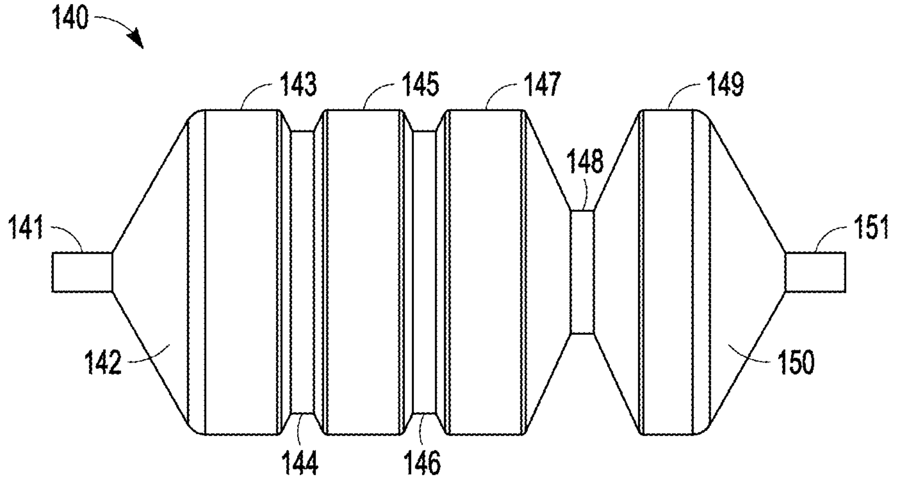
FIG. 3C illustrates a balloon catheter having three neck sections, in accordance with various embodiments.

In some embodiments, the balloon can include three necks and is free of other neck sections, such that the balloon includes four sections separated by the three necks. The three neck sections can be positioned in any suitable way along the length of the balloon. The four main sections formed by the three neck sections can have equal or different lengths. The three neck sections can have equal diameters, or different diameters. In some embodiments two of the neck sections have an equal diameter that is smaller than the diameter of the other neck section. FIG. 3C illustrates an embodiment of a balloon catheter having three neck sections with four main sections each having an approximately equal length, wherein two of the neck sections have an equal diameter that is smaller than the diameter of the other neck section.

In various embodiments, the present invention provides a balloon catheter for delivering a therapeutic agent to a target site of a body lumen. The balloon catheter can include an elongated balloon having multiple main, or body, sections and at least one neck section with a smaller diameter than that of the main sections. The balloon catheter can include an elongated balloon having a main diameter, such as multiple main sections having the main diameter or having an average diameter equal to the main diameter. The multiple-sectioned balloon with a smaller diameter neck section mechanically anchors the balloon in the body lumen; therefore, it can prevent slipping of the balloon in the body lumen. If the balloon slips away from the targeted diseased site it can be missed and the site of health lumen can be injured. The balloon catheter can include at least one neck section on the balloon including a smaller diameter than the main diameter. The balloon catheter can also include a coating layer overlying an exterior surface of the balloon. The coating can include the polymer-encapsulated drug particles that include the therapeutic agent and the one or more polymers that encapsulate the therapeutic agent; or the drug-releasing coating including the polymer-encapsulated drug particles; or a composition including a therapeutic agent and one or more additives; or a combination thereof. The coating layer can include one or more water-soluble additives and one or more water-insoluble or partially water-soluble additives an initial drug load of a therapeutic agent (e.g., from paclitaxel, docetaxel, taxol, an mTOR inhibitor, rapamycin, sirolimus, zotarolimus, everolimus, tacrolimus, umirolimus, an analogue thereof, and combinations thereof). In a method of using the balloon catheter, feature (a), or (b), or (c), or (a) and (b), or (a) and (c), or (b) and (c), or (a) and (b) and (c), can be present: (a) the ratio of the inflated balloon diameter to a strictured or stenosed body lumen diameter at the target site is about 1.0 to about 40; or (b) the inflating includes inflating the balloon to a pressure equal to or greater than a nominal pressure of the balloon catheter, and the stretch ratio of a nominal diameter of the balloon catheter to a strictured or stenosed body lumen diameter at the target site is about 1.0 to about 40; or (c) the inflating includes inflating to a pressure greater than the nominal pressure of the balloon catheter, and the nominal diameter of the balloon catheter is less than the inflated balloon diameter; or (d) a combination of (a), (b), and (c).

The main diameter of the balloon can be the diameter of the main sections of the balloon when the balloon is inflated. In some embodiments, the inflated pressure used to determine the main diameter can be any pressure that eliminates any folded or creased areas of the balloon and achieves tautness of the balloon. The inflated pressure used to determine the main diameter can be a pressure such that the inflated balloon has a shape and size that corresponds to the desired shape and size of the balloon during the intended treatment of the body lumen. The inflated pressure used to determine the main diameter can be the nominal pressure of the balloon, such that the nominal diameter of the balloon catheter is equal to the main diameter of the balloon.

In one embodiment, the drug-coated balloon includes two main sections at both ends with the same diameters, one neck section with a smaller diameter between the two main sections, and the two cones at proximal and distal balloon body. The balloon catheter includes at least one neck section on the balloon including a smaller diameter than the balloon diameter of the main sections. The balloon catheter can include an elongated (e.g., cylindrical) balloon having multiple sections with various diameters. Feature (a), or (b), or (c), or (a) and (b), or (a) and (c), or (b) and (c), or (a) and (b) and (c), are present: (a) the ratio of the inflated balloon diameter to a body lumen diameter at the target site is about 1.0 to about 40; or (b) the inflating includes inflating the balloon to a pressure equal to or greater than a nominal pressure of the balloon catheter, and the stretch ratio of a nominal diameter of the balloon catheter to a body lumen diameter at the target site is about 1.0 to about 40; or (c) the inflating includes inflating to a pressure greater than the nominal pressure of the balloon catheter, and the nominal diameter of the balloon catheter is less than the inflated balloon diameter; or (d) a combination of (a), (b), and (c). The multiple sectioned balloon with smaller necks can increase friction between the balloon and the body lumen; therefore, it can prevent the slipping of the balloon in the body lumen.

Figures 4A, 4B, 4C, 4D:
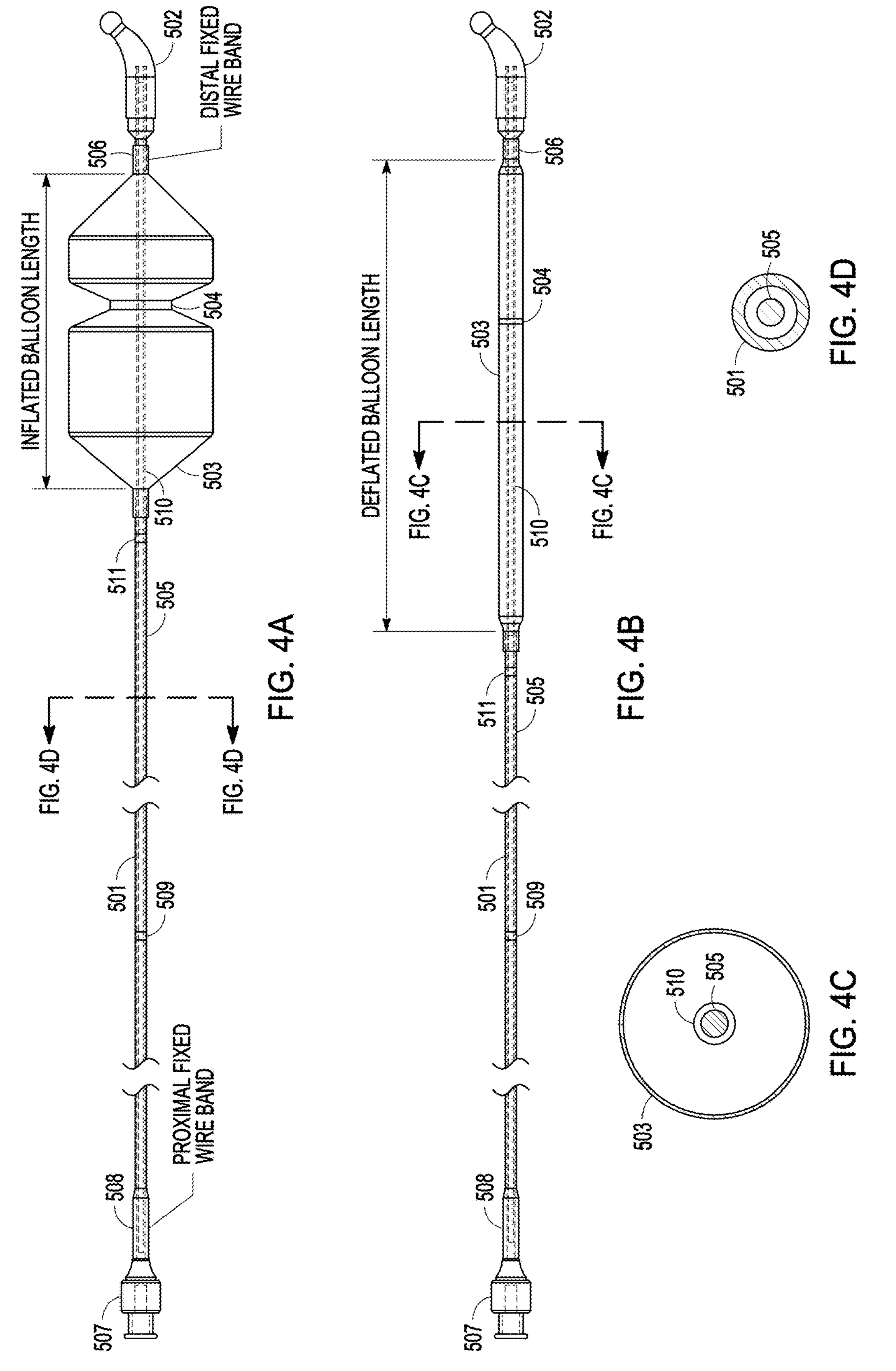
FIG. 4A-4D illustrate a balloon catheter that includes an elongated rigid member, in accordance with various embodiments.

In some embodiments, the catheter shaft can include an elongated rigid component, such as a rod, mandrel, or wire, aligned longitudinally with the catheter shaft. FIG. 4A to 4D illustrate a balloon catheter that includes an elongated rigid component or, core wire 505. FIG. 4A illustrates the embodiment with the balloon inflated and FIG. 4B illustrates the balloon in the non-expanded state. At the proximal end of the shaft, core wire 505 is attached to catheter shaft 501 under strain relief 508. Core wire 505 extends distally in catheter shaft 501. In some embodiments, catheter shaft is made from 72D PEBA polymer. The shaft 501 is made from a material that exhibits an amount of elasticity when under tension. Under balloon 503, core wire 505 is covered by a hypotube 510. Hypotube 510 provides lateral strength to core wire 505 so that it does not buckle when the balloon 503 is inflated. Near the distal end of the catheter, hypotube 510 and core wire 505 are bonded to tip 502. Tip extrusion 506 connects tip 502 to hypotube 510 and core wire 505. The space between shaft 501 and core wire 505 is the inflation lumen for balloon 503, with the interior of balloon 503 being in fluid communication with Luer hub 507. While this embodiment can be used with any suitable balloons of the invention, FIGS. 4A and 4B show balloon 510 503 with one neck, with polyethylene fiber 504 used to reinforce the neck.

The elongated rigid component can have a cross-sectional profile that is cylindrical, tapered, rectangular, hexagonal, or another shape and can be made from metal or a non-metallic material that is relatively non-compressible. The elongated component can run from the proximal side of the balloon to the distal side of the balloon, or from a location proximal to the proximal side of the balloon to the distal side of the balloon. The elongated component can float freely within a central lumen of the catheter shaft, can be positioned in a dedicated lumen in a multilumen catheter shaft, or can run longitudinally on the outside of the main catheter shaft. The elongated component can be anchored at a single point, at two points, or at more than two points along the catheter shaft. The elongated component can be anchored by thermally fusing it directly to the catheter shaft, adhesively or chemically bonding it to the catheter shaft, swaging or crimping to one or more portions of the catheter, overmolding, or via any other suitable method. The elongated component can be reinforced along its entire length or along certain sections such as under the balloon to prevent buckling; for example, the elongated metallic component can be a reinforced wire. The reinforcement can be constructed using any rigid material such as stainless steel, Nitinol (i.e., nickel titanium alloy), steel, tungsten, iridium, superalloys contain elements, including nickel (Ni) chromium (Cr), aluminum (Al), titanium (Ti), tungsten (W), niobium (Nb), tantalum (Ta) and cobalt (Co), or Polyether ether ketone (PEEK) and can have any suitable cross-sectional shape. In some embodiments, the reinforcement is a tube that is cylindrical, rectangular, hexagonal, or having any suitable outer profile. The elongated component can be disposed inside of the reinforcement tube as shown in FIG. 4C, or along the outside of the reinforcement tube.

Figure 5:
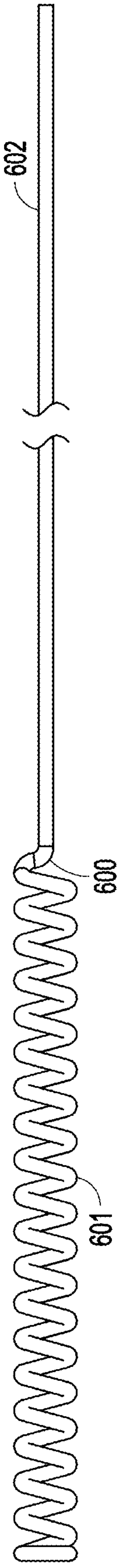
FIG. 5 illustrates an elongated rigid member that is a spring, in accordance with various embodiments.

As shown in FIGS. 4A and 4B, the catheter can include a balloon length-control mechanism which stretches and elongates the balloon when it is in a deflated state, giving the balloon a smaller cross-sectional deflated profile for tracking through the body lumen and for removal after treatment. When the balloon is inflated, the length-control mechanism can allow the balloon to shorten in overall length and inflate to the predetermined inflated diameter and length for the balloon (e.g., as created during the molding or forming process). In one embodiment the force generated from balloon inflation could be transferred from the distal end of the balloon, such as via a balloon bond to the elongated metallic component or via a connection between the catheter tip and the elongated metallic component, back through the catheter shaft by the elongated rigid metallic component to the catheter shaft proximal to the balloon, such as via a connection between the elongated metallic component and the catheter shaft at the proximal end of the balloon or proximal to the proximal end of the balloon. This transfer of force to the catheter shaft would allow the catheter shaft material to act as a spring while working in the elastic region of the catheter shaft material's stress-strain curve. Energy can be stored in the catheter shaft material during balloon inflation, when the catheter shaft is elongated under tension due to balloon inflation and can be released by the catheter shaft to press on elongated metallic component during deflation to elongate the balloon. In some embodiments, a spring oriented longitudinally along the catheter shaft can be used to store and release force for the balloon length-control mechanism. FIG. 5 illustrates an embodiment of the spring, 600, which can be used as an alternative to core wire 505 shown in FIGS. 4A and 4D. Referring to FIG. 5, spring 600 has a spring section 601 and wire section 602. In some embodiments, spring section 601 can be located at the proximal end of the catheter shaft. The spring can be located within a lumen in the catheter shaft, outside the lumen but within the catheter shaft, or outside the catheter shaft. The spring can be within the balloon, or can be located separately from the balloon, such as proximally to the proximal end of the balloon, or a combination thereof. As compared to the length of the inflated balloon, the elongated length of the deflated balloon can be about 0.1 mm longer to about 100 mm longer, or less than, equal to, or greater than about 0.1 mm longer, 0.2, 0.4, 0.6, 0.8, 1, 1.5, 1, 2.5, 3, 4, 5, 6, 8, 10, 12, 15, 20, 25, 30, 40, 50, 60, 70, 80, 90, or about 100 mm longer or more. The catheter shaft can include various materials to achieve the desired amount of force to elongate the balloon, such as polyamides, nylon (e.g., nylon 6,6, or nylon 12), a polyether block amide (PEBA) (e.g., 35D PEBA, 55D PEBA, or 72D PEBA), polyurethanes, silicones, rubbers, another thermoplastic polymer, or a combination thereof. The catheter shaft can be uniform in composition or can include a combination of materials that are distributed along one or more portions of the catheter shaft to create the desired elongation force. Different materials can yield different elastic strain and different force applied to the elongated rigid metallic component for balloon elongation. The catheter shaft can be an extruded catheter shaft.

The drug-coated balloon catheter can be a medical device for the treatment of benign prostatic hyperplasia (BPH). The balloon catheter can dilate the prostatic urethra and can include a catheter shaft for insertion into the urethra and a compliant, semi-compliant, or non-compliant balloon for inflation in the prostatic urethra. The balloon can be coated with a coating including a therapeutic agent which is delivered to the prostate tissue and prostatic urethra upon balloon inflation. The balloon can be positioned within the prostate using any suitable method, such as via a separate location balloon in the bladder, a location balloon in the bulbous urethra, marker bands under the balloon visible with fluoroscopy, or the catheter shaft can be scope—(e.g., cystoscope-) compatible allowing placement via direct visualization, or the catheter can be side by side with the scope. For example, several possible catheter designs allow direct visualization of the balloon during positioning and inflation.

In some embodiments, when treating the prostate, the balloon catheter can be sized so that the main body section(s) of the catheter are between the bladder neck sphincter (at the outlet of the bladder) and the external sphincter. In other embodiments, the main body section(s) of the catheter are above the external sphincter, placed through the prostate and one or more body sections go through the bladder neck sphincter and sit in the bladder. In these embodiments, preferably, a neck region of the balloon catheter is aligned with the bladder neck. As discussed herein, a scope equipped with visualization can be used to properly size and place the balloon catheter.

In some embodiments where the balloon catheter includes a soft tip, a Coude tip, or the like, the tip can be used to aid in device insertion and tracking through the urethra. In other embodiments the balloon catheter includes a lumen or channel designed to allow insertion and tracking to the target site or prostate through the urethra.

An achalasia stricture is a rare disorder that makes it difficult for food and liquid to pass from the esophagus to the stomach. In some embodiments, when treating an achalasia stricture, the balloon catheter as shown in FIG. 3A should be sized so that the proximal main body section(s) of the catheter are in the achalasia stricture and above the lower esophageal sphincter. In these embodiments, the neck region of the balloon catheter can be aligned with the lower esophageal sphincter neck. As discussed herein, a scope equipped with visualization can be used to properly size and place the balloon catheter. In embodiments where the balloon catheter includes a soft tip, the tip can be inserted into the sphincter (e.g., the lower esophageal sphincter) or the stomach to aid in placing the balloon catheter in the desired location.

The balloon catheter can alleviate the lower urinary tract symptoms (LUTS) due to BPH through the direct dilation of the prostatic tissue. Dilation of the prostate with the balloon with ratio of inflated balloon diameter of body lumen diameter at the target site of 1.0 to 40, or with a balloon having a stretch ratio of the nominal balloon diameter to the body lumen diameter at the target site of 1.0 to 40, can create a commissurotomy at the natural plane that separates the lateral sections in the transition zone of the prostate. Concurrently, drug can be released from the coating into the prostatic tissue, which can, for example, prevent enlargement of the prostate and re-narrowing of the newly formed opening.

In various embodiments, during inflation of the balloon in a body lumen (e.g., during performance of a method of the present invention), the nominal balloon diameter of the catheter (e.g., the diameter normally achieved at nominal pressure) can be such that the ratio of the nominal balloon diameter to the diameter of the body lumen at the location of treatment is any suitable ratio, such as about 1.01 to about 40, or about 1.01 to about 15, or about 1.2 to about 10, or about 1.31 to about 8, or less than, equal to, or greater than about 1.1, 1.2, 1.3, 1.4, 1.5, 1.6, 1.8, 2, 3, 4, 5, 6, 7, 8, 9, 10, 12, 14, 16, 18, or about 40 or more. In some embodiments, the inflated diameter of the balloon at the target site during inflation to the nominal pressure is equal to the nominal diameter; however, during actual use, some strictures can prevent achievement of the nominal diameter, or can constrain the inflated balloon to form “dog-bone” shape. The nominal balloon diameter at predetermined pressure (e.g., 2 atm, 3 atm, 6 atm, or 9 atm) can be different for different diameters of balloons for various diseases. For example, nominal diameters of urethral stricture balloons can be 6 mm, 8 mm, 10 mm, 12 mm, and 14 mm with balloon lengths of 20 mm, 25 mm, 30 mm, 35 mm, 40 mm, 45 mm, and 50 mm for 6 mm, 8 mm, 10 mm, 12 mm, and 14 mm balloon catheters at 4 atm, 5 atm, 6 atm, 8 atm, or 12 atm inflation. The nominal diameters of the BPH stricture balloons can be 25 mm, 30 mm, 35 mm, 40 mm, and 45 mm with balloon lengths of 20 mm, 25 mm, 30 mm, 35 mm, 40 mm, 45 mm, 50 mm, 55 mm, and 60 mm balloon catheters at nominal pressure of 2 atm, 3 atm, 4 atm, 6 atm, or 9 atm inflation. Table 1 illustrates examples of nominal balloon sizes, nominal pressures, and ratios of minimal balloon diameter to lumen diameter for used to treat strictures of various diseases. Nominal pressure is the pressure required to bring the balloon to its labeled nominal diameter in an unconstrained pressure ramp test. Nominal diameter is the desired diameter that the product is labeled with. All physicians purchase balloons and select balloons for use according to the nominal diameter. The rated burst pressure is the maximum pressure that the balloon can be inflated to and have a very high confidence that it will not burst, a labeling requirement for balloon catheters that is calculated from a statistical analysis of the pressures observed when the balloons burst in an unconstrained pressure ramp test.

TABLE 1

Examples of nominal balloon sizes, nominal pressures, and ratios of minimal balloon diameter to stricture diameter for used to treat strictures of various diseases. The ratios assume a stricture diameter of 3 mm.

| Disease | Nominal balloon diameter × length (mm) | Nominal pressure (atm) | Rated burst pressure (atm) | Ratio of nominal balloon diameter/ stricture diameter |
|---|---|---|---|---|
| BPH | 20-50 × 20-80, such as 30-40 × 30-50 | 1.5 minimum, such as 2 or more | 2 minimum, such as 4 or more | 6.7-16.7 |
| Urethral stricture | 6-14 × 20-180, such as 6-14 × 30-50 | 3 minimum, such as 8 or more | 8 minimum, such as 10-12 | 2-4.7 |
| Esophageal stricture | 6-20 × 30-80 | 3 minimum | 9 minimum | 2-6.7 |
| Achalasia (stricture of lower esophagus) | 30-40 × 80-100 | 1.5 minimum | 9 minimum | 10-16.7 |
| Gastrointestinal strictures | 6-20 × 40-60 | 3 minimum | 9 minimum | 2-6.7 |
| Biliary strictures | 4-10 × 20-40 | 3 minimum | 9 minimum | 1.3-3.3 |

In various embodiments, the balloon catheter can be sufficient such that at a predetermined pressure (e.g., the nominal pressure) the balloon can have any suitable ratio of inflated balloon catheter diameter to a diameter of the body lumen at the location of treatment; for example, at a pressure of about 1 atm (304 kPa) to about 30 atm (3040 kPa) (e.g., about 1 atm or less, or less than, equal to, or more than about 4 atm, 5, 6, 7, 8, 9, 10, 11, 12, 13, 14, 15, 16, 17, 18, 19, 20, 22, 24, 26, 28, or about 30 atm or more).

The inflated diameter of the balloon can be any suitable diameter that is achieved during or throughout the inflation period such that a desired ratio of the inflated balloon diameter to the diameter of the body lumen is achieved. The inflated diameter of the balloon can correspond to the pressure used to inflate the balloon during the inflation period. The inflation pressure can be in the range of nominal inflation pressure to rated burst pressure. The nominal pressure is the pressure at the nominal diameter of the inflated balloon catheter. The nominal diameter is the diameter at the nominal pressure of the balloon catheter and is specified on the product labeling. In some embodiments, the inflated pressure can be the nominal pressure for the balloon, and the inflated diameter of the balloon can be about equal to the nominal diameter of the balloon, or can be less than the nominal diameter of the balloon due to constraint from the stricture. In some embodiments, the inflated pressure of the balloon during the inflation period can be above or below the nominal pressure and the inflated diameter of the balloon can be, correspondingly, above or below the nominal diameter of the balloon.

In various embodiments, the balloon catheter of the present invention is compatible with flexible or rigid scopes that allow visualization of the treatment zone, allowing more accurate and more efficient placement than other balloon catheters. The scope can be a gastroscope, enteroscope, duodenoscope, colonoscope, sigmoidoscope, rectoscope, anoscope, rhinoscope, bronchoscope, or a cystoscope. In various embodiments, the balloon catheter of the present invention is self-seeking, in that the neck section of the balloon catheter directs the balloon catheter to a proper position during inflation (e.g., with the neck section of the balloon catheter, such as a distal-most neck section, in the bladder neck) even if the balloon catheter is slightly off-position at the time of initiation of inflation.

In various embodiments, the balloon catheter has one or more neck sections separating one or more main sections, and the at least one neck section of the balloon catheter of the present invention, or the configuration of the one or more neck sections, allows the balloon catheter to stay in place during treatment more consistently and effectively to dilate the stricture and deliver the drug, as compared to other balloon catheters lacking such a neck section or configuration of neck sections.

The drug-coated balloon catheter can include an elongated balloon body with multiple main sections, two cones at distal and proximal ends of the balloon body, an inflation lumen, and a wire lumen, wherein the balloon body includes at least two main sections with a larger diameter and at least one neck section with a smaller diameter, wherein the main section with a larger diameter and neck section are aligned alternatively and adjacently. The elongated balloon can have a generally cylindrical shape, with the exception of any neck section on the balloon, any tapered sections (e.g., cones) between the neck section and the main sections having the main diameter, and any tapered or shaped sections at the longitudinal ends of the balloon. The elongated balloon can have any suitable profile taken perpendicular to a longitudinal direction of the balloon, such as circular (e.g., cylindrical balloon), oval, or polygonal (e.g., pentagonal, hexagonal, heptagonal, octagonal, and the like), or a combination thereof. The diameter of a non-cylindrical balloon can be the largest or smallest size perpendicular to the longitudinal direction.

The balloon can have any suitable size. The balloon can be designed to fit within the prostatic urethra with the distal section of the balloon being positioned in the bladder. Main diameters and nominal balloon diameters can range from about 5 mm to about 50 mm, 25 mm up to 45 mm, at least 10 mm, at least 15 mm, at least 20 mm, at least 30 mm, such as about 5 mm or less, or less than, equal to, or greater than about 6 mm, 7, 8, 9, 10, 11, 12, 13, 14, 15, 16, 17, 18, 19, 20, 21, 22, 23, 24, 25, 26, 27, 28, 29, 30, 32, 34, 36, 38, 40, 41, 42, 43, 44, 45, 46, 47, 48, 49, or about 50 mm or more; main section diameters can independently range from any of these ranges or specific sizes. The balloon can have a length of about 20 mm to about 160 mm, 40 mm to about 80 mm, or about 20 mm or less, or less than, equal to, or greater than about 22 mm, 24, 26, 28, 30, 32, 34, 36, 38, 40, 42, 44, 46, 48, 50, 52, 54, 56, 58, 60, 62, 64, 66, 68, 70, 72, 74, 76, 78 mm, or about 80 mm or more. Balloon length and diameter can be selected based on the unique prostate anatomy of the patient.

The neck section can be a rigid or semi-rigid neck section, such that the diameter of the neck section (e.g., the portion of the neck section having the neck section diameter) remains substantially static during inflation of the balloon. The neck section can include a substantially nonelastic (e.g., non-compliant, or minimally non-compliant) portion of the balloon, a reinforced portion of the balloon, or a combination thereof. The neck section can include an inelastic material circulated around a circumference of the neck section, such as a suture or monofilament or multifilaments of such material, such as nylon, polyamide, aromatic polyamides, ultra high molecular weight polyethylene (UHMWPE), polyesters, aromatic polyesters, polyethylene terephthalate (PET) or a combination thereof.

The catheter shaft, the balloon, or a combination thereof, can include single or multiple markings along its length to aid in positioning and alignment with certain anatomical structures. The markings can have any suitable orientation, such as circumferential, or longitudinally along the catheter shaft or balloon. Marks on the catheter shaft or balloon can be used to aid in positioning the balloon in the treatment area, indicate that the balloon is fully recovered in the sheath, or locate the device within a patient's anatomy. Markings on the catheter shaft can be visualized using an endoscope, cystoscope, or with the unaided eye, or markings can include radiologically distinguishable components such as radiopaque materials. Markings can be created by thermally bonding polymer to the surface of the catheter shaft having a distinguishable color, via pad print, via laser marking, or via any other method. FIGS. 4A and 4B illustrate an embodiment of balloon recapture mark 509 and positioning mark 511. Balloon recapture mark 509 can be used when the balloon catheter includes a sheath that covers the balloon. Mark 509 can be located just proximal of the proximal end of the sheath when the sheath is covering the balloon. After the user advances the catheter to the desired location, removes the sheath, and inflates the balloon, the user may want to later advance the sheath so that the balloon is covered for removal. In this case, after deflating, the user will distally advance the sheath until the recapture mark 509 is visible. Positioning mark 511 can be used to aid the user in positioning the catheter within a body lumen. For example, when a single neck balloon, as shown in FIGS. 4A and 4B, is used for a BPH treatment, the positioning mark which can be located just proximal of the proximal end of the balloon, can be placed just proximal of the external sphincter. In various embodiments, the user can see mark 511 through the scope and when the mark is just proximal of the external sphincter, the user can be confident that the balloon is properly positioned.

The balloon catheter can include a catheter tip at the distal end which is inserted into the body first. The catheter tip can facilitate passage of the balloon through the body lumen. The tip can be an atraumatic tip that helps prevent damage to the body lumen during insertion therein. The tip can be a Coude atraumatic tip. The atraumatic Coude tip is designed to facilitate passage of the catheter through the bends in the body lumen while preventing damage to the body lumen walls during tracking. It can be a low durometer biocompatible material overmolded onto the catheter shaft or adhesively bonded onto the shaft. For example, the Coude tip can be formed from a PEBAX® or liquid silicone rubber.

In some embodiments, the catheter can include an insertion sheath that covers the balloon during insertion (e.g., the coated and folded/pleated balloon) and can be removed completely from the body during treatment. The sheath can be designed to couple with an obturator or dilator to facilitate reinsertion of the sheath into the body lumen. The sheath can include one material, or more than one material. The sheath can have a laminated construction where several different layers of materials are combined to create the sheath or can be constructed using simple extrusion or co-extrusion. In one embodiment the sheath includes an inner layer that includes a fluoropolymer such as PTFE or FEP, a middle reinforcing layer that includes a braided or coiled wire filament such as stainless steel, Nitinol, PEEK, or other material, and an outer layer including a polymer such as PEBAX®, nylon, polyurethane, or another thermoplastic material. The durometer of the outer sheath material and the pitch of the braid or coil reinforcement can be uniform or can vary along the length of the sheath. The obturator can be an extruded tube or can be molded into a specific geometry and can include a wide range of materials such as LDPE, HDPE, PE, PEBA, nylons, silicones, polyurethanes or other biocompatible materials. The distal tip (inserted into the body) of the obturator can include a taper, radius, or some combination that facilities passage through a body lumen. The sheath and obturator can have overmolded, swaged, crimped, or adhesively-bonded hub connections which allow them to interface together. Alternately, the obturator can be flared at the proximal side to create a grasping feature and create an interference connection with the sheath. After treatment, the obturator and sheath can be inserted through the body lumen to the proximal side of the balloon. Once in position, the obturator can be separated from the sheath, and the sheath can be replaced over the deflated balloon to facilitate removal of the balloon catheter.

FIG. 4 illustrates an embodiment of the balloon catheter used for treating BPH including a catheter shaft, catheter tip, and Tuohy Borst adapter/stopcock assembly.

The main sections of the balloon can be formed with identical or similar diameters. In some embodiments, the diameters of the various main sections can differ from each other by as much as 30%, when measured at nominal balloon diameter. In FIGS. 3A, 3B, 3C, and 4, the main sections of the balloon are shown with equal diameters, that is the diameter of each main section is constant. In practice, at higher pressures, the diameter of the main sections will become slightly bowed out, in that the diameter of the mid part of the main sections can have a slightly larger diameter than the edges of the main sections near the balloon cone and/or near the neck sections.

For embodiments where the balloon has neck and main sections, as shown in FIGS. 3A, 3B, 3C, and 4, and where the balloon has no neck sections, as shown in FIG. 1, after the balloon catheter is assembled, the balloon can be coated with the at least one water-soluble additive and drug as discussed herein. In some embodiments where the balloon has multiple main sections, the distal main section may not be coated. The balloon can be coated according to the process discussed herein. If a sheath is used, it can be put over the balloon after the balloon is coated. The catheter is then packaged, sterilized, and labeled as is known in the art.

In FIG. 3A, in one embodiment, a balloon with one neck section is shown. Balloon 100 has waist 101, cone 102, first body section 103, neck 104, second body section 105, cone 106, and waist 107. When assembled into a balloon catheter, as is known in the art, waists 101 and 107 will be attached or bonded or the like to the catheter shaft (not shown). During inflation, waists 101 and 107 do not inflate as they are attached to the catheter shaft. Sections 102, 103, 104, 105, and 106 can all be inflated simultaneously through a single inflation point in communication with the catheter shaft and external Luer hub. In FIG. 3B, in one embodiment, a balloon with two neck sections is shown. Balloon 120 has waist 121, cone 122, first body section 123, first neck 124, second body section 125, second neck 126, third body section 127, cone 128, and waist 129. When assembled into a balloon catheter, as is known in the art, waists 121 and 129 will be attached or bonded or the like to the catheter shaft. During inflation, waists 121 and 129 do not inflate as they are attached to the catheter shaft. Sections 122, 123, 124, 125, 126, 127, and 128 can all be inflated simultaneously through a single inflation point in communication with the catheter shaft and external Luer hub. While neck sections 124 and 126 are shown as being the same diameter at the present state of inflation, they can be the same or different diameters with the same or different compliance. In FIG. 3C, in one embodiment, a balloon with three neck sections is shown. Balloon 140, has waist 141, cone 142, first body section 143, first neck 144, second body section 145, second neck 146, third body section 147, third neck 148, fourth body section 149, cone 150, and waist 151. When assembled into a balloon catheter, as is known in the art, waists 141 and 151 will be attached or bonded or the like to the catheter shaft. During inflation, waists 141 and 151 do not inflate as they are attached to the catheter shaft. Sections 142, 143, 144, 145, 146, 147, 148, 149, and 150 can all be inflated simultaneously through a single inflation point in communication with the catheter shaft and external Luer hub. While neck sections 144, 146, and 148 are shown with different diameters at the present state of inflation, they can be the same or different diameters with the same of different compliance.

In various embodiments, the balloon catheter can be assembled with a sheath. The catheter assembly and scope (e.g., cystoscope) are inserted transurethrally into the prostatic urethra and they are positioned side by side near the external sphincter. Using the live video feed from the scope, the external sphincter can be located. The balloon can be positioned adjacent to the external sphincter and within the prostatic urethra. The balloon dilation, drug release, and balloon deflation can be visualized by the scope.

Coating Design and Formulation.

Figure 2A:
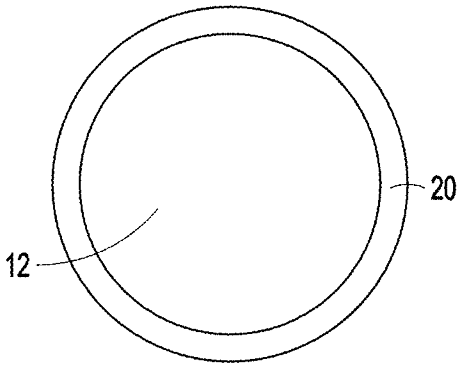
FIGS. 2A-2C are cross-sectional views of different embodiments of the distal portion of the balloon catheter of FIG. 1 at line A-A, showing exemplary coating layers, in accordance with various embodiments.
Figure 2B:
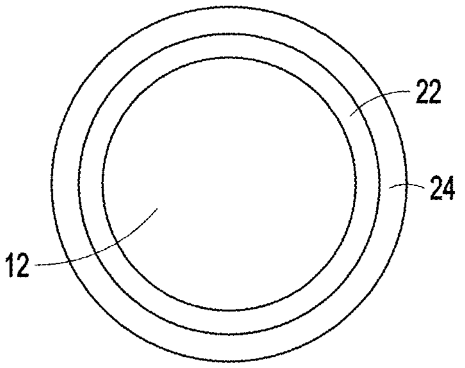
Figure 2C:
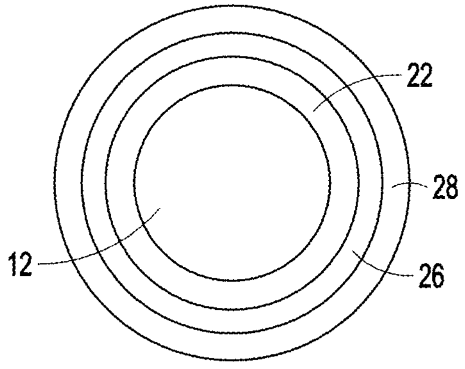

In one embodiment, the present invention provides a balloon catheter for delivering a therapeutic agent to a tissue, such as a vascular tissue or a nonvascular tissue. The device can include a coating applied to an exterior surface of the balloon catheter. The coating can include the polymer-encapsulated drug particles that include the therapeutic agent and the one or more polymers that encapsulate the therapeutic agent; or the drug-releasing coating including the polymer-encapsulated drug particles; or a composition including a therapeutic agent and one or more additives; or a combination thereof. The layer can include a composition including a therapeutic agent and one or more additives. The additive can be any suitable additive. The layer can include one additive, or the layer can include more than one additive, such as a water-soluble first additive and a water-soluble second additive. For example, as shown in the embodiment depicted in FIG. 2A, the balloon 12 is coated with a layer 20 that includes the polymer-encapsulated drug particles that include the therapeutic agent and the one or more polymers that encapsulate the therapeutic agent; or the drug-releasing coating including the polymer-encapsulated drug particles; or a composition including a therapeutic agent and one or more additives; or a combination thereof. In some embodiments, the layer consists essentially of a therapeutic agent and an additive, e.g., the layer includes only the therapeutic agent and the additive, without any other materially significant components. In some embodiments, the device can optionally include an adherent layer. For example, as shown in the embodiment depicted in FIG. 2B, the balloon 12 is coated with an adherent layer 22. A layer 24 can be overlying the adherent layer, wherein the layer 24 includes the polymer-encapsulated drug particles that include the therapeutic agent and the one or more polymers that encapsulate the therapeutic agent; or the drug-releasing coating including the polymer-encapsulated drug particles; or a composition including a therapeutic agent and one or more additives; or a combination thereof. The adherent layer, which is a separate layer underlying the drug coating layer, improves the adherence of the drug coating layer to the exterior surface of the medical device and protects coating integrity. For example, if drug and additive differ in their adherence to the medical device, the adherent layer can prevent differential loss of components and maintain drug-to-additive ratio in the coating during transit to a target site for therapeutic intervention. Furthermore, the adherent layer can function to facilitate rapid release of coating layer components off the device surface upon contact with tissues at the target site. In other embodiments, the device can include a top layer. For example, as shown in the embodiment depicted in FIG. 2C, the balloon 12 is coated with an adherent layer 22, a coating layer 26 including therapeutic agent and overlying the adherent layer, and a top layer 28. The top layer can reduce loss of the drug layer before it is brought into contact with target tissues, for example during transit of the balloon 12 to the site of therapeutic intervention or during the first moments of inflation of balloon 12 before coating layer 20 is pressed into direct contact with target tissue.

In various embodiments the coating that overlays the balloon portion of the catheter has a single layer or multiple layers that contain a one or more therapeutic agents. In some embodiments the layer in contact with the expandable portion of the catheter has no therapeutic agent and is formulated with ingredients that allow the entire or a substantial portion of the coating to transfer to the stricture or stenosis upon inflation of the balloon catheter. In some embodiments the layer in contact with the balloon portion of the catheter has no therapeutic agent and is formulated with ingredients that allow the coating to adhere to the balloon.

Embodiments of the present invention relate to balloon catheters having a rapid drug-releasing coating and methods for preparing such coated devices. The drug-releasing coating can include the polymer-encapsulated drug particles that include the therapeutic agent and the one or more polymers that encapsulate the therapeutic agent; or the drug-releasing coating including the polymer-encapsulated drug particles; or a composition including a therapeutic agent and one or more additives; or a combination thereof. The therapeutic agent according to embodiments of the present invention does not require a delayed or long-term release and instead, for example, the therapeutic agent is released in a very short time period to provide a therapeutic effect upon contact with tissue. An object of embodiments of the present invention is to facilitate rapid and efficient uptake of drug by target tissue during transitory device deployment at a target site. Other embodiments of the present invention relate to balloon catheters having a drug coating which includes particles of a therapeutic agent encapsulated in an additive, or encapsulated by one or more polymers. After inflation of the drug-coated balloon, the particles of the therapeutic agent are embedded into the lumen wall and provide long term drug delivery.

In one embodiment, the present invention provides a balloon catheter for delivering a therapeutic agent to a tissue, such as a vascular tissue or a nonvascular tissue. The device includes a layer applied to an exterior surface of the balloon catheter. The layer includes the polymer-encapsulated drug particles that include the therapeutic agent and the one or more polymers that encapsulate the therapeutic agent; or the drug-releasing coating including the polymer-encapsulated drug particles; or a composition including a therapeutic agent and one or more additives; or a combination thereof. The additive can be any suitable additive. The layer can include one additive, or the layer can include more than one additive, such as a water-soluble first additive and a water-soluble second additive. The layer can also include a water-insoluble or partially water-soluble additive or the layer can include more than one water-insoluble or partially water-soluble additive. In some embodiments therapeutic agent and excipient is dispersed in one of the coating layers. The range of dispersion can vary from a molecular dispersion to dispersions that have drug particles that are tens of micron in size. In one embodiment the therapeutic agent is less then 10 μm in size, in another embodiment the therapeutic agent is 5 μm or less. In another embodiment the therapeutic agent is at least 75% crystalline, or more preferably at least 90% crystalline. In another embodiment the drug is amorphous with no molecular orientation. Techniques to determine if the drug is crystalline or amorphous include powder X-ray diffraction (pXRD), modulated differential scanning calorimetry (mDSC), or confocal raman spectroscopy.

In one embodiment, the concentration density of the at least one therapeutic agent applied to the surface of the medical device is from about 1 to 20 $\mu g/mm^2$, or from about 2 to 6 $\mu g/mm^2$, or about 0.5 $microgram/mm^2$ or less, or less than, equal to, or greater than about 1, 2, 3, 4, 5, 6, 7, 8, 9, 10, 12, 14, 16, 18, or about 20 $micrograms/mm^2$ or more. If the medical device is a balloon, these measurements are calculated at nominal diameter. The ratio of additives to drug by weight in the coating layer in embodiments of the present invention can be about 20 to 0.05, about 10 to 0.1, or about 6 to 0.15.

The ratio by weight of the therapeutic agent in the coating layer to the total weight of the one or more additives in the coating layer can be about 0.05 to about 20, about 0.1 to about 10, about 0.1 to about 5, about 0.5 to about 8, about 0.5 to about 3, about 2 to about 6, or about 0.05 or less, or less than, equal to, or greater than about 1, 2, 3, 4, 5, 6, 7, 8, 9, 10, 11, 12, 13, 14, 15, 16, 17, 18, 19, or about 20 or more.

The drug coating can cover any suitable proportion of the exterior surface of the balloon (e.g., proportion of the surface of the balloon that obtains the main diameter during inflation to the nominal pressure, excluding necks and end-cones), such as about 1% to about 100%, or about 50% to about 100%, to about 80% to about 100%, or about 10% or less, or less than, equal to, or greater than 20%, 30, 40, 50, 60, 70, 75, 80, 85, 90, 95, 96, 97, 98, 99, or about 100% or more.

The balloon can have thereon a residual drug amount after the withdrawing. Any suitable residual drug amount can remain after the withdrawing, such as greater than, equal to, or less than about 70 wt %, 65, 60, 55, 50, 45, 40, 35, 30, 25, 20, 15, 10, 5 wt %, or about 0 wt %.

In some embodiments, the one or more additives, or the one or more polymers, or the first and/or second ionic or zwitterionic additive, can promote a rapid release of the therapeutic agent from the balloon, and whereby the rapid release includes a residual drug amount of the therapeutic agent remaining on the balloon after the balloon is inflated at the target site of the nonvascular body lumen for an inflation period of from about 0.1 minutes to 10 minutes and subsequently removed from the nonvascular lumen.

A coating layer overlying the exterior of the medical device can include one or more water-soluble additives (e.g., a water-soluble first additive, a water-soluble second additive, and a water-soluble third additive).

The water-soluble additive can include a first water-soluble additive that is a surfactant such as a PEG sorbitan monolaurate, a PEG sorbitan monooleate, or a combination thereof. The water-soluble additive can include a second water-soluble additive that is a chemical compound with one or more moieties that are hydroxyl, amine, carbonyl, carboxyl, or ester, such as sorbitol, sorbitan, xylitol, gluconolactone, or a combination thereof. The drug coating can include both the first water-soluble additive and the second water-soluble additive. In some embodiments, the distal end of the balloon can be free of the therapeutic agent.

In some embodiments, the additive is at least one of a surfactant and a chemical compound. A coating layer overlying the exterior of the medical device can include one or more water-soluble additives and one or more water-insoluble or partially water-soluble additives. The water-soluble additive can be neutral, anionic, cationic, or zwitterionic. The water-insoluble additive can be neutral, anionic, cationic, or zwitterionic.

In some embodiments the coating with the therapeutic agent releases off the balloon into aqueous media in less than 30 seconds with no agglomerated particles or individual particles greater than 20 μm. In some embodiments the coating released has particles or agglomerated particles less than 10 μm, or preferably less than 5 μm particles.

The device can be capable of releasing the therapeutic agent and delivering the therapeutic agent to the tissue in about 0.1 to 10 minutes.

In some embodiments, the additives can enhance release of the therapeutic agent off the balloon. The additive can enhance penetration and absorption of the therapeutic agent in tissue. The additive can have a water and ethanol solubility of at least 1 mg/mL and the therapeutic agent can be water-insoluble.

In some embodiments, the layer overlying the exterior surface of the medical device can include a therapeutic agent and at least two additives, wherein each of the additives includes a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, and wherein each additive is soluble in polar organic solvent and is soluble in water. In one aspect of this embodiment, the polar organic solvent is chosen from methanol, ethanol, isopropanol, acetone, dimethylformide, tetrahydrofuran, methylethyl ketone, dimethylsulfoxide, acetonitrile, ethyl acetate, and chloroform and mixtures of these polar organic solvents with water. In another aspect of this embodiment, the device further includes a top layer overlying the surface of the layer overlying the exterior surface of the medical device to reduce loss of drug during transit through a body to the target tissue.

Methods for Treating Strictures and Stenosis.

The present invention provides novel methods for treatment of body lumen strictures to have a long term and persistent effect. The new methods open the lumen and prevents, reduces, or minimizes re-narrowing and recurrent nonvascular or vascular strictures. Vascular lumens include arteries, veins, or any lumens with blood. Nonvascular lumens include those lumens without blood. The methods involve delivering of a drug coating including the polymer-encapsulated drug particles that include the therapeutic agent and the one or more polymers that encapsulate the therapeutic agent; or the drug-releasing coating including the polymer-encapsulated drug particles; or a composition including a therapeutic agent and one or more additives; or a combination thereof. The drug coating can have more than one layer and includes an effective amount of therapeutic agents such as anti-inflammatory and antiproliferative drugs (e.g., from paclitaxel, docetaxel, taxol, an mTOR inhibitor, rapamycin, sirolimus, zotarolimus, everolimus, tacrolimus, umirolimus, an analogue thereof, and combinations thereof). The coating can include one or more water-soluble additives and one or more water-insoluble or partially water-soluble additives to a stricture or stenosis. The treatment is intended for a variety of animals, such as premature neonates to adult humans.

In various embodiments, the present invention provides a minimally invasive method for treatment or prevention of nonvascular strictures of the upper and lower urinary tract. These urinary tract strictures can include; trauma induced urethral strictures, iatrogenic urethral strictures, idiopathic urethral strictures, ureteral strictures, prostate cancer treatment- or stricturotomy-induced bladder neck contractures, and Benign Prostatic Hyperplasia (BPH) due to lateral lobe and or median lobe obstruction. The method includes inserting a balloon catheter through the urethra and tracking it to the urinary tract stricture. The balloon catheter includes an elongated balloon and drug coating. The method includes inflating the balloon to contact the coating layer with the urinary tract stricture tissue until the balloon achieves an inflated balloon diameter for an inflation period. The method includes deflating the balloon after the inflation period and withdrawing from the urethra. In some embodiments, the method further includes performing a surgical procedure such as prostate cancer treatment, BPH treatment, or stricturotomy prior to the insertion of the balloon catheter into the target site. In some embodiments, the prostate cancer treatment includes radical prostatectomy (RP), radiotherapy, cryotherapy, or high intensity focused ultrasound (HIFU). In some embodiments, the BPH procedure includes, transurethral resection of the prostate, photoselective laser vaporization of the prostate, or holmium laser enucleation of the prostate. In some embodiments, the stricturotomy includes hot or cold knife urethrotomy or direct vision internal urethrotomy (DVIU).

In various embodiments, the present invention provides a method for treatment of benign prostate hyperplasia. The method includes 1) inserting a rigid cystoscope (including optics and bridge with irrigation capability) with a sheath into the urethra and tracking the cystoscope tip into the bladder. The method includes 2) removing the bridge and optics and inserting a drug-coated balloon catheter through the length of the cystoscope and then removing the cystoscope while leaving the drug coated balloon in the bladder. The method includes 3) reinserting the reassembled cystoscope, with optics and bridge with irrigation capability, side by side with the drug coated balloon shaft, letting the coating hydrate in the irrigation fluid until the coating is soaked and putting the tip of the scope and the proximal edge of the balloon side by side near the external sphincter. The method includes 3) inflating to the initial pressure (for example 0.5 atm, 1 atm or 1.5 atm) and maintaining the initial pressure until the pressure no longer drops for 1-2 minutes. The method includes 4) inflating to the next higher pressure with an 0.5, 1, or 1.5 atm increase from the previous pressure and maintaining the higher pressure until the pressure no longer drops, for 1-2 minutes. The method includes 5) repeating the steps of 4) until the prostatic tissue yield and the commissurotomy is formed. The method includes 6) keeping the balloon inflated for 1 minute to 7 days, 1 minute to 1 day, or 1-10 minutes to release the drug into tissue and to prevent bleeding. The method includes 7) deflating the balloon catheter. The method includes 8) withdrawing the scope and balloon catheter assembly from the body lumen. Feature (a), or (b), or (c), or (a) and (b), or (a) and (c), or (b) and (c), or (a) and (b) and (c), can be present: (a) the ratio of the inflated balloon diameter to a body lumen diameter at the target site is about 1.0 to about 40; or (b) the inflating includes inflating the balloon to a pressure equal to or greater than a nominal pressure of the balloon catheter, and the stretch ratio of a nominal diameter of the balloon catheter to a body lumen diameter at the target site is about 1.0 to about 40; or (c) the inflating includes inflating to a pressure greater than the nominal pressure of the balloon catheter, and the nominal diameter of the balloon catheter is less than the inflated balloon diameter; or (d) a combination of (a), (b), and (c).

In some embodiments, when treating the prostate, it is preferable to place the proximal balloon waist in the external sphincter so that the external sphincter is not dilated. It is also preferable to size the balloon so that when the balloon waist is in the external sphincter, a balloon neck (e.g., a distal-most balloon neck) is aligned with the bladder neck. This arrangement provides holding forces so that the balloon will not slip during expansion. If a balloon neck cannot be aligned with the bladder neck, it can be preferable to inflate the balloon slowly so that the prostate can yield as the balloon is inflated.

Once properly positioned, the balloon is inflated, such as using an inflation device with a pressure gauge. The balloon can be inflated slowly, allowing the prostatic tissue to yield and reducing the propensity for the balloon to slip proximally into the bladder and slip backward distally. Although a single- or multi-necked shape of the balloon can prevent balloon movement by aligning the distal-most neck with the bladder neck, in some abnormal situations such as with an enlarged median lobe (e.g., about 10-15% of cases) the neck of the balloon may not stay aligned to the neck of the bladder during inflation and additional techniques can be useful to further prevent balloon migration. In some examples, inflating at a rate of about 0.5 to 1 atm/min can prevent balloon movement. As the tissue yields, the balloon pressure correspondingly drops, allowing for additional fluid to be instilled within the balloon without increasing the pressure. When the pressure is stable for about 1-2 minutes the pressure can be increased in 0.5 or 1 atm increments and maintained in a similar method. The pressure can be continually increased, following this method of increasing pressure, allowing pressure to stabilize after pressure drops, and continuing to increase pressure, until a commissurotomy or a split is achieved. Alternatively, a very slow inflation can prevent balloon migration to achieve a commissurotomy or a prostate split. Once a commissurotomy or a prostatic urethra and prostate split is observed and confirmed with the video feed from the scope, mechanical decompression can be achieved. The balloon can remain inflated for a period of about 1 minute to 7 days, 1 minute to 1 day, or 1-10 minutes to allow the drug in the coating to transfer into the tissue. Once the treatment is completed, the balloon can be deflated and the catheter and scope can be removed from the body lumen of the patient.

In some embodiments, when treating the prostate, it can be desirable to predilate the stricture. In this embodiment, the predilation catheter can be shorter and/or of less diameter than the drug-coated balloon treatment catheter. In this scenario, the predilation catheter is positioned with the proximal waist of the balloon in the external sphincter and a neck region aligned with the bladder neck. The balloon is slowly inflated as described herein to aid in yielding the prostate while protecting against balloon slippage. Once inflated, the predilation balloon is deflated and removed and the drug-coated treatment balloon is inserted. The treatment balloon's proximal waist is aligned with the external sphincter. If the prostate was properly predilated, it is not as necessary to align a balloon neck with the bladder neck as the balloon will not be as prone to slipping as it would be in a non-predilated body lumen.

In one embodiment, the present invention relates to a method for treating at least one of a benign prostatic hyperplasia and prostate cancer, the method includes flushing the prostate with water, saline solution, or a water solution including at least one water-soluble additive; inserting a balloon catheter into a target site in the prostate, the balloon catheter including a balloon and a coating layer overlying external surfaces of the balloon. The coating layer can include the polymer-encapsulated drug particles that include the therapeutic agent and the one or more polymers that encapsulate the therapeutic agent; or the drug-releasing coating including the polymer-encapsulated drug particles; or a composition including a therapeutic agent and one or more additives; or a combination thereof. The method can include inflating the balloon until the coating layer contacts walls of the benign prostatic hyperplasia or prostate cancer at the target site and the balloon achieves an inflated balloon diameter for an inflation period; deflating the balloon after the inflation period, wherein the inflation period is from 0.1 minutes to 10 minutes; and withdrawing the balloon catheter from the prostate. The ratio of the inflated balloon diameter to the stricture diameter of the body lumen can be 1.0 to 40, 1.1 to 40, 1.2 to 40, 1.3 to 40, or 1.4 to 40 (e.g., 1, or greater than, less than, or equal to 1.1, 1.2, 1.3, 1.4, 1.5, 1.6, 1.7, 1.8, 1.9, 2, 2.2, 2.4, 2.6, 2.8, 3, 3.5, 4, 4.5, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or40 or less, or any value therebetween). Optionally the inflating can include inflating to a pressure equal to or greater than the nominal pressure of the balloon catheter.

In one embodiment, the present invention relates to a method for treating a urethral stricture, the method including flushing the urethral stricture with water, saline solution, or a water solution including at least one water-soluble additive so as to soak or wet the drug coating; inserting a balloon catheter into a target site in the urethral stricture, the balloon catheter including a balloon and a coating layer overlying external surfaces of the balloon. The coating layer can include the polymer-encapsulated drug particles that include the therapeutic agent and the one or more polymers that encapsulate the therapeutic agent; or the drug-releasing coating including the polymer-encapsulated drug particles; or a composition including a therapeutic agent and one or more additives; or a combination thereof. The ratio by weight of the therapeutic agent in the coating layer to the total weight of the one or more water-insoluble or slightly or partially water-insoluble and one or more water-soluble additives in the coating layer can be from about 0.05 to 20. The method can include inflating the balloon until the coating layer contacts walls of the urethral stricture at the target site and the balloon achieves an inflated balloon diameter for an inflation period; deflating the balloon after the inflation period, wherein the inflation period is from 0.1 minutes to 10 minutes; and withdrawing the balloon catheter from the urethral stricture. The ratio of the inflated balloon diameter to a diameter of the urethra in the location of the stricture can be about 1.0 to about 40, or about 1.01 to about 15, or about 1.01 or less, or less than, equal to, or greater than about 1.1, 1.2, 1.3, 1.4, 1.5, 1.6, 1.8, 2, 3, 4, 5, 6, 7, 8, 9, 10, 12, 14, 16, 18, or about 40 or more. After dilation, the diameter of the urethral stricture can be 6.7 mm or more, such as about 6.7 mm to about 20 mm, or about 6.7 mm to about 15 mm, or less than, equal to, or greater than about 6.7, 6.8, 6.9, 7.0, 7.2, 7.4, 7.6, 7.8, 8, 8.5, 9, 9.5, 10, 11, 12, 13, 14, 15 mm or more. Optionally the inflating can include inflating to a pressure equal to or greater than the nominal pressure of the balloon catheter.

In various embodiments, the present invention provides a minimally invasive method for treatment or prevention of strictures in the gastrointestinal tract or digestive body lumens. The gastrointestinal strictures include esophageal strictures, achalasia strictures, biliary strictures, stomach strictures, gastrectomy induced stomach stricture, small intestine strictures, duodenum strictures, jejunum strictures, ileum strictures, colon strictures, rectum strictures, ileoanal J-pouch strictures, and large intestine strictures. The strictures include esophageal stricture due to eosinophilic esophagitis or barrett's esophagus, radiation induced strictures, Crohn's disease induced strictures, ulcerative colitis induced stricture, chronic inflammatory bowel disease (IBD) induced strictures, and any anastomotic strictures of the gastrointestinal tract. The method includes inserting a balloon catheter into the stricture of the gastrointestinal tract, the balloon catheter includes an elongated balloon and drug coating. The method can include flushing the gastrointestinal stricture with water, saline solution, or a water solution including at least one water-soluble additive so as to soak or wet the drug coating. The method includes inflating the balloon at the target site to contact the coating layer with walls of the body lumen at the location of the stricture of digestive body lumen until the balloon achieves an inflated balloon diameter for an inflation period. The method includes deflating the balloon after the inflation period. The method includes withdrawing the balloon catheter from the body lumen. In some embodiments, the method further includes performing a surgical procedure such as a stricturotomy or resection prior to the insertion of the balloon catheter into the target site. In some embodiments, the stricturotomy or resection includes needle knife electroincision, endoscopic mucosal resection (EMR), or endoscopic sub-mucosal dissection (ESD).

In various embodiments, the present invention provides a method for treatment of or prevention of an inflammatory disease-induced (IBD) non-vascular stricture. IBDs can include Crohn's disease and ulcerative colitis. In some embodiments, the stricture is a small intestine stricture, duodenum stricture, jejunum stricture, ileum stricture, colon stricture, rectum stricture, large intestine stricture, colorectal stricture, ileocolonic stricture, or gastrointestinal stricture. The method includes inserting a balloon catheter into a target site in a body lumen including the inflammatory disease-induced non-vascular stricture, the balloon catheter including an elongated balloon and the drug coating. The method can include flushing the inflammatory disease-induced non-vascular stricture with water, saline solution, or a water solution including at least one water-soluble additive so as to soak or wet the drug coating. The method includes inflating the balloon at the target site to contact the coating layer with walls of the body lumen at the location of the inflammatory disease-induced non-vascular stricture until the balloon achieves an inflated balloon diameter for an inflation period. The method includes deflating the balloon after the inflation period. The method includes withdrawing the balloon catheter from the body lumen.

In one embodiment, the present invention relates to a method for treating an esophageal stricture including achalasia stricture, the method including optionally flushing the esophageal stricture prior to, during, or after insertion of the balloon catheter with water, saline solution or a water solution including at least one water-soluble additive; and inserting a balloon catheter into a target site in the esophageal stricture, the balloon catheter including a balloon and the drug coating. The drug-coated balloon catheter can be delivered to the esophageal stricture with minimally invasive methods by placing an endoscope in the mouth or the nose to access the esophagus. The drug-coated balloon can then be placed through the working channel of a scope or tracked on a previously placed guidewire so that the working portion of the balloon is centered on the stricture. The scope used can be a gastroscope, colonoscope, enteroscope, rhinoscope, or any other endoscope suitable for tracking to the esophageal stricture treatment site. The method can include flushing the esophageal stricture with water, saline solution, or a water solution including at least one water-soluble additive so as to soak or wet the drug coating. The method can include inflating the balloon until the coating layer contacts walls of the esophageal stricture at the target site and the balloon achieves an inflated balloon diameter for an inflation period; deflating the balloon after the inflation period, wherein the inflation period is from 0.1 minutes to 10 minutes; and withdrawing the balloon catheter from the esophageal stricture. The ratio of the balloon diameter to a diameter of the esophagus at the location of the stricture can be about 1.0 to 40, 1.1 to 40, 1.2 to 40, 1.3 to 40, or 1.4 to 40 (e.g., 1, or greater than, less than, or equal to 1.1, 1.2, 1.3, 1.4, 1.5, 1.6, 1.7, 1.8, 1.9, 2, 2.2, 2.4, 2.6, 2.8, 3, 3.5, 4, 4.5, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 or less, or any value therebetween). In some embodiments, the balloon catheter properties are equal or similar to those given in Table 2, having a growth rate that slows at higher pressures. Compliance is the percent change in balloon diameter from nominal diameter to rated burst pressure (RBP) diameter, calculated as: ((Diameter @RBP−Diameter @nominal pressure)/Diameter @nominal pressure)*100%. Optionally the inflating can include inflating to a pressure equal to or greater than the nominal pressure of the balloon catheter.

TABLE 2

Examples of properties of balloon catheters for treating esophageal and gastrointestinal strictures.

| Nominal diameter (mm) | Rated burst pressure diameter (mm) | Nominal pressure (atm) | Rated burst pressure (atm) | Compliance (%) |
|---|---|---|---|---|
| 4 | 6 | 3 | 12 | 50 |
| 6 | 8 | 3 | 10 | 30 |
| 8 | 10 | 3 | 9 | 25 |
| 10 | 12 | 3 | 8 | 20 |
| 12 | 15 | 3 | 8 | 17 |
| 15 | 18 | 3 | 7 | 20 |
| 18 | 20 | 3 | 6 | 11 |
| 20 | 23 | 3 | 6 | 15 |
| 23 | 25 | 3 | 6 | 9 |
| 30 | 34 | 2 | 4 | 13 |
| 35 | 40 | 2 | 4 | 14 |
| 40 | 45 | 2 | 4 | 12 |

In some embodiments, the balloon catheter properties are equal or similar to those given in Table 3, a single balloon catheter having the ability to achieve a wide range of balloon diameters at relatively high working pressures compared to conventional compliant balloons. Balloons in Table 3 have a unique feature that there are three increasing balloon diameters at three increasing inflation pressure stages. The nominal inflation diameter is the diameter at stage I. The diameter increases about 0.5-4 mm, preferably 0.75-3 mm, most preferably 0.9-2 mm for every stage of pressure increase. For example, a balloon that has a diameter of 15 mm at Pressure I (3 atm) has a diameter of 16.5 mm at pressure II (4.5 atm) and has a diameter of 18 mm at pressure III (7 atm).

TABLE 3

Examples of properties of balloon catheters for treating esophageal and gastrointestinal strictures.

| Three inflation pressure stages (atm) | Diameter at pressure stage I (mm) [Nominal Diameter] | Diameter at pressure stage II (mm) | Diameter at pressure stage III (mm) |
|---|---|---|---|
| 3, 6, 10 | 4 | 5 | 6 |
| 3, 6, 10 | 6 | 7 | 8 |
| 3, 5.5, 9 | 8 | 9 | 10 |
| 3, 5, 8 | 10 | 11 | 12 |
| 3, 4.5, 8 | 12 | 13.5 | 15 |
| 3, 4.5, 7 | 15 | 16.5 | 18 |
| 3, 4.5, 6 | 18 | 19 | 20 |
| 3, 4.5, 5.5 | 20 | 21.5 | 23 |
| 3, 4, 5 | 23 | 24 | 25 |
| 2, 3.5, 4.5 | 30 | 32.5 | 35 |
| 2, 3, 4 | 35 | 37.5 | 40 |
| 2, 3, 4 | 40 | 42.5 | 45 |

In various embodiments, the present invention provides a minimally invasive method for treatment or prevention of vaginal stricture or stenosis. The method includes inserting a balloon catheter into the vagina and tracking it to stricture site. The balloon catheter includes an elongated balloon, a coating layer, or more than one drug coating layers overlying the exterior surface of the balloon. The method includes inflating the balloon to contact the coating layer with the vaginal wall until the balloon achieves an inflated balloon diameter for an inflation period. The method includes deflating the balloon after the inflation period and withdrawing from the vagina.

In various embodiments, the present invention provides a minimally invasive method for treatment of a cancer treatment-induced non-vascular stricture. The method includes inserting a balloon catheter into a target site in a body lumen including the cancer treatment-induced non-vascular stricture, the balloon catheter including an elongated balloon, and a drug coating layer, overlying an exterior surface of the balloon. The method includes inflating the balloon at the target site to contact the coating layer with walls of the body lumen at the location of the cancer treatment-induced non-vascular stricture until the balloon achieves an inflated balloon diameter for an inflation period. The method includes deflating the balloon after the inflation period. The method includes withdrawing the balloon catheter from the body lumen. In some embodiments, the cancer treatment is radiation treatment of the prostate, EMR or ESD.

In various embodiments, the present invention provides a minimally invasive method for reducing or preventing recurrence of cancer. The method includes inserting a balloon catheter into a target site in a body lumen, wherein the target site is at, proximate to, proximal to, or distal to a site of a performed cancer treatment, the balloon catheter including an elongated balloon and the drug coating. The method includes inflating the balloon at the target site to contact the coating layer with walls of the body lumen at the target site until the balloon achieves an inflated balloon diameter for an inflation period. The method includes deflating the balloon after the inflation period. The method includes withdrawing the balloon catheter from the body lumen. In some embodiments, the method further includes performing the cancer treatment of the body lumen at, proximate to, proximal to, or distal to the target site prior to the insertion of the balloon catheter into the target site. In some embodiments the cancer treatment performed is radiation treatment of the prostate, transurethral resection of the prostate, or EMR or ESD of the gastrointestinal tract.

In various embodiments, the present invention provides a method for treatment or reducing the occurrence of a surgical anastomosis-induced non-vascular stricture, including the treatment of an anastomosis at the time the anastomosis is formed and/or before a stricture forms. The method includes inserting a balloon catheter into a target site in a body lumen including the surgical anastomosis-induced non-vascular stricture, the balloon catheter including an elongated balloon and the drug coating. The method can include flushing the anastomosis site with water, saline solution, or a water solution including at least one water-soluble additive so as to soak or wet the drug coating. The method includes inflating the balloon at the target site to contact the coating layer with walls of the body lumen at the location of the surgical anastomosis-induced non-vascular stricture until the balloon achieves an inflated balloon diameter for an inflation period. The method includes deflating the balloon after the inflation period. The method includes withdrawing the balloon catheter from the body lumen. In some embodiments, the stricture is a fibrotic stricture. In some embodiments, the stricture is an esophageal stricture, stomach stricture, small intestine stricture, duodenum stricture, jejunum stricture, ileum stricture, colon stricture, rectum stricture, large intestine stricture, colorectal stricture, a stricture resulting from gastric bypass, ileocolonic stricture, gastrointestinal stricture, urethral stricture, ureteral stricture, vaginal stricture or stenosis, J-pouch strictures, or a bladder neck stricture. The anastomosis including two or more body structures joined together, the one or more body structures can come from an autologous source (i.e., same individual, such as bowel resections and arterio-venous fistulas), an allogeneic source (i.e., another individual, such as in organ transplants), or an xenogeneic source (i.e., different species, such as decellularized grafts).

In various embodiments, the present invention provides a method for treatment or prevention of surgical procedure induced strictures. Surgical procedures that can induce non-vascular strictures are needle knife electroincision, episiotomy, urethrotomy, direct vision internal urethrotomy (DVIU), endoscopic mucosal resection (EMR), or endoscopic sub-mucosal dissection (ESD). The method includes inserting a balloon catheter into a target site in a body lumen including the needle knife electroincision-, urethrotomy-, direct vision internal urethrotomy (DVIU)-, endoscopic mucosal resection (EMR)-, or endoscopic sub-mucosal dissection (ESD)-induced non-vascular stricture, the balloon catheter including an elongated balloon and the drug coating. The method can include flushing the surgical site with water, saline solution, or a water solution including at least one water-soluble additive so as to soak or wet the drug coating. The method includes inflating the balloon at the surgical procedure site to contact the coating layer with walls of the body lumen at the surgical procedure site until the balloon achieves an inflated balloon diameter for an inflation period. The method includes deflating the balloon after the inflation period. The method includes withdrawing the balloon catheter from the body lumen.

Various embodiments of this invention relate to a method for treating nonvascular body lumen strictures using endoscopes to visualize the stricture. The endoscope can be a gastroscope, enteroscope, duodenoscope, colonoscope, sigmoidoscope, rectoscope, anoscope, rhinoscope, bronchoscope, or a cystoscope. The scope can be used to ensure that the balloon catheter is properly positioned within the targeted lumen. The method includes inserting the endoscope in the body lumen which can be any bodily orifice such as mouth, nose, anus, ear canal, vagina or urethra and traversing to the stricture site to visualize the stricture. A guidewire can be delivered via the working channel of the endoscope so it passes through the stricture prior to inserting a balloon catheter. The method includes inserting the balloon catheter of FIG. 1 or 4B to a target site in the body lumen. The method can include inserting the balloon catheter on a guidewire and an endoscope to a target site in the body lumen side by side or with the balloon catheter in the working channel of the endoscope. The method can include, prior to, during, or after the insertion of the balloon to the target site, flushing the body lumen with water, saline solution, or a water solution including at least one water-soluble additive. The method includes inflating the balloon until the coating layer contacts walls of the stricture in the body lumen at the target site and the balloon achieves an inflated balloon diameter for an inflation period. Feature (a), or (b), or (c), or (a) and (b), or (a) and (c), or (b) and (c), or (a) and (b) and (c), can be present: (a) the ratio of the inflated balloon diameter to a body lumen stricture diameter at the target site is about 1.0 to about 40; or (b) the inflating includes inflating the balloon to a pressure equal to or greater than a nominal pressure of the balloon catheter, and the stretch ratio of a nominal diameter of the balloon catheter to the body lumen stricture diameter at the target site is about 1.0 to about 40; or (c) the inflating includes inflating to a pressure greater than the nominal pressure of the balloon catheter, and the nominal diameter of the balloon catheter is less than the inflated balloon diameter; or (d) a combination of (a), (b), and (c). The method includes deflating the balloon after the inflation period. The method also includes withdrawing the balloon catheter from the stricture and endoscope and withdrawing the endoscope from in the body lumen.

In various embodiments, the present invention provides a method for treatment or prevention of vascular stenosis. The vascular stenosis can be one of coronary artery stenosis, carotid artery stenosis, brachial artery stenosis, radial artery stenosis, renal artery stenosis, iliac artery stenosis, superficial femoral artery stenosis, popliteal artery stenosis, anterior tibial artery, posterior tibial artery, peroneal artery and other arteries of the foot. The method includes inserting a balloon catheter and/or stent into a target site in the vasculature, the balloon catheter including an elongated balloon and balloon and/or stent including the drug coating. The method includes inflating the balloon and/or expanding the stent at the target site to contact the coating layer with the inner luminal wall and dilate the stenosis until the balloon achieves an inflated balloon diameter for an inflation period or until the stent achieves an expanded diameter. The method can include deflating the balloon after the inflation period. The method can include withdrawing the balloon catheter from the body lumen. In various embodiments, a sheath that covers the coated balloon and/or coated stent can be used to prevent the drug from washing off during while advancing the balloon catheter or stent to the target site in a blood vessel.

In some embodiments, when treating the stenosed artery, it can be desirable to predilate the stenosis with an uncoated pre-dilation balloon catheter prior to treating it with a drug-coated balloon. In some embodiments the pre-dilation balloon catheter has cutting or scoring elements on the balloon that are used to break calcified plaque. In some embodiments, the predilation catheter can be shorter and/or of less diameter than the drug-coated balloon treatment catheter. In this scenario, the predilation catheter is positioned such that the center of the balloon body is aligned with the center of the stenosis. Once inflated, the predilation balloon is deflated and removed and the drug-coated treatment balloon is inserted. The size of the drug-coated balloon is chosen such that the balloon diameter and the balloon length is larger than the pre-dilation balloon catheter to ensure the drug coating comes in contact with the entire luminal wall of the predilated stenosis.

In some embodiments, when treating the stenosed artery, it can be desirable to debulk or remove tissue from the stenosis with an atherectomy device prior to treating it with a drug-coated balloon. Any suitable atherectomy device type such as laser, directional, rotational, or jet can be used. After atherectomy is conducted an angiogram can be taken so the size of the drug-coated balloon can be chosen such that the balloon diameter and the balloon length is large enough to ensure the drug coating comes in contact with the entire luminal wall of the debulked stenosis.

In various embodiments, the present invention provides a method for treatment or prevention of in-stent restenosis including but not limited to; coronary artery stenosis, superficial femoral artery stenosis, popliteal artery stenosis, anterior tibial artery, posterior tibial artery, peroneal artery and other arteries of the foot. The method includes inserting a balloon catheter into a target site of the in-stent restenosis, the balloon catheter including an elongated balloon and the drug coating. The method includes inflating the balloon at the target site to contact the coating layer with the inner luminal wall and dilate the stenosis until the balloon achieves an inflated balloon diameter for an inflation period. The method includes deflating the balloon after the inflation period. The method includes withdrawing the balloon catheter from the body lumen.

In various embodiments, the present invention provides a method for treatment or prevention of stenosed arterial venous fistulas. The method includes inserting a balloon catheter into a target site in the vasculature, the balloon catheter including an elongated balloon and the drug coating. The method includes inflating the balloon at the target site to contact the coating layer with the inner luminal wall and dilate the stenosis until the balloon achieves an inflated balloon diameter for an inflation period. The method includes deflating the balloon after the inflation period. The method includes withdrawing the balloon catheter from the body lumen.

In various embodiments, the present invention provides a method for treatment or prevention of stenosed heart valves. The method includes inserting a balloon catheter into a target site in the heart valve, the balloon catheter including an elongated balloon and the drug coating. The method includes inflating the balloon at the target site to contact the coating layer with the inner luminal wall and dilate the heart valve stenosis until the balloon achieves an inflated balloon diameter for an inflation period. The method includes deflating the balloon after the inflation period. The method includes withdrawing the balloon catheter from the body lumen.

In various embodiments, the present invention provides a method for treating a body lumen including inserting a balloon catheter, such as any balloon catheter described herein, to a target site in a body lumen. In some embodiments, the balloon is inflated until the drug coating layer contacts walls of the stricture and the stricture is dilated, with simultaneous transfer of the drug to the stricture. In some embodiments, the balloon is inflated until the drug coating layer contacts walls of the stricture, the inflation dilates the stricture to increase its diameter, such that the contacting with the stricture can provide full circumferential transfer of the drug to the wall of the stricture. In some embodiments, the portion of the balloon that includes the drug (e.g., in embodiments including less than 100% of the surface area coated with the drug) can contact the stricture uniformly. In other embodiments, the contacting of various portions of the surface of the balloon with the stricture is non-uniform.

In various embodiments, the method includes measuring the body lumen stricture to be treated. The distal and proximal healthy tissue diameter and the length of the stricture can be assessed to select the drug-coated balloon to be used. The physician will select a balloon based on the diameter of the body lumen stricture and achieving a stretch ratio of the nominal diameter of the balloon to the diameter of the body lumen stricture of 1.0-40. The physician can then inflate the balloon to at least the nominal pressure, and in some cases, can inflate the balloon past the nominal pressure, up to the rated burst pressure of the balloon. The range of pressure used during the inflation period can be called the working pressure range of the drug-coated balloon. In some cases, the method can include exceeding the rated burst pressure of the balloon. Because the nominal diameter of the balloon is determined without any constrictions, the inflated diameter of the balloon during treatment while in the stricture will be about the same or less or greater than the nominal diameter. At or above or below burst pressure, the inflated diameter of the balloon can be less than the nominal diameter, equal to the nominal diameter, or can exceed the nominal diameter. For example, a body lumen stricture can be measured to have a diameter of 10 mm. The physician can choose a 14 mm nominal diameter drug-coated balloon that has a nominal pressure of 6 atm and a rated burst pressure of 10 atm. The stretch ratio is 1.4. The physician would inflate the balloon to at least 6 atm and in some cases inflate to 8 atm or 10 atm and in some cases inflate to over 10 atm to achieve the desired inflated balloon diameter during treatment.

Various embodiments provide a method of treating a benign prostatic hyperplasia (BPH) stricture, a urethral stricture, a ureteral stricture, a vaginal stricture or stenosis, prostate cancer, an esophageal stricture, a biliary tract stricture, stomach strictures, small intestine strictures, duodenum strictures, jejunum strictures, ileum strictures, colon strictures, rectum strictures, large intestine strictures, colorectal strictures, strictures after gastric bypass, ileocolonic strictures, gastrointestinal strictures, J-pouch strictures, bladder neck strictures (e.g., stenosis), fibrostenotic strictures of eosinophilic esophagitis, Crohn's disease (CD)- and ulcerative colitis (UC)-induced strictures, radiation-induced strictures, endoscopic resection (EMR and ESD) induced stricture, surgery-related anastomotic strictures, achalasia strictures, gastrectomy-induced strictures, asthma, or chronic obstructive pulmonary disease (COPD). The method is a method of treating a stricture in the body lumen, such as a urethral stricture, a benign prostatic hyperplasia (BPH) stricture, a ureteral stricture, an esophageal stricture, a sinus stricture, stomach strictures, small intestine strictures, duodenum strictures, jejunum strictures, ileum strictures, colon strictures, rectum strictures, large intestine strictures, and biliary tract strictures. The stricture in the body lumen can be a benign prostatic hyperplasia (BPH) stricture, a urethral structure, or an esophageal stricture. The method can be a method of treating benign prostatic hyperplasia, prostate cancer, or a combination thereof, wherein the body lumen is a prostate.

The body lumen can be a prostate, wherein inserting the balloon catheter includes positioning the balloon catheter in the prostate using a scope (e.g., flexible or rigid, such as a cystoscope). The balloon catheter can include a scope, and the method can include using video feed from the scope to locate the target site. The method can include using video feed from the scope to position the balloon catheter at the target site.

The body lumen can be a prostate, the balloon can have multiple main sections divided by one or more necks, and inserting the balloon catheter can include positioning one of the balloon catheter main sections in the prostate and positioning a second main section of the balloon catheter in the bladder.

The inserting can include positioning the at least one neck section of the balloon in a bladder neck. The at least one neck section of the balloon catheter can be a distal neck section, and the inserting can include positioning the distal neck section in the bladder neck. The balloon catheter can include a proximal neck section, and the inserting can include positioning the proximal neck section in the prostatic urethra.

The inflation period can be any suitable inflation period, such as about 0.1 minutes to about 10 minutes, about 0.5 minutes to about 2 minutes, or about 0.1 minutes or less, or about 0.2 minutes, 0.3, 0.4, 0.5, 0.6, 0.7, 0.8, 0.9, 1, 1.1, 1.2, 1.3, 1.4, 1.5, 1.6, 1.8, 2, 2.2, 2.4, 2.6, 2.8, 3, 3.5, 4, 4.5, 5, 6, 7, 8, 9, or about 10 minutes or more.

The inflating can include increasing pressure within the balloon at any suitable rate (e.g., which can exclude periods wherein pressure drops due to tissue yielding and pressure can be maintained during these times), such as about 0.1 atm/minute to about 10 atm/minute, or about 0.5 to about 1.5 atm/minute, or about 0.1 atm/minute or less, or less than, equal to, or greater than about 0.2 atm/minute, 0.3, 0.4, 0.5, 0.6, 0.7, 0.8, 0.9, 1, 1.1, 1.2, 1.3, 1.4, 1.5, 1.6, 1.8, 2, 2.2, 2.4, 2.6, 2.8, 3, 3.5, 4, 4.5, 5, 6, 7, 8, 9, or about 10 atm/minute or more.

Embodiments of the present invention are directed to the treatment of strictures in body lumens by delivering of an effective amount of therapeutic agents, such as anti-inflammatory and antiproliferative drugs (e.g., rapamycin, paclitaxel, or their analogues). The strictures in a body lumen include vascular stenosis, urethral strictures, ureteral strictures, vaginal stricture or stenosis, esophageal strictures, achalasia strictures, strictures in stents, sinus strictures, stomach strictures, small intestine strictures, duodenum strictures, jejunum strictures, ileum strictures, colon strictures, rectum strictures, large intestine strictures, and biliary tract strictures. Embodiments of the present invention are directed to methods for treating at least one of vascular stenosis, benign prostatic hyperplasia (BPH), urethral issues, prostate cancer, colorectal strictures, strictures after gastric bypass, ileocolonic strictures, gastrointestinal strictures, J-pouch strictures, bladder neck strictures (e.g., stenosis), fibrostenotic eosinophilic esophagitis strictures, Crohn's disease (CD)- and ulcerative colitis (UC)-induced strictures, radiation-induced strictures, endoscopic resection (EMR and ESD)-induced strictures, surgery-related anastomotic strictures, achalasia strictures, gastrectomy-induced strictures, asthma, and chronic obstructive pulmonary disease (COPD). According to embodiments, the method involves inflating the balloon catheter and releasing the drug to a wall of the stricture, deflating the balloon; and withdrawing the balloon catheter, wherein the residual drug can be about 1 to 70% of the total loading drug on the balloon catheter, wherein the drug in the wall of body lumen can be about 0.1 to 25% of the total loading drug on the balloon catheter. In one aspect of this embodiment, the additive enhances absorption of the drug into tissue of the stricture in the body lumen.

Therapeutic Agent.

The therapeutic agent which can be used in embodiments of the present invention, can be any drugs or biologically active materials. The therapeutic agent can be a hydrophobic therapeutic agent, an antiproliferative therapeutic agent, an anti-inflammatory agent, or a combination thereof. The drugs can be of various physical states, e.g., molecular distribution, crystal forms or cluster forms. Examples of drugs that are especially useful in embodiments of the present invention are lipophilic substantially water-insoluble drugs, such as paclitaxel, docetaxel, taxol, rapamycin, sirolimus, zotarolimus, everolimus, tacrolimus, umirolimus, an analogue thereof, and combinations thereof, daunorubicin, doxorubicin, lapachone, vitamin D2 and/or D3, their analogues or derivatives thereof, or combinations thereof. Therapeutic agents, such as antiproliferative drugs, such as paclitaxel, taxol, docetaxel, rapamycin, sirolimus, zotarolimus, tacrolimus, umirolimus, everolimus, mTOR inhibitors (i.e., a class of drugs that inhibit the mechanistic target of rapamycin), or their analogues, can be delivered to the wall of a body lumen to treat the narrowing or stricture.

Other drugs that can be useful in embodiments of the present invention include, without limitation, glucocorticoids (e.g., dexamethasone, betamethasone), hirudin, angiopeptin, aspirin, growth factors, antisense agents, anti-cancer agents, antiproliferative agents, oligonucleotides, and, more generally, anti-platelet agents, anti-coagulant agents, anti-mitotic agents, antioxidants, anti-metabolite agents, anti-chemotactic, anti-inflammatory agents, and combinations thereof.

Some drugs that can be useful in various embodiments, such as particularly for the airway, sinus, and other nasal lumens but also for urethral applications are corticosteroids such as, budesonide, flunisolide, triamcinolone, beclomethasone, fluticasone, mometasone, mometasone furoate, dexamethasone, hydrocortisone, methylprednisolone, prednisone, cortisone, betamethasone, triamcinolone acetonide, or the like. Some other suitable drugs are terbutaline, albuterol, ipratropium, pirbuterol, epinephrine, salmeterol, levalbuterol, formoterol, or the like; the drug can be a bronchodilator or a vasoconstrictor.

Also useful in embodiments of the present invention are polynucleotides, antisense, RNAi, or siRNA, for example, that inhibit inflammation and/or smooth muscle cell or fibroblast proliferation.

Anti-platelet agents can include drugs such as aspirin and dipyridamole. Aspirin is classified as an analgesic, antipyretic, anti-inflammatory and anti-platelet drug. Dipyridamole is a drug similar to aspirin in that it has anti-platelet characteristics. Dipyridamole is also classified as a coronary vasodilator. Anti-coagulant agents for use in embodiments of the present invention can include drugs such as heparin, protamine, hirudin and tick anticoagulant protein. Antioxidant agents can include probucol. Antiproliferative agents can include drugs such as amlodipine and doxazosin. Anti-mitotic agents and anti-metabolite agents that can be used in embodiments of the present invention include drugs such as methotrexate, azathioprine, vincristine, vinblastine, 5-fluorouracil, adriamycin, and mutamycin. Antibiotic agents for use in embodiments of the present invention include penicillin, cefoxitin, oxacillin, tobramycin, and gentamicin. Suitable antioxidants for use in embodiments of the present invention include probucol. Additionally, genes or nucleic acids, or portions thereof can be used as the therapeutic agent in embodiments of the present invention. Furthermore, collagen-synthesis inhibitors, such as tranilast, can be used as a therapeutic agent in embodiments of the present invention.

Photosensitizing agents for photodynamic or radiation therapy, including various porphyrin compounds such as porfimer, for example, are also useful as drugs in embodiments of the present invention.

Drugs for use in embodiments of the present invention also include everolimus, somatostatin, tacrolimus, roxithromycin, dunaimycin, ascomycin, bafilomycin, erythromycin, midecamycin, josamycin, concanamycin, clarithromycin, troleandomycin, folimycin, cerivastatin, simvastatin, lovastatin, fluvastatin, rosuvastatin, atorvastatin, pravastatin, pitavastatin, vinblastine, vincristine, vindesine, vinorelbine, etoposide, teniposide, nimustine, carmustine, lomustine, cyclophosphamide, 4-hydroxycyclophosphamide, estramustine, melphalan, ifosfamide, trofosfamide, chlorambucil, bendamustine, dacarbazine, busulfan, procarbazine, treosulfan, temozolomide, thiotepa, daunorubicin, doxorubicin, aclarubicin, epirubicin, mitoxantrone, idarubicin, bleomycin, mitomycin, dactinomycin, methotrexate, fludarabine, fludarabine-5'-dihydrogenphosphate, cladribine, mercaptopurine, thioguanine, cytarabine, fluorouracil, gemcitabine, capecitabine, docetaxel, carboplatin, cisplatin, oxaliplatin, amsacrine, irinotecan, topotecan, hydroxycarbamide, miltefosine, pentostatin, aldesleukin, tretinoin, asparaginase, pegaspargase, anastrozole, exemestane, letrozole, formestane, aminoglutethimide, adriamycin, azithromycin, spiramycin, cepharantin, smc proliferation inhibitor-2w, epothilone A and B, mitoxantrone, azathioprine, mycophenolatmofetil, c-myc-antisense, b-myc-antisense, betulinic acid, camptothecin, lapachol, beta.-lapachone, podophyllotoxin, betulin, podophyllic acid 2-ethylhydrazide, molgramostim (rhuGM-CSF), peginterferon a-2b, lenograstim (r-HuG-CSF), filgrastim, macrogol, dacarbazine, basiliximab, daclizumab, selectin (cytokine antagonist), CETP inhibitor, cadherines, cytokinin inhibitors, COX-2 inhibitor, NFkB, angiopeptin, ciprofloxacin, camptothecin, fluoroblastin, monoclonal antibodies, which inhibit the muscle cell proliferation, bFGF antagonists, probucol, prostaglandins, 1,11-dimethoxycanthin-6-one, 1-hydroxy-11-methoxycanthin-6-one, scopoletin, colchicine, NO donors such as pentaerythritol tetranitrate and syndnoeimines, S-nitrosoderivatives, tamoxifen, staurosporine, beta.-estradiol, a-estradiol, estriol, estrone, ethinylestradiol, fosfestrol, medroxyprogesterone, estradiol cypionates, estradiol benzoates, tranilast, kamebakaurin and other terpenoids, which are applied in the therapy of cancer, verapamil, tyrosine kinase inhibitors (tyrphostines), cyclosporine A, 6-a-hydroxy-paclitaxel, baccatin, taxotere and other macrocyclic oligomers of carbon suboxide (MCS) and derivatives thereof, mofebutazone, acemetacin, diclofenac, lonazolac, dapsone, o-carbamoylphenoxyacetic acid, lidocaine, ketoprofen, mefenamic acid, piroxicam, meloxicam, chloroquine phosphate, penicillamine, hydroxychloroquine, auranofin, sodium aurothiomalate, oxaceprol, celecoxib, β-sitosterin, ademetionine, myrtecaine, polidocanol, non ivamide, levomenthol, benzocaine, aescin, ellipticine, D-24851 (Calbiochem), colcemid, cytochalasin A-E, indanocine, nocodazole, S 100 protein, bacitracin, vitronectin receptor antagonists, azelastine, guanidyl cyclase stimulator tissue inhibitor of metal proteinase-1 and -2, free nucleic acids, nucleic acids incorporated into virus transmitters, DNA and RNA fragments, plasminogen activator inhibitor-1, plasminogen activator inhibitor-2, antisense oligonucleotides, VEGF inhibitors, IGF-1, active agents from the group of antibiotics such as cefadroxil, cefazolin, cefaclor, cefotaxim, tobramycin, gentamycin, penicillins such as dicloxacillin, oxacillin, sulfonamides, metronidazol, antithrombotics such as argatroban, aspirin, abciximab, synthetic antithrombin, bivalirudin, coumadin, enoxaparin, desulphated and N-reacetylated heparin, tissue plasminogen activator, GpIIb/IIIa platelet membrane receptor, factor Xa inhibitor antibody, heparin, hirudin, r-hirudin, PPACK, protamin, prourokinase, streptokinase, warfarin, urokinase, vasodilators such as dipyramidole, trapidil, nitroprussides, PDGF antagonists such as triazolopyrimidine and seramin, ACE inhibitors such as captopril, cilazapril, lisinopril, enalapril, losartan, thiol protease inhibitors, prostacyclin, vapiprost, interferon α, β- and γ, histamine antagonists, serotonin blockers, apoptosis inhibitors, apoptosis regulators such as $p^{65}$ NF-kB or Bcl-xL antisense oligonucleotides, halofuginone, nifedipine, tranilast, molsidomine, tea polyphenols, epicatechin gallate, epigallocatechin gallate, Boswellic acids and derivatives thereof, leflunomide, anakinra, etanercept, sulfasalazine, etoposide, dicloxacillin, tetracycline, triamcinolone, mutamycin, procainamide, retinoic acid, quinidine, disopyramide, flecamide, propafenone, sotalol, amidorone, natural and synthetically obtained steroids such as bryophyllin A, inotodiol, maquiroside A, ghalakinoside, mansonine, strebloside, hydrocortisone, betamethasone, dexamethasone, non-steroidal substances (NSAIDS) such as fenoprofen, ibuprofen, indomethacin, naproxen, phenylbutazone and other antiviral agents such as acyclovir, ganciclovir and zidovudine, antimycotics such as clotrimazole, flucytosine, griseofulvin, ketoconazole, miconazole, nystatin, terbinafine, antiprozoal agents such as chloroquine, mefloquine, quinine, moreover natural terpenoids such as hippocaesculin, barringtogenol-C21-angelate, 14-dehydroagrostistachin, agroskerin, agrostistachin, 17-hydroxyagrostistachin, ovatodiolids, 4,7-oxycycloanisomelic acid, baccharinoids B1, B2, B3 and B7, tubeimoside, bruceanol A, B and C, bruceantinoside C, yadanziosides N and P, isodeoxyelephantopin, tomenphantopin A and B, coronarin A, B, C and D, ursolic acid, hyptatic acid A, zeorin, iso-iridogermanal, maytenfoliol, effusantin A, excisanin A and B, longikaurin B, sculponeatin C, kamebaunin, leukamenin A and B, 13,18-dehydro-6-a-senecioyloxychaparrin, taxamairin A and B, regenilol, triptolide, moreover cymarin, apocymarin, aristolochic acid, anopterin, hydroxyanopterin, anemonin, protoanemonin, berberine, cheliburin chloride, cictoxin, sinococuline, bombrestatin A and B, cudraisoflavonei A, curcumin, dihydronitidine, nitidine chloride, 12-beta-hydroxypregnadien-3,20-dione, bilobol, ginkgol, ginkgolic acid, helenalin, indicine, indicine-N-oxide, lasiocarpine, inotodiol, glycoside 1a, podophyllotoxin, justicidin A and B, larreatin, malloterin, mallotochromanol, isobutyrylmallotochromanol, maquiroside A, marchantin A, maytansine, lycoridicin, margetine, pancratistatin, liriodenine, bisparthenolidine, oxoushinsunine, aristolactam-AII, bisparthenolidine, periplocoside A, ghalakinoside, ursolic acid, deoxypsorospermin, psychorubin, ricin A, sanguinarine, manwu wheat acid, methylsorbifolin, sphatheliachromen, stizophyllin, mansonine, strebloside, akagerine, dihydrousambarensine, hydroxyusambarine, strychnopentamine, strychnophylline, usambarine, usambarensine, berberine, liriodenine, oxoushinsunine, daphnoretin, lariciresinol, methoxylariciresinol, syringaresinol, umbelliferon, afromoson, acetylvismione B, desacetylvismione A, and vismione A and B.

A combination of drugs can also be used in embodiments of the present invention. Some of the combinations have additive effects because they have a different mechanism, such as paclitaxel and rapamycin, paclitaxel and active vitamin D, paclitaxel and lapachone, rapamycin and active vitamin D, rapamycin and lapachone. Because of the additive effects, the dose of the drug can be reduced as well. These combinations can reduce complications from using a high dose of the drug.

Some drugs for use in various embodiments that are considered particularly suitable for the airway, sinus and other nasal lumens are corticosteroids such as, budesonide, flunisolide, triamcinolone, beclomethasone, fluticasone, mometasone, mometasone furoate, dexamethasone, hydrocortisone, methylprednisolone, prednisone, cortisone, betamethasone, triamcinolone acetonide, or the like.

In one embodiment of the balloon catheter, the ratio by weight of the therapeutic (e.g., hydrophobic) agent in the coating layer to the total weight of the one or more additives in the coating layer can be about 0.05 to about 20, about 0.1 to about 10, about 0.1 to about 5, about 0.5 to about 8, about 0.5 to about 3, about 2 to about 6, or about 0.05 or less, or less than, equal to, or greater than about 1, 2, 3, 4, 5, 6, 7, 8, 9, 10, 11, 12, 13, 14, 15, 16, 17, 18, 19, or about 20 or more. In one embodiment of the balloon catheter, the ratio by weight of the therapeutic agent in the coating layer to the total weight of the one or more additives (e.g., a first and second additive in the coating layer, or to the total weight of a first, second, and third additive) in the coating layer, is from about 0.05 to about 20, about 0.1 to about 10, about 0.1 to about 5, about 0.5 to about 8, about 0.5 to about 3, about 2 to about 6, or about 0.05 or less, or less than, equal to, or greater than about 1, 2, 3, 4, 5, 6, 7, 8, 9, 10, 11, 12, 13, 14, 15, 16, 17, 18, 19, or about 20 or more.

Additives.

The excipients according to embodiments of the present invention can facilitate rapid drug elution and superior permeation of drug into tissues at a disease site. Thus, coatings according to embodiments of the present invention provide an enhanced rate and/or extent of absorption of the antiproliferative therapeutic agent in nonvascular diseased tissues or nonvascular body lumens. In embodiments of the present invention, the coated device delivers antiproliferative therapeutic agent to nonvascular tissues during a very brief deployment time of less than 10 minutes, less than 2 minutes, and reduces re-narrowing and reoccurring of the strictures of a nonvascular body lumen.

In some embodiments, the additive reduces crystal size and number of particles of the therapeutic agent, and wherein the additive is water-soluble, and the therapeutic agent is not water-soluble. The additive can have a fatty chain of an acid, ester, ether, or alcohol, wherein the fatty chain can directly insert into lipid membrane structures of the tissue. The additive can penetrate into and rearrange lipid membrane structures of the tissue. The additive can have one or more functional groups which have affinity to the drug by hydrogen bonding and/or van der Waals interactions. In some embodiments, the additive can be at least one of a surfactant and a chemical compound, and wherein the additive has a molecular weight of 50 to 750 g/mol (e.g., 50 g/mol or more, or less than, equal to, or greater than 75 g/mol, 100, 125, 150, 175, 200, 225, 250, 275, 300, 325, 350, 375, 400, 425, 450, 475, 500, 525, 550, 575, 600, 625, 650, 675, 700, 725 g/mol, or 750 g/mol or less. The chemical compound can have more than four hydroxyl groups. In some embodiments, the chemical compound having more than four hydroxyl groups has a melting point of 120° C. or less, and the chemical compound is an alcohol or an ester. In some embodiments, the therapeutic agent is not water-soluble or is only sparingly water-soluble.

In one aspect of this embodiment, the additive enhances absorption of the drug into tissue of the nonvascular and vascular body lumens. In another aspect of this embodiment, the additive includes a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions. The drug affinity part of the additive can bind the lipophilic drug, such as rapamycin or paclitaxel or their analogues. The hydrophilic portion accelerates diffusion and increases permeation of the drug into tissue. It can facilitate rapid movement of drug off the medical device during deployment at the target site by preventing hydrophobic drug molecules from clumping to each other and to the device, increasing drug solubility in interstitial spaces, and/or accelerating drug lumen through polar head groups to the lipid bilayer of cell membranes of target tissues. The additives of various embodiments of the present invention can have two parts that function together to facilitate rapid release of drug off the device surface and uptake by target tissue during deployment (by accelerating drug contact with tissues for which drug has high affinity) while preventing the premature release of drug from the device surface prior to device deployment at the target site.

In embodiments of the present invention, the therapeutic agent is rapidly released after the medical device is brought into contact with tissue and is readily absorbed. For example, certain embodiments of devices of the present invention include drug-coated balloon catheters that deliver a therapeutic agent such as a lipophilic antiproliferative pharmaceutical (such as paclitaxel or rapamycin) to nonvascular tissue through brief, direct pressure contact at high drug concentration during balloon dilation. The lipophilic drug, for example, is retained in target tissue at the delivery site, where it inhibits hyperplasia and restenosis yet allows epithelization. In these embodiments, coating formulations of the present invention not only facilitate rapid release of drug from the balloon surface and transfer of drug into target tissues during deployment, but also prevent drug from diffusing away from the device during transit through tortuous anatomy prior to reaching the target site and from dislodging from the device during the initial phase of balloon inflation, before the drug coating is pressed into direct contact with the surface of the body lumen.

The additive according to certain embodiments has a drug affinity part and a hydrophilic part. The drug affinity part is a hydrophobic part and/or has an affinity to the therapeutic agent by hydrogen bonding and/or van der Waals interactions. The drug affinity part can include aliphatic and aromatic organic hydrocarbon compounds, such as benzene, toluene, and alkanes, among others. These parts are not water-soluble. They can bind both hydrophobic drug, with which they share structural similarities, and lipids of cell membranes. The drug affinity part can include functional groups that can form hydrogen bonds with drug and with itself. The hydrophilic part can include hydroxyl groups, amine groups, amide groups, carbonyl groups, carboxylic acid and anhydrides, ethyl oxide, ethyl glycol, polyethylene glycol, ascorbic acid, amino acid, amino alcohol, glucose, sucrose, sorbitan, glycerol, polyalcohol, phosphates, sulfates, organic salts and their substituted molecules, among others. One or more hydroxyl, carboxyl, acid, amide or amine groups, for example, can be advantageous since they easily displace water molecules that are hydrogen-bound to polar head groups and surface proteins of cell membranes and can function to remove this barrier between hydrophobic drug and cell membrane lipid. These parts can dissolve in water and polar solvents. The additive of embodiments of the present invention has components to both bind drug and facilitate its rapid movement off the medical device during deployment and into target tissues.

The additives in embodiments of the present invention can be surfactants and/or chemical compounds with one or more hydroxyl, amino, carbonyl, carboxyl, acid, amide, or ester moieties. The surfactants include ionic, nonionic, aliphatic, and aromatic surfactants. The chemical compounds with one or more hydroxyl, amino, carbonyl, carboxyl, acid, amide, or ester moieties are chosen from amino alcohols, hydroxyl carboxylic acid and anhydrides, ethyl oxide, ethyl glycols, amino acids, peptides, proteins, sugars, glucose, sucrose, sorbitan, glycerol, polyalcohol, phosphates, sulfates, organic acids, esters, salts, vitamins, and their substituted molecules.

The terms "hydrophilic" and "hydrophobic" are relative terms. To function as an additive in various embodiments of the present invention, the compound includes polar or charged hydrophilic moieties as well as non-polar hydrophobic (lipophilic) moieties.

An empirical parameter commonly used in medicinal chemistry to characterize the relative hydrophilicity and hydrophobicity of pharmaceutical compounds is the partition coefficient, P, the ratio of concentrations of unionized compound in the two phases of a mixture of two immiscible solvents, usually octanol and water, such that P=([solute] octanol/[solute]water). Compounds with higher log Ps are more hydrophobic, while compounds with lower log Ps are more hydrophilic. Lipinski's rule suggests that pharmaceutical compounds having log P<5 can be more membrane permeable. For purposes of certain embodiments of the present invention, for example, the additive has log P less than log P of the drug to be formulated (as an example, log P of paclitaxel is 7.4). A greater log P difference between the drug and the additive can facilitate phase separation of drug. For example, if log P of the additive is much lower than log P of the drug, the additive can accelerate the release of drug in an aqueous environment from the surface of a device to which drug might otherwise tightly adhere, thereby accelerating drug delivery to tissue during brief deployment at the site of intervention. In certain embodiments of the present invention, log P of the additive is negative. In other embodiments, log P of the additive is less than log P of the drug. While a compound's octanol-water partition coefficient P or log P is useful as a measurement of relative hydrophilicity and hydrophobicity, it is merely a rough guide that can be useful in defining suitable additives for use in embodiments of the present invention.

Suitable additives that can be used in embodiments of the present invention include, without limitation, organic and inorganic pharmaceutical excipients, natural products and derivatives thereof (such as sugars, vitamins, amino acids, peptides, proteins, and fatty acids), low molecular weight oligomers, surfactants (anionic, cationic, non-ionic, and ionic), and mixtures thereof. The additives described herein as useful in the present invention are provided for exemplary purposes only and is not intended to be comprehensive. Many other additives can be useful for purposes of the present invention. The additive can include the first ionic or zwitterionic additive, the second ionic or zwitterionic additive, or a combination thereof.

Surfactants.

In embodiments including a surfactant, the surfactant can be any surfactant suitable for use in pharmaceutical compositions. Such surfactants can be anionic, cationic, zwitterionic or non-ionic. Mixtures of surfactants are also within the scope of various embodiments of the invention, as are combinations of surfactant and other additives. Surfactants often have one or more long aliphatic chains such as fatty acids that can insert directly into lipid bilayers of cell membranes to form part of the lipid structure, while other components of the surfactants loosen the lipid structure and enhance drug penetration and absorption. The contrast agent iopromide does not have these properties.

An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Using HLB values as a rough guide, hydrophilic surfactants are generally considered to be those compounds having an HLB value greater than about 10, as well as anionic, cationic, or zwitterionic compounds for which the HLB scale is not generally applicable. Similarly, hydrophobic surfactants are compounds having an HLB value less than about 10. In certain embodiments of the present invention, a higher HLB value is utilized, since increased hydrophilicity can facilitate release of hydrophobic drug from the surface of the device. In one embodiment, the HLB of the surfactant additive is higher than 10. The additive HLB can be higher than 14. Alternatively, surfactants having lower HLB can be utilized to prevent drug loss prior to device deployment at the target site, for example in a top coat over a drug layer that has a very hydrophilic additive.

The HLB value of a surfactant is merely a rough guide generally used to enable formulation of industrial, pharmaceutical and cosmetic emulsions, for example. For many important surfactants, including several polyethoxylated surfactants, it has been reported that HLB values can differ by as much as about 8 HLB units, depending upon the empirical method chosen to determine the HLB value (Schott, J. Pharm. Sciences, 79(1), 87-88 (1990)). Keeping these inherent difficulties in mind, and using HLB values as a guide, surfactants can be identified that have suitable hydrophilicity or hydrophobicity for use in embodiments of the present invention, as described herein.

PEG-Fatty Acids and PEG-Fatty Acid Mono and Diesters.

Although polyethylene glycol (PEG) itself does not function as a surfactant, a variety of PEG-fatty acid esters have useful surfactant properties. Among the PEG-fatty acid monoesters, esters of lauric acid, oleic acid, and stearic acid are most useful in embodiments of the present invention. Examples of hydrophilic surfactants include PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate and PEG-20 oleate. The HLB values are in the range of 4-20.

Polyethylene glycol fatty acid diesters are also suitable for use as surfactants in the compositions of embodiments of the present invention. Hydrophilic surfactants include PEG-20 dilaurate, PEG-20 dioleate, PEG-20 distearate, PEG-32 dilaurate and PEG-32 dioleate. The HLB values are in the range of 5-15.

In general, mixtures of surfactants are also useful in embodiments of the present invention, including mixtures of two or more commercial surfactants as well as mixtures of surfactants with another additive or additives. Several PEG-fatty acid esters are marketed commercially as mixtures or mono- and di-esters.

Polyethylene Glycol Glycerol Fatty Acid Esters.

Hydrophilic surfactants can include PEG-20 glyceryl laurate, PEG-30 glyceryl laurate, PEG-40 glyceryl laurate, PEG-20 glyceryl oleate, and PEG-30 glyceryl oleate.

Alcohol-Oil Transesterification Products.

Many surfactants of different degrees of hydrophobicity or hydrophilicity can be prepared by reaction of alcohols or polyalcohol with a variety of natural and/or hydrogenated oils. Most commonly, the oils used are castor oil or hydrogenated castor oil, or an edible vegetable oil such as corn oil, olive oil, peanut oil, palm kernel oil, apricot kernel oil, or almond oil. Alcohols include glycerol, propylene glycol, ethylene glycol, polyethylene glycol, sorbitol, and pentaerythritol. Among these alcohol-oil transesterified surfactants, hydrophilic surfactants are PEG-35 castor oil (Incrocas-35), PEG-40 hydrogenated castor oil (Cremophor RH 40), PEG-25 trioleate (TAGAT$^{T}$M TO), PEG-60 corn glycerides (Crovol M70), PEG-60 almond oil (Crovol A70), PEG-40 palm kernel oil (Crovol PK70), PEG-50 castor oil (Emalex C-50), PEG-50 hydrogenated castor oil (Emalex HC-50), PEG-8 caprylic/capric glycerides (Labrasol), and PEG-6 caprylic/capric glycerides (Softigen 767). For example, hydrophobic surfactants in this class include PEG-5 hydrogenated castor oil, PEG-7 hydrogenated castor oil, PEG-9 hydrogenated castor oil, PEG-6 corn oil (Labrafil™ M 2125 CS), PEG-6 almond oil (Labrafil™ M 1966 CS), PEG-6 apricot kernel oil (Labrafil™ M 1944 CS), PEG-6 olive oil (Labrafil™ M 1980 CS), PEG-6 peanut oil (Labrafil$^{M}$ M 1969 CS), PEG-6 hydrogenated palm kernel oil (Labrafil™ M 2130 BS), PEG-6 palm kernel oil (Labrafil$^{M}$ M 2130 CS), PEG-6 triolein (Labrafil™ b M 2735 CS), PEG-8 corn oil (Labrafil™ WL 2609 BS), PEG-20 corn glycerides (Crovol M40), and PEG-20 almond glycerides (Crovol A40).

Polyglyceryl Fatty Acids.

Polyglycerol esters of fatty acids are also suitable surfactants for use in embodiments of the present invention. Among the polyglyceryl fatty acid esters, hydrophobic surfactants include polyglyceryl oleate (Plurol Oleique), polyglyceryl-2 dioleate (Nikkol DGDO), polyglyceryl-10 trioleate, polyglyceryl stearate, polyglyceryl laurate, polyglyceryl myristate, polyglyceryl palmitate, and polyglyceryl linoleate. Hydrophilic surfactants include polyglyceryl-10 laurate (Nikkol Decaglyn 1-L), polyglyceryl-10 oleate (Nikkol Decaglyn 1-0), and polyglyceryl-10 mono, dioleate (Caprol™ PEG 860), polyglyceryl-10 stearate, polyglyceryl-10 laurate, polyglyceryl-10 myristate, polyglyceryl-10 palmitate, polyglyceryl-10 linoleate, polyglyceryl-6 stearate, polyglyceryl-6 laurate, polyglyceryl-6 myristate, polyglyceryl-6 palmitate, and polyglyceryl-6 linoleate. Polyglyceryl polyricinoleates (Polymuls) are also surfactants.

Propylene Glycol Fatty Acid Esters.

Esters of propylene glycol and fatty acids are suitable surfactants for use in embodiments of the present invention. In this surfactant class, hydrophobic surfactants include propylene glycol monolaurate (Lauroglycol FCC), propylene glycol ricinoleate (Propymuls), propylene glycol monooleate (Myverol P-06), propylene glycol dicaprylate/dicaprate (Captex™ 200), and propylene glycol dioctanoate (Captex™ 800).

Sterol and Sterol Derivatives.

Sterols and derivatives of sterols are suitable surfactants for use in embodiments of the present invention. Derivatives include the polyethylene glycol derivatives. A surfactant in this class is PEG-24 cholesterol ether (Solulan C-24).

Polyethylene Glycol Sorbitan Fatty Acid Esters.

A variety of PEG-sorbitan fatty acid esters are available and are suitable for use as surfactants in embodiments of the present invention. Among the PEG-sorbitan fatty acid esters, surfactants include PEG-20 sorbitan monolaurate (Tween-20), PEG-20 sorbitan monopalmitate (Tween-40), PEG-20 sorbitan monostearate (Tween-60). PEG-20 sorbitan monooleate (Tween-80). In some embodiments, laurate esters are utilized because they have a short lipid chain compared with oleate esters, increasing drug absorption.

Sugar and its Derivatives.

Sugar derivatives are suitable surfactants for use in embodiments of the present invention. Surfactants in this class include sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-nonyl-β-D-glucopyranoside, octanoyl-N-methylglucamide, n-octyl-β-D-glucopyranoside, and octyl-β-D-thioglucopyranoside.

Polyethylene Glycol Alkyl Phenols.

Several PEG-alkyl phenol surfactants are available, such as PEG-10-100 nonyl phenol and PEG-15-100 octyl phenol ether, Tyloxapol, octoxynol, octoxynol-9, nonoxynol, and are suitable for use in embodiments of the present invention.

Polyoxyethylene-Polyoxypropylene (POE-POP) Block Copolymers.

The POE-POP block copolymers are a unique class of polymeric surfactants. The unique structure of the surfactants, with hydrophilic POE and hydrophobic POP moieties in well-defined ratios and positions, provides a wide variety of surfactants suitable for use in embodiments of the present invention. These surfactants are available under various trade names, including Synperonic PE series (ICI); Pluronic™ series (BASF), Emkalyx, Lutrol (BASF), Supronic, Monolan, Pluracare, and Plurodac. The generic term for these polymers is "poloxamer" (CAS 9003-11-6). These polymers have the formula: $HO(C_2H_4O)_a(C_3H_6O)_b(C_2H_4O)_aH$ where "a" and "b" denote the number of polyoxyethylene and polyoxypropylene units, respectively.

Hydrophilic surfactants of this class include Poloxamers 108, 188, 217, 238, 288, 338, and 407. Hydrophobic surfactants in this class include Poloxamers 124, 182, 183, 212, 331, and 335.

Sorbitan Fatty Acid Esters.

Sorbitan esters of fatty acids are suitable surfactants for use in embodiments of the present invention. Among these esters, hydrophobic surfactants include sorbitan monolaurate (Arlacel 20), sorbitan monopalmitate (Span-40), and sorbitan monooleate (Span-80), sorbitan monostearate.

The sorbitan monopalmitate, an amphiphilic derivative of Vitamin C (which has Vitamin C activity), can serve two important functions in solubilization systems. First, it possesses effective polar groups that can modulate the microenvironment. These polar groups are the same groups that make vitamin C itself (ascorbic acid) one of the most water-soluble organic solid compounds available: ascorbic acid is soluble to about 30 wt/wt % in water (very close to the solubility of sodium chloride, for example). Second, when the pH increases so as to convert a fraction of the ascorbyl palmitate to a more soluble salt, such as sodium ascorbyl palmitate.

Ionic Surfactants.

Ionic surfactants, including cationic, anionic and zwitterionic surfactants, are suitable hydrophilic surfactants for use in embodiments of the present invention. Ionic surfactants include quaternary ammonium salts, fatty acid salts and bile salts. Specifically, ionic surfactants include benzalkonium chloride, benzethonium chloride, cetylpyridinium chloride, docecyl trimethyl ammonium bromide, cetyl trimethyl ammonium chloride, trimethyl-tetradecylammonium chloride, trimethyloctylammonium chloride, lauryl triethyl ammonium chloride, DOTAP—1,2-dioleoyl-3-trimethylammonium-propane (chloride salt or methyl sulfate salt), DOTMA—1,2-di-O-octadecenyl-3-trimethylammonium propane (chloride salt), DC-Cholesterol—3β-[N—(N',N'-dimethylaminoethane)-carbamoyl]cholesterol hydrochloride, DODMA—1,2-dioleyloxy-3-dimethylaminopropane, GL67—N4-Cholesteryl-Spermine HCl Salt, DDAB—Dimethyldioctadecylammonium (Bromide Salt), MVL5—N1-[2-((1S)-1-[(3-aminopropyl)amino]-4-[di(3-amino-propyl)amino]butylcarboxamido)ethyl]-3,4-di[oleyloxy]-benzamide, EPC—1,2-dioleoyl-sn-glycero-3-ethylphosphocholine (chloride salt), sodium docecylsulfates, dialkyl methylbenzyl ammonium chloride, edrophonium chloride, domiphen bromide, dialkylester of sodium sulfonsuccinic acid, sodium dioctyl sulfosuccinate, sodium cholate, and sodium taurocholate. They can be dissolved in both organic solvents (such as ethanol, acetone, and toluene) and water. This is especially useful for medical device coatings because it simplifies the preparation and coating process and has good adhesive properties. Water-insoluble drugs are commonly dissolved in organic solvents.

Some of the surfactants described herein are very stable under heating. They survive an ethylene oxide sterilization process. They do not react with drugs such as paclitaxel or rapamycin under the sterilization process. The hydroxyl, ester, amide groups are utilized because they are unlikely to react with drug, while amine and acid groups often do react with paclitaxel or rapamycin during sterilization. Furthermore, surfactant additives improve the integrity and quality of the coating layer, so that particles do not fall off during handling. When the surfactants described herein are formulated with paclitaxel, experimentally it can protect the drug from premature release during the device delivery process while facilitating rapid release and elution of paclitaxel during a very brief deployment time of 0.2 to 10 minutes at the target site. Drug absorption by tissues at the target site can be experimentally determined to be high.

Chemical Compounds with One or More Hydroxyl, Amino, Carbonyl, Carboxyl, Acid, Amide, or Ester Moieties.

The chemical compounds with one or more hydroxyl, amino, carbonyl, carboxyl, acid, amide, or ester moieties include creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl) urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, N-acetylglucosamine, N-octyl-D-gluconamide, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-Lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate (e.g., Labrasol®), PEG caprate, PEG caproate, glyceryl monocaprylate, glyceryl monocaprate, glyceryl monocaproate, monolaurin, monocaprin, monocaprylin, monomyristin, monopalmitolein, and monoolein.

The chemical compounds with one or more hydroxyl, amino, carbonyl, carboxyl, acid, amide, or ester moieties include amino alcohols, hydroxyl carboxylic acid, ester, anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohols and organic acids, and their substituted molecules. Hydrophilic chemical compounds with one or more hydroxyl, amino, carbonyl, carboxyl, acid, amide, or ester moieties having a molecular weight less than 5,000-10,000 are utilized in certain embodiments. In other embodiments, molecular weight of the additive with one or more hydroxyl, amino, carbonyl, carboxyl, acid, amide, or ester moieties is less than 1000-5,000, or less than 750-1,000, or less than 750. In these embodiments, the molecular weight of the additive is to be less than that of the drug to be delivered. Further, the molecular weight of the additive is to be higher than 80 since molecules with molecular weight less than 80 very easily evaporate and do not stay in the coating of a medical device. Small molecules can diffuse quickly. They can release themselves easily from the delivery balloon, accelerating release of drug, and they can diffuse away from drug when the drug binds tissue of the body lumens.

In certain embodiments, additives with more than four hydroxyl groups are utilized, for example in the case of a high molecular weight additive. Large molecules diffuse slowly. If the molecular weight of the additive or the chemical compound is high, for example if the molecular weight is above 800, above 1000, above 1200, above 1500, or above 2000; large molecules can elute off the surface of the medical device too slowly to release drug under 2 minutes. If these large molecules contain more than four hydroxyl groups they have increased hydrophilic properties, which is necessary for relatively large molecules to release drug quickly. The increased hydrophilicity can help to elute the coating off the balloon, accelerate release of drug, and improve and/or facilitate drug movement through water barrier and polar head groups of lipid bilayers to penetrate tissues. In one embodiment, the hydroxyl group is utilized as the hydrophilic moiety because it is unlikely to react with water-insoluble drug, such as paclitaxel or rapamycin. In some embodiments, the chemical compound having more than four hydroxyl groups has a melting point of 120° C. or less. In some embodiments, the chemical compound having more than four hydroxyl groups has three adjacent hydroxyl groups that in stereo configuration are all on one side of the molecule. For example, sorbitol and xylitol have three adjacent hydroxyl groups that in stereo configuration are all on one side of the molecule, while galactitol does not. The difference impacts the physical properties of the isomers such as the melting temperature. The stereo configuration of the three adjacent hydroxyl groups can enhance drug binding. This will lead to improved compatibility of the water-insoluble drug and hydrophilic additive, and improved tissue uptake and absorption of drug.

Some of the chemical compounds with one or more hydroxyl, amine, carbonyl, carboxyl, or ester moieties described herein are very stable under heating. They survive an ethylene oxide sterilization process and do not react with the water-insoluble drug such as paclitaxel or rapamycin during sterilization. L-ascorbic acid and its salt and diethanolamine, on the other hand, do not necessarily survive such a sterilization process, and they react with paclitaxel. A different sterilization method is therefore utilized for L-ascorbic acid and diethanolamine. For example, hydroxyl, ester, and amide groups are utilized because they are unlikely to react with therapeutic agents such as paclitaxel or rapamycin. Sometimes, amine and acid groups do react with paclitaxel, for example, experimentally, benzoic acid, gentisic acid, diethanolamine, and ascorbic acid were not stable under ethylene oxide sterilization, heating, and aging process and reacted with paclitaxel. When the chemical compounds described herein are formulated with paclitaxel, a top coat layer can be advantageous to prevent premature drug loss during the device delivery process before deployment at the target site, since hydrophilic small molecules sometimes release drug too easily. The chemical compounds herein can rapidly elute drug off the balloon during deployment at the target site. Surprisingly, even though some drug can be lost during transit of the device to the target site when the coating contains these additives, experimentally drug absorption by tissue is high after only 0.2-10 minutes of deployment, for example, with the additive hydroxyl lactones such as ribonic acid lactone and gluconolactone.

Fat-Soluble Vitamins and Salts Thereof.

Vitamins A, D, E and K in many of their various forms and provitamin forms are considered as fat-soluble vitamins and in addition to these several other vitamins and vitamin sources or close relatives are also fat-soluble and have polar groups, and relatively high octanol-water partition coefficients. Clearly, the general class of such compounds has a history of safe use and high benefit to risk ratio, making them useful as additives in embodiments of the present invention.

The following examples of fat-soluble vitamin derivatives and/or sources are also useful as additives: alpha-tocopherol, beta-tocopherol, gamma-tocopherol, delta-tocopherol, tocopherol acetate, ergosterol, 1-alpha-hydroxycholecal-ciferol, vitamin D2, vitamin D3, alpha-carotene, beta-carotene, gamma-carotene, vitamin A, fursultiamine, methylolriboflavin, octotiamine, prosultiamine, riboflavine, vintiamol, dihydrovitamin K1, menadiol diacetate, menadiol dibutyrate, menadiol disulfate, menadiol, vitamin K1, vitamin K1 oxide, vitamins K2, and vitamin K—S(II). Folic acid is also of this type, and although it is water-soluble at physiological pH, it can be formulated in the free acid form. Other derivatives of fat-soluble vitamins useful in embodiments of the present invention can easily be obtained via well-known chemical reactions with hydrophilic molecules.

Water-Soluble Vitamins and their Amphiphilic Derivatives.

Vitamins B, C, U, pantothenic acid, folic acid, and some of the menadione-related vitamins/provitamins in many of their various forms are considered water-soluble vitamins. These can also be conjugated or complexed with hydrophobic moieties or multivalent ions into amphiphilic forms having relatively high octanol-water partition coefficients and polar groups. Again, such compounds can be of low toxicity and high benefit to risk ratio, making them useful as additives in embodiments of the present invention. Salts of these can also be useful as additives in the present invention. Examples of water-soluble vitamins and derivatives include, without limitation, acetiamine, benfotiamine, pantothenic acid, cetotiamine, cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U. Also, as mentioned above, folic acid is, over a wide pH range including physiological pH, water-soluble, as a salt.

Compounds in which an amino or other basic group is present can easily be modified by simple acid-base reaction with a hydrophobic group-containing acid such as a fatty acid (especially lauric, oleic, myristic, palmitic, stearic, or 2-ethylhexanoic acid), low-solubility amino acid, benzoic acid, salicylic acid, or an acidic fat-soluble vitamin (such as riboflavin). Other compounds might be obtained by reacting such an acid with another group on the vitamin such as a hydroxyl group to form a linkage such as an ester linkage, etc. Derivatives of a water-soluble vitamin containing an acidic group can be generated in reactions with a hydrophobic group-containing reactant such as stearylamine or riboflavine, for example, to create a compound that is useful in embodiments of the present invention. The linkage of a palmitate chain to vitamin C yields ascorbyl palmitate.

Amino Acids and their Salts.

Alanine, arginine, asparagines, aspartic acid, cysteine, cystine, glutamic acid, glutamine, glycine, histidine, proline, isoleucine, leucine, lysine, methionine, phenylalanine, serine, threonine, tryptophan, tyrosine, valine, and derivatives thereof are other useful additives in embodiments of the invention.

Certain amino acids, in their zwitterionic form and/or in a salt form with a monovalent or multivalent ion, have polar groups, relatively high octanol-water partition coefficients, and are useful in embodiments of the present invention. In the context of the present disclosure we take "low-solubility amino acid" to mean an amino acid which has solubility in unbuffered water of less than about 4% (40 mg/mL). These include cystine, tyrosine, tryptophan, leucine, isoleucine, phenylalanine, asparagine, aspartic acid, glutamic acid, and methionine.

Amino acid dimers, sugar-conjugates, and other derivatives are also useful. Through simple reactions well-known in the art hydrophilic molecules can be joined to hydrophobic amino acids, or hydrophobic molecules to hydrophilic amino acids, to make additional additives useful in embodiments of the present invention.

Catecholamines, such as dopamine, levodopa, carbidopa, and DOPA, are also useful as additives.

Oligopeptides, Peptides and Proteins.

Oligopeptides and peptides are useful as additives, since hydrophobic and hydrophilic amino acids can be easily coupled and various sequences of amino acids can be tested to maximally facilitate permeation of tissue by drug.

Proteins are also useful as additives in various embodiments of the present invention. Serum albumin, for example, is a useful additive since it is water-soluble and contains significant hydrophobic parts to bind drug: paclitaxel is 89% to 98% protein-bound after human intravenous infusion, and rapamycin is 92% protein bound, primarily (97%) to albumin. Furthermore, paclitaxel solubility in PBS increases over 20-fold with the addition of BSA. Albumin is naturally present at high concentrations in serum and is thus very safe for human use.

Other useful proteins include, without limitation, other albumins, immunoglobulins, caseins, hemoglobins, lysozymes, immunoglobins, a-2-macroglobulin, fibronectins, vitronectins, firbinogens, lipases, and the like.

Organic Acids and their Esters and Anhydrides.

Examples include acetic acid and anhydride, benzoic acid and anhydride, diethylenetriaminepentaacetic acid dianhydride, ethylenediaminetetraacetic dianhydride, maleic acid and anhydride, succinic acid and anhydride, diglycolic anhydride, glutaric anhydride, ascorbic acid, citric acid, tartaric acid, lactic acid, oxalic acid aspartic acid, nicotinic acid, 2-pyrrolidone-5-carboxylic acid, and 2-pyrrolidone.

These esters and anhydrides are soluble in organic solvents such as ethanol, acetone, methylethylketone, ethylacetate. The water-insoluble drugs can be dissolved in organic solvent with these esters and anhydrides, then coated easily on to the medical device, then hydrolyzed under high pH conditions. The hydrolyzed anhydrides or esters are acids or alcohols, which are water-soluble and can effectively carry the drugs off the device into the walls of the body lumen.

Antimicrobials.

The antimicrobial properties of various fatty acids, alkyl glyceryl ethers and monoglycerides of C8-C12 fatty acids have been investigated for many years. The studies have confirmed that fatty acids, alkyl glyceryl ethers and monoglycerides can inhibit the growth of numerous types of bacteria and viruses. The coating formulation of the present invention can include various fatty acids, alkyl glyceryl ethers and monoglycerides of C8-C12 fatty acids, such as caprylic acid, monocaprilin, capric acid, monocaprin, lauric acid, dodecyl glycerol and monolaurin, as one of the additives for the treatment of various nonvascular and vascular strictures.

Other Chemical Compounds with One or More Hydroxyl, Amine, Carbonyl, Carboxyl, or Ester Moieties.

The additives according to various embodiments can include amino alcohols, alcohols, amines, acids, amides, and hydroxyl acids in both cyclo and linear aliphatic and aromatic groups. Examples are L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sorbitol, glucitol, sugar phosphates, glucopyranose phosphate, sugar sulphates, sinapic acid, vanillic acid, vanillic acid diethylamide, vanillin, methyl paraben, propyl paraben, xylitol, 2-ethoxyethanol, sugars, galactose, glucose, ribose, mannose, xylose, sucrose, lactose, maltose, arabinose, lyxose, fructose, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and amine described herein, polyglycidol, glycerol, multiglycerols (e.g., chemical compounds with multiple hydroxyl, amino, carbonyl, carboxyl, or ester moieties), galactitol, di(ethylene glycol), tri(ethylene glycol), tetra(ethylene glycol), penta(ethylene glycol), poly(ethylene glycol) oligomers, di(propylene glycol), tri (propylene glycol), tetra(propylene glycol, and penta(propylene glycol), poly(propylene glycol) oligomers, a block copolymer of polyethylene glycol and polypropylene glycol, and derivatives and combinations thereof.

Combinations of additives can also be useful for purposes of the present invention. One embodiment includes the combination or mixture of two additives, for example, a first additive including a surfactant and a second additive including a chemical compound with one or more hydroxyl, amine, carbonyl, carboxyl, or ester moieties.

The combination or mixture of the surfactant and the small water-soluble molecule (the chemical compounds with one or more hydroxyl, amine, carbonyl, carboxyl, or ester moieties) can have advantages. Formulations including mixtures of the two additives with water-insoluble drug are in certain cases superior to mixtures including either additive alone. The hydrophobic drugs bind extremely water-soluble small molecules more poorly than they do surfactants. They are often phase separated from the small water-soluble molecules, which can lead to suboptimal coating uniformity and integrity. The water-insoluble drug has Log P higher than both that of the surfactant and that of small water-soluble molecules. However, Log P of the surfactant is typically higher than Log P of the chemical compounds with one or more hydroxyl, amine, carbonyl, carboxyl, or ester moieties. The surfactant has a relatively high Log P (usually above 0) and the water-soluble molecules have low Log P (e.g., below 0). Some surfactants, when used as additives in embodiments of the present invention, adhere so strongly to the water-insoluble drug and the surface of the medical device that drug is not able to rapidly release from the surface of the medical device at the target site. On the other hand, some of the water-soluble small molecules (with one or more hydroxyl, amine, carbonyl, carboxyl, or ester moieties) adhere so poorly to the medical device that they release drug before it reaches the target site, for example, into serum during the transit of a coated balloon catheter to the site targeted for intervention. Surprisingly, by adjusting the ratio of the concentrations of the small hydrophilic molecule and the surfactant in the formulation, the inventor has found that the coating stability during transit and rapid drug release when inflated and pressed against tissues of the lumen wall at the target site of therapeutic intervention in certain cases is superior to a formulation including either additive alone. Furthermore, the presence of the surfactant improves the miscibility and compatibility of the water-insoluble drug and the highly water-soluble molecules. The surfactant also improves coating uniformity and integrity by its good adhesion to the drug and the small molecules. The long chain hydrophobic part of the surfactant binds the drug tightly while the hydrophilic part of the surfactant binds the water-soluble small molecules.

The surfactants in the mixture or the combination include all of the surfactants described herein for use in embodiments of the invention. The surfactant in the mixture can be chosen from PEG sorbitan fatty esters; PEG omega-3 fatty esters, ethers, and alcohols; glycerol fatty esters, sorbitan fatty esters, PEG glyceryl fatty esters, PEG fatty esters and alcohols, sugar fatty esters, PEG sugar esters, Tween 20, Tween 40, Tween 60, p-isononylphenoxypolyglycidol, PEG laurate, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate, PEG sorbitan monolaurate, PEG sorbitan monolaurate, PEG sorbitan monooleate, PEG sorbitan stearate, PEG oleyl ether, PEG laurayl ether, Tween 20, Tween 40, Tween 60, Tween 80, octoxynol, octoxynol-9, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-nonyl-β-D-glucopyranoside, octanoyl-N-methylglucamide, n-octyl-β-D-glucopyranoside, octyl-β-D-thioglucopyranoside and their derivatives.

Embodiments of the chemical compound with one or more hydroxyl, amine, carbonyl, carboxyl, or ester moieties in the mixture or the combination can include any of the chemical compounds with one or more hydroxyl, amine, carbonyl, carboxyl, or ester moieties described herein for use in embodiments of the invention. In various embodiments, the chemical compound with one or more hydroxyl, amine, carbonyl, carboxyl, or ester moieties in the mixture has at least one hydroxyl group, such as four hydroxyl groups. In certain embodiments, additives with more than four hydroxyl groups are utilized, for example in the case of a high molecular weight additive. In some embodiments, the chemical compound having more than four hydroxyl groups has a melting point of 120° C. or less. Large molecules diffuse slowly. If the molecular weight of the additive or the chemical compound is high, for example if the molecular weight is above 800, above 1000, above 1200, above 1500, or above 2000; large molecules can elute off the surface of the medical device too slowly to release drug under 2 minutes. If these large molecules contain more than four hydroxyl groups they have increased hydrophilic properties, which is necessary for relatively large molecules to release drug quickly. The increased hydrophilicity helps elute the coating off the balloon, accelerates release of drug, and improves or facilitates drug movement through water barrier and polar head groups of lipid bilayers to penetrate tissues. In one embodiment, the hydroxyl group is utilized as the hydrophilic moiety because it is unlikely to react with water-insoluble drug, such as paclitaxel or rapamycin.

The chemical compound with one or more hydroxyl, amine, carbonyl, carboxyl, or ester moieties in the mixture is chosen from L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sorbitol, glucitol, sugar phosphates, glucopyranose phosphate, sugar sulphates, sinapic acid, vanillic acid, vanillin, methyl paraben, propyl paraben, xylitol, 2-ethoxyethanol, sugars, galactose, glucose, ribose, mannose, xylose, sucrose, lactose, maltose, arabinose, lyxose, fructose, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and amine described herein, polyglycidol, glycerol, multiglycerols, galactitol, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, di(ethylene glycol), tri(ethylene glycol), tetra(ethylene glycol), penta(ethylene glycol), poly (ethylene glycol) oligomers, di(propylene glycol), tri(propylene glycol), tetra(propylene glycol, and penta(propylene glycol), poly(propylene glycol) oligomers, a block copolymer of polyethylene glycol and polypropylene glycol, and derivatives and combinations thereof.

Mixtures or combinations of a surfactant and a water-soluble small molecule can confer the advantages of both additives or operate synergistically. The water-insoluble drug often has a poor compatibility with highly water-soluble chemical compounds, and the surfactant improves compatibility. The surfactant also improves the coating quality, uniformity, and integrity, and particles do not fall off the balloon during handling. The surfactant reduces drug loss during transit to a target site. The water-soluble chemical compound improves the release of drug off the balloon and absorption of the drug in the tissue. Experimentally, the combination was surprisingly effective at preventing drug release during transit and achieving high drug levels in tissue after very brief 0.2 to 2 minute deployment. Furthermore, in animal studies it effectively reduced stenosis and late lumen loss.

Some of the mixtures or combinations of surfactants and water-soluble small molecules are very stable under heating. They survived an ethylene oxide sterilization process and do not react with the water-insoluble drugs, paclitaxel or rapamycin, during sterilization. In one embodiment, the hydroxyl, ester, amide groups are utilized because they are unlikely to react with therapeutic agents such as paclitaxel or rapamycin. Sometimes amine and acid groups do react with paclitaxel and are not stable under ethylene oxide sterilization, heating, and aging. When the mixtures or combinations described herein are formulated with paclitaxel, a top coat layer can be advantageous in order to protect the drug layer and from premature drug loss during the device.

Examples of additives include p-isononylphenoxypolyglycidol, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate, PEG sorbitan monolaurate, PEG sorbitan monolaurate, PEG sorbitan monooleate, PEG sorbitan stearate, octoxynol, octoxynol-9, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-nonyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine (amino acids), cetotiamine, cyclothiamine, dexpanthenol, niacinamide, nicotinic acid and its salt, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U (vitamins); albumin, immunoglobulins, caseins, hemoglobins, lysozymes, immunoglobins, a-2-macroglobulin, fibronectins, vitronectins, firbinogens, lipases, benzalkonium chloride, benzethonium chloride, dodecyl trimethyl ammonium bromide, sodium docecylsulfates, dialkyl methylbenzyl ammonium chloride, and dialkylesters of sodium sulfonsuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, xylitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerol, multiglycerols, galactitol, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl) urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, di(ethylene glycol), tri(ethylene glycol), tetra(ethylene glycol), penta(ethylene glycol), poly (ethylene glycol) oligomers, di(propylene glycol), tri(propylene glycol), tetra(propylene glycol, and penta(propylene glycol), poly(propylene glycol) oligomers, a block copolymer of polyethylene glycol and polypropylene glycol, and derivatives and combinations thereof (chemical compounds with one or more hydroxyl, amino, carbonyl, carboxyl, or ester moieties). Some of these additives are both water-soluble and organic solvent-soluble. They have good adhesive properties and adhere to the surface of polyamide medical devices, such as balloon catheters. They can therefore be used in the adherent layer, top layer, and/or in the drug layer of embodiments of the present invention. The aromatic and aliphatic groups increase the solubility of water-insoluble drugs in the coating solution, and the polar groups of alcohols and acids accelerate drug permeation of tissue.

Other additives according to embodiments of the invention include hydroxyl ketone, hydroxyl lactone, hydroxyl acid, hydroxyl ester, and hydroxyl amide. Examples are gluconolactone, D-glucoheptono-1,4-lactone, glucooctanoic lactone, gulonic acid lactone, mannoic lactone, erythronic acid lactone, ribonic acid lactone, glucuronic acid, gluconic acid, gentisic acid, lactobionic acid, lactic acid, acetaminophen, vanillic acid, sinapic acid, hydroxybenzoic acid, methyl paraben, propyl paraben, and derivatives thereof.

From a structural point of view, these additives share structural similarities and are compatible with water-insoluble drugs (such as paclitaxel and rapamycin). They often contain double bonds such as C═C, C═N, C═O in aromatic or aliphatic structures. These additives also contain amine, alcohol, ester, amide, anhydride, carboxylic acid, and/or hydroxyl groups. They can form hydrogen bonds and/or van der Waals interactions with drug. They are also useful in the top layer in the coating. Compounds containing one or more hydroxyl, carboxyl, or amine groups, for example, are especially useful as additives since they facilitate drug release from the device surface and easily displace water next to the polar head groups and surface proteins of cell membranes and can thereby remove this barrier to hydrophobic drug permeability. They accelerate movement of a hydrophobic drug off the balloon to the lipid layer of cell membranes and tissues for which it has very high affinity. They can also carry or accelerate the movement of drug off the balloon into more aqueous environments such as the interstitial space, for example, of nonvascular tissues that have been injured by balloon angioplasty or stent expansion. Additives such as polyglyceryl fatty esters, ascorbic ester of fatty acids, sugar esters, alcohols and ethers of fatty acids have fatty chains that can integrate into the lipid structure of target tissue membranes, carrying drug to lipid structures. Some of the amino acids, vitamins and organic acids have aromatic C═N groups as well as amino, hydroxyl, and carboxylic components to their structure. They have structural parts that can bind or complex with hydrophobic drug, such as paclitaxel or rapamycin, and they also have structural parts that facilitate tissue penetration by removing barriers between hydrophobic drug and lipid structure of cell membranes.

For example, isononylphenylpolyglycidol (Olin-10 G and Surfactant-10G), PEG glyceryl monooleate, sorbitan monolaurate (Arlacel 20), sorbitan monopalmitate (Span-40), sorbitan monooleate (Span-80), sorbitan monostearate, polyglyceryl-10 oleate, polyglyceryl-10 laurate, polyglyceryl-10 palmitate, and polyglyceryl-10 stearate all have more than four hydroxyl groups in their hydrophilic part. These hydroxyl groups have very good affinity for walls of the body lumen and can displace hydrogen-bound water molecules. At the same time, they have long chains of fatty acid, alcohol, ether, and ester that can both complex with hydrophobic drug and integrate into the lipid structure of the cell membranes to form the part of the lipid structure. This deformation or loosening of the lipid membrane of target cells can further accelerate permeation of hydrophobic drug into tissue.

In another example, L-ascorbic acid, thiamine, maleic acids, niacinamide, and 2-pyrrolidone-5-carboxylic acid all have a very high water and ethanol solubility and a low molecular weight and small size. They also have structural components including aromatic C═N, amino, hydroxyl, and carboxylic groups. These structures have very good compatibility with paclitaxel and rapamycin and can increase the solubility of these water-insoluble drugs in water and enhance their absorption into tissues. However, they often have poor adhesion to the surface of medical devices. They are therefore used in combination with other additives in the drug layer and top layer where they are useful to enhance drug absorption. Vitamin D2 and D3 are especially useful because they themselves have anti-restenotic effects and reduce thrombosis, especially when used in combination with paclitaxel.

The relative amount of the therapeutic agent and the additive in the coating layer, can vary depending on applicable circumstances. The optimal amount of the additive can depend upon, for example, the particular therapeutic agent and additive selected, the critical micelle concentration of the surface modifier if it forms micelles, the hydrophilic-lipophilic-balance (HLB) of a surfactant or an additive's octonol-water partition coefficient (P), the melting point of the additive, the water solubility of the additive and/or therapeutic agent, the surface tension of water solutions of the surface modifier, and the like.

Other considerations will further inform the choice of specific proportions of different additives. These considerations can include the degree of bioacceptability of the additives and/or the desired dosage of therapeutic agent to be provided.

In one embodiment, the present invention relates to a balloon catheter for delivering a therapeutic agent to a target site of a body lumen stricture, the balloon catheter including a coating layer overlying an exterior surface of a balloon. The coating layer can include the polymer-encapsulated drug particles that include the therapeutic agent and the one or more polymers that encapsulate the therapeutic agent; or the drug-releasing coating including the polymer-encapsulated drug particles; or a composition including a therapeutic agent and one or more additives; or a combination thereof. The therapeutic agent can be chosen from paclitaxel, docetaxel, taxol, an mTOR inhibitor, rapamycin, sirolimus, zotarolimus, everolimus, tacrolimus, umirolimus, an analogue thereof, and combinations thereof. The additive can be a non-water-soluble additive chosen from cholesteryl acetate, cholesteryl phenylacetate, cholesteryl laurate, cholesteryl palmitate, cholesteryl stearate, cholesteryl n-valerate, cholesteryl benzoate, cholesteryl heptylate, cholesteryl decylate, cholesteryl caproate, cholesteryl oleate, cholesteryl oleyl carbonate, cholesteryl linoleate, cholesteryl pelargonate, cholesteryl erucate, cholesteryl caprylate, 5α-cholestane, 5α-cholestan-3-one, and combinations thereof.

In one embodiment, the present invention relates to a balloon catheter for delivering a therapeutic agent to a target site of a body lumen stricture or stenosis, the balloon includes a polyester, a polyamide, a nylon 12, a nylon 11, a polyamide 12, a block copolymer of a polyether and a polyamide, a polyether block amide, a polyurethane, a block copolymer of a polyether and a polyester, or a combination thereof. The balloon catheter includes a coating layer overlying an exterior surface of a balloon. The coating layer includes the polymer-encapsulated drug particles that include the therapeutic agent and the one or more polymers that encapsulate the therapeutic agent; or the drug-releasing coating including the polymer-encapsulated drug particles; or a composition including a therapeutic agent and one or more additives; or a combination thereof. The therapeutic agent can be chosen from paclitaxel, docetaxel, taxol, an mTOR inhibitor, rapamycin, sirolimus, zotarolimus, everolimus, tacrolimus, umirolimus, an analogue thereof, and combinations thereof. The additive can be a water-insoluble or slightly or partial water-insoluble first additive that includes at least one alkyl fatty group or cholesteryl group with the first additive having a molecular weight of 50 to 750, a water-soluble second additive that is more hydrophilic or more water-soluble than the first additive and that includes —($CH_2CH_2O$)— unit with a molecular weight of 750 to 100,000, preferable 1000 to 50,000, most preferable 2000 to 10,000. The water-insoluble or slightly or partial water-insoluble first additive with cholesteryl group can be chosen from cholesteryl acetate, cholesteryl phenylacetate, cholesteryl laurate, cholesteryl palmitate, cholesteryl stearate, cholesteryl n-valerate, cholesteryl benzoate, cholesteryl heptylate, cholesteryl decylate, cholesteryl caproate, cholesteryl oleate, cholesteryl oleyl carbonate, cholesteryl linoleate, cholesteryl pelargonate, cholesteryl erucate, cholesteryl caprylate, 5α-cholestane, 5α-cholestan-3-one, and combinations thereof. The water-insoluble or slightly or partial water-insoluble first additive with alkyl fatty group (e.g., C4-C30, such as equal to or greater than C1, 2, 3, 4, 5, 6, 7, 8, 9, 10, 11, 12, 13, 14, 15, 16, 17, 18, 19, 20, 21, 22, 23, 24, 25, 26, 27, 28, 29, or C30) can be chosen from alkyl glyceryl ethers, monoglycerides of C8-C12 fatty acids, alkyl alcohol, alkyl ether, alkyl ester, caprylic acid, monocaprilin, capric acid, monocaprin, lauric acid, dodecyl glycerol, butanoic acid, hexanoic acid, octanoic acid, decanoic acid, dodecanoic acid, tetradecanoic acid, hexadecanoic acid, octadecanoic acid, octadecatrienoic acid, eicosanoic acid, eicosenoic acid, eicosatetraenoic acid, eicosapentaenoic acid, docosahexaenoic acid, tocotrienol, butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, natural or synthetic phospholipids, mono-, di-, or triacylglycerols, cardiolipin, phosphatidylglycerol, phosphatidic acid, phosphatidylcholine, alpha tocoferol, phosphatidylethanolamine, sphingomyelin, phosphatidylserine, phosphatidylinositol, dimyristoylphosphatidylcholine, dioleoylphosphatidylcholine, dipalmitoylphosphatidylcholine, distearoylphosphatidylcholine, phosphatidylethanolamines phosphatidylglycerols, sphingolipids, prostaglandins, gangliosides, neobee, niosomes, derivatives thereof, and combinations thereof. The water-soluble second additive can be chosen from cholesteryl-polyethylene glycol 600 sebacate, polyoxyethanyl α-tocopheryl sebacate, methylated polyethylene glycol cholesterol (mPEG cholesterol), polyethylene glycol cholesterol (PEG cholesterol), polyethylene glycol ester cholesterol (PEG cholesterol), polyethylene glycol ether cholesterol (PEG cholesterol), methylated polyethylene glycol-amide-cholesterol (mPEG cholesterol), polyethylene glycol-amide-cholesterol (PEG cholesterol), polyethylene glycol (PEG)-cholesteryl sebacate, polyethylene glycol cholesterol, PEG amide ester cholesterol, PEG amide ether cholesterol, mPEG amide ester cholesterol, DSPE-PEG-cholesterol, PEGylated phospholipid, methylated PEGylated phospholipid, PEG caprylic/capric diglycerides, PEG8 caprylic/capric glycerides, PEG caprylate, PEG caprate, PEG caproate, PEG-20 sorbitan monolaurate (Tween-20), PEG-20 sorbitan monopalmitate (Tween-40), PEG-20 sorbitan monostearate (Tween-60), PEG-20 sorbitan monooleate (Tween-80), PEG laurate, PEG oleate, PEG stearate, PEG glyceryl laurate, and PEG-30 glyceryl oleate, polyglyceryl fatty acid esters, polyglyceryl oleate (Plurol Oleique), polyglyceryl-2 dioleate (Nikkol DGDO), polyglyceryl-10 trioleate, polyglyceryl stearate, polyglyceryl laurate, polyglyceryl myristate, polyglyceryl palmitate, polyglyceryl linoleate, polyglyceryl-10 laurate (Nikkol Decaglyn 1-L), polyglyceryl-10 oleate (Nikkol Decaglyn 1-0), polyglyceryl-10 mono/dioleate ($Caprol^T$ PEG 860), polyglyceryl-10 stearate, polyglyceryl-10 laurate, polyglyceryl-10 myristate, polyglyceryl-10 palmitate, polyglyceryl-10 linoleate, polyglyceryl-6 stearate, polyglyceryl-6 laurate, polyglyceryl-6 myristate, polyglyceryl-6 palmitate, polyglyceryl-6 linoleate, and combinations thereof.

Coating Solution.

The coating layer can include the polymer-encapsulated drug particles that include the therapeutic agent and the one or more polymers that encapsulate the therapeutic agent; or the drug-releasing coating including the polymer-encapsulated drug particles; or a composition including a therapeutic agent and one or more additives; or a combination thereof. Solvents for preparing of the coating layer can include, as examples, one or combination of the following: (a) water, (b) alkanes such as hexane, octane, cyclohexane, and heptane, (c) aromatic solvents such as benzene, toluene, and xylene, (d) alcohols such as ethanol, propanol, and isopropanol, diethylamide, ethylene glycol monoethyl ether, Trascutol, and benzyl alcohol (e) ethers such as dioxane, dimethyl ether and tetrahydrofuran, (f) esters/acetates such as ethyl acetate and isobutyl acetate, (g) ketones such as acetone, acetonitrile, diethyl ketone, and methyl ethyl ketone, and (h) mixture of water and organic solvents such as water/ethanol, water/acetone, water/methanol, water/tetrahydrofuran. A solvent in the top coating layer can be, for example, methanol, ethanol, and/or acetone.

Organic solvents, such as short-chained alcohol, dioxane, tetrahydrofuran, dimethylformamide, acetonitrile, dimethylsulfoxide, and the like, can be useful solvents in embodiments of the present invention because these organic solvents generally disrupt colloidal aggregates and co-solubilize all the components in the coating solution.

Various embodiments provide a method for preparing coating solution. The content of the therapeutic agent in the coating solution can be from 0.5-50% by weight based on the total weight of the solution. The content of the additive in the coating solution can be from about 0.1 wt % to about 45 wt %, about 0.2 wt % to about 40 wt % by weight, about 0.3 to about 15 wt %, or about 0.1 wt % or less, or less than, equal to, or greater than about 0.2 wt %, 0.3, 0.4, 0.5, 0.6, 0.8, 1, 2, 3, 4, 5, 6, 7, 8, 9, 10, 12, 14, 16, 18, 20, 22, 24, 26, 28, 30, 35, 40, or about 45 wt % or more, based on the total weight of the solution. The amount of solvent used depends on the coating process and viscosity. It will affect the uniformity of the drug-additive coating but will be evaporated.

In other embodiments, two or more solvents, two or more therapeutic agents, and/or two or more additives can be used in the coating solution.

The medical device coating for delivering a drug to a nonvascular tissue or nonvascular stricture can be prepared from a mixture. The coating can be prepared from a mixture including an organic phase containing drug particles dispersed therein and an aqueous phase containing one or more water-soluble additives. The water-soluble additive can be chosen from polyethylene glycol, polyvinyl alcohol, polyvinylpyrrolidinone, polypeptides, water-soluble surfactants, water-soluble vitamins, and proteins. Alternatively, the coating can be prepared from a two-phase mixture that contains small drug particles suspended in a liquid. The liquid can consist of any suitable antisolvent for the drug particles such as water, heptane, hexane, or cycleohexane. The suspended drug particles can be stabilized by other additives that are dissolved in the liquid phase.

The medical device coating solution for delivering a drug to a nonvascular tissue or nonvascular stricture that can be prepared from a mixture. The coating solution can be prepared from a mixture including water and a water-miscible solvent, a water-soluble additive and a water-insoluble or partially water-soluble additive containing mostly insoluble drug particles dispersed therein. The water-miscible solvent can be one or more chosen from acetone, methanol, ethanol, isopropanol, butanol, THF, acetonitrile, dimethylformamide, dimethyl sulfoxide, dioxane, and acetic acid. The water-soluble additive can be chosen from water-soluble surfactants, water-soluble salts, water-soluble vitamins, water-soluble sterols, proteins, and mixtures thereof. In one embodiment all or a portion of the one or more water-soluble additives are dissolved in the water and added to the microfluidizer. Next the drug can be added to be processed in the microfluidizer and the mixture is processed under high shear conditions and high pressure to reduce the particle size of the drug to less than 10 μm, or more preferably less than 5 μm. Next the water-insoluble or partially water-soluble additive can be dissolved in the water-miscible solvent and added to the microfluidizer and processed under high shear conditions. The processing can be one of microfluidization, homogenization, rotator-stator milling, high or low energy bead milling, or high-power ultrasonic probe homogenization.

In one embodiment preparing a coating solution includes a) mixing water, water-miscible solvent, therapeutic agent, and a water-soluble additive to form a premix; b) processing the premix to reduce the particle size of the therapeutic agent; c) mixing insoluble water additive, the water-soluble additive, water, and water-miscible solvent to form a second premix; d) mixing the second premix with the first processed premix to form a coating solution. The therapeutic agent is one of from paclitaxel, docetaxel, taxol, an mTOR inhibitor, rapamycin, sirolimus, zotarolimus, everolimus, tacrolimus, umirolimus, an analogue thereof, and combinations thereof; the therapeutic agent is crystalline, partially crystalline, amorphous, partially amorphous, or a combination thereof. The coating solution is an aqueous suspension of the therapeutic agent. The particle size of the therapeutic agent is in the range of 0.2 micron to 5 microns. The first additive, the second additive, or a combination thereof encapsulates the therapeutic agent, the additive-encapsulated therapeutic agent has a larger particle size than the therapeutic agent itself, and the particle size of the additive-encapsulated therapeutic agent in the coating is in the range of 0.3 micron to 10 micron. The processing is one of microfluidization, homogenization, rotator-stator milling, high or low energy bead milling, or high-power ultrasonic probe homogenization. The first additive includes a water-insoluble or slightly or partially water-insoluble additive including at least one alkyl fatty group or cholesteryl group. The first additive can have a molecular weight of 50 to 750. The first additive in the coating has a lower melting temperature than that of the first additive in its pure form. The first additive in the coating has a lower crystallinity than that of the first additive in its pure form. The second additive is more hydrophilic or more water-soluble than the first additive and that includes a polyethylene glycol ($—(CH_2CH_2O)—$) or a polyglycerol ($—(CH_2—CHOH—CH_2O)—$) unit. The second additive has a molecular weight in the range of 750 to 100,000, or 750 to 50,000, or 750 to 10,000. Medical device coating.

The medical device and the coating layers of embodiments of the present invention can be made according to various methods. A coating solution can include the polymer-encapsulated drug particles that include the therapeutic agent and the one or more polymers that encapsulate the therapeutic agent; or the drug-releasing coating including the polymer-encapsulated drug particles; or a composition including a therapeutic agent and one or more additives; or a combination thereof. Coating techniques can be used for applying a coating solution to a medical device such as casting, fixed volume liquid dispensing, metering (e.g., dispense a fixed amount of coating solution based on volume onto the balloon or stent), spinning, spraying, dipping (e.g., immersing), ink jet printing, electrostatic techniques, and combinations of these processes. During the application of the coating solution, the balloon can be at least partially inflated. The metering can be performed in any suitable way, such as by pumping liquid coating solution from a reservoir to a nozzle that is proximate the surface of the medical device (e.g., the surface of an at least partially inflated balloon, or the surface of a stent). The nozzle can dispense the liquid therefrom, which can be immediately transferred to the exterior of the medical device due to its proximity to the nozzle (e.g., the nozzle can be so close to the balloon or stent that the liquid emerging from the nozzle can contact and be transferred to the exterior of the medical device before forming a drop of liquid that leaves the nozzle). The nozzle can dispense the liquid to the exterior of the medical device such that substantially none of the liquid is lost. The medical device can be rotated around its longitudinal axis during the dispensing of the liquid from the nozzle. The nozzle can be attached to a programmable x-y stage to allow it to move during the dispensing, such as along the exterior of the medical device parallel to the longitudinal axis of a cylindrical balloon or stent or along the profile of a non-cylindrically shaped medical device such as a balloon or a non-continuous shaped medical device such as a stent. In some embodiments, the medical device can be rotated around its longitudinal axis during the dispensing, and the nozzle can move parallel to the longitudinal axis of the medical device, such that substantially all of the medical device surface is coated with the coating solution (e.g., similar to the movement of a woodworker's chisel on a cylindrical piece of spinning wood in a lathe). The nozzle can be moved once along the length of the medical device or it can be moved back and forth conducting multiple passes along the length of the medical device. If the medical device is a stent, the stent can be coated at the manufactured, crimped, or expanded diameter, or at a diameter in-between.

Choosing an application technique can depend on the viscosity and surface tension of the solution. In some embodiments of the present invention, metering can be utilized because it makes it easier to control the uniformity of the thickness of the coating layer as well as the concentration of the therapeutic agent applied to the medical device.

In one embodiment of the present invention, the balloon is inflated or partially inflated, the coating solution is applied to the inflated balloon by metering it on while the balloon is inflated and rotating along its longitudinal axis. The balloon is then allowed to dry before being deflated, folded, and sheathed.

The description of an embodiment of an application device, fixture, and metering technique is an example. Any suitable metering or other technique can be used for coating the balloon catheter.

After the medical device is coated with the coating solution, the coated medical device can be subjected to a drying in which the solvent in the coating solution is evaporated. This produces a coating matrix on the medical device containing the therapeutic agent. One example of a drying technique is placing a coated medical device into an oven at approximately 20° C. or higher for approximately 24 hours. Any other suitable method of drying the coating solution can be used. The time, temperature, and relative humidity can vary with particular additives and therapeutic agents.

In one embodiment, a method for coating a balloon catheter includes preparing an aqueous suspension coating solution including mixing water, water-miscible solvent, therapeutic agent, and a water-soluble additive to form a premix; processing the premix to reduce the particle size of the therapeutic agent; mixing insoluble water additive, the water-soluble additive, water, and water-miscible solvent to form a second premix; mixing the second premix with the first processed premix to form a coating solution; wherein the therapeutic agent is chosen from an from paclitaxel, docetaxel, taxol, an mTOR inhibitor, rapamycin, sirolimus, zotarolimus, everolimus, tacrolimus, umirolimus, an analogue thereof, and combinations thereof; wherein the therapeutic agent is crystalline, partially crystalline, amorphous, partially amorphous, or a combination thereof; wherein the coating solution is an aqueous suspension of the therapeutic agent; wherein the particle size of the therapeutic agent is in the range of 0.2 micron to 5 micron. The first additive, the second additive, or a combination thereof encapsulates the therapeutic agent, the additive-encapsulated therapeutic agent has a larger particle size than the therapeutic agent itself, and the particle size of the additive-encapsulated therapeutic agent in the coating is in the range of 0.3 micron to 10 micron. The first additive includes a water-insoluble or slightly or partially water-insoluble additive including at least one alkyl fatty group or cholesteryl group. The first additive can have a molecular weight of 50 to 750. The first additive in the coating has a lower melting temperature than that of the first additive in its pure form. The first additive in the coating has a lower crystallinity than that of the first additive in its pure form. The second additive is more hydrophilic or more water-soluble than the first additive and that includes a polyethylene glycol ($—(CH_2CH_2O)—$) or a polyglycerol ($—(CH_2—CHOH—CH_2O)—$) unit. The second additive has a molecular weight in the range of 750 to 100,000, or 750 to 50,000, or 750 to 10,000. The method includes preparing a balloon catheter including; inflating the balloon catheter; cleaning the surface of the balloon; fixturing the balloon so it can be mounted inside a coating machine horizontally and rotated at a fixed speed. The method includes dispensing the coating solution onto the surface of the balloon while the nozzle is translating laterally across the balloon. The method includes continuing to rotate the balloon to evaporate the solvent at room temperature or higher than room temperature. The method includes pleating and folding the balloon catheter. The method includes sterilizing the balloon.

Balloon Preparation.

Various embodiments of the present invention provide a method of forming a balloon. The method can include placing a tube including balloon material or extruding the balloon material into a mold having any suitable shape, such as a balloon mold having a shape including a proximal cone, at least one main body section, at least one neck section having a diameter less than the at least one main body section, another at least one main body section, and a distal cone. The method can include heating the balloon material tube to a temperature above the glass transition temperature thereof, pressurizing the interior of the balloon material tube, and stretching the balloon material to reduce the balloon thickness. The method can also include expanding the balloon material tube into contact with the interior of the mold.

Various embodiments of the present invention provide a method of forming a balloon and then shrinking it to get a large diameter range. The method includes placing a tube including balloon material into a balloon mold wherein the balloon mold has a shape including a proximal cone, at least one main body section, and a distal cone. The method includes pressurizing the interior of the balloon material tube. The method includes expanding the balloon material tube into contact with the interior of the mold at pressures of 200-400 psi and temperatures of 100-200° C. The formed balloon is then shrunk by annealing the balloon at a temperature lower than the forming process with low inflation pressure for a specified amount of time, preferably 1-30 psi at 70-90° C., for 3-30 seconds. Once the balloon is shrunk it can be attached to a catheter shaft and coated with drug. Any of the manufacturing techniques, methods of treating body lumens, or balloons described in the following patents, which are hereby incorporated by reference as if they were reproduced herein in their entirety, can be used in embodiments of the present invention: U.S. Pat. Nos. 7,163,522 and 7,108,826.

Expandable Neck.

In various embodiments, the balloon catheter of the present invention is free of an expandable neck. In other embodiments, the balloon of the balloon catheter include at least one expandable neck. The balloon can include a first main section and a second main section on opposite sides of the neck section. During an inflated state of the balloon, the expandable neck section can have an inflated diameter than the main diameter of the first and second main sections when the balloon is inflated. During the inflating the inflated diameter of the neck section can be the smallest diameter of the balloon catheter between the first and second main sections. The neck section can be expandable, such that during the inflating the inflated diameter of the neck section is greater than a diameter of the neck section prior to inflation.

In various embodiments, the balloon catheter including a balloon with an expandable neck can be used to treat a urethral stricture or benign prostatic hyperplasia (BPH). The balloon can be inflated such that the first main section of the balloon catheter is in the prostatic urethra, the second main section of the balloon catheter is in the bladder, and the neck section is in the bladder neck.

The inflating of the balloon can include simultaneous inflation of the first main section, the neck section, and the second main section. For example, the inflating can include inflating the first main section, the second main section, and the neck section simultaneously via a single inflation lumen.

The at least one neck section can include an area of reduced compliance during inflation relative to the first main section and the second main section. In some embodiments, the neck section can include a reinforcing material around a circumference of the neck section to reduce compliance of the neck section during the inflation. The reinforcing material can include any suitable material, such as a suture, monofilament, or multifilament, wherein the reinforcing material comprises nylon, a polyamide, an aromatic polyamide, ultra high molecular weight polyethylene (UHMWPE), a polyester, an aromatic polyester, polyethylene terephthalate (PET), or a combination thereof.

The balloon including the expandable neck on the balloon catheter can include a drug coating. The drug coating can be on the first main section, the second main section, the neck, or a combination thereof. The drug coating can be on the neck. The drug coating can be on the first main section and the neck.

Flushing and Soaking of the Coating.

The method of using the balloon catheter that includes the balloon with the drug coating in the body lumen can include a combination of flushing and soaking. Flushing the lumen and allowing the drug coating to soak in the flushing media can increase the rate of drug release from the balloon, and can increase the overall proportion of the drug in the coating that is delivered to the target site in the lumen.

The method can include flushing the body lumen target site with a flushing media. The flushing media can be any suitable liquid flushing media. The flushing media can include water, saline solution, or a water solution including at least one water-soluble additive.

The balloon catheter can be inserted into the body lumen before, during, or after the flushing. The balloon catheter can be inserted into the body lumen after the flushing. After inserting the balloon catheter into the lumen such that the balloon is posited at the target site, the method can include holding the balloon catheter in position for a soaking period prior to inflation to hydrating the coating layer in the flushing media. The soaking period can be predetermined prior to the holding of the balloon catheter in position for the soaking period. The soaking period can be any suitable period, such as 1 minute to 2 hours, or 1 minute to 60 minutes, or equal to or greater than 1 minute, 2, 3, 4, 5, 6, 7, 8, 9, 10, 12, 14, 16, 18, 20, 22, 24, 26, 28, 30, 35, 40, 45, 50, 55, 60 minutes, 1.2 h, 1.4, 1.6, 1.8, or 2 h.

The flushing and the soaking period, combined with the inflation period and the composition of the drug coating, can be sufficient such that the residual drug amount after the withdrawal of the balloon catheter from the body lumen is 70% or less of the initial drug load of the drug in the drug coating prior to insertion of the balloon catheter into the body lumen. For example, the residual drug amount can be 70% or less of the initial drug load, or equal to or less than 68%, 66, 64, 62, 60, 58, 56, 54, 52, 50, 48, 46, 44, 42, 40, 38, 36, 34, 32, 30, 28, 26, 24, 22, 20, 18, 16, 14, 12, 10, 8, 6, 4, 2, 1%, or less than 1%. The contact of the drug coating and the lumen during the inflation period can be sufficient to release 37-1$^{00}$% of the initial drug load (e.g., such that when the residual drug in the coating is compared to the initial drug load in the coating prior to the insertion into the lumen, 37-1$^{00}$% of the drug has been released from the drug coating), or 37-97%, or equal to or greater than 37%, 38, 40, 42, 44, 46, 48, 50, 52, 54, 56, 58, 60, 62, 64, 66, 68, 70, 72, 74, 76, 78, 80, 82, 84, 86, 88, 90, 92, 94, 95, 96, 97, 98%, or 99% of the initial drug load.

Scope.

The method of using the balloon catheter that includes the balloon with the drug coating in the body lumen can include the use of a scope. For example, the inserting of the balloon catheter into the body lumen can include inserting both the balloon catheter and a scope into the body lumen. The balloon catheter and the scope can be positioned in any suitable way. For example, the balloon catheter and the scope can be posited side-by-side, or the balloon catheter can be loaded into the scope. In some embodiments, the balloon catheter can be positioned with a working channel of the scope prior to inserting the scope into the body lumen. In some embodiments, the balloon catheter can be positioned within a working channel of the scope after inserting the scope into the body lumen.

The balloon catheter can be visualizable with the scope. For example, the method can include visualizing the balloon catheter with the scope before and/or during the inflating of the balloon. The method can include visualizing the therapeutic agent that deposits from the balloon onto the body lumen stricture via the scope.

The scope can be any suitable scope. For example, the scope can include an endoscope, enteroscope, colonoscope, sigmoidoscope, rectoscope, anoscope, rhinoscope, bronchoscope, or a cystoscope.

Although various embodiments are specifically illustrated and described herein, it will be appreciated that modifications and variations of the present invention are covered by the above teachings and are within the purview of the appended claims without departing from the spirit and intended scope of the invention.

Other than the operating examples, or where otherwise indicated, all numbers expressing quantities of components in a layer, reaction conditions, and so forth used in the specification and claims are to be understood as being modified in all instances by the term “about.” Accordingly, unless otherwise indicated to the contrary, the numerical parameters set forth in this specification and attached claims are approximations that can vary depending upon the desired properties sought to be obtained by the present disclosure.

EXAMPLES

Various embodiments of the present invention can be better understood by reference to the following Examples which are offered by way of illustration. The present invention is not limited to the Examples given herein.

Throughout the Examples, unless otherwise indicated, the stretch ratio was calculated as the ratio of the diameter of the nominal balloon to the diameter of the body lumen stricture at the location of treatment. The diameter of the body lumen at the location of treatment is the normal diameter for the body lumen at the location of treatment and can be calculated as the average of the diameters of healthy tissue adjacent to the stricture, stenosis, or lesion, that is proximal and distal of the stricture or stenosis or lesion of the lumen. The inflated balloon diameter was about equal to the nominal balloon diameter for the pressure used during the inflation period and was within 10% of the nominal balloon diameter.

Part I. Preclinical and Bench Testing.

Example I-1. Preparation of Coating Solutions

Formulation 23: 50-150 mg (0.06-0.18 mmole) paclitaxel, 5-75 mg pentaerythritol ethoxylate (15/4), 10-200 mg pentaerythritol ethoxylate (3/4), and 1-6 ml ethanol were mixed.

Formulation 24: 50-150 mg (0.06-0.2 mmole) paclitaxel, 25-300 mg trimethylpropane ethoxylate (Mw~170)), and 1-6 ml ethanol were mixed.

Formulation S16: 45-200 mg (0.05-0.22 mmole) sirolimus, 5-75 mg pentaerythritol ethoxylate (15/4), 23-100 mg Brij 52 Cetyl Ether, and 1-6 ml (10/90 v/v) methanol/water were mixed.

Formulation S21: 45-200 mg (0.05-0.22 mmole) sirolimus, 5-75 mg monolaurin, and 1-6 ml (10/90 v/v) methanol/water were mixed.

Formulation S22: 45-300 mg (0.05-0.22 mmole) sirolimus, 5-80 mg pentaerythritol ethoxylate (15/4), 23-100 mg Brij 52 Cetyl Ether, 23-150 mg D-α-Tocopherol polyethylene glycol 1000 succinate (TPGS), and 1-6 ml (25/75 v/v) methanol/water were mixed.

Formulation S44: 45-300 mg (0.05-0.22 mmole) sirolimus, 5-80 mg pentaerythritol ethoxylate (15/4), 23-100 mg dodecyl glycerol, and 1-6 ml (25/75 v/v) methanol/water were mixed.

Formulation S47a: 45-200 mg (0.05-0.22 mmole) sirolimus, 4.5-20 mg polyoxyethanyl α-tocopheryl sebacate, 23-100 mg dodecyl glycerol, and 1-6 ml (25/75 v/v) methanol/water were mixed.

Formulation S47b: 45-200 mg (0.05-0.22 mmole) sirolimus, 4.5-20 mg polyoxyethanyl α-tocopheryl sebacate, 23-100 mg dodecyl glycerol, and 1-6 ml (25/75 v/v) ethanol/water were mixed.

Formulation S57: 45-200 mg (0.05-0.22 mmole) sirolimus, 4.5-20 mg polyoxyethanyl α-tocopheryl sebacate, 23-100 mg cholesteryl acetate, 23-100 mg dodecyl glycerol, and 1-6 ml (25/75 v/v) ethanol/water were mixed.

Formulation S58: 45-200 mg (0.05-0.22 mmole) sirolimus, 4.5-20 mg polyoxyethanyl α-tocopheryl sebacate, 23-100 mg mPEG-cholesterol, MW 5 k, 23-100 mg dodecyl glycerol, and 1-6 ml (25/75 v/v) ethanol/water were mixed.

Formulation S59: 45-200 mg (0.05-0.22 mmole) sirolimus, 23-100 mg mPEG-cholesteryl MW 5 k, 23-100 mg dodecyl glycerol, and 1-6 ml (25/75 v/v) ethanol/water were mixed.

Formulation CC6F2: 45-200 mg (0.05-0.22 mmole) sirolimus, 4.5-20 mg polyoxyethanyl α-tocopheryl sebacate, 23-100 mg cholesteryl decylate, 23-100 mg dodecyl glycerol, and 1-6 ml (20/80 v/v) cyclohexane/water were mixed.

Formulation CC6F4: 45-200 mg (0.05-0.22 mmole) sirolimus, 4.5-20 mg polyoxyethanyl α-tocopheryl sebacate, 23-100 mg cholesteryl acetate, 23-100 mg dodecyl glycerol, and 1-6 ml (20/80 v/v) cyclohexane/water were mixed.

Formulation S16 was prepared by using a rotor-stator process. 123 mg of sirolimus was added to a vial along with 3 mL of water. Next the rotor-stator was used to conduct a particle size reduction on the sirolimus. Next a premix was made in a separate vial consisting of; 55 mg of Brij 52 cetyl ether, 27.5 mg of pentaerythritol ethoxylate 15/4, 0.36 mL of methanol and 0.64 mL of water. This premix was added to the vial with the drug and mixed with the rotor-stator for approximately 5 minutes. This solution was used to coat balloons.

Formulation S22 was prepared by using a low energy bead milling process. Ajar mill with 5 mm diameter by 5 mm length yttrium stabilized zirconium grinding beads was used to conduct a sirolimus particle size reduction. 200 mg of sirolimus was added to ajar along with 8 mL of grinding beads. Next a premix was made in a separate vial consisting of, 100 mg of TPGS, 0.5 mL of methanol and 3 mL of water. This premix was added to the jar with the drug and milled for approximately 3-hours. Lastly a second premix of 25 mg of Brij 52 cetyl ether, 75 mg of pentaerythritol ethoxylate 15/4, 0.75 mL of methanol and 0.75 mL of water was prepared. All materials were fully solubilized in the second premix. The second premix was added to the jar containing the drug and milled overnight for approximately 16 hours. This solution was used to coat balloons.

Formulation S59 was prepared by using a high energy ultrasonic probe process. An ultrasound system, Sonics Vibra-cell VCX 130 with 6 mm probe, was used to conduct a sirolimus particle size reduction. 200 mg of sirolimus was added to a vial. Then 3 mL of ethanol/water (25/75 v/v) was added to separate vial. The vial was placed in an ice water bath and the mixture was sonicated with the ultrasound system for 5 minutes. Next a premix was made by dissolving 200 mg of dodecyl glycerol and 200 mg of mPEG-cholesteryl MW 5 k into 0.72 mL of ethanol. Then 0.24 mL of water was added to the second premix. All materials were fully solubilized in the second premix. The second premix was added to the drug suspension vial and sonicated further for 5 minutes and used to coat balloons.

Figure 6:
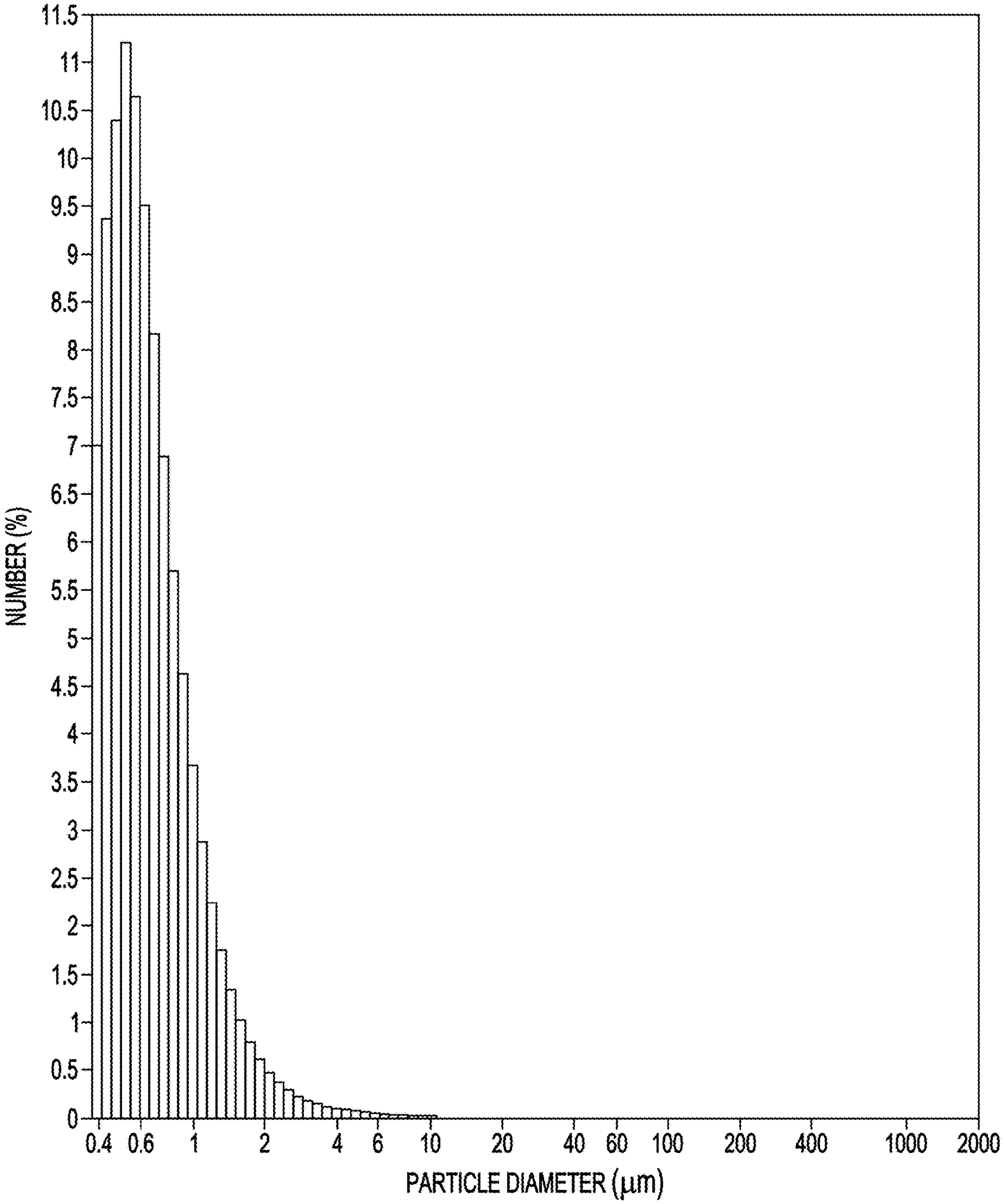
FIG. 6 is a diagram and table showing an example of drug coating particle size analysis using a Beckman Coulter LS 13 320 Particle Sizing Analyzer with Liquid Analyzer Module, in accordance with various embodiments.
Figure 10:
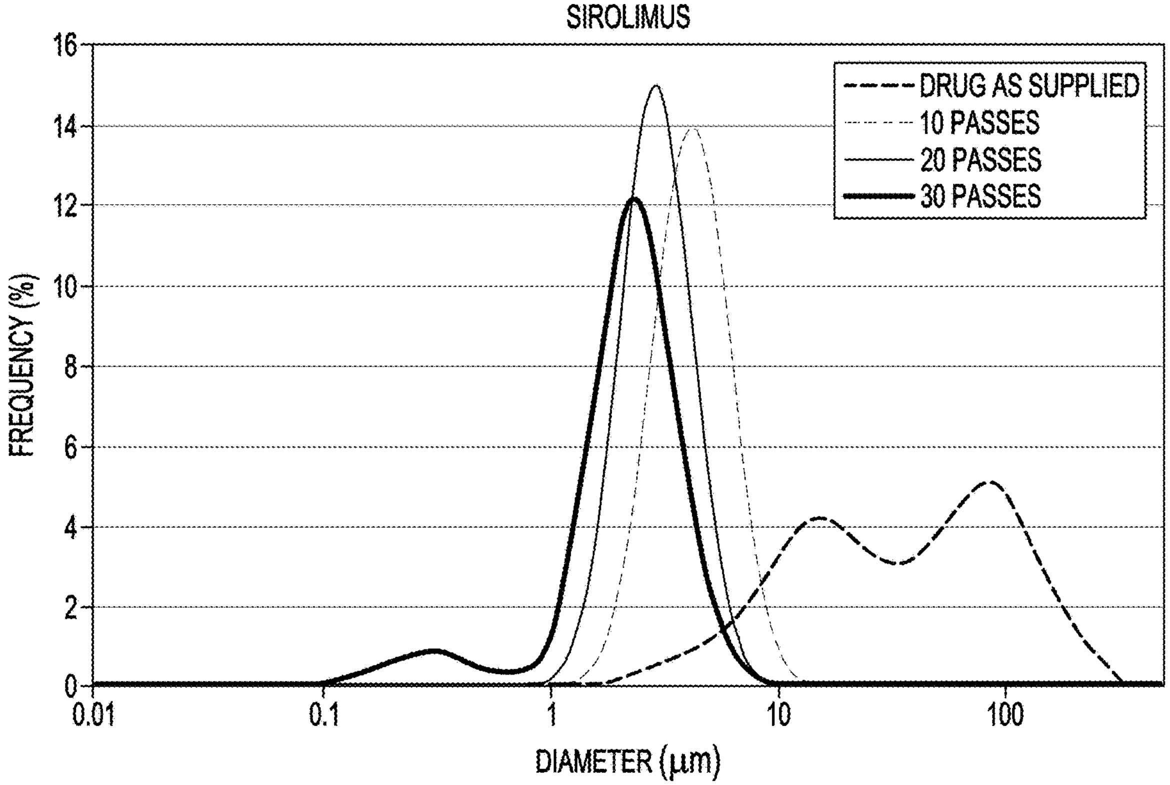
FIG. 10 illustrates a diagram of the sirolimus particle size reduction obtained with a high-pressure homogenizer, in accordance with various embodiments.

Formulation S47a was prepared by using a high-pressure homogenization process. A Microfluidizer was used to conduct a sirolimus particle size reduction. The Microfluidizer has a product recirculation loop and a heat exchanger to allow product cooling. 1.4 g of polyoxyethanyl α-tocopheryl sebacate was premixed with 34.5 mL of water. The premix was added to the microfluidizer. Once the premix was charged into the homogenizer vessel the microfluidizer was put into recirculation mode at a pressure of 30,000 psi. 4 g of sirolimus was slowly added to the vessel. Then the aqueous drug suspension was recirculated for 2 hours while periodically checking the particle size via laser light diffraction. The particle size was reduced from a $D_{90}$ of 124 μm to a $D_{90}$ of 3.78 μm. See FIG. 10, which illustrates a diagram of the sirolimus particle size reduction obtained with a high-pressure homogenizer. Next a second premix was made by dissolving 2 g of dodecyl glycerol and 1.29 g of polyoxyethanyl α-tocopheryl sebacate in 9 mL of ethanol. Then 3 mL of water was added to the second premix. All materials were fully solubilized in the second premix. The second premix was added to the drug suspension already being recirculated in the microfluidizer. The final mixture was further recirculated for an additional 1 hour. Coating solution S47a were characterized for particle size using laser light diffraction. Results are shown in FIG. 6. The $D_{90}$ was 1.149 μm, $D_{75}$ was 0.817 μm, $D_{50}$ was 0.607 μm, $D_{25}$ was 0.489 μm and the $D_{10}$ was 0.425 μm. Calculations were from 0.375 μm to 2000 μm. Mean was 0.746 μm; median was 0.607 μm; mean/median ratio was 1.230; mode was 0.520 μm; S.D. was 0.532 μm; variance was 0.283 $\mu m^2$; C.V. was 71.4%; skewness was 6.796 right skewed; kurtosis was 80.59 leptokurtic.

Formulation S47a was coated on 12 mm diameter by 50 mm length balloons using the following process. A special coating machine was used to dispense Formulation S47a onto the surface of the balloon. The solution was pumped to a dispense nozzle near the rotating balloon catheter. The balloon catheter was mounted into a fixture such that the balloon longitudinal axis was horizontal and the balloon could be spun on its longitudinal axis at a precise speed. The dispense nozzle was mounted onto a linear stage to allow for controlled motion of the nozzle along the length of the balloon while simultaneously dispensing liquid Formulation S47a onto the balloon. The nozzle made seven back and forth passes along the length of the balloon during coating solution dispensing and the balloon was maintained at a rotational speed of 75 RPM. After dispensing the nozzle was moved away and the balloon maintained rotation while simultaneously using a hot air gun to further dry the coating. The hot air nozzle was directed at the balloon and the temperature of the hot air was maintained at 120° F. until the balloon was completely dried for 3 minutes. This process was repeated for all balloons to be coated. Once the balloon were dried they were put in a humidification oven for 4 hours at 45° C., and 80% RH. After that the balloons were pleat and folded and sheathed. Then they were placed in Tyvek packaging and sent out to get ethylene oxide sterilized.

Figure 7A:
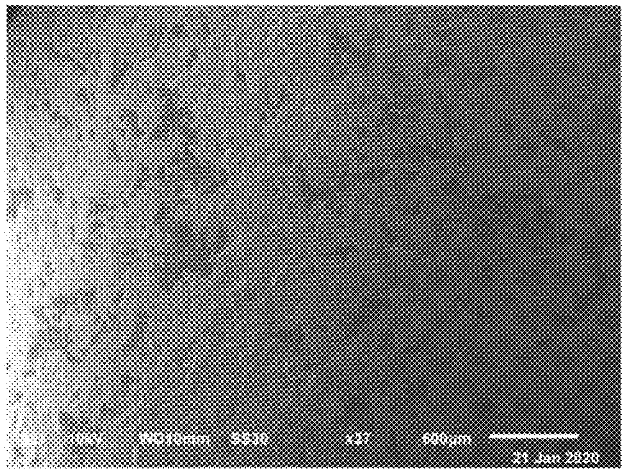
FIGS. 7A-C illustrate SEM images of an example of a sirolimus coated balloon, with FIG. 7A showing 37×, FIG. 7B showing 1,600×, and FIG. 7C showing 7,500×, in accordance with various embodiments.
Figure 7B:
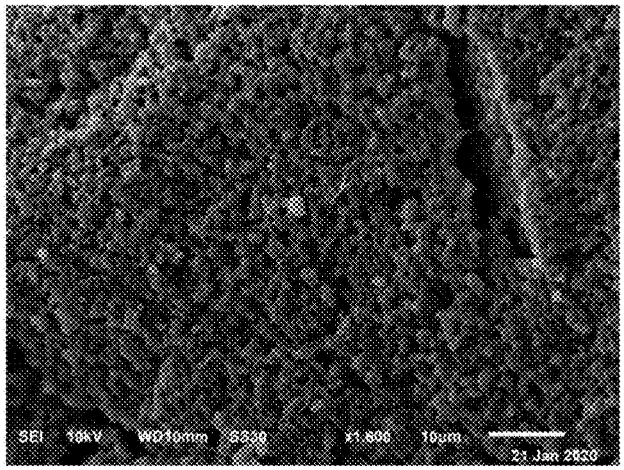
Figure 7C:
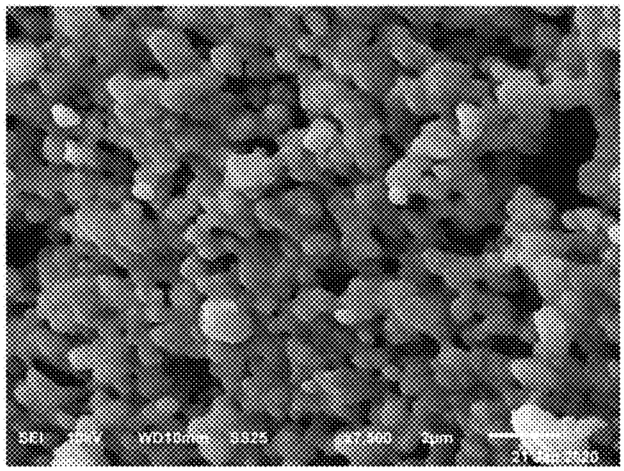

Sterilized balloons with S47a coating on them where characterized using scanning electron microscopy the results show that there were no observable particles greater than 10 μm and many of the particles were sub 1 micron in size. See FIG. 7, which illustrates SEM images of the sirolimus-coated balloon, with image (A) showing 37×, image (B) showing 1,600×, image (C) showing 7,500×, in accordance with various embodiments.

Figure 8A:
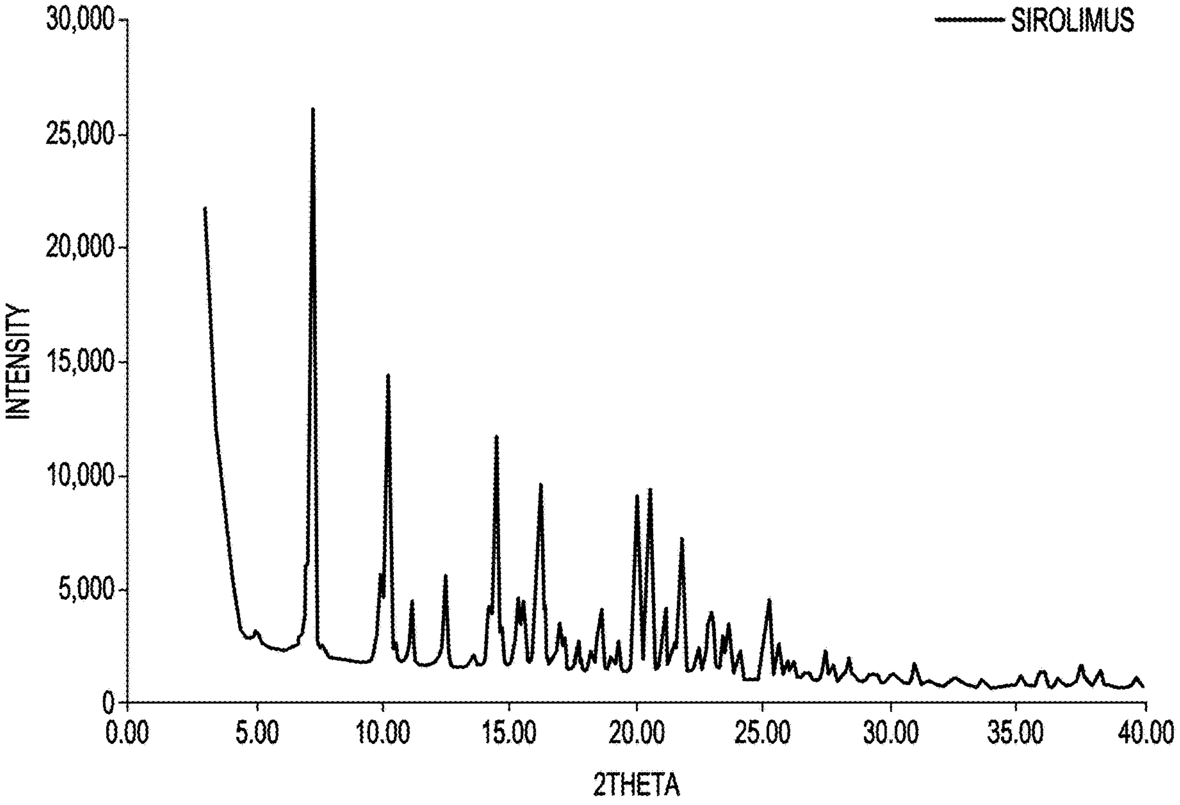
Figure 8B:
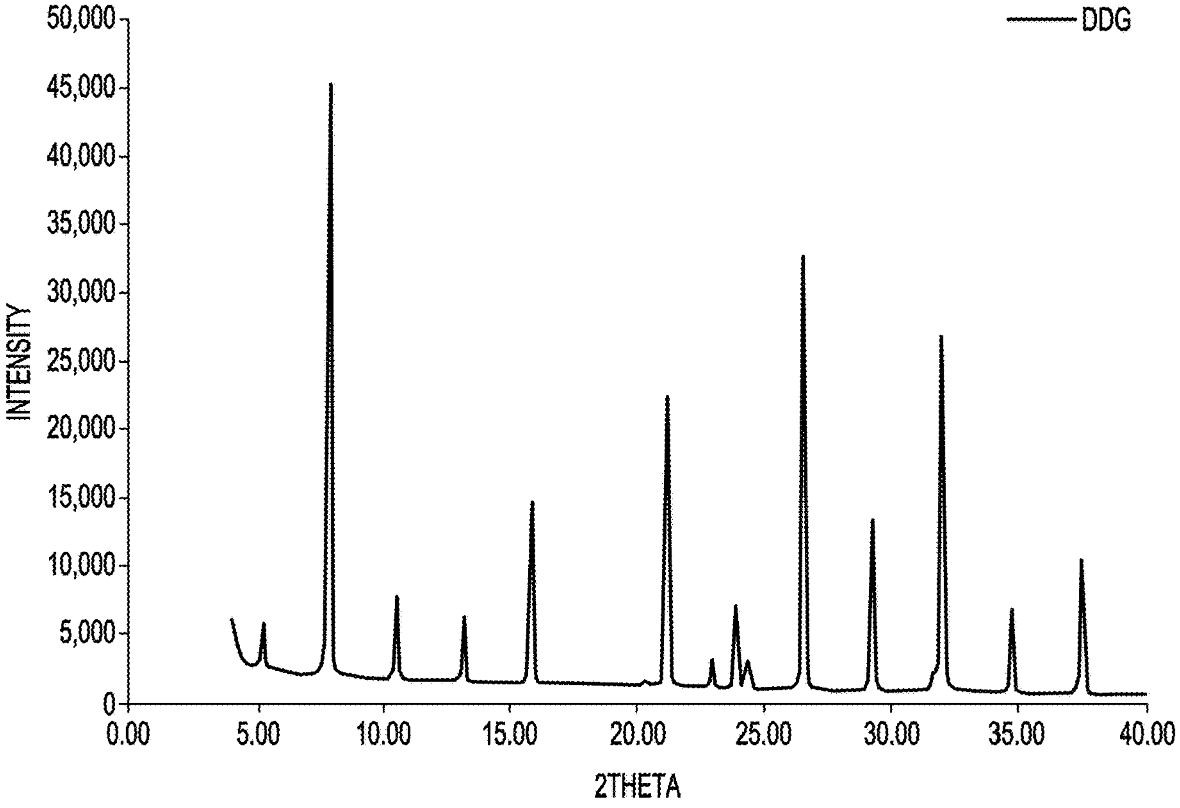
Figure 8C:
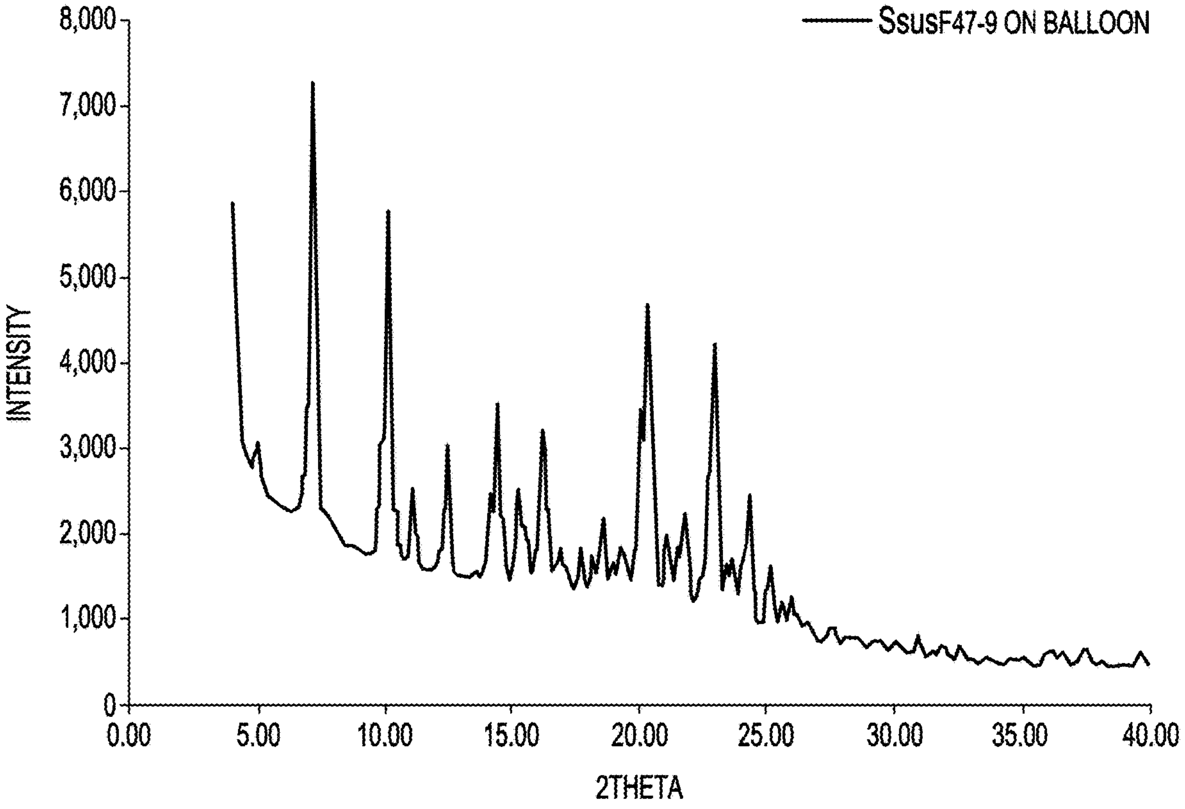
Figure 9A:
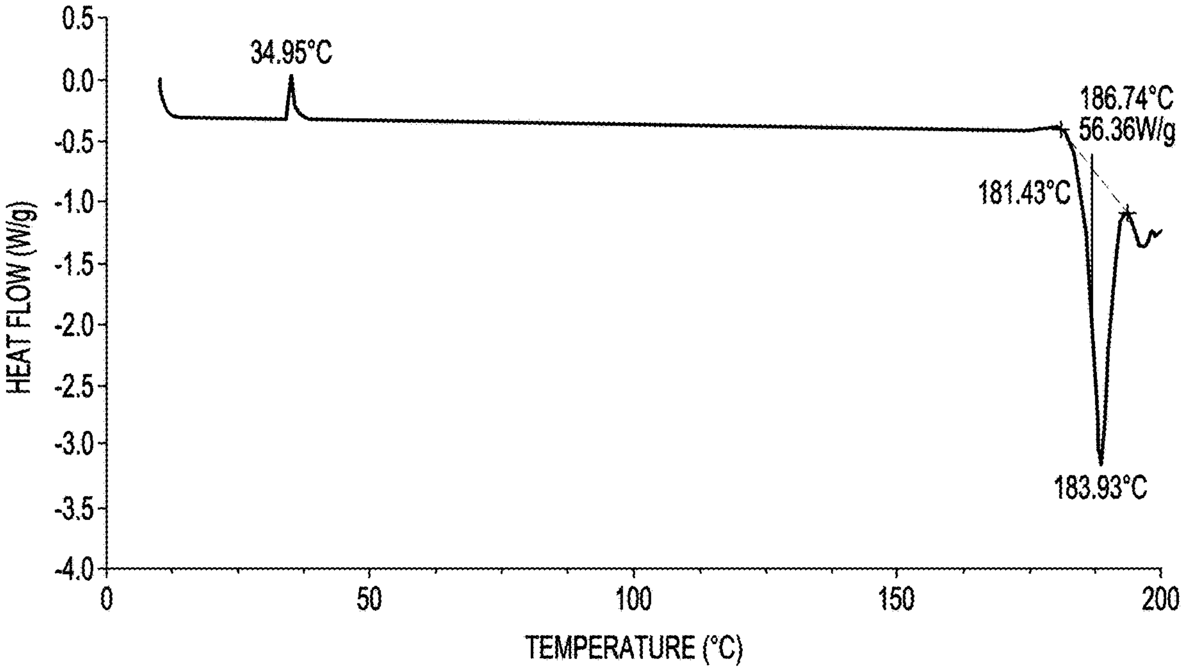
Figure 9B:
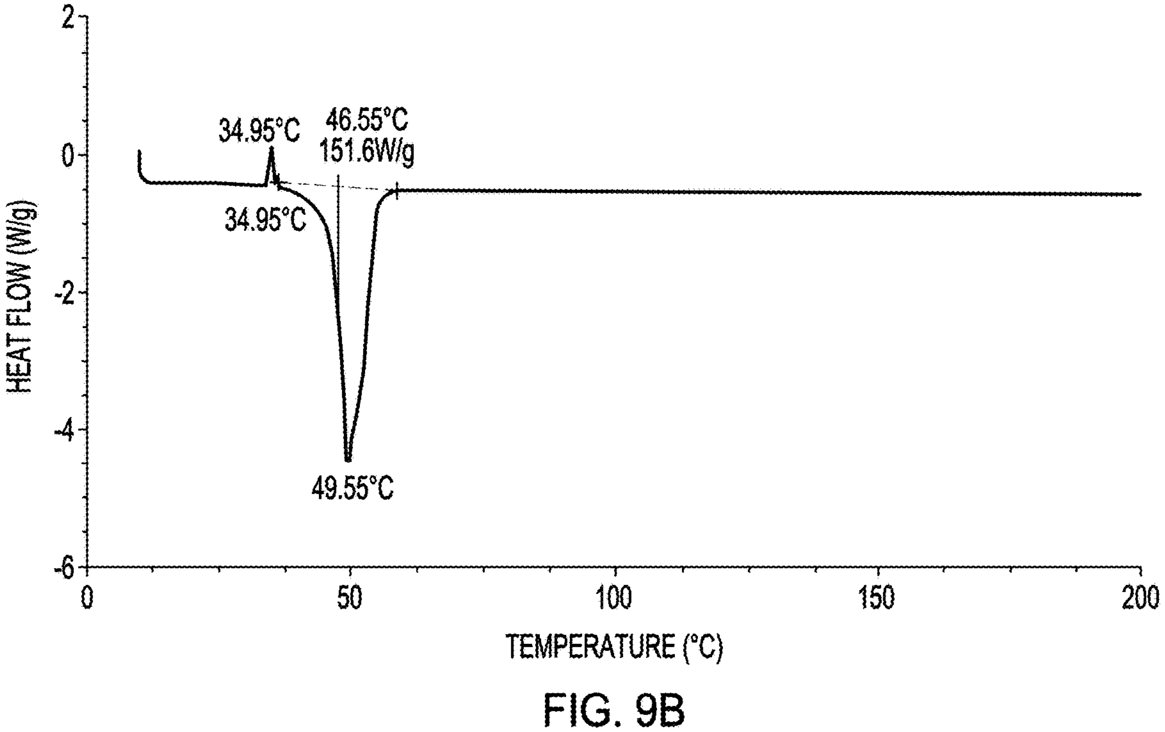
Figure 9C:
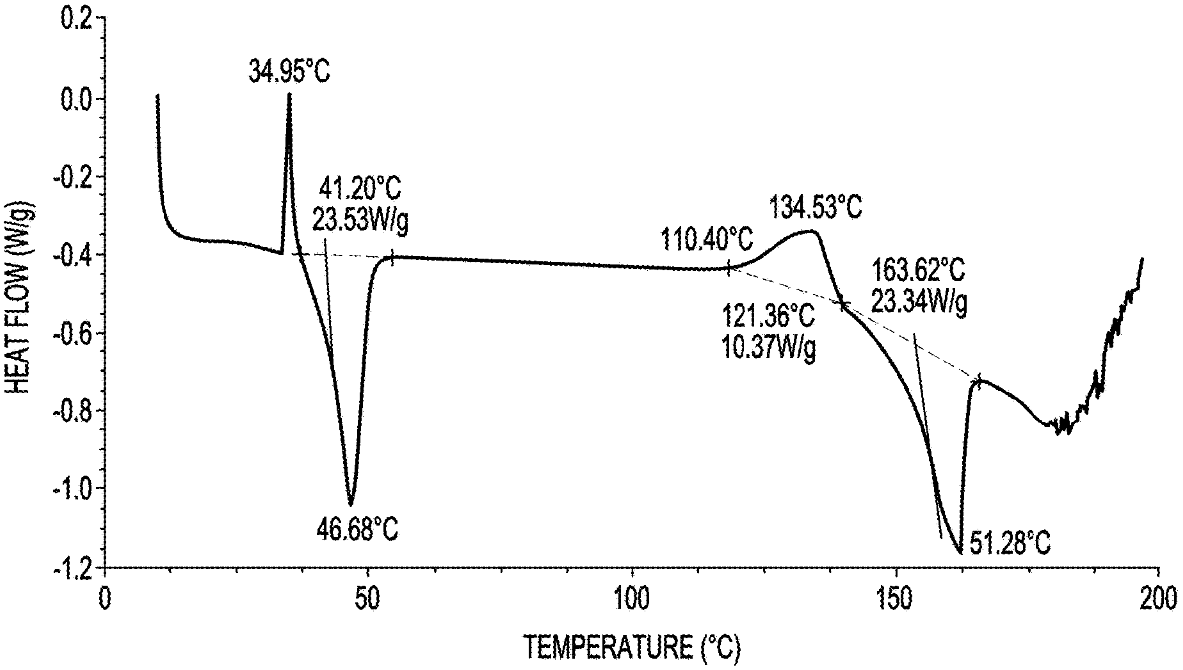

Sterilized balloons with S47a coating on them along with pure sirolimus samples and pure additive (DDG-dodecyl glycerol) samples where characterized using powder x-ray diffraction and modulated Differential Scanning Calorimetry. The results showed that the sirolimus in the sterilized coating S47a is crystalline. See FIG. 8. The DSC measurements were used to calculate the percent crystallinity of the coating. The results show the Sirolimus was 77.3 to 93.9% crystalline by weight. The DSC scans also showed that the melting temperature of the additive (DDG-dodecyl glycerol) was reduced 2-4° C., and the melting temperature for the drug was reduced 25-27° C. See FIGS. 9A-C and Table 4. FIGS. 9A-C illustrate diagrams of DSC scans of (A) crystalline sirolimus, (B) dodecyl glycerol, (C) drug (S47A)-coated balloon.

TABLE 4

DSC data of coating on balloon from Formulation S47a.

| Specimen | $1^{st}$ onset temp. (° C.) | $1^{st}$ peak temp. (° C.) | $1^{st}$ Peak enthalpy (J/g) | $2^{nd}$ onset temp. (° C.) | $2^{nd}$ peak temp. (° C.) | $2^{nd}$ Peak enthalpy (J/g) | $3^{rd}$ peak temp. (° C.) | $3^{rd}$ Peak enthalpy (J/g) | % crystallinity sirolimus |
|---|---|---|---|---|---|---|---|---|---|
| Sample 1 | 36.48 | 46.56 | 17.04 | 124.96 | 140.76 | 10.47 | 163.4 | 25.92 | 83.0 |
| Sample 2 | 36.9 | 46.85 | 16.18 | 124.96 | 139.79 | 8.07 | 163.14 | 24.15 | 77.3 |
| Sample 3 | 36.69 | 46.75 | 20.58 | 124.75 | 139.16 | 10.14 | 164.21 | 29.08 | 93.1 |
| Sample 4 | 37.12 | 46.97 | 18.91 | 124.54 | 138.97 | 8.55 | 162.7 | 26.58 | 85.1 |
| Sample 5 | 36.9 | 46.73 | 20.58 | 124.96 | 138.73 | 8.83 | 162.69 | 29.32 | 93.9 |
| Average | 36.82 | 46.77 | 18.66 | 124.83 | 139.48 | 9.21 | 163.23 | 27.01 | 86.5 |
| S.D. | 0.24 | 0.15 | 2.01 | 0.19 | 0.82 | 1.04 | 0.63 | 2.19 | 7.0 |

Example I-2. Studies on Various Coating Formulations

Porcine Animal Study with Formulation S79.

Formulation S79, an aqueous microcrystalline sirolimus suspension with dissolved 1,2-dilauroyl-sn-glycero-3-phosphatidylcholine, was prepared by using a high-pressure homogenization process. A Microfluidizer was used to conduct a sirolimus crystal particle size reduction. The Microfluidizer has a product recirculation loop and a tube in shell heat exchanger to allow for product cooling. The cooling media that was recirculated through the heat exchanger was maintained at 5° C. using a Recirculating Chiller. A premix of 4.0 g of 1,2-dilauroyl-sn-phosphatidylcholine dissolved in 9.4 mL of ethanol was added to 28.1 mL of water. This premix was added to the microfluidizer. Once the premix was charged into the homogenizer vessel the microfluidizer was put into recirculation mode at a pressure of 30,000 psi. 4.0 g of sirolimus was slowly added to the vessel. Then the aqueous drug suspension was recirculated for 2 hours. Lastly the homogenized mixture was packed out into a trace clean bottle and 12.5 mL of 75/25 water/ethanol was chased through the microfluidizer and added to the bottle to recover as much crystalline drug particles as possible. Formulation S79 was uniformly coated onto balloons of various sizes for acute drug transfer testing in a pig. The balloons were coated using an automated coating machine that precisely dispensed a prespecified volume of coating solution onto the surface of the balloon. The prespecified volume of solution was calculated based on the coating solution concentration and the desired nominal drug dose per balloon. The balloon sizes, diameter×length, were 6×30 and 18×65. The amount of drug per square millimeter for each balloon was 2. This gave nominal drug dosing of 1165 μg and 7572 μg for each respective balloon size. The 6 mm balloons were used in the pig's urethra with a stretch ratio of 1.0 to 2.0. Lastly the 18 mm balloons were used in the pig's esophagus, small intestine, and colon with stretch ratios of 1.0-2.0. For the urological and gastrointestinal treatments the balloon was tracked into position and the coating was allowed to hydrate for 1 minute prior to inflation. For the gastrointestinal treatments a gastroscope, enteroscope, or colonoscope was used to visualize the treatment site and flush the wall of the treatment site prior to use of the DCB. After all treatments, the pig was alive for 24 hours prior to sacrifice, then the treated tissue was excised in the necropsy lab and assayed for drug content. The measured sirolimus drug concentration in the various tissues can be seen in Table 5. The residual amount of drug on the balloon after treatment was measured and can be seen in Table 6.

TABLE 5

Formula S79 measured drug concentrations

| Treatment site | Sirolimus Concentration (ug/g) |
|---|---|
| Esophagus-Treatment (Prox) | 0.255 |
| Esophagus-Treatment (Dist) | 0.224 |
| Duodenum-Treatment (Dist) | 0.680 |
| Colon-Treatment (Mid) | 5.27 |

TABLE 6

Formula S79 residual drug on balloon after treatment.

| Treatment Location | Residual Balloon Content (% of Dose) |
|---|---|
| Colon-Treatment (Mid) | 52.40% |
| Duodenum-Treatment (Dist) | 2.50% |
| Esophagus-Treatment (Prox) | 15.90% |
| Esophagus-Treatment (Dist) | 23.00% |

Porcine Animal Study with Formulation S96, S97, and S98.

Formula S96 Sirolimus Coating Solution Preparation. Formulation S96, an aqueous microcrystalline sirolimus suspension encapsulated in lipids with dissolved 1,2 dihexanoyl-sn-glycero-3-phosphatidylcholine, 1,2-dilauroyl-sn-glycero-3-phosphatidylcholine and 1,2-dipalmitoyl-sn-glycero-3-ethylphosphocholine (chloride salt), was prepared by using a sonic probe process. A first premix of 75 mg cetyl palmitate, 150 mg of cholesterol stearate and 75 mg of cholesterol acetate was dissolved in 0.7 mL of cyclohexane. Next 200 mg of crystalline sirolimus was added to this first premix. An ultrasound system, Sonics Vibra-cell VCX 130 with 6 mm probe, was used to conduct a sirolimus particle size reduction on the first premix. A second aqueous premix was made by adding 0.35 mL of ethanol to 5 mL of water. While maintaining ultrasonic agitation the first premix was added to the second premix to make a solid particle in oil with water emulsion. The emulsion was mixed with sonic agitation for 5 minutes to allow the lipids to solidify thus coating the sirolimus drug particles. Lastly a third premix was made by dissolving 27.78 mg of 1,2 dihexanoyl-sn-glycero-3-phosphatidylcholine, 138.89 mg of 1,2-dipalmitoyl-sn-glycero-3-ethylphosphocholine (chloride salt), and 166.67 mg of 1,2-dilauroyl-sn-glycero-3-phosphatidylcholine in 1.635 mL of ethanol. Then 1.015 mL of water was added to the third premix. The third premix was added to the drug particle emulsion mixture to complete the coating solution.

Formula S97 Sirolimus Coating Solution Preparation. Formulation S97, an aqueous microcrystalline sirolimus suspension encapsulated in lipids with dissolved 1,2 dihexanoyl-sn-glycero-3-phosphatidylcholine, 1,2-dilauroyl-sn-glycero-3-phosphatidylcholine, Poly(1-vinylpyrrolidone-co-2-dimethylaminoethyl methacrylate), and DC-Cholesterol, was prepared by using a sonic probe process. A first premix of 75 mg cetyl palmitate, 150 mg of cholesterol stearate and 75 mg of cholesterol acetate was dissolved in 0.7 mL of cyclohexane. Next 200 mg of crystalline sirolimus was added to this first premix. An ultrasound system, Sonics Vibra-cell VCX 130 with 6 mm probe, was used to conduct a sirolimus particle size reduction on the first premix. A second aqueous premix was made by adding 0.35 mL of ethanol to 5 mL of water. While maintaining ultrasonic agitation the first premix was added to the second premix to make a solid particle in oil with water emulsion. The emulsion was mixed with sonic agitation for 5 minutes to allow the lipids to solidify thus coating the sirolimus drug particles. Lastly a third premix was made by dissolving 50.0 mg of 1,2 dihexanoyl-sn-glycero-3-phosphatidylcholine, 50.0 mg of Poly(1-vinylpyrrolidone-co-2-dimethylaminoethyl methacrylate), 66.7 mg of DC-cholesterol and 166.67 mg of 1,2-dilauroyl-sn-glycero-3-phosphatidylcholine in 1.635 mL of ethanol. Then 1.015 mL of water was added to the third premix. The third premix was added to the drug particle emulsion mixture to complete the coating solution.

Formula S98 Sirolimus Coating Solution Preparation. Formulation S98, an aqueous microcrystalline sirolimus suspension encapsulated in lipids with dissolved 1,2 dihexanoyl-sn-glycero-3-phosphatidylcholine, 1,2-dilauroyl-sn-glycero-3-phosphatidylcholine and DC-Cholesterol, was prepared by using a sonic probe process. A first premix of 75 mg cetyl palmitate, 150 mg of cholesterol stearate and 75 mg of cholesterol acetate was dissolved in 0.7 mL of cyclohexane. Next 200 mg of crystalline sirolimus was added to this first premix. An ultrasound system, Sonics Vibra-cell VCX 130 with 6 mm probe, was used to conduct a sirolimus particle size reduction on the first premix. A second aqueous premix was made by adding 0.35 mL of ethanol to 5 mL of water. While maintaining ultrasonic agitation the first premix was added to the second premix to make a solid particle in oil with water emulsion. The emulsion was mixed with sonic agitation for 5 minutes to allow the lipids to solidify thus coating the sirolimus drug particles. Lastly a third premix was made by dissolving 25.0 mg of 1,2 dihexanoyl-sn-glycero-3-phosphatidylcholine, 108.3 mg of DC-cholesterol and 200.0 mg of 1,2, dilauroyl-sn-glycero-3-phosphatidylcholine in 1.635 mL of ethanol. Then 1.015 mL of water was added to the third premix. The third premix was added to the drug particle emulsion mixture to complete the coating solution.

Formulations S96, S97, and S98 were uniformly coated onto balloons of various sizes for acute drug transfer testing in a pig. The balloons were coated using an automated coating machine that precisely dispensed a prespecified volume of coating solution onto the surface of the balloon. The prespecified volume of solution was calculated based on the coating solution concentration and the desired nominal drug dose per balloon. The balloon sizes, diameter×length, were 6×30 and 18×65. The amount of drug per square millimeter for each balloon was 2 micrograms/$mm^2$ at nominal inflation pressure. This gave nominal drug dosing of 1165 μg and 7572 μg for each respective balloon size The 6 mm balloons were used in the pig's urethra with a stretch ratio of 1.0 to 2.0. Lastly the 18 mm balloons were used in the pig's esophagus, small intestine, and colon with stretch ratios of 1.0-2.0. For the urological and gastrointestinal treatments the balloon was tracked into position and the coating was allowed to hydrate for 1 minute prior to inflation. For the gastrointestinal treatments a gastroscope, enteroscope, or colonoscope was used to visualize the treatment site and flush the wall of the treatment site prior to use of the DCB. After all treatments, the pig was alive for 24 hours prior to sacrifice, then the treated tissue was excised in the necropsy lab and assayed for drug content. The measured sirolimus drug concentration in the various tissues can be seen in Table 7.

TABLE 7

Formulations S96, S97, and S98 measured drug concentrations in various tissues.

| Sample | Formula | Sirolimus [ug/g] |
|---|---|---|
| Esophagus-prox | S98 | 0.00 |
| Esophagus-mid | S96 | 0.00 |
| Esophagus-dist | S97 | 0.00 |
| Duodenum-prox | S97 | 0.12 |
| Duodenum-dist | S96 | 0.00 |
| Colon-prox | S96 | 2.65 |
| Colon-dist | S98 | 1.56 |
| Urethra-prox | S96 | 0.17 |
| Urethra-mid | S97 | 0.11 |
| Urethra-dist | S98 | 0.15 |

Polymer Encapsulated Drug Particles (PEDPs) and Charged Polymer Encapsulated Drug Particles (CPEDPs).

MSF5, a PEDPs, were made by first creating a dispersed phase (DP) premix by dissolving 304.7 mg of PLGA 5050 and 203 mg of sirolimus in 2.74 g of dichloromethane (DCM). Next a continuous phase (CP) premix was made by dissolving 1.08 g of Mowiol 4-88 (polyvinyl alcohol, 88% hydrolyzed) with heating to 60° C. in 58.7 g of purified water. Once the Mowiol 4-88 was fully dissolved the solution was allowed to cool and 180 mg of DCM was added to it. Next the DP was added into the CP while stirring the CP using a rotor-stator mixer to create an emulsion. Then the emulsion was added to 140 mL of purified water to precipitate the PEDPs from the emulsion. After precipitation the mixture was centrifuged to collect the PEDPs in the bottom of the centrifuge tube. Next the supernatant was poured off and the PEDPs were dispersed in a 250 mL of purified water and centrifuged again to wash the PEDPs. Next the wash supernatant was poured off and the PEDPs were dispersed in a small amount of water and vacuum dried overnight.

MSF4, a CPEDPs, were made by first creating a dispersed phase (DP) premix by dissolving 507.8 mg of PLGA 7525, 101.6 mg of Eudragit E, and 406.3 mg of sirolimus in 5.48 g of dichloromethane (DCM). Next a continuous phase (CP) premix was made by dissolving 0.585 g of Mowiol 4-88 (polyvinyl alcohol, 88% hydrolyzed) with heating to 60° C. in 31.8 g of purified water. Once the Mowiol 4-88 was fully dissolved the solution was allowed to cool and 98 mg of DCM was added to it. Next the DP was added into the CP while stirring the CP using a rotor-stator mixer to create an emulsion. Then the emulsion was added to 280 mL of purified water to precipitate the CPEDPs from the emulsion. After precipitation the mixture was centrifuged to collect the CPEDPs in the bottom of the centrifuge tube. Next the supernatant was poured off and the CPEDPs were dispersed in a 250 mL of purified water and centrifuged again to wash the CPEDPs. Next the wash supernatant was poured off and the CPEDPs were dispersed in a small amount of water and vacuum dried overnight.

MSF12, a CPEDPs, were made by first creating a dispersed phase (DP) premix by dissolving 464 mg of PLGA 7525, 166 mg of PLGA 5050, 50.0 mg of 1,2 disteroyl-sn-glycero-3-phosphatidylcholine, 20 mg of butylated hydroxytoluene, and 300.0 mg of sirolimus in 5.40 g of dichloromethane (DCM). Next a continuous phase (CP) premix was made by dissolving 0.576 g of Mowiol 4-88 (polyvinyl alcohol, 88% hydrolyzed) with heating to 60° C. in 31.3 g of purified water. Once the Mowiol 4-88 was fully dissolved the solution was allowed to cool and 96 mg of DCM was added to it. Next the DP was added into the CP while stirring the CP using a rotor-stator mixer to create an emulsion. Then the emulsion was added to 320 mL of purified water to precipitate the CPEDPs from the emulsion. After precipitation the mixture was centrifuged to collect the CPEDPs in the bottom of the centrifuge tube. Next the supernatant was poured off and the CPEDPs were dispersed in a 250 mL of purified water and centrifuged again to wash the CPEDPs. Next the wash supernatant was poured off and the CPEDPs were dispersed in a small amount of water and vacuum dried overnight.

MSF12, a CPEDPs, were made by first creating a dispersed phase (DP) premix by dissolving 464 mg of PLGA 7525, 166 mg of PLGA 5050, 50.0 mg of 1,2 disteroyl-sn-glycero-3-phosphatidylcholine, 20 mg of butylated hydroxytoluene, and 300.0 mg of sirolimus in 5.40 g of dichloromethane (DCM). Next a continuous phase (CP) premix was made by dissolving 0.576 g of Mowiol 4-88 (polyvinyl alcohol, 88% hydrolyzed) with heating to 60° C. in 31.3 g of purified water. Once the Mowiol 4-88 was fully dissolved the solution was allowed to cool and 96 mg of DCM was added to it. Next the DP was added into the CP while stirring the CP using a rotor-stator mixer to create an emulsion. Then the emulsion was added to 320 mL of purified water to precipitate the CPEDPs from the emulsion. After precipitation the mixture was centrifuged to collect the CPEDPs in the bottom of the centrifuge tube. Next the supernatant was poured off and the CPEDPs were dispersed in a 250 mL of purified water and centrifuged again to wash the CPEDPs. Next the wash supernatant was poured off and the CPEDPs were dispersed in a small amount of water and vacuum dried overnight.

MSF13, a CPEDP, were made by first creating a dispersed phase (DP) premix by dissolving 480 mg of PLGA 7525, 180 mg of PLGA 5050, 20.0 mg of 1,2 disteroyl-sn-glycero-3-phosphatidylcholine, 20 mg of butylated hydroxytoluene, and 300.0 mg of sirolimus in 5.40 g of dichloromethane (DCM). Next a continuous phase (CP) premix was made by dissolving 0.576 g of Mowiol 4-88 (polyvinyl alcohol, 88% hydrolyzed) with heating to 60° C. in 31.3 g of purified water. Once the Mowiol 4-88 was fully dissolved the solution was allowed to cool and 96 mg of DCM was added to it. Next the DP was added into the CP while stirring the CP using a rotor-stator mixer to create an emulsion. Then the emulsion was added to 320 mL of purified water to precipitate the CPEDPs from the emulsion. After precipitation the mixture was centrifuged to collect the CPEDPs in the bottom of the centrifuge tube. Next the supernatant was poured off and the CPEDPs were dispersed in a 250 mL of purified water and centrifuged again to wash the CPEDPs. Next the wash supernatant was poured off and the CPEDPs were dispersed in a small amount of water and vacuum dried overnight.

Wet coating process of MSF13 with 1,2 disterovl-sn-glycero-3-phosphatidylcholine, DMAEMA, Eudragit E. After drying MSF13 were added to a vial that contained 6 mm yttrium stabilized zirconium cylindrical beads. The vial was placed on a 300 tilted roller mill for 15 minutes to break up aggregates of MSF13. Next a 2 mg/mL solution was made by adding the coating material (1,2 disteroyl-sn-glycero-3-phosphatidylcholine, DMAEMA, Eudragit E) into a separate vial and dissolving it in a 4/96 ethanol/cyclopentane solvent. Then the solution was added to the vial containing MSF13 and was placed back on the 30° tilted roller mill without a cap and rotated till all the solvent evaporated. The coated MSF13 CPEDPs were collected for further testing.

MSF14, a CPEDP, were made by first creating a dispersed phase (DP) premix by dissolving 464 mg of PLGA 7525, 166 mg of PLGA 5050, 50.0 mg of 1,2 disteroyl-sn-glycero-3-phosphatidylcholine, 20 mg of butylated hydroxytoluene, and 300.0 mg of sirolimus in 5.40 g of dichloromethane (DCM). Next a continuous phase (CP) premix was made by dissolving 0.576 g of Mowiol 4-88 (polyvinyl alcohol, 88% hydrolyzed) with heating to 60° C. in 31.3 g of purified water. Once the Mowiol 4-88 was fully dissolved the solution was allowed to cool and 96 mg of DCM was added to it. Next the DP was added into the CP while stirring the CP using a rotor-stator mixer to create an emulsion. Then the emulsion was added to 320 mL of purified water to precipitate the CPEDPs from the emulsion. After precipitation the mixture was centrifuged to collect the CPEDPs in the bottom of the centrifuge tube. Next the supernatant was poured off and the CPEDPs were dispersed in a 250 mL of purified water and centrifuged again to wash the CPEDPs. Next the wash supernatant was poured off and the CPEDPs were dispersed in a small amount of water and vacuum dried overnight.

Dry coating process of MSF14 with 1% 1,2 disteroyl-sn-glycero-3-phosphatidylcholine. After drying 400 mg of MSF14 were added to a vial that contained 11 grams of 6 mm yttrium stabilized zirconium cylindrical beads and 4 mg of 1,2 distearoyl-sn-glycero-3-phosphatidylcholine (1,2 disteroyl-sn-glycero-3-phosphatidylcholine). The vial was placed on a roller mill for 2 hours to mechanically coat the outside of MSF14.

Wet coating process of MSF14 with 1% 1,2 disterovl-sn-glycero-3-phosphatidylcholine. After drying 400 mg MSF14 were added to a vial that contained 6 mm yttrium stabilized zirconium cylindrical beads. The vial was placed on a 30° tilted roller mill for 15 minutes to break up any aggregates of MSF14. Next a 2 mg/mL solution was made by adding 4 mg of 1,2 disteroyl-sn-glycero-3-phosphatidylcholine into a separate vial and dissolving it in 2 mL of a 4/96 ethanol/cyclopentane solvent. Then the solution was added to the vial containing MSF14 and was placed back on the 30° tilted roller mill without a cap and rotated till all the solvent evaporated. The coated MSF14 CPEDPs were collected for further testing.

MSF25, a CPEDP, was made by first creating a dispersed phase (DP) premix by dissolving 360 mg of PLGA 7525, 2,200 mg of PLGA 8515, 160.0 mg of 1,2 disteroyl-sn-glycero-3-phosphatidylcholine, 80 mg of butylated hydroxytoluene, and 1,320.0 mg of sirolimus in 50.55 g of dichloromethane (DCM). Next a continuous phase (CP) premix was made by dissolving 1.312 g of Mowiol 4-88 (polyvinyl alcohol, 88% hydrolyzed) with heating to 60° C. in 162.19 g of purified water. Once the Mowiol 4-88 was fully dissolved the solution was allowed to cool and 492 mg of DCM was added to it. Next the DP was added into the CP while stirring the CP using a rotor-stator mixer to create an emulsion. Then the emulsion was added to 1148 mL of purified water to harden the CPEDPs. After hardening the mixture was centrifuged to collect the CPEDPs in the bottom of the centrifuge tube. Next the supernatant was poured off and the CPEDPs were dispersed in a 1148 mL of purified water and centrifuged again to wash the CPEDPs. Next the wash supernatant was poured off and the CPEDPs were dispersed in a small amount of water and vacuum dried overnight.

Zeta Potential of Polymer Encapsulated Drug Particles (PEDPs) and Charged Polymer Encapsulated Drug Particles (CPEDPs).

The zeta potential of the PEDPs and CPEDPs was measured using a Beckman Coulter Delsa Nano Particle Analyzer to characterize the zeta potential via electrophoretic light scattering (ELS) of MSF4, MSF5, and MSF12 as it is desired to have positive surface charge for particle adhesion to live tissue. Samples were created by dispersing 8-12 mg of each type of PEDP or CPADP in approximately 1 mL of purified water using an ultrasound bath for the dispersion process. The zeta potential measurements were then conducted by depositing a few drops of dispersion in a clean flow though cell with 25° C. purified water prior to measurement. The zeta potential measurements can be seen in Table 8.

TABLE 8

Zeta potential measurements.

| Sample | PEDP and CPEDP Configuration | Zeta Potential |
|---|---|---|
| MSF5 | Nonionic Ingredients: PLGA 5050 with Sirolimus Drug | −19.9 |
| MSF4 | Eudragit E Cationic polymer mixed with PLGA 7525 and Sirolimus Drug | +14.69 |
| MSF12 | 5% Zwitter-ionic phosphatidylcholine mixed with PLGA 7525 and PLGA 5050 | +7.35 |
| MSF13 | 2% 1,2 disteroyl-sn-glycero-3-phosphatidylcholine, 48% PLGA 7525, 18% PLGA 5050, 2% BHT, 30% Sirolimus Drug | +5.47 |
| MSF13 + 1,2 disteroyl-sn-glycero-3-phosphatidylcholine coating, 1% of microsphere mass | MSF13 with outside coating of zwitter-ionic phosphatidylcholine using wet coating process | +7.35 |
| MSF13 + DMAEMA coating, 1% of microsphere mass | MSF13 with outside coating of cationic polymer using wet coating process | +35.26 |
| MSF13 + Eudragit E coating, 1% of microsphere mass | MSF13 with outside coating of cationic polymer using wet coating process | +34.02 |
| MSF14 | 2% 1-palmitoyl-2-stearoyl-sn-glycero-3-phosphocholine, 56% PLGA 7525, 10% PLGA 5050, 2% BHT, 30% Sirolimus Drug | −13.34 |
| MSF14 + 1,2 disteroyl-sn-glycero-3-phosphatidylcholine coating, 1% of microsphere mass | MSF14 with outside coating of zwitter-ionic phosphatidylcholine using dry coating process | −2.09 |
| MSF14 + 1,2 disteroyl-sn-glycero-3-phosphatidylcholine coating, 1% of microsphere mass | MSF14 with outside coating of zwitter-ionic phosphatidylcholine using wet coating process | +1.57 |
| MSF25 no Drug or DSPC | 82.0% PLGA 8515, 16.0% PLGA 7525, 2% BHT | NA |
| MSF25 no DSPC | 56.9% PLGA 8515, 11.1% PLGA 7525, 2% BHT, 30% Sirolimus Drug | NA |
| MSF25-5 | 4% 1,2 disteroyl-sn-glycero-3-phosphatidylcholine, 55% PLGA 8515, 9% PLGA 7525, 2% BHT, 30% Sirolimus Drug | NA |
| MSF25-5 + 1,2 disteroyl-sn-glycero-3-phosphatidylcholine coating, 3% of microsphere mass | MSF25-5 with outside coating of zwitterionic phosphatidylcholine using wet coating process | NA |

Porcine Animal Study with Formulation MS122, MS123, and MS124.

Formula MS122 Sirolimus Coating Solution Preparation. Coating Solution Formula MS122 a charged polymer encapsulated drug particle (CPEDP) aqueous formulation was made. First MSF13, a CPEDPs, was made using the process described above. Then MSF13 was coated with 1% Eudragit E using the wet coating process described above. Next 313 mg of the coated MSF13 was added to a vial and dispersed in 2.06 mL of purified water. This solution was sonicated for 5-10 minutes to fully disperse the CPEDPs. Then in a separate vial a premix of 301 mg of 1-palmitoyl-2-lauroyl-sn-glycero-3-phosphocholine and 32 mg of 1,2-dilauroyl-sn-glycero-3-phosphatidylcholine was dissolved in 1.37 mL ethanol. Once dissolved 2.06 mL of water was added to dilute the premix. Next the premix was added to the dispersed CPEDPs and sonicated for 5-10 minutes. This solution, Formula MS122, was used to coat balloons for drug transfer testing in pigs.

Formula MS123 Sirolimus Coating Solution Preparation. Coating Solution Formula MS123 a charged polymer encapsulated drug particle (CPEDP) aqueous formulation was made. First MSF13, a CPEDPs, was made using the process described above. Then MSF13 was coated with 1% 1,2 disteroyl-sn-glycero-3-phosphatidylcholine using the wet coating process described above. Next 392 mg of the coated MSF13 was added to a vial and dispersed in 2.44 mL of purified water. This solution was sonicated for 5-10 minutes to fully disperse the CPEDPs. Then in a separate vial a premix of 333 mg of 1-palmitoyl-2-lauroyl-sn-glycero-3-phosphocholine and 38 mg of 1,2-dilauroyl-sn-glycero-3-phosphatidylcholine was dissolved in 1.62 mL ethanol. Once dissolved 2.44 mL of water was added to dilute the premix. Next the premix was added to the dispersed CPEDPs and sonicated for 5-10 minutes. This solution, Formula MS123, was used to coat balloons for drug transfer testing in pigs.

Formula MS124 Sirolimus Coating Solution Preparation. Coating Solution Formula MS124 a charged polymer encapsulated drug particle (CPEDP) and crystalline drug particle aqueous formulation was made. First MSF13, a CPEDPs, was made using the process described above. Then MSF13 was coated with 1% 1,2 disteroyl-sn-glycero-3-phosphatidylcholine using the wet coating process described above. Next 124 mg of crystalline sirolimus was added to a vial with 2.44 mL of purified water. Then a sonic probe was used to conduct a particle size reduction on the crystalline drug. Next 196 mg of the coated MSF13 was added to the vial containing the crystalline sirolimus particles. Then in a separate vial a premix of 194 mg of 1-palmitoyl-2-lauroyl-sn-glycero-3-phosphocholine and 136 mg of 1,2-dilauroyl-sn-glycero-3-phosphatidylcholine was dissolved in 1.61 mL ethanol. Once dissolved 2.44 mL of water was added to dilute the premix. Next the premix was added to the dispersed CPEDPs and sonicated for 5-10 minutes to fully disperse the CPEDPs and the crystalline sirolimus particles. This solution, Formula MS124, was used to coat balloons for drug transfer testing in pigs.

Formulations MS122, MS123, and MS124 were uniformly coated onto balloons of various sizes for acute drug transfer testing in a pig. The balloons were coated using an automated coating machine that precisely dispensed a prespecified volume of coating solution onto the surface of the balloon. The prespecified volume of solution was calculated based on the coating solution concentration and the desired nominal drug dose per balloon. The balloon sizes, diameter×length, were 6×30, and 18×65. The amount of drug per square millimeter for each balloon was 3.0 for the 18 mm diameter balloons. The amount of drug per square millimeter for each balloon was 3.5 for the 6 mm diameter balloons. This gave nominal drug dosing of 906 μg, and 11358 μg for the respective 6.0 and 18 mm diameter balloons. The 6 mm balloons were used in the pig's urethra with a stretch ratio of 1.0 to 2.0. Lastly the 18 mm balloons were used in the pig's esophagus, small intestine, and colon with stretch ratios of 1.0 to 2.0. For the urological and gastrointestinal treatments the balloon was tracked into position and the coating was allowed to hydrate for 1 minute prior to inflation. For the gastrointestinal treatments a gastroscope, enteroscope, or colonoscope was used to visualize the treatment site and flush the wall of the treatment site prior to use of the DCB. After all treatments the pig was survived for 24 hours then the treated tissue was excised in the necropsy lab and assayed for drug content. The measured sirolimus drug concentration in the various tissues can be seen in Table 9. The residual amount of drug left on the balloons post treatment can be seen in Table 10.

TABLE 9

Formulations MS122, MS123, and MS124 measured drug concentrations in various tissues

| Sample | Formula | Sirolimus [ug/g] |
|---|---|---|
| Prox Urethra | MS122 | 2.200 |
| Mid Urethra | MS123 | 0.375 |
| Dist Urethra | MS124 | 1.690 |
| Prox Esophagus | MS122 | 0.127 |
| Mid Esophagus | MS124 | 0.104 |
| Dist Esophagus | MS123 | Below limit of quantification |
| Prox Duodenum | MS122 | Below limit of quantification |
| Mid Duodenum | MS123 | 10.400 |
| Dist Duodenum | MS124 | Below limit of quantification |
| Prox Colon | MS124 | 9.470 |
| Dist Colon | MS123 | 8.230 |

TABLE 10

Residual amount of drug left on the balloons post treatment for MSF122, MSF123, and MS124.

| Sample | Formula Balloon | Sirolimus [ug] | % of Dose |
|---|---|---|---|
| Dist Urethra | MS124-6x50-2 | 1372.79 | 40.4 |
| Prox Colon | MS124-18x65-1 | 6201.47 | 54.6 |
| Dist Duodenum | MS124-18x65-4 | 113.58 | 1.0 |
| Mid Esophagus | MS124-18x65-3 | 1453.82 | 12.8 |
| Mid Urethra | MS123-6x50-3 | 683.00 | 20.1 |
| Dist Esophagus | MS123-18x65-2 | 2419.25 | 21.3 |
| Mid Duodenum | MS123-18x65-3 | 2226.17 | 19.6 |
| Distal Colon | MS123-18x65-1 | 6485.42 | 57.1 |
| Prox Urethra | MS122-6x50-2 | 1077.17 | 31.7 |
| Prox Duodenum | MS122-18x65-3 | 34.07 | 0.3 |
| Prox Esophagus | MS122-18x65-2 | 147.65 | 1.3 |

Formula C6SsusF9 Sirolimus Coating Solution Preparation. Coating Solution Formula C6SsusF9 a charged polymer encapsulated drug particle (CPEDP) dispersed in predominantly nonpolar organic solvent with dissolved phospholipids was made. First MSF 18, a CPEDP, was made using the same process described above to make MSF13 and MSF14. Then 328 mg of dried MSF18 was coated with 9.84 mg (3% of CPEDPs) 1,2-distearoyl-sn-glycero-3-phosphocholine using the wet coating process described above. Then in a separate vial 328 mg of 1-palmitoyl-2-stearoyl-sn-glycero-3-phosphocholine was dissolved in 5 mL of 4/96 ethanol/cyclohexane v/v solvent. Once dissolved this solution was added to the vial containing the coated CPEDPs.

Next the full mixture was a sonicated for 2-5 minutes to fully disperse the CPEDPs. This solution, C6SsusF9, was collected and assayed for drug concentration. The resulting measurement was 17.5 mg/mL sirolimus.

Formula C6SsusF11 Sirolimus Coating Solution Preparation. Coating Solution Formula C6SsusF 11, a polymer encapsulated drug particle (CPEDP) dispersed in nonpolar organic solvent with dissolved mismatched, unsaturated acyl group phospholipids, was made. First, MSF21, a CPEDP, was made using the same process described above to make MSF13 and MSF14. Then 303 mg of MSF21 was weighed into a vial and 2 mL of cyclohexane was added to it. The contents of the vial were sonicated to disperse the CPEDPs to create premix 1. Then in a separate vial 303 mg of 1-palmitoyl-2-oleoyl-sn-glycero-3-phosphocholine was dissolved with mild heat in 2 mL cyclohexane solvent to create premix 2. Next premix 2 was added to premix 1 and the full mixture was a sonicated for 2-5 minutes to fully disperse the CPEDPs. This solution, C6SsusF11, was collected and assayed for drug concentration. The resulting measurement was 20.0 mg/mL sirolimus.

Formula C6SsusF12 Sirolimus Coating Solution Preparation. Coating Solution Formula C6SsusF12, a polymer encapsulated drug particle (CPEDP) dispersed in nonpolar organic solvent with dissolved matched, unsaturated acyl group phospholipids, was made. First, MSF21, a CPEDPs, was made using the same process described above to make MSF13 and MSF14. Then 302 mg of MSF21 was weighed into a vial and 2 mL of cyclohexane was added to it. The contents of the vial were sonicated to disperse the CPEDPs to create premix 1. Then in a separate vial 304 mg of 1,2-dioleoyl-sn-glycero-3-phosphocholine was dissolved with mild heat in 2 mL cyclohexane solvent to create premix 2. Next premix 2 was added to premix 1 and the full mixture was a sonicated for 2-5 minutes to fully disperse the CPEDPs. This solution, C6SsusF12, was collected and assayed for drug concentration. The resulting measurement was 20.6 mg/mL sirolimus.

Formula C6SsusF13 Sirolimus Coating Solution Preparation. Coating Solution Formula C6SsusF13, a polymer encapsulated drug particle (CPEDP) dispersed in nonpolar organic solvent with dissolved matched, unsaturated acyl group phospholipids, was made. First, MSF21, a CPEDP, was made using the same process described above to make MSF13 and MSF14. Then 304 mg of MSF21 was weighed into a vial and 2 mL of cyclohexane was added to it. The contents of the vial were sonicated to disperse the CPEDPs to create premix 1. Then in a separate vial 30.3 mg of 1,2-dioleoyl-sn-glycero-3-phosphocholine and 272.7 mg of 1-palmitoyl-2-oleoyl-sn-glycero-3-phosphocholine was dissolved with mild heat in 2 mL cyclohexane solvent to create premix 2. Next premix 2 was added to premix 1 and the full mixture was a sonicated for 2-5 minutes to fully disperse the CPEDPs. This solution, C6SsusF12, was collected and assayed for drug concentration. The resulting measurement was 20.1 mg/mL sirolimus.

Formula C6SsusF13-3, MSF25 Sirolimus Coating Solution Preparation. Coating Solution Formula C6SsusF13-3, a polymer encapsulated drug particle (CPEDP) dispersed in nonpolar organic solvent with dissolved matched, unsaturated acyl group phospholipids, was made. First, MSF25, a CPEDP, was made using the methods described above. Then 2.622 g of MSF25 was weighed into a bottle and 22.5 mL of cyclohexane was added to it. The contents of the vial were sonicated to disperse the CPEDPs to create premix 1. Then in a separate vial 262.2 mg of 1,2-dioleoyl-sn-glycero-3-phosphocholine and 2.360.1 g of 1-palmitoyl-2-oleoyl-sn-glycero-3-phosphocholine was dissolved with mild heat in 22.5 mL cyclohexane solvent to create premix 2. Next premix 2 was added to premix 1 and the full mixture was a sonicated for 2-5 minutes to fully disperse the CPEDPs. This solution, C6SsusF13-3, was collected and assayed for drug concentration. The resulting measurement was 17.98 mg/mL sirolimus. 18 mm diameter by 65 mm length balloon catheters of were coated using this formulation. The target dose for the catheters was 9.2 mg. The balloons were pleat and folded, packaged, vacuum dried, and sterilized. These balloons were used to treat 6 pigs in their esophagus, duodenum, and colon detailed in Example IV-4 below.

Part II. Human Clinical Testing Urethral Strictures.

Uroflowmetry ($Q_{max}$ measurement). Uroflowmetry is performed by urinating into a special urinal, toilet, or disposable device that has a measuring device built into it. The parameter, $Q_{max}$, is the maximum flow rate measured during a uroflowmetery test. This method was used prior to treatment (baseline) and at follow-up visits of 14 days, 1, 3, 6, a12 months, and 2 years to demonstrate the longevity of the treatment.

Post-void residual (PVR) is a measurement of the volume of urine left in the bladder after voiding. It is measured using ultrasound prior to treatment (baseline) and at follow-up visits of 14 days, 1, 3, 6, 12 months, and 2 years to demonstrate the longevity of the treatment.

International Prostate Symptom Score (IPSS). The IPSS is based on the answers to eight questions—seven regarding disease symptoms and one question related to the patient's quality of life: 1) Incomplete Emptying; How often have you had the sensation of not emptying your bladder? 2) Frequency; How often have you had to urinate less than every two hours? 3) Intermittency; How often have you found you stopped and started again several times when you urinated? 4) Urgency; How often have you found it difficult to postpone urination? 5) Weak Stream; How often have you had a weak urinary stream? 6) Straining; How often have you had to strain to start urination? 7) Nocturia; How many times did you typically get up at night to urinate? 8) Quality of Life Due to Urinary Symptoms; If you were to spend the rest of your life with your urinary condition just the way it is now, how would you feel about that? Although the IPSS was developed for BPH it can be applied to other bladder outlet obstructive diseases such as stricture to determine if obstructive symptoms are improved after a medical treatment. For the symptom questions, the patient is asked to choose the rating that best represents their condition. The scale ranges from 0 to 5, with 5 representing the most symptomatic disease. The seven symptom scores are summed to give an overall maximum possible score of 35. The answer to the quality of life question is scored on a scale of 0 to 6. According to these scoring systems, the scores can be categorized as follows: symptoms are mild if the score is 7 or less; symptoms are moderate if the score is 8 to 19; and symptoms are severe if the score is 20 to 35. This questionnaire was given prior to treatment (baseline) and at follow-up visits of 14 days, 1, 3, 6, 12 months, and 2 years to demonstrate the longevity of the treatment.

Example II-1. Testing of Drug-Coated Balloons in Urethral Strictures of Human Subjects Drug-coated balloon catheters with a dose density of 3.5 µg of paclitaxel per millimeter squared of balloon surface area were used to treat human subjects that had stricture disease in a clinical study. The drug-coated balloon catheters had nominal diameters of 6, 8, 10, 12, and 14 mm and lengths of 30 and 50 mm at nominal pressure of 6 atm. The paclitaxel (PTX) dosing per balloon size can be seen in Table 11.

TABLE 11

| Paclitaxel (PTX) dosing per balloon size. | | |
|---|---|---|
| Diameter (mm) | 30 mm Length | 50 mm Length |
| 6 | 1979 μg PTX | 3299 μg PTX |
| 8 | 2639 μg PTX | 4398 μg PTX |
| 10 | 3299 μg PTX | 5498 μg PTX |
| 12 | 3958 μg PTX | 6597 μg PTX |
| 14 | 4618 μg PTX | 7697 μg PTX |

The drug-coated balloon catheters had a dual lumen shaft design with a single inflatable balloon. One lumen was sized to accommodate a 0.038" guide wire lumen. The other lumen was the inflation port lumen and allows the balloon to be inflated with mixture of saline and contrast fluid. The drug-coated balloon catheter had a manifold with two Luer-style connections, one connection was compatible with an inflation syringe, the other allowed the guidewire to protrude out of the manifold so the balloon catheter could freely slide onto the guidewire. The 6 and 8 mm drug-coated balloon catheters had a rated burst pressure of 12 atmospheres. The 10, 12, and 14 mm drug-coated balloon catheters had a rated burst pressure of 10 atmospheres. The balloon was made of polyamide.

Treatments were performed for 53 patients for bulbar urethral strictures. Of these patients, 5 were retreated due to stricture recurrence, bring the total number of treatments to 58. All patients were male as the study excluded female patients. Subjects enrolled in the study had a minimum of 1 and a maximum of 3 prior interventions for urethral stricture. The age range was 50.7±15.47 years. The etiologies of urethral stricture across the patient population were 50.9% traumatic, 45.3% iatrogenic, and 3.8% idiopathic. Of 53 patients, 7 had a suprapubic catheter at baseline. The stricture length on average was 0.9 cm and the average stricture diameter was 2.47 mm.

The clinical treatment strategy involved predilation of the stricture with direct vision internal urethrotomy (DVIU), an uncoated non-compliant balloon, or a combination of both. An uncoated balloon was used to predilate 32 patients, 16 patients were predilated with both an uncoated balloon and DVIU, and 10 patients were predilated with DVIU only. Following predilation all subjects were treated with the paclitaxel drug-coated balloons. 26 patients were treated with the 8×30 mm balloons. 27 patients were treated with the 10×30 mm balloons.

Clinical subjects were evaluated at 14, 30, 90, 180, 365 days, and 2 years after the index procedure. Evaluations included analysis of stricture free rate, uroflowmetry including $Q_{max}$, and PVR. Additionally, pharmacokinetic analysis was completed for the paclitaxel content in the blood, urine, semen, and residual drug on the drug-coated balloons.

On average patient IPSS improved from a baseline average of 25.2, to 5.2 at 14 days, 4.3 at 30 days, 6.1 at 90 days, 4.6 at 180 days, 4.5 at 365 days, and 6.9 at 2 years. Average patient $Q_{max}$ at baseline was 5.0 mL/sec and improved to 22.2 mL/sec at 14 days, 22.8 mL/sec at 30 days, 21.4 mL/sec at 90 days, 19.8 mL/sec at 180 days, 20.1 mL/sec at 365 days, and 17.5 mL/sec at 2 years. Average patient PVR was 141.4 mL at baseline and improved to 35.7 mL at 14 days, 36.1 mL at 30 days, 38.8 mL at 90 days, 30.1 mL at 180 days, 24.6 mL at 365 days, and 45.5 mL at 2 years. Stricture free rate was 75.5% (37/49) at day 180 and 74.5% (37/47) at 365 days.

Human plasma paclitaxel concentration on average was 0.1 ng/mL immediately post treatment and was below the level of quantification for all other later time points, 1 hour, 3 hours, 5 hours, 10 hours, 24 hours, and 5 days. Human urine paclitaxel concentration on average was 184 ng/mL immediately post procedure, 2.6 ng/mL at 5 days, 0.3 ng/mL at 14 days, and 0.1 ng/mL at 30 days. Human semen paclitaxel concentration on average was 2.5 ng/mL at 14 days and 1.0 ng/mL at 30 days.

Residual drug content on the balloons used to treat human subject was on average 2.7% of the original dose with a range of 0.1% to 28.0%.

Example II-3. Human Clinical Subject B from Example III-1 Treated with an Uncoated Predilation Balloon Followed by a 10 mm Nominal Diameter Drug-Coated Balloon Catheter Subject B had a 1.8 cm length by 2.0 mm diameter stricture in his anterior urethra. Specifically, the bulbar portion of the anterior urethra. This was determined by conducting a retrograde urethragram. The human clinical subject had a baseline $Q_{max}$ of 8 mL/second, PVR of 45 mL, and a baseline IPSS score of 30. First a cystoscope was inserted into the urethra. Then a guidewire was inserted into the working channel of the cystoscope. Next a predilation balloon that had a nominal diameter of 10 mm and a length of 20 mm was inserted into the urethra over the guidewire and positioned so the balloon crossed the stricture. The predilation balloon was inflated to 20 atmospheres with a syringe that had a pressure gauge on it. The syringe contained a mixture of saline and contrast media. A fluoroscopic image was acquired to ensure the balloon had a uniform expansion. Once this was confirmed the balloon was deflated and withdrawn from the urethra. Next a drug-coated balloon that had a nominal diameter of 10 mm and a length of 30 mm was inserted into the urethra over the guidewire. The drug-coated balloon was positioned such that the balloon body completely covered the predilated stricture area. The drug-coated balloon was held in position for at least 1 minute prior to inflating to hydrate the coating. Then the drug-coated balloon was inflated with a mixture of saline and contrast media using the syringe that had a pressure gauge on it. The balloon was inflated to 10 atmospheres for 5 minutes. Then the balloon was deflated and withdrawn from the human subject. The stretch ratio for the 10 mm nominal diameter drug-coated balloon was 1.3 to 1.5. The diameter of the dilated stricture was 10 mm after dilation. The residual drug remaining on the balloon after use was analyzed. The residual amount of paclitaxel left on the balloon was 49.1 μg (1.5 percent of the initial drug load). The human clinical subject had follow-up visits at 14, 30, 90, 180, 365 days, and 2 years to measure maximum urine flow rate, PVR, and IPSS score. Additionally, the urethral caliber of the human clinical subject was assessed at 6 and 12 months to determine if the urethra was greater than 16 French (5.3 mm) by visualizing and passing a flexible cystoscope past the previously treated area. The human clinical subject had a maximum urine flow rate improvement from 8 mL/second to 25, 29, 36, 34, 34, and 23 mL/second at follow-up visits of 14, 30, 90, 180, 365 days, and 2 years respectively. The human clinical subject had PVR improvement from 45 mL to 30, 28, 35, 26, 3, and 10 mL at follow-up visits of 14, 30, 90, 180, 365 days, and 2 years respectively. The human clinical subject had an IPSS improvement from 30 to 4, 3, 5, 2, 3, and 3 at follow-up visits of 14, 30, 90, 180 365 days, and 2 years respectively. The human clinical subject had a urethra caliber greater than 16 French (5.3 mm) at 6 and 12 months.

Part III. Human Clinical Testing Benign Prostatic Hyperplasia.

Example III-1. BPH Human Clinical Testing: Single Lumen & Reinforced Fixed Wire Drug-Coated Balloon Catheter Drug-coated balloon catheters with a dose density of 2.4 μg of paclitaxel per millimeter squared were used to treat human subjects that had benign prostatic hyperplasia disease in a clinical study. The balloons had a single neck positioned approximately 10 mm from the distal cone of the balloon. The neck length was 2 mm for all the balloons. The proximal lobe or treatment lobe had a range of different diameters and length, while the distal lobe or bladder lobe was always the same 10 mm length and matched the diameter of the treatment lobe. The drug-coated balloon catheters had nominal diameters of 30, 35, 40, and 45 mm and dilation lengths of 30, 35, 40, 45, and 50 mm at a nominal inflation pressure of 2 atm. For balloon diameters of 30 mm the neck diameter was 12 mm, for balloon diameters of 35 mm the neck diameter was 15 mm, for balloon diameters of 40 mm the neck diameter was 20 mm, and for balloon diameters of 45 mm the neck diameter was 23 mm. All balloons sizes had a rated burst pressure of 4 atm. The balloons were coated with paclitaxel from halfway up the proximal cone, over the entire treatment lobe, over the entire neck section, and the body portion of the bladder lobe. The paclitaxel (PTX) dosing per balloon size can be seen in Table 12.

TABLE 12

Paclitaxel (PTX) dosing per balloon size.

| Diameter (mm) | 30 mm Length | 35 mm Length | 40 mm Length | 45 mm Length | 50 mm Length |
|---|---|---|---|---|---|
| 30 | 9586 μg PTX | 11433 μg PTX | 12567 μg PTX | 13661 μg PTX | 15256 μg PTX |
| 35 | 12403 μg PTX | 13915 μg PTX | 15238 μg PTX | 16561 μg PTX | 18073 μg PTX |
| 40 | 15220 μg PTX | 16543 μg PTX | 18055 μg PTX | 19567 μg PTX | 20890 μg PTX |
| 45 | 18037 μg PTX | 19455 μg PTX | 20872 μg PTX | 22290 μg PTX | 23707 μg PTX |

Two catheter designs were used in this study. The balloon shape, material, and dimensions were identical across the two catheter platforms. The difference between the two balloon catheters was the catheter shaft design. The first design was a single lumen design without a Luer hub and was designed to be back loaded into a cystoscope. The second design was a reinforce fixed wire catheter shaft with a Luer hub attached and was designed to be positioned side-by-side with a cystoscope.

Single lumen design: The drug-coated balloon catheters had a single lumen nylon 12 shaft design with holes punched under the balloon to allow inflation of the drug-coated balloon. The catheter shaft did not have a Luer and was designed to connect to a Tuohy Borst valve and Luer compatible stopcock after passing through the working channel of a cystoscope. The balloon neck was reinforced with ultra-high molecular weight polyethylene (UHMWPE) fibers that were fixed in place to minimize diameter growth during inflation. The balloon neck anchors into the bladder neck during balloon inflation and prevents migration of the proximal balloon lobe into the bladder. The proximal lobe of the balloon (treatment lobe) is located in the prostatic urethra and sized to fit the prostate. The distal balloon lobe is used for positioning and provides dilation of the bladder neck and any intra prostatic protrusion present during balloon inflation. The balloon is made of a high durometer polyether block amide (74D PEBA). At the distal end of the catheter a silicone Coude tip is attached that allows the catheter to be tracked in the prostatic urethra. The Coude tip is specially curved to conform to the male urethra anatomy and is atraumatic to prevent damage during insertion. The balloon portion of the catheter was pleat and folded down to a caliber of 19 French and a sheath was place over the balloon. The delivery sheath had three functions. One was to cover and protect the balloon. Two was to form a smooth cylindrical catheter body that allows the balloon catheter to be tracked through the urethra and positioned into the prostatic urethra. The last was to recapture the balloon after the treatment to facilitate removal of the device. Balloon catheters with a diameter of 30 or 35 mm had a 21Fr sheath while balloon catheters with a diameter of 40 or 45 mm had a 24 Fr sheath. The sheath was constructed with an inner layer of etched PTFE liner, a middle layer of a flat coiled wire, and an outer layer of polyether block amine (35D PEBA). The sheath and Coude tip were sized identically and have mating features to make a single smooth insertion surface.

Reinforce fixed wire design: The drug-coated balloon catheters had a catheter shaft that consisted of a single lumen extrusion of high durometer polyether block amide (72D PEBA). Within the extrusion lumen a cylindrical 304 stainless steel mandrel ran the length of the catheter and under the balloon. The mandrel is thermally bonded into the distal tip and the proximal end of the catheter near the Luer hub. The mandrel is reinforced under the balloon section with a 304 stainless steel tube to prevent buckling. The catheter shaft extrusion is terminated under the proximal balloon bond allowing inflation of the drug-coated balloon. At the proximal end of the catheter shaft a female Luer hub is adhesively bonded to the catheter shaft extrusion to allow connection to an inflation device. The balloon neck is reinforced with ultra-high molecular weight polyethylene (UHMWPE) fibers that were fixed in place to minimize diameter growth during inflation. The balloon neck anchors into the bladder neck during balloon inflation and prevents migration of the proximal balloon lobe into the bladder. The proximal lobe of the balloon (treatment lobe) is located in the prostatic urethra and sized to fit the prostate. The distal balloon lobe is used for positioning and provides dilation of the bladder neck and any intra prostatic protrusion present during balloon inflation. The balloon was made of a high durometer polyether block amide (74D PEBA). At the distal end of the catheter a silicone Coude tip is attached that allows the catheter to be tracked in the prostatic urethra. The Coude tip is specially curved to conform to the male urethra anatomy and is atraumatic to prevent damage during insertion. The balloon portion of the catheter was pleat and folded down to a caliber of 19 French and a sheath was place over the balloon. The delivery sheath had three functions. One was to cover and protect the balloon. Two was to form a smooth cylindrical catheter body that allows the balloon catheter to be tracked through the urethra and positioned into the prostatic urethra. The last was to recapture the balloon after the treatment to facilitate removal of the device. Balloon catheters with a diameter of 30 and 35 mm had a 21 Fr sheath while balloon catheters with a diameter of 40 and 45 mm had a 24Fr sheath. The sheath was constructed with an inner layer of etched PTFE liner, a middle layer of a flat coiled wire, and an outer layer of polyether block amine (72D PEBA). The sheath and Coude tip were sized identically and have mating features to make a single smooth insertion surface. This design also included a preloaded obturator place over the top of the catheter shaft. The obturator was made of LDPE, had a radiused distal tip, and had a flared proximal end to interface with the sheath. The combined sheath and obturator were used to track through the urethra and recapture the balloon after the treatment.

In total 80 patients were treated for benign prostatic hyperplasia. All patients were male as the study excluded female patients. Subjects enrolled in the study had a minimum IPSS score of 13, a $Q_{max}$ ranging from 5 to 15 mL, prostate volumes between 20 and 80 grams, and prostatic urethral lengths between 35 and 55 mm. The average age was 65.8±7.82 years.

The clinical treatment strategy involved predilation of the prostate to create a commissurotomy between the lateral lobes. The predilation balloon was an uncoated balloon catheter identical in size or smaller than the selected drug-coated balloon. The predilation balloons were designed identically to the drug-coated balloons. 49 patients were treated with the single lumen catheter shaft design and 31 patients were treated with the reinforced fixed wire catheter shaft design. 18 patients were treated with a 30×35 mm drug-coated balloon, 32 patients were treated with a 35×35 mm drug-coated balloon, 8 patients were treated with a 35×45 mm drug-coated balloon, and 22 patients were treated with a 40×45 mm drug-coated balloon.

Clinical subjects were evaluated at 14, 30, 90, 180, and 365 days after the index procedure. Evaluations included analysis IPSS, uroflowmetry including $Q_{max}$, and PVR. Additionally, pharmacokinetic analysis was completed for the paclitaxel content in the blood, urine, semen, and residual drug on the drug-coated balloons.

On average patient IPSS improved from a baseline average of 22.3, to 10.7 at 14 days, 9.0 at 30 days, 8.1 at 90 days, 8.0 at 180 days, and 8.3 at 365 days. Average patient $Q_{max}$ at baseline was 10.9 mL/sec and improved to 18.5 mL/sec at 14 days, 20.1 mL/sec at 30 days, 20.4 mL/sec at 90 days, 20.1 mL/sec at 180 days, and 18.3 mL/sec at 365 days. Average patient PVR was 64.0 mL at baseline and improved to 41.4 mL at 14 days, 28.4 mL at 30 days, 33.9 mL at 90 days, 29.7 mL at 180 days, and 31.7 mL at 365 days.

Human plasma paclitaxel concentration on average was 0.2 ng/mL immediately post treatment, 0.2 ng/mL at 1 hour, 0.1 ng/mL at 3 hours, 0.1 ng/mL at 5 hours, 0.07 ng/mL at 10 hours, 0.03 ng/mL at 24 hours, and 0.02 ng/mL at 4 days. Human urine paclitaxel concentration on average was 598 ng/mL immediately post procedure, 202 ng/mL at 4 days, 5.2 ng/mL at 14 days, and 5.1 ng/mL at 30 days. Human semen paclitaxel concentration on average was 5.3 ng/mL at 14 days, 3.2 ng/mL at 30 days, and 0.12 ng/mL at 6 months.

Residual drug content on the balloons used to treat human subject was on average 23.0% of the original dose with a range of 7.7% to 47.1%.

Part IV. Preclinical Testing Drug-Coated Balloons in the Gastrointestinal (GI) Tract.

Example IV-1. GI Preclinical Study 1

Twenty-eight balloon catheters (10, 15 and 18 mm in diameter and 55 mm in length) were inflated to 1 atmosphere and wiped with an ethanol wipe to clean the balloon surface. The balloons were coated using Formulation 23 from Example I-1 with sufficient coating solution to achieve 3.5 microgram paclitaxel per square mm of balloon surface. The balloons were then dried, folded, sheathed, packaged in a Tyvek pouch and ethylene oxide sterilized in preparation for animal testing.

For this study male pigs were used. Pretreatment endoscopy was conducted to measure the inner diameter of the esophagus, duodenum, and colon treatment sites before drug-coated balloon treatment. For biliary tract treatments endoscopic retrograde cholangiopancreatography (ERCP) with sphincterotomy of the ampula of vater was conducted to take a cholangiogram of the biliary tract and identify the treatment sites. The esophagus, duodenum and colon treatment site diameters were approximately 15-18 mm. The biliary tract treatment site diameters were 4-8 mm. The balloon catheters were chosen such that the stretch ratio for the treatments was approximately 1.1-2.2. Drug-coated balloon catheters were used with nonoverlapping treatments in the esophagus, duodenum, biliary tract and colon. An endoscope was used to visualize the treatment site. The treatment site was flushed with sterile saline prior to tracking the balloons in. The drug-coated balloon catheters were tracked down the working channel of the endoscope until they reached the treatment site. Prior to inflation the drug coating was allowed to hydrate for 1 minute. The drug-coated balloon catheters were then inflated to rated burst pressure at the treatment sites for 2 min to release drug and additive, then deflated and withdrawn from the pigs. The pigs were sacrificed so the tissue drug content could be measured after 1 hour and the residual drug remaining on the balloon after use was analyzed.

The pig tissue drug concentration from the esophagus, duodenum, biliary tract and colon samples was 19.5, 28.7, 309.0 and 5.5 μg/g respectively at 1 hour. The residual balloon content as a percent of the original drug loading from the samples ranged from 1.35-65.5%.

Example IV-2. GI Preclinical Study 2

Eighty balloon catheters (10, 15 and 18 mm in diameter and 55 mm in length) were inflated to 1 atmosphere and wiped with an ethanol wipe to clean the balloon surface. The balloons were coated using Formulation 23 from Example I-1 with sufficient coating solution to achieve 3.5 microgram paclitaxel per square mm of balloon surface. The balloons were then dried, folded, sheathed, packaged in a Tyvek pouch and ethylene oxide sterilized in preparation for animal testing.

For this study male pigs were used. Pretreatment endoscopy was conducted to measure the inner diameter of the esophagus, duodenum, and colon treatment sites before drug-coated balloon treatment. The esophagus, duodenum and colon treatment site diameters were approximately 15-18 mm. The balloon catheters were chosen such that the stretch ratio for the treatments was approximately 1.1-2.2. Drug-coated balloon catheters were used with nonoverlapping treatments in the esophagus, duodenum and colon. An endoscope was used to visualize the treatment site. The treatment site was flushed with sterile saline prior to tracking the balloons in. The drug-coated balloon catheters were tracked down the working channel of the endoscope until they reached the treatment site. Prior to inflation the drug coating was allowed to hydrate for 1 minute. The drug-coated balloon catheters were then inflated to rated burst pressure at the treatment sites for 2 min to release drug and additive, then deflated and withdrawn from the pigs. The tissue drug content was measured after 1 hour. The pig tissue drug concentration from the esophagus, duodenum, and colon samples was 66.1, 40.3, and 127.0 μg/g respectively at 1 hour.

Example IV-3. GI Preclinical Study 3

Twenty-eight balloon catheters (6 and 8 mm in diameter by 30 mm in length) were inflated to 1 atmosphere and wiped with an ethanol wipe to clean the balloon surface. The balloons were coated using Formulation 23 from Example I-1 with sufficient coating solution to achieve 3.5 microgram paclitaxel per square mm of balloon surface. The balloons were then dried, folded, sheathed, packaged in a Tyvek pouch and ethylene oxide sterilized in preparation for animal testing.

For this study male pigs were used. Endoscopic retrograde cholangiopancreatography (ERCP) with sphincterotomy of the ampula of vater was conducted to take a cholangiogram of the biliary tract and identify the treatment sites. The biliary tract treatment site diameters were 4-8 mm. The balloon catheters were chosen such that the stretch ratio for the treatments was approximately 1.5-2.2. Drug-coated balloon catheters were used with nonoverlapping treatments in the biliary tract. The drug-coated balloon catheters were tracked down the working channel of the duodenoscope until they reached the treatment site. Prior to inflation the drug coating was allowed to hydrate for 1 minute. The drug-coated balloon catheters were then inflated to rated burst pressure at the treatment sites for 2 min to release drug and additive, then deflated and withdrawn from the pigs. The tissue drug content was measured after 1 hour. The pig tissue drug concentration from the biliary tract samples was 170.0 μg/g at 1 hour.

Example IV-4. Chronic GI Preclinical Study with Sirolimus Coated Balloon Catheters 42 balloon catheters (18 mm in diameter and 65 mm in length) were inflated to 1 atmosphere and wiped with an ethanol wipe to clean the balloon surface. The balloons were evenly coated using Formulation C6SsusF13-3, MSF25 from Example I-1 with sufficient coating solution to achieve 9.2 mg drug dosing. The DCBs were used with nonoverlapping treatments in the esophagus, duodenum and colon. An endoscope was used to visualize the treatment site. The treatment site was flushed with sterile saline prior to tracking the balloons in. The drug-coated balloon catheters were tracked down the working channel of the endoscope until they reached the treatment site. Prior to inflation the drug coating was allowed to hydrate for 1 minute. The drug-coated balloon catheters were then inflated to rated burst pressure at the treatment sites for 2 min to release drug and additive, then deflated and withdrawn from the pigs and collected for residual drug content measurements. After treatments the pigs were survived for 1 hours, 7 day, and 28 days and then the treated tissue was excised and bisected in the necropsy lab with one half of the sample being assayed for drug content and the other half sample going to histology. The measured sirolimus drug concentration in the various tissues can be seen in Table 13. The residual amount of drug left on the balloons post treatment can be seen in Table 14.

TABLE 13

Formulation C6SsusF13-3, MSF25 Sirolimus Coating measured drug concentrations in various tissues.

| Subject | Segment | Sample weight (g) | Rapamycin Conc. (ng/g) | Total Rapamycin (ng) | Day Collected |
|---|---|---|---|---|---|
| 20P1311 | Esophagus Prox | 4.8272 | 6430 | 31000 | 0.04 |
| 20P1311 | Esophagus Distal | 4.1582 | 7600 | 31600 | 0.04 |
| 20P1311 | Duodenum Prox | 4.1988 | 1300 | 5460 | 0.04 |
| 20P1311 | Duodenum Distal | 4.1128 | 1040 | 4280 | 0.04 |
| 20P1311 | Colon Prox | 7.4891 | 1820 | 13600 | 0.04 |
| 20P1311 | Colon Distal | 6.7983 | 1920 | 13100 | 0.04 |
| 20P1311 | Urethra Prox | 2.3321 | 950 | 2220 | 0.04 |
| 20P1311 | Urethra Distal | 2.2199 | 23700 | 52600 | 0.04 |
| 20P1389 | Esophagus Prox | 1.7552 | 76.1 | 134 | 7 |
| 20P1389 | Esophagus Distal | 2.0545 | 37.7 | 77.5 | 7 |
| 20P1389 | Duodenum Prox | 3.1134 | 52.0 | 162 | 7 |
| 20P1389 | Duodenum Distal | 3.3873 | 63.4 | 215 | 7 |
| 20P1389 | Colon Prox | 2.8320 | 73.2 | 207 | 7 |
| 20P1389 | Colon Distal | 4.7838 | 78.8 | 377 | 7 |
| 20P1389 | Urethra Prox | 0.7627 | 46.7 | 35.6 | 7 |
| 20P1389 | Urethra Distal | 0.4232 | 25.7 | 10.9 | 7 |
| 20P1390 | Esophagus Prox | 2.2717 | 75.4 | 171 | 7 |
| 20P1390 | Esophagus Distal | 1.9296 | 56.5 | 109 | 7 |
| 20P1390 | Duodenum Prox | 3.6512 | 77.5 | 283 | 7 |
| 20P1390 | Duodenum Distal | 4.0159 | 57.4 | 231 | 7 |
| 20P1390 | Colon Prox | 2.2745 | 92.5 | 210 | 7 |
| 20P1390 | Colon Distal | 5.1932 | 107 | 556 | 7 |
| 20P1309 | Esophagus Prox | 3.5945 | 5.34 | 19.2 | 28 |
| 20P1309 | Esophagus Distal | 4.5356 | 1.96 | 8.89 | 28 |
| 20P1309 | Duodenum Prox | 2.6779 | 5.70 | 15.3 | 28 |
| 20P1309 | Duodenum Distal | 2.8140 | 4.63 | 13.0 | 28 |
| 20P1309 | Colon Prox | 3.0973 | 20.7 | 64.1 | 28 |
| 20P1309 | Colon Distal | 4.3016 | 6.79 | 29.2 | 28 |
| 20P1309 | Urethra Prox | 2.3129 | 5.88 | 13.6 | 28 |
| 20P1309 | Urethra Distal | 0.9159 | 3.52 | 3.22 | 28 |
| 20P1310 | Esophagus Prox | 3.3146 | 5.21 | 17.3 | 28 |
| 20P1310 | Esophagus Distal | 2.8290 | 1.55 | 4.38 | 28 |
| 20P1310 | Duodenum Prox | 3.6420 | 4.51 | 16.4 | 28 |
| 20P1310 | Duodenum Distal | 3.3454 | 2.31 | 7.73 | 28 |
| 20P1310 | Colon Prox | 3.0805 | 4.35 | 13.4 | 28 |
| 20P1310 | Colon Distal | 8.0090 | 6.54 | 52.4 | 28 |

TABLE 14

Residual amount of drug left on the balloons post treatment for C6SsusF13-3, MSF25.

| Subject | Treatment Location | Residual Sirolimus (mg) | % of Dose |
|---|---|---|---|
| 20P1309 | Prox Duo | 0.5 | 5.7% |
| 20P1309 | Dist Eso | 2.3 | 25.4% |
| 20P1309 | Prox Colon | 1.2 | 13.5% |
| 20P1309 | Dist Duo | 1.1 | 11.9% |
| 20P1309 | Dist Colon | 4.5 | 49.2% |
| 20P1309 | Prox Eso | 3.4 | 36.8% |
| 20P1310 | Prox Eso | 2.6 | 27.9% |
| 20P1310 | Dist Duo | 1.5 | 16.8% |
| 20P1310 | Colon Dist | 4.2 | 45.8% |
| 20P1310 | Prox Colon | 4.1 | 44.7% |
| 20P1310 | Dist Eso | 2.5 | 26.8% |
| 20P1310 | Prox Duo | 0.8 | 9.2% |
| 20P1311 | Dist Duo | 1.0 | 10.4% |
| 20P1311 | Dist Colon | 2.2 | 23.6% |
| 20P1311 | Prox Duo | 1.6 | 17.5% |
| 20P1311 | Dist Eso | 4.5 | 48.6% |
| 20P1311 | Prox Colon | 1.2 | 13.4% |
| 20P1311 | Prox Eso | 3.6 | 39.6% |
| 20P1389 | Prox Colon | 1.9 | 20.1% |
| 20P1389 | Prox Duo | 0.5 | 5.0% |
| 20P1389 | Dist Eso | 2.0 | 21.3% |
| 20P1389 | Prox Eso | 2.6 | 28.4% |
| 20P1389 | Dist Duo | 4.5 | 49.0% |
| 20P1389 | Dist Colon | 0.2 | 2.0% |
| 20P1390 | Prox Colon | 5.7 | 62.3% |
| 20P1390 | Dist Colon | 2.5 | 27.4% |

TABLE 14-continued

Residual amount of drug left on the balloons post treatment for C6SsusF13-3, MSF25.

| Subject | Treatment Location | Residual Sirolimus (mg) | % of Dose |
|---|---|---|---|
| 20P1390 | Dist Eso | 1.7 | 18.3% |
| 20P1390 | Prox Duo | 0.4 | 4.0% |
| 20P1390 | Dist Duo | 1.3 | 14.7% |
| 20P1390 | Prox Eso | 2.0 | 21.6% |
| 21P0012 | Prox Duo | 0.4 | 4.4% |
| 21P0012 | Prox Eso | 1.6 | 17.1% |
| 21P0012 | Dist Eso | 3.7 | 40.7% |
| 21P0012 | Dist Duo | 1.3 | 14.2% |
| 21P0012 | Prox Colon | 2.2 | 24.1% |
| 21P0012 | Dist Colon | 2.9 | 32.0% |

Part V. Human Clinical Testing Drug-Coated Balloons in the Gastrointestinal Tract.

Example V-1. Human Clinical Subject a with an Esophageal Stricture Treated with an Uncoated Predilation Balloon Followed by an 18 mm Nominal Diameter Drug-Coated Balloon Catheter 75-year-old male subject A had a 2.0 cm length by 9 mm diameter stricture in his esophagus. Specifically located ⅔rds the length of the esophagus from the mouth. This was determined by conducting an esophogram. The human clinical subject had a baseline dysphagia handicap index score of 42. First a gastroscope was inserted into the mouth and down the esophagus to the stricture. Next a predilation balloon that had a nominal diameter of 12 mm and a length of 55 mm was tracked into the working channel of the gastroscope and positioned so the balloon crossed the stricture. The predilation balloon was inflated to 9 atmospheres with a syringe that had a pressure gauge on it and held at pressure for 5 minutes. The syringe contained a mixture of saline and contrast media. A fluoroscopic image was acquired to ensure the balloon had a uniform expansion. Next the predilation balloon was removed and another predilation balloon that had a nominal diameter of 15 mm and a length of 55 mm was tracked into the working channel of the gastroscope and positioned so the balloon crossed the stricture. The second predilation balloon was inflated to 7 atmospheres which corresponded to a diameter of 16.5 mm and was held at pressure for 5 minutes. Next a drug-coated balloon that had a nominal diameter of 18 mm and a length of 55 mm was inserted into the gastroscope. The drug-coated balloon was positioned such that the balloon body completely covered the predilated stricture area. The drug-coated balloon was held in position for at least 1 minute prior to inflating to hydrate the coating. Then the drug-coated balloon was inflated with a mixture of saline and contrast media using the syringe that had a pressure gauge on it. The balloon was inflated to 4.5 atmospheres, achieved an inflated diameter of 19 mm, and was held at the inflation pressure for 5 minutes. Then the balloon was deflated and withdrawn from the human subject. The stretch ratio for the 18 mm nominal diameter drug-coated balloon was 2.1. The diameter of the dilated stricture was 18 mm after dilation. The human clinical subject had follow-up visits at 30, 90, and 180 days to measure esophagus diameter, dysphagia handicap index score, and body mass. The human clinical subject had an esophagus diameter increase from 9.0 mm to 20.0 (122% increase), 20.0 (122% increase), and 20.0 mm (122% increase) at follow-up visits of 30, 90, and 180 days respectively. The human clinical subject had dysphagia handicap index score improvement from 42 to 6 (86% reduction), 6 (86% reduction), and 2 (95% reduction) at follow-up visits of 30, 90, and 180 days respectively. The human clinical subject had body mass change from 65 kg to 66.5, 65, and 64.5 kg at follow-up visits of 30, 90, and 180 days respectively. Patient A did not receive any stricture reinterventions after being treated with a drug-coated balloon.

Example V-2. Human Clinical Subject B with a Large Bowel Stricture Treated with an Uncoated Predilation Balloon Followed by an 18 mm Nominal Diameter Drug-Coated Balloon Catheter 35-year-old subject B had a 0.5 cm length by 12 mm diameter stricture in his colon. Specifically located at the colon-rectum junction. This was determined by conducting an colonoscopy. The human clinical subject had a baseline obstructive symptom score of 69 with severe constipation, inability of have a bowel movement, swelling and distention of the abdomen, and vomiting. First a colonoscope was inserted into the anus and up adjacent to the stricture. Next a predilation balloon that had a nominal diameter of 18 mm and a length of 55 mm was tracked into the working channel of the colonoscope and positioned so the balloon crossed the stricture. The predilation balloon was inflated to 6 atmospheres with a syringe that had a pressure gauge on it and held at pressure for 5 minutes. The syringe contained a mixture of saline and contrast media. A fluoroscopic image was acquired to ensure the balloon had a uniform expansion. Next the predilation balloon was removed and a drug-coated balloon that had a nominal diameter of 18 mm and a length of 55 mm was inserted into the colonoscope. The drug-coated balloon was positioned such that the balloon body completely covered the predilated stricture area. The drug-coated balloon was held in position for at least 1 minute prior to inflating to hydrate the coating. Then the drug-coated balloon was inflated with a mixture of saline and contrast media using the syringe that had a pressure gauge on it. The balloon was inflated to 6 atmospheres, achieved an inflated diameter of 20 mm, and was held at the inflation pressure for 5 minutes. Then the balloon was deflated and withdrawn from the human subject. The stretch ratio for the 18 mm nominal diameter drug-coated balloon was 1.7. The diameter of the dilated stricture was 19 mm after dilation. The human clinical subject had follow-up visits at 30, 90, and 180 days to measure obstructive symptoms. The human clinical subject had obstructive symptom score improvement from 69 to 0 (100% reduction), 0 (100% reduction), and 0 (100% reduction) at follow-up visits of 30, 90, and 180 days respectively. Patient A did not receive any stricture reinterventions after being treated with a drug-coated balloon.

Figure 11:
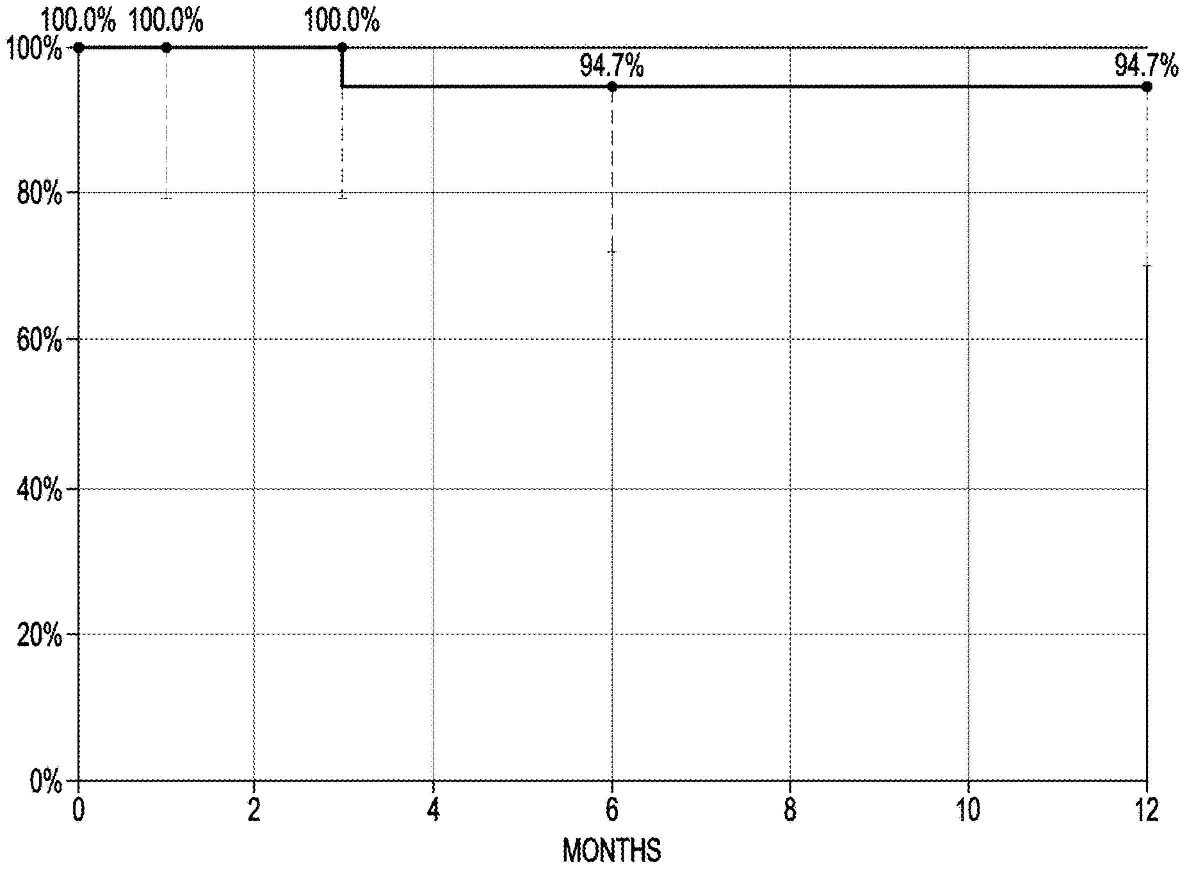
FIG. 11 illustrates a freedom from reintervention Kaplan-Meier curve for paclitaxel-coated balloon treatment in esophagus and bowel, in accordance with various embodiments.

Example V-3. Kaplan-Meier Freedom from Reintervention of Esophageal and Bowel Strictures A total of 19 subjects were treated with paclitaxel coated balloons in their esophagus and bowel and only one patient required retreatment through 12 months follow-up. FIG. 11 shows a survival curve analysis (i.e., freedom from reintervention Kaplan-Meier curve), and shows an estimate for freedom from reintervention at 12 months to be 94.7%.

Example V-4. Human Clinical Subject C with a Biliary Tract Stricture Treated with an Uncoated Predilation Balloon Followed by an 8 mm Nominal Diameter Drug-Coated Balloon Catheter 68-year-old male subject C had a 1.0 cm length by 4 mm diameter stricture in his biliary tract. Specifically located between the common bile duct and common hepatic duct. This was determined by conducting ERCP. The human clinical subject had an indwelling biliary drainage tube prior to being treated. First a duodenoscope was inserted into the mouth and positioned near the ampulla of vater. Next a snare was used to remove the indwelling drainage tube. Next a sphincterotome was used to cannulate the biliary duct and advance a guidewire. Next a predilation balloon that had a nominal diameter of 6 mm and a length of 40 mm was tracked into the working channel of the duodenoscope and positioned so the balloon crossed the stricture. The predilation balloon was inflated to 11 atmospheres with a syringe that had a pressure gauge on it and held at pressure for 3 minutes. The syringe contained a mixture of saline and contrast media. A fluoroscopic image was acquired to ensure the balloon had a uniform expansion. The residual stenosis was originally 70% and was reduced to 40% post predilation. Next the predilation balloon was removed and a drug-coated balloon that had a nominal diameter of 8 mm and a length of 50 mm was inserted into the duodenoscope. The drug-coated balloon was positioned such that the balloon body completely covered the predilated stricture area. The drug-coated balloon was held in position for at least 1 minute prior to inflating to hydrate the coating. Then the drug-coated balloon was inflated with a mixture of saline and contrast media using the syringe that had a pressure gauge on it. The balloon was inflated to 6 atmospheres, achieved an inflated diameter of 8.8 mm, and was held at the inflation pressure for 5 minutes. The residual stenosis was originally 40% and was reduced to 12% post DCB treatment. Then the balloon was deflated and withdrawn from the human subject. The stretch ratio for the 8 mm nominal diameter drug-coated balloon was 2.2. The diameter of the dilated stricture was 8 mm after dilation. The human clinical subject had follow-up visits at 180 days to measure stricture diameter. The human clinical subject had biliary duct diameter improvement from 4 to 9 mm at 180 days. Patient C did not receive any stricture reinterventions after being treated with a drug-coated balloon.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

Exemplary Embodiments

The following exemplary embodiments are provided, the numbering of which is not to be construed as designating levels of importance:

Embodiment 1 provides a polymer-encapsulated drug particles comprising: a therapeutic agent; and one or more polymers that encapsulate the therapeutic agent.

Embodiment 2 provides the polymer-encapsulated drug particles of Embodiment 1, wherein the polymer-encapsulated drug particle has a positive zeta potential.

Embodiment 3 provides the polymer-encapsulated drug particles of any one of Embodiments 2, wherein the polymer-encapsulated drug particle has a zeta potential of greater than zero.

Embodiment 4 provides the polymer-encapsulated drug particles of any one of Embodiments 2-3, wherein the polymer-encapsulated drug particle has a zeta potential of −1 to−50 or 1-50.

Embodiment 5 provides the polymer-encapsulated drug particles of any one of Embodiments 2-4, wherein the polymer-encapsulated drug particle has a zeta potential of −2 to−40 or 2-40.

Embodiment 6 provides the polymer-encapsulated drug particles of any one of Embodiments 1-5, wherein the therapeutic agent is crystalline, partially crystalline, amorphous, partially amorphous, or a combination thereof.

Embodiment 7 provides the polymer-encapsulated drug particles of any one of Embodiments 1-6, wherein the therapeutic agent is crystalline and/or partially crystalline.

Embodiment 8 provides the polymer-encapsulated drug particles of any one of Embodiments 1-7, wherein the polymer is at least one polymer chosen from polylactic acid, (PL), polyglycolic acid (GA), a polylactic acid/polyglycolic acid copolymer (PLGA), polydioxanone, polycaprolactone, polyphosphazene, collagen, gelatin, chitosan, glycosoaminoglycans, and copolymers thereof.

Embodiment 9 provides the polymer-encapsulated drug particles of any one of Embodiments 1-8, wherein the polymer-encapsulated drug particles have a largest dimension of 0.2 micron to 30 microns.

Embodiment 10 provides the polymer-encapsulated drug particles of any one of Embodiments 1-9, wherein the therapeutic agent has a largest dimension of 0.1 to 29.9 microns.

Embodiment 11 provides the polymer-encapsulated drug particles of any one of Embodiments 1-10, wherein the polymer-encapsulated drug particles are polymer encapsulated drug particles (PEDP) and/or charged polymer encapsulated drug particles (CPEDP).

Embodiment 12 provides the polymer-encapsulated drug particles of Embodiment 11, wherein a positive charge density of the CPEDP is higher than that of the PEDP.

Embodiment 13 provides the polymer-encapsulated drug particles of any one of Embodiments 11-12, wherein a positive charge density of the CPEDP is higher than that of the therapeutic agent in the absence of the polymer encapsulant.

Embodiment 14 provides the polymer-encapsulated drug particles of any one of Embodiments 11-13, wherein a zeta potential of the CPEDP is higher than that of the PEDP.

Embodiment 15 provides the polymer-encapsulated drug particles of any one of Embodiments 11-14, wherein a zeta potential of the CPEDP is higher than that of the therapeutic agent in the absence of the polymer encapsulant.

Embodiment 16 provides the polymer-encapsulated drug particles of any one of Embodiments 1-15, wherein the polymer-encapsulated drug particles further comprise a first ionic or zwitterionic additive, wherein the first ionic or zwitterionic additive is in the polymer-encapsulated drug particles, coated on a surface of the polymer-encapsulated drug particles, or a combination thereof, or the polymer comprises an anionic, cationic, or zwitterionic polymer, or the polymer comprises a neutral polymer, or a combination thereof.

Embodiment 17 provides the polymer-encapsulated drug particles of Embodiment 16, wherein the first ionic or zwitterionic additive comprises a cationic molecule, an anionic additive, or a zwitterionic additive.

Embodiment 18 provides the polymer-encapsulated drug particles of any one of Embodiments 16-17, wherein the first ionic or zwitterionic additive is coated on the surface of the polymer-encapsulated drug particles.

Embodiment 19 provides the polymer-encapsulated drug particles of Embodiment 18, wherein the zeta potential of the polymer-encapsulated drug particles is higher than that of a corresponding polymer-encapsulated drug particle that is free of the surface coating of the first ionic or zwitterionic additive.

Embodiment 20 provides the polymer-encapsulated drug particles of any one of Embodiments 16-19, wherein the first ionic or zwitterionic additive comprises a charged polymer, a charged lipid, a phospholipid, a phosphocholine, a phosphatidylcholine, a phosphatidylethanolamine, a phosphatidylserine, a phosphatidylinositol, and combinations thereof.

Embodiment 21 provides the polymer-encapsulated drug particles of Embodiment 20, wherein two acyl groups of the charged lipid or two acyl groups of the charged phospholipid comprise mis-matched acyl groups.

Embodiment 22 provides the polymer-encapsulated drug particles of Embodiment 21, wherein the mis-matched acyl groups have lengths of C6-C34.

Embodiment 23 provides the polymer-encapsulated drug particles of any one of Embodiments 21-22, wherein the mis-matched acyl groups differ by length, degree of saturation, substituents thereon, substitution patterns thereon, or combinations thereof.

Embodiment 24 provides the polymer-encapsulated drug particles of any one of Embodiments 20-23, wherein the charged polymer is chosen from polycation-containing cyclodextrin, amino cyclodextrin or a derivative thereof, amino dextran, a histone, a protamine, cationized human serum albumin, an aminopolysaccharide, chitosan, a peptide, poly-L-lysine, poly-L-ornithine, poly(4-hydroxy-L-proline ester), a polyethylenimine, a polyallylamine, a polypropylenimine, a polyamidoamine dendrimer, a cationic polyoxazoline, a poly(beta-aminoester), a PEG-PEI copolymer, a PLGA-PEI copolymer, a positively charged gelatin, hydroxy-terminated poly(2-methyl-2-oxazoline), poly(2-ethyl-2-oxazoline), stearic acid-modified branched polyethylenimine, branched PEI-g-PEG, poly(1-vinylpyrrolidone-co-2-dimethylaminoethyl methacrylate), poly(1-vinylpyrrolidone)-graft-(1-triacontene), polylysine, polyarginine, poly(N,N-dimethylaminoethyl methacrylate), a cationic copolymer of dimethylaminoethyl methacrylate/butyl methacrylate/methyl methacrylate, an anionic copolymer of methacrylic acid/methyl methacrylate, a copolymer of ethyl acrylate/methyl methacrylate/methacrylic acid ester with quaternary ammonium groups, and combinations thereof.

Embodiment 25 provides the polymer-encapsulated drug particles of any one of Embodiments 20-24, wherein the charged lipid is chosen from 1,2-dipalmitoyl-sn-glycero-3-ethylphosphocholine (chloride salt), 1,2-distearoyl-sn-glycero-3-ethylphosphocholine (chloride salt), cholic acid, deoxycholic acid, chenodeoxycholic acid, lithocholic acid, 1,2-dilauroyl-sn-glycero-3-phosphoglycerol, sodium salt, 1,2-dihexanoyl-sn-glycero-3-phosphocholine, 1,2-diheptanoyl-sn-glycero-3-phosphocholine, 1,2-dioctanoyl-sn-glycero-3-phosphocholine, 1,2-dinonanoyl-sn-glycero-3-phosphocholine, 1,2-decanoyl-sn-glycero-3-phosphocholine, 1,2-diundecanoyl-sn-glycero-3-phosphocholine, 1,2-dilauroyl-sn-glycero-3-phosphocholine, 1,2-dimyristoyl-sn-glycero-3-phosphocholine, 1,2-dipalmitoyl-sn-glycero-3-phosphocholine, 1,2-distearoyl-sn-glycero-3-phosphocholine, 1-palmitoyl-2-stearoyl-sn-glycero-3-phosphocholine, 1-stearoyl-2-palmitoyl-sn-glycero-3-phosphocholine, 1-palmitoyl-2-lauroyl-sn-glycero-3-phosphocholine, 1,2-dioleoyl-sn-glycero-3-phosphocholine (DOPC), 1-palmitoyl-2-oleoyl-glycero-3-phosphocholine (POPC), 1-stearoyl-2-hydroxy-sn-glycero-3-phosphocholine, 1-lauroyl-2-hydroxy-sn-glycero-3-phosphocholine, 1-myristoyl-2-hydroxy-sn-glycero-3-phosphocholine, 1-palmitoyl-2-hydroxy-sn-glycero-3-phosphocholine, dieicosenoyl phosphatidylcholine (1,2-dieicosenoyl-sn-glycero-3-phosphocholine, C20:1 PC), diarachidonoyl phosphatidylcholine (1,2-diarachidoyl-sn-glycero-3-phosphocholine, C20:0 PC), dierucoyl phosphatidylcholine (1,2-dierucoyl-sn-glycero-3-phosphocholine, C22:1 PC), didocosahexaenoyl phosphatidylcholine (1,2-didocosahexaenoyl-sn-glycero-3-phosphocholine, C22:6 PC), heneicosenoyl phosphatidylcholine (1,2-heneicosenoyl-sn-glycero-3-phosphocholine, C21:1 PC), and dinervonyl phosphatidylcholine (1,2-dinervonoyl-sn-glycero-3-phosphocholine, C24:1 PC), and combinations thereof.

Embodiment 26 provides the polymer-encapsulated drug particles of any one of Embodiments 16-25, wherein the first ionic or zwitterionic additive is chosen from 1,2-dipalmitoyl-sn-glycero-3-ethylphosphocholine (chloride salt), 1,2-distearoyl-sn-glycero-3-ethylphosphocholine (chloride salt), cholic acid, deoxycholic acid, chenodeoxycholic acid, lithocholic acid, 1,2-dilauroyl-sn-glycero-3-phosphoglycerol, sodium salt, 1,2-dihexanoyl-sn-glycero-3-phosphocholine, 1,2-diheptanoyl-sn-glycero-3-phosphocholine, 1,2-dioctanoyl-sn-glycero-3-phosphocholine, 1,2-dinonanoyl-sn-glycero-3-phosphocholine, 1,2-decanoyl-sn-glycero-3-phosphocholine, 1,2-diundecanoyl-sn-glycero-3-phosphocholine, 1,2-dilauroyl-sn-glycero-3-phosphocholine, 1,2-dimyristoyl-sn-glycero-3-phosphocholine, 1,2-dipalmitoyl-sn-glycero-3-phosphocholine, 1,2-distearoyl-sn-glycero-3-phosphocholine, 1-palmitoyl-2-stearoyl-sn-glycero-3-phosphocholine, 1-stearoyl-2-palmitoyl-sn-glycero-3-phosphocholine, 1-palmitoyl-2-lauroyl-sn-glycero-3-phosphocholine, 1,2-dioleoyl-sn-glycero-3-phosphocholine (DOPC), 1-palmitoyl-2-oleoyl-glycero-3-phosphocholine (POPC), 1-stearoyl-2-hydroxy-sn-glycero-3-phosphocholine, 1-lauroyl-2-hydroxy-sn-glycero-3-phosphocholine, 1-myristoyl-2-hydroxy-sn-glycero-3-phosphocholine, 1-palmitoyl-2-hydroxy-sn-glycero-3-phosphocholine, and a combination thereof.

Embodiment 27 provides the polymer-encapsulated drug particles of any one of Embodiments 16-26, wherein the first ionic or zwitterionic additive comprises a water-insoluble or slightly or partial water-insoluble additive including at least one acyl group, the first ionic or zwitterionic additive having a molecular weight of 50 to 750, 750 to 100,000, or 750 to 50,000, or 750 to 10,000.

Embodiment 28 provides the polymer-encapsulated drug particles of any one of Embodiments 16-27, wherein the first ionic or zwitterionic additive has a lower melting temperature than that of the additive in its pure form.

Embodiment 29 provides the polymer-encapsulated drug particles of any one of Embodiments 16-28, wherein the first ionic or zwitterionic additive has a lower crystallinity than that of the additive in its pure form.

Embodiment 30 provides the polymer-encapsulated drug particles of any one of Embodiments 1-29, wherein the therapeutic agent is chosen from paclitaxel, docetaxel, taxol, an mTOR inhibitor, rapamycin, sirolimus, zotarolimus, everolimus, tacrolimus, umirolimus, an analogue thereof, and combinations thereof.

Embodiment 31 provides the polymer-encapsulated drug particles of any one of Embodiments 1-30, wherein the polymer-encapsulated drug particles are on a balloon catheter, a drug-coated catheter, a drug-eluting stent, a drug-eluting stent on a balloon, a drug-eluting stent on a drug-coated balloon, a stent on a drug-coated balloon, or a combination thereof.

Embodiment 32 provides a drug-releasing coating comprising: the polymer-encapsulated drug particles of any one of Embodiments 1-31; and a release matrix comprising a second ionic or zwitterionic additive.

Embodiment 33 provides the drug-releasing coating of Embodiment 32, wherein the second ionic or zwitterionic additive has the same molecular structure as the first ionic or zwitterionic additive.

Embodiment 34 provides the drug-releasing coating of Embodiment 32, wherein the second ionic or zwitterionic additive has a different molecular structure from the first ionic or zwitterionic additive.

Embodiment 35 provides the drug-releasing coating of any one of Embodiments 32-34, wherein the polymer-encapsulated drug particles are 10 wt % to 80 wt % of the drug-releasing coating by dry measure.

Embodiment 36 provides the drug-releasing coating of any one of Embodiments 32-35, wherein the polymer-encapsulated drug particles are 25 wt % to 70 wt % of the drug-releasing coating by dry measure.

Embodiment 37 provides the drug-releasing coating of any one of Embodiments 32-36, wherein the polymer-encapsulated drug particles are 40 wt % to 60 wt % of the drug-releasing coating by dry measure.

Embodiment 38 provides the drug-releasing coating of any one of Embodiments 32-37, wherein the release matrix further comprises particles of the therapeutic agent that are free of encapsulation by the polymer of the polymer-encapsulated drug particles.

Embodiment 39 provides the drug-releasing coating of Embodiment 38, wherein the particles of the therapeutic agent that are free of encapsulation by the polymer of the polymer-encapsulated drug particles comprise crystalline particles of the therapeutic agent.

Embodiment 40 provides the drug-releasing coating of any one of Embodiments 38-39, wherein the particles of the therapeutic agent that are free of encapsulation by the polymer of the polymer-encapsulated drug particles are homogeneously distributed in the release matrix.

Embodiment 41 provides the drug-releasing coating of any one of Embodiments 32-40, wherein the polymer-encapsulated drug particles are homogeneously distributed in the release matrix.

Embodiment 42 provides the drug-releasing coating of any one of Embodiments 32-41, wherein the second ionic or zwitterionic additive comprises a cationic molecule, an anionic additive, or a zwitterionic additive.

Embodiment 43 provides the drug-releasing coating of any one of Embodiments 32-42, wherein the second ionic or zwitterionic additive in the release matrix is chosen from a charged polymer, a charged lipid, a phospholipid, a phosphatidylcholine, a phosphatidylethanolamine, a phosphatidylserine, a phosphatidylinositol, and combinations thereof.

Embodiment 44 provides the drug-releasing coating of Embodiment 43, wherein two acyl groups of the charged lipid or two acyl groups of the charged phospholipid comprise mis-matched acyl groups.

Embodiment 45 provides the drug-releasing coating of Embodiment 44, wherein the mis-matched acyl groups have lengths of C6-C34.

Embodiment 46 provides the drug-releasing coating of any one of Embodiments 44-45, wherein the mis-matched acyl groups differ by length, degree of saturation, substituents thereon, substitution patterns thereon, or combinations thereof.

Embodiment 47 provides the drug-releasing coating of any one of Embodiments 43-46, wherein the charged polymer is chosen from polycation-containing cyclodextrin, amino cyclodextrin or a derivative thereof, amino dextran, a histone, a protamine, cationized human serum albumin, an aminopolysaccharide, chitosan, a peptide, poly-L-lysine, poly-L-ornithine, poly(4-hydroxy-L-proline ester), a polyethylenimine, a polyallylamine, a polypropylenimine, a polyamidoamine dendrimer, a cationic polyoxazoline, a poly(beta-aminoester), a PEG-PEI copolymer, a PLGA-PEI copolymer, a positively charged gelatin, hydroxy-terminated poly(2-methyl-2-oxazoline), poly(2-ethyl-2-oxazoline), stearic acid-modified branched polyethylenimine, branched PEI-g-PEG, poly(1-vinylpyrrolidone-co-2-dimethylaminoethyl methacrylate), poly(1-vinylpyrrolidone)-graft-(1-triacontene), polylysine, polyarginine, poly(N,N-dimethylaminoethyl methacrylate), a cationic copolymer of dimethylaminoethyl methacrylate/butyl methacrylate/methyl methacrylate, an anionic copolymer of methacrylic acid/methyl methacrylate, a copolymer of ethyl acrylate/methyl methacrylate/methacrylic acid ester with quaternary ammonium groups, and combinations thereof.

Embodiment 48 provides the drug-releasing coating of any one of Embodiments 43-47, wherein the charged lipid is chosen from 1,2-dipalmitoyl-sn-glycero-3-ethylphosphocholine (chloride salt), 1,2-distearoyl-sn-glycero-3-ethylphosphocholine (chloride salt), cholic acid, deoxycholic acid, chenodeoxycholic acid, lithocholic acid, 1,2-dilauroyl-sn-glycero-3-phosphoglycerol, sodium salt, 1,2-dihexanoyl-sn-glycero-3-phosphocholine, 1,2-diheptanoyl-sn-glycero-3-phosphocholine, 1,2-dioctanoyl-sn-glycero-3-phosphocholine, 1,2-dinonanoyl-sn-glycero-3-phosphocholine, 1,2-decanoyl-sn-glycero-3-phosphocholine, 1,2-diundecanoyl-sn-glycero-3-phosphocholine, 1,2-dilauroyl-sn-glycero-3-phosphocholine, 1,2-dimyristoyl-sn-glycero-3-phosphocholine, 1,2-dipalmitoyl-sn-glycero-3-phosphocholine, 1,2-distearoyl-sn-glycero-3-phosphocholine, 1-palmitoyl-2-stearoyl-sn-glycero-3-phosphocholine, 1-stearoyl-2-palmitoyl-sn-glycero-3-phosphocholine, 1-palmitoyl-2-lauroyl-sn-glycero-3-phosphocholine, 1,2-dioleoyl-sn-glycero-3-phosphocholine (DOPC), 1-palmitoyl-2-oleoyl-glycero-3-phosphocholine (POPC), 1-stearoyl-2-hydroxy-sn-glycero-3-phosphocholine, 1-lauroyl-2-hydroxy-sn-glycero-3-phosphocholine, 1-myristoyl-2-hydroxy-sn-glycero-3-phosphocholine, 1-palmitoyl-2-hydroxy-sn-glycero-3-phosphocholine, dieicosenoyl phosphatidylcholine (1,2-dieicosenoyl-sn-glycero-3-phosphocholine, C20:1 PC), diarachidonoyl phosphatidylcholine (1,2-diarachidoyl-sn-glycero-3-phosphocholine, C20:0 PC), dierucoyl phosphatidylcholine (1,2-dierucoyl-sn-glycero-3-phosphocholine, C22:1 PC), didocosahexaenoyl phosphatidylcholine (1,2-didocosahexaenoyl-sn-glycero-3-phosphocholine, C22:6 PC), heneicosenoyl phosphatidylcholine (1,2-heneicosenoyl-sn-glycero-3-phosphocholine, C21:1 PC), and dinervonyl phosphatidylcholine (1,2-dinervonoyl-sn-glycero-3-phosphocholine, C24:1 PC), and combinations thereof.

Embodiment 49 provides the drug-releasing coating of any one of Embodiments 43-48, wherein the second ionic or zwitterionic additive is chosen from 1,2-dipalmitoyl-sn-glycero-3-ethylphosphocholine (chloride salt), 1,2-distearoyl-sn-glycero-3-ethylphosphocholine (chloride salt), cholic acid, deoxycholic acid, chenodeoxycholic acid, lithocholic acid, 1,2-dilauroyl-sn-glycero-3-phosphoglycerol, sodium salt, 1,2-dihexanoyl-sn-glycero-3-phosphocholine, 1,2-diheptanoyl-sn-glycero-3-phosphocholine, 1,2-dioctanoyl-sn-glycero-3-phosphocholine, 1,2-dinonanoyl-sn-glycero-3-phosphocholine, 1,2-decanoyl-sn-glycero-3-phosphocholine, 1,2-diundecanoyl-sn-glycero-3-phosphocholine, 1,2-dilauroyl-sn-glycero-3-phosphocholine, 1,2-dimyristoyl-sn-glycero-3-phosphocholine, 1,2-dipalmitoyl-sn-glycero-3-phosphocholine, 1,2-distearoyl-sn-glycero-3-phosphocholine, 1-palmitoyl-2-stearoyl-sn-glycero-3-phosphocholine, 1-stearoyl-2-palmitoyl-sn-glycero-3-phosphocholine, 1-palmitoyl-2-lauroyl-sn-glycero-3-phosphocholine, 1,2-dioleoyl-sn-glycero-3-phosphocholine (DOPC), 1-palmitoyl-2-oleoyl-glycero-3-phosphocholine (POPC), 1-stearoyl-2-hydroxy-sn-glycero-3-phosphocholine, 1-lauroyl-2-hydroxy-sn-glycero-3-phosphocholine, 1-myristoyl-2-hydroxy-sn-glycero-3-phosphocholine, 1-palmitoyl-2-hydroxy-sn-glycero-3-phosphocholine, and a combination thereof.

Embodiment 50 provides the drug-releasing coating of any one of Embodiments 43-49, wherein the second ionic or zwitterionic additive comprises a water-insoluble or slightly or partial water-insoluble additive including at least one acyl group, the second ionic or zwitterionic additive having a molecular weight of 50 to 750, 750 to 100,000, or 750 to 50,000, or 750 to 10,000.

Embodiment 51 provides the drug-releasing coating of any one of Embodiments 43-50, wherein the second ionic or zwitterionic additive in the coating has a lower melting temperature than that of the additive in its pure form.

Embodiment 52 provides the drug-releasing coating of any one of Embodiments 43-51, wherein the second ionic or zwitterionic additive in the coating has a lower crystallinity than that of the additive in its pure form.

Embodiment 53 provides the drug-releasing coating of any one of Embodiments 32-52, wherein the coating is on a balloon catheter, a drug-coated catheter, a drug-eluting stent, a drug-eluting stent on a balloon, a drug-eluting stent on a drug-coated balloon, a stent on a drug-coated balloon, or a combination thereof.

Embodiment 54 provides a method for treating or preventing a nonvascular or vascular stricture or stenosis, the method comprising:

- inserting a catheter comprising the balloon or stent of any one of Embodiments 31 or 53 into the body lumen;
- expanding the balloon or stent to contact the coating layer with the stricture, stenosis, or area wherein the stricture or stenosis is to be prevented;
- when a balloon is used, the method further comprises deflating the balloon; and
- when a balloon is used, the method further comprises removing the balloon from the body lumen.

Embodiment 55 provides a method of making the polymer-encapsulated drug particles of any one of Embodiments 1-31, the method comprising:

- forming a suspension comprising the therapeutic agent and the polymer;
- processing the suspension to reduce particle size of the suspension; and
- adding an aqueous premix to the suspension to form polymer-encapsulated drug particles in the suspension.

Embodiment 56 provides the method of Embodiment 55, wherein the processing comprising sonicating.

Embodiment 57 provides the method of any one of Embodiments 55-56, further comprising adding a first ionic or zwitterionic additive to the suspension to coat the formed particles therewith.

Embodiment 58 provides the method of any one of Embodiments 55-57, further comprising adding a second ionic or zwitterionic additive to the suspension to form the drug-releasing coating of any one of Embodiments 32-53.

Embodiment 59 provides a method of making the polymer-encapsulated drug particles of any one of Embodiments 1-31, the method comprising:

- forming an organic premix comprising an organic solvent, the one or more polymers, the therapeutic agent, and optionally the first ionic or zwitterionic additive;
- forming an aqueous premix comprising water and a water-soluble polymer or surfactant; adding an organic solvent to the aqueous premix;
- combining the aqueous premix and the organic premix together;
- agitating the combined aqueous premix and organic premix to form an emulsion comprising the polymer-encapsulated drug particles.

Embodiment 60 provides the method of Embodiment 59, wherein the therapeutic agent, the one or more polymers, and the optional first ionic or zwitterionic additive if present are dissolved in the organic premix.

Embodiment 61 provides the method of any one of Embodiments 59-60, wherein the organic solvent of the organic premix and the organic solvent added to the aqueous premix are the same organic solvent.

Embodiment 62 provides the method of any one of Embodiments 59-61, wherein the organic solvent of the organic premix and the organic solvent added to the aqueous premix are a polar organic solvent.

Embodiment 63 provides the method of any one of Embodiments 59-62, further comprising adding water to the emulsion comprising the polymer-encapsulated particles.

Embodiment 64 provides the method of any one of Embodiments 59-63, further comprising separating the polymer-encapsulated drug particles from the combined aqueous premix and organic premix.

Embodiment 65 provides the method of any one of Embodiments 59-64, further comprising washing the polymer-encapsulated drug particles with an aqueous liquid, drying the polymer-encapsulated drug particles, or a combination thereof.

Embodiment 66 provides the method of any one of Embodiments 59-65, further comprising

- forming a first mixture comprising the polymer-encapsulated drug particles and an organic solvent;
- forming a second mixture comprising a second ionic or zwitterionic additive and an organic solvent;
- combining the first mixture and second mixture; and
- drying the combined first mixture and second mixture, to form the drug-releasing coating of any one of Embodiments 32-53.

Embodiment 67 provides the method of Embodiment 66, wherein the organic solvent of the first mixture and the second mixture is a nonpolar organic solvent.

Embodiment 68 provides the method of any one of Embodiments 66-67, further comprising agitating the combined first mixture and second mixture prior to the drying to homogeneously disperse the polymer-encapsulated drug particles therein.

Embodiment 69 provides a method of making a balloon catheter, the method comprising:

applying the polymer-encapsulated drug particles of any one of Embodiments 1-31 or the drug-releasing coating of any one of Embodiments 32-53 to an exterior of a balloon of a balloon catheter.

Embodiment 70 provides a balloon catheter comprising: an elongated balloon; and a coating layer overlying an exterior surface of the balloon, the coating layer comprising the polymer-encapsulated drug particles of any one of Embodiments 1-31, or the drug-releasing coating of any one of Embodiments 32-53, or a composition comprising a therapeutic agent chosen from paclitaxel, docetaxel, taxol, an mTOR inhibitor, rapamycin, sirolimus, zotarolimus, everolimus, tacrolimus, umirolimus, an analogue thereof, and combinations thereof, the therapeutic agent having a particle size of 0.2 micron to 10 microns, a first additive comprising a water-insoluble or partially water-insoluble additive comprising at least one alkyl fatty group or cholesteryl group, and a second additive that is more hydrophilic or more water-soluble than the first additive and that comprises a polyethylene glycol (—$(CH_2CH_2O)$—) or a polyglycerol (—$(CH_2$—CHOH—$CH_2O)$—) unit, wherein the second additive has a molecular weight in the range of 750 to 100,000, or a combination thereof.

Embodiment 71 provides the balloon catheter of Embodiment 70, wherein the balloon comprises a polyester, a polyamide, a nylon 12, a nylon 11, a polyamide 12, a block copolymer of a polyether and a polyamide, a polyether block amide, a polyurethane, a block copolymer of a polyether and a polyester, or a combination thereof.

Embodiment 72 provides the balloon catheter of any one of Embodiments 70-71, wherein the balloon catheter is for delivering the therapeutic agent to a body lumen stricture or stenosis, wherein the body lumen stricture or stenosis is chosen from urethral stricture, prostatic urethral stricture, ureteral stricture, esophageal stricture, sinus stricture, stomach stricture, small intestine stricture, colon stricture, rectum stricture, large intestine stricture, bladder neck stricture, a biliary tract stricture, vaginal stricture, in-stent restenosis, coronary artery stenosis, superficial femoral artery stenosis, popliteal artery stenosis, anterior tibial artery stenosis, posterior tibial artery stenosis, and peroneal artery stenosis.

Embodiment 73 provides the balloon catheter of any one of Embodiments 70-72, wherein the balloon catheter is for delivering the therapeutic agent to a target site of a body lumen, wherein the target site of the body lumen is chosen from urethral stricture, prostatic urethral stricture, ureteral stricture, esophageal stricture, sinus stricture, stomach stricture, small intestine stricture, colon stricture, rectum stricture, large intestine stricture, bladder neck stricture, a biliary tract stricture, vaginal stricture, in-stent restenosis, coronary artery stenosis, superficial femoral artery stenosis, popliteal artery stenosis, anterior tibial artery stenosis, posterior tibial artery stenosis, and peroneal artery stenosis.

Embodiment 74 provides the balloon catheter of any one of Embodiments 70-73, wherein the first additive, the second additive, or a combination thereof encapsulates the therapeutic agent.

Embodiment 75 provides the balloon catheter of Embodiment 74, wherein the additive-encapsulated therapeutic agent has a larger particle size than the therapeutic agent itself.

Embodiment 76 provides the balloon catheter of any one of Embodiments 74-75, wherein the particle size of the additive-encapsulated therapeutic agent in the coating is in the range of 0.3 micron to 10 microns.

Embodiment 77 provides the balloon catheter of any one of Embodiments 70-76, wherein the first additive in the coating has a lower melting temperature than that of the first additive in its pure form.

Embodiment 78 provides the balloon catheter of any one of Embodiments 70-77, wherein the first additive in the coating has a lower crystallinity than that of the first additive in its pure form.

Embodiment 79 provides the balloon catheter of any one of Embodiments 70-78, wherein the first additive with cholesteryl group is chosen from cholesterol, cholesteryl acetate, cholesteryl phenylacetate, cholesteryl laurate, cholesteryl palmitate, cholesteryl stearate, cholesteryl n-valerate, cholesteryl benzoate, cholesteryl heptylate, cholesteryl decylate, cholesteryl caproate, cholesteryl oleate, cholesteryl oleyl carbonate, cholesteryl linoleate, cholesteryl pelargonate, cholesteryl erucate, cholesteryl caprylate, 5α-cholestane, 5α-cholestan-3-one, and combinations thereof.

Embodiment 80 provides the balloon catheter of any one of Embodiments 70-79, wherein the first additive comprising at least one alkyl fatty group is chosen from alkyl glyceryl ethers, monoglycerides of C8-C12 fatty acids, alkyl alcohol, alkyl ether, alkyl ester, caprylic acid, monocaprilin, capric acid, monocaprin, lauric acid, dodecyl glycerol, butanoic acid, hexanoic acid, octanoic acid, decanoic acid, dodecanoic acid, tetradecanoic acid, hexadecanoic acid, octadecanoic acid, octadecatrienoic acid, eicosanoic acid, eicosenoic acid, eicosatetraenoic acid, eicosapentaenoic acid, docosahexaenoic acid, tocotrienol, butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, natural or synthetic phospholipids, mono-, di-, or triacylglycerols, cardiolipin, phosphatidylglycerol, phosphatidic acid, phosphatidylcholine, alpha tocoferol, phosphatidylethanolamine, sphingomyelin, phosphatidylserine, phosphatidylinositol, dimyristoylphosphatidylcholine, dioleoylphosphatidylcholine, dipalmitoylphosphatidylcholine, distearoylphosphatidylcholine, phosphatidylethanolamines phosphatidylglycerols, sphingolipids, prostaglandins, gangliosides, neobee, niosomes, derivatives thereof, and combinations thereof.

Embodiment 81 provides the balloon catheter of any one of Embodiments 70-80, wherein the second additive is chosen from cholesteryl-polyethylene glycol 600 sebacate, polyoxyethanyl α-tocopheryl sebacate, methylated polyethylene glycol cholesterol (mPEG cholesterol), polyethylene glycol cholesterol (PEG cholesterol), polyethylene glycol ester cholesterol (PEG cholesterol), polyethylene glycol ether cholesterol (PEG cholesterol), methylated polyethylene glycol-amide-cholesterol (mPEG cholesterol), polyethylene glycol-amide-cholesterol (PEG cholesterol), polyethylene glycol (PEG)-cholesteryl sebacate, polyethylene glycol cholesterol, PEG amide ester cholesterol, PEG amide ether cholesterol, mPEG amide ester cholesterol, DSPE-PEG-cholesterol, PEGylated phospholipid, methylated PEGylated phospholipid, PEG caprylic/capric diglycerides, PEG8 caprylic/capric glycerides, PEG caprylate, PEG caprate, PEG caproate, PEG-20 sorbitan monolaurate (Tween-20), PEG-20 sorbitan monopalmitate (Tween-40), PEG-20 sorbitan monostearate (Tween-60), PEG-20 sorbitan monooleate (Tween-80), PEG laurate, PEG oleate, PEG stearate, PEG glyceryl laurate, PEG-30 glyceryl oleate, polyglyceryl fatty acid esters, polyglyceryl oleate, polyglyceryl-2 dioleate, polyglyceryl-10 trioleate, polyglyceryl stearate, polyglyceryl laurate, polyglyceryl myristate, polyglyceryl palmitate, polyglyceryl linoleate, polyglyceryl-10 laurate, polyglyceryl-10 oleate, polyglyceryl-10 mono/dioleate, polyglyceryl-10 stearate, polyglyceryl-10 laurate, polyglyceryl-10 myristate, polyglyceryl-10 palmitate, polyglyceryl-10 linoleate, polyglyceryl-6 stearate, polyglyceryl-6 laurate, polyglyceryl-6 myristate, polyglyceryl-6 palmitate, polyglyceryl-6 linoleate, and combinations thereof.

Embodiment 82 provides a balloon catheter for delivering a therapeutic agent to a target site of a body lumen stricture or stenosis, the balloon catheter comprising:

an elongated balloon; and a coating layer overlying an exterior surface of the balloon, wherein the coating layer comprising the polymer-encapsulated drug particles of any one of Embodiments 1-31, or the drug-releasing coating of any one of Embodiments 32-53, or a composition comprising a therapeutic agent chosen from paclitaxel, docetaxel, taxol, an mTOR inhibitor, rapamycin, sirolimus, zotarolimus, everolimus, tacrolimus, umirolimus, an analogue thereof, and combinations thereof, the therapeutic agent having a particle size of 0.2 micron to 5 microns, a first additive, and a second additive, or a combination thereof;

wherein the balloon comprises a polyester, a polyamide, a nylon 12, a nylon 11, a polyamide 12, a block copolymer of a polyether and a polyamide, a polyether block amide, a polyurethane, a block copolymer of a polyether and a polyester, or a combination thereof; wherein the therapeutic agent is crystalline, partially crystalline, or a combination thereof;

wherein the first additive, the second additive, or a combination thereof encapsulates the therapeutic agent, the additive-encapsulated therapeutic agent has a larger particle size than the therapeutic agent itself, and the particle size of the additive-encapsulated therapeutic agent in the coating is in the range of 0.3 micron to 10 micron;

wherein the first additive comprises a water-insoluble or slightly or partially water-insoluble additive comprising at least one alkyl fatty group or cholesteryl group, the first additive having a molecular weight of 50 to 750;

wherein the first additive in the coating has a lower melting temperature than that of the first additive in its pure form;

wherein the first additive in the coating has a lower crystallinity than that of the first additive in its pure form;

wherein the second additive is more hydrophilic or more water-soluble than the first additive and that comprises polyethylene glycol (—$(CH_2CH_2O)$—) or a polyglycerol (—$(CH_2$—CHOH—$CH_2O)$—) unit, and the second additive has a molecular weight in the range of 750 to 100,000;

wherein the body lumen stricture or stenosis is chosen from urethral stricture, prostatic urethral stricture, ureteral stricture, esophageal stricture, sinus stricture, stomach stricture, small intestine stricture, colon stricture, rectum stricture, large intestine stricture, bladder neck stricture, a biliary tract stricture, vaginal stricture, in-stent restenosis, coronary artery stenosis, superficial femoral artery stenosis, popliteal artery stenosis, anterior tibial artery stenosis, posterior tibial artery stenosis, and peroneal artery stenosis;

wherein first additive with cholesteryl group is chosen from cholesterol, cholesteryl acetate, cholesteryl phenylacetate, cholesteryl laurate, cholesteryl palmitate, cholesteryl stearate, cholesteryl n-valerate, cholesteryl benzoate, cholesteryl heptylate, cholesteryl decylate, cholesteryl caproate, cholesteryl oleate, cholesteryl oleyl carbonate, cholesteryl linoleate, cholesteryl pelargonate, cholesteryl erucate, cholesteryl caprylate, 5α-cholestane, 5α-cholestan-3-one, and combinations thereof;

wherein the water-insoluble or slightly or partial water-insoluble first additive with alkyl fatty group is chosen from alkyl glyceryl ethers, monoglycerides of C8-C12 fatty acids, alkyl alcohol, alkyl ether, alkyl ester, caprylic acid, monocaprilin, capric acid, monocaprin, lauric acid, dodecyl glycerol, butanoic acid, hexanoic acid, octanoic acid, decanoic acid, dodecanoic acid, tetradecanoic acid, hexadecanoic acid, octadecanoic acid, octadecatrienoic acid, eicosanoic acid, eicosenoic acid, eicosatetraenoic acid, eicosapentaenoic acid, docosahexaenoic acid, tocotrienol, butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, natural or synthetic phospholipids, mono-, di-, or triacylglycerols, cardiolipin, phosphatidylglycerol, phosphatidic acid, phosphatidylcholine, alpha tocoferol, phosphatidylethanolamine, sphingomyelin, phosphatidylserine, phosphatidylinositol, dimyristoylphosphatidylcholine, dioleoylphosphatidylcholine, dipalmitoylphosphatidylcholine, distearoylphosphatidylcholine, phosphatidylethanolamines phosphatidylglycerols, sphingolipids, prostaglandins, gangliosides, neobee, niosomes, derivatives thereof, and combinations thereof; and wherein the water-soluble second additive is chosen from cholesteryl-polyethylene glycol 600 sebacate, polyoxyethanyl α-tocopheryl sebacate, methylated polyethylene glycol cholesterol (mPEG cholesterol), polyethylene glycol cholesterol (PEG cholesterol), polyethylene glycol ester cholesterol (PEG cholesterol), polyethylene glycol ether cholesterol (PEG cholesterol), methylated polyethylene glycol-amide-cholesterol (mPEG cholesterol), polyethylene glycol-amide-cholesterol (PEG cholesterol), polyethylene glycol (PEG)-cholesteryl sebacate, polyethylene glycol cholesterol, PEG amide ester cholesterol, PEG amide ether cholesterol, mPEG amide ester cholesterol, DSPE-PEG-cholesterol, PEGylated phospholipid, methylated PEGylated phospholipid, PEG caprylic/capric diglycerides, PEG8 caprylic/capric glycerides, PEG caprylate, PEG caprate, PEG caproate, PEG-20 sorbitan monolaurate (Tween-20), PEG-20 sorbitan monopalmitate (Tween-40), PEG-20 sorbitan monostearate (Tween-60), PEG-20 sorbitan monooleate (Tween-80), PEG laurate, PEG oleate, PEG stearate, PEG glyceryl laurate, PEG-30 glyceryl oleate, polyglyceryl fatty acid esters, polyglyceryl oleate, polyglyceryl-2 dioleate, polyglyceryl-10 trioleate, polyglyceryl stearate, polyglyceryl laurate, polyglyceryl myristate, polyglyceryl palmitate, polyglyceryl linoleate, polyglyceryl-10 laurate, polyglyceryl-10 oleate, polyglyceryl-10 mono/dioleate, polyglyceryl-10 stearate, polyglyceryl-10 laurate, polyglyceryl-10 myristate, polyglyceryl-10 palmitate, polyglyceryl-10 linoleate, polyglyceryl-6 stearate, polyglyceryl-6 laurate, polyglyceryl-6 myristate, polyglyceryl-6 palmitate, polyglyceryl-6 linoleate, and combinations thereof.

Embodiment 83 provides a method for prevention or treatment of strictures in the digestive body lumen or the gastrointestinal tract, the method comprising:

- inserting a balloon catheter into a target site in a body lumen comprising the non-vascular stricture, the balloon catheter comprising
  - an elongated balloon, and
  - a coating layer overlying an exterior surface of the balloon, the coating layer comprising
    - the polymer-encapsulated drug particles of any one of Embodiments 1-31, or
    - the drug-releasing coating of any one of Embodiments 32-53, or
    - a composition comprising
      - a therapeutic agent chosen from paclitaxel, docetaxel, taxol, an mTOR inhibitor, rapamycin, sirolimus, zotarolimus, everolimus, tacrolimus, umirolimus, an analogue thereof, and combinations thereof, the therapeutic agent having a particle size of 0.2 micron to 10 microns,
      - a first additive comprising a water-insoluble or partially water-insoluble additive, and
      - a second additive that is more hydrophilic or more water-soluble than the first additive, or
    - a combination thereof;
- inflating the balloon at the target site to contact the coating layer with walls of the body lumen at the location of the non-vascular stricture until the balloon achieves an inflated balloon diameter for an inflation period; deflating the balloon after the inflation period; and
- withdrawing the balloon catheter from the body lumen;
- wherein the first additive; the second additive; or a combination thereof encapsulates the therapeutic agent; the additive-encapsulated therapeutic agent has a larger particle size than the therapeutic agent itself; and the particle size of the additive-encapsulated therapeutic agent in the coating is in the range of 0.3 micron to 10 micron;
- wherein the strictures in the digestive body lumen or the gastrointestinal tracts comprise esophageal strictures; achalasia strictures; biliary strictures; stomach strictures; small intestine strictures; duodenum strictures; jejunum strictures; ileum strictures; colon strictures; rectum strictures; ileoanal J-pouch strictures; large intestine strictures; or a combination thereof; and wherein the strictures in the digestive body lumen or the gastrointestinal tracts comprise esophageal stricture of eosinophilic esophagitis; radiation induced strictures; Crohn's disease induced strictures; ulcerative colitis induced strictures; chronic inflammatory bowel disease (IBD) induced strictures; anastomotic strictures of surgical procedures; or a combination thereof.

Embodiment 84 provides a method for prevention or treatment of stenosis or stricture in a vascular body lumen; the method comprising:

- inserting a balloon catheter into a target site in a body lumen comprising the vascular stenosis or stricture; the balloon catheter comprising
  - an elongated balloon; and
  - a coating layer overlying an exterior surface of the balloon; wherein the coating layer comprising
    - the polymer-encapsulated drug particles of any one of Embodiments 1-31; or
    - the drug-releasing coating of any one of Embodiments 32-53; or
    - a composition comprising
      - a therapeutic agent comprising paclitaxel, docetaxel, taxol, an mTOR inhibitor, rapamycin, sirolimus, zotarolimus, everolimus, tacrolimus, umirolimus, an analogue thereof, and combinations thereof,
      - a first additive, and
      - a second additive, or
    - a combination thereof,
  - wherein
    - the therapeutic agent is crystalline, partially crystalline, amorphous, partially amorphous, or a combination thereof,
    - the particle size of the therapeutic agent is in the range of 0.2 micron to 5 micron,
    - the first additive, the second additive, or a combination thereof encapsulates the therapeutic agent, the additive-encapsulated therapeutic agent has a larger particle size than the therapeutic agent itself, and the particle size of the additive-encapsulated therapeutic agent in the coating is in the range of 0.3 micron to 10 micron,
    - the first additive comprises a water-insoluble or slightly or partially water- insoluble additive comprising at least one alkyl fatty group or cholesteryl group, the first additive having a molecular weight of 50 to 750,
    - the first additive in the coating has a lower melting temperature than that of the first additive in its pure form,
    - the first additive in the coating has a lower crystallinity than that of the first additive in its pure form,
    - the second additive is more hydrophilic or more water-soluble than the first additive and that comprises polyethylene glycol ($—(CH_2CH_2O)—$) or a polyglycerol ($-(CHz- CHOH—CH_2O)—$) unit, and
    - the molecular weight of the second additive is in the range of 750 to 100,000,
- inflating the balloon at the target site to contact the coating layer with walls of the body lumen at the location of the stenosis or stricture until the balloon achieves an inflated balloon diameter for an inflation period,
- deflating the balloon after the inflation period, and
- withdrawing the balloon catheter from the body lumen.

Embodiment 85 provides a method for preparing a coated balloon catheter, the method comprising:

- processing a therapeutic agent chosen from paclitaxel, docetaxel, taxol, an mTOR inhibitor, rapamycin, sirolimus, zotarolimus, everolimus, tacrolimus, umirolimus, an analogue thereof, and combinations thereof, so that a majority of the therapeutic agent crystals have a particle size of 0.2 microns to 5.0 microns;

mixing a fluid in which the therapeutic agent is substantially insoluble with the therapeutic agent, a first water-insoluble additive, and a second water-soluble additive; and applying the mixture to the external surface of a balloon catheter, wherein the first additive, the second additive, or a combination thereof encapsulates the therapeutic agent, the additive-encapsulated therapeutic agent has a larger particle size than the therapeutic agent itself, and the particle size of the additive-encapsulated therapeutic agent in the coating is in the range of 0.3 micron to 10 micron.

Embodiment 86 provides the method of Embodiment 85, further comprising:

preparing the balloon catheter comprising
  inflating the balloon catheter;
  cleaning the surface of the balloon; and
  fixturing the balloon so it is mountable inside a coating machine horizontally and rotated at a fixed speed;

dispensing the mixture onto the surface of the balloon while the nozzle is translating laterally across the balloon; and continuing to rotate the balloon to evaporate the solvent at room temperature or higher than room temperature.

Embodiment 87 provides the method of Embodiment 86, further comprising pleating and folding the balloon catheter; and sterilizing the coated balloon catheter.

Embodiment 88 provides the method of any one of Embodiments 85-87, wherein the first additive is chosen from cholesterol, cholesteryl acetate, cholesteryl phenylacetate, cholesteryl laurate, cholesteryl palmitate, cholesteryl stearate, cholesteryl n-valerate, cholesteryl benzoate, cholesteryl heptylate, cholesteryl decylate, cholesteryl caproate, cholesteryl oleate, cholesteryl oleyl carbonate, cholesteryl linoleate, cholesteryl pelargonate, cholesteryl erucate, cholesteryl caprylate, 5α-cholestane, 5α-cholestan-3-one, and combinations thereof.

Embodiment 89 provides the method of any one of Embodiments 85-88, wherein the first additive is chosen from alkyl glyceryl ethers, monoglycerides of C8-C12 fatty acids, alkyl alcohol, alkyl ether, alkyl ester, caprylic acid, monocaprilin, capric acid, monocaprin, lauric acid, dodecyl glycerol, butanoic acid, hexanoic acid, octanoic acid, decanoic acid, dodecanoic acid, tetradecanoic acid, hexadecanoic acid, octadecanoic acid, octadecatrienoic acid, eicosanoic acid, eicosenoic acid, eicosatetraenoic acid, eicosapentaenoic acid, docosahexaenoic acid, tocotrienol, butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, natural or synthetic phospholipids, mono-, di-, or triacylglycerols, cardiolipin, phosphatidylglycerol, phosphatidic acid, phosphatidylcholine, alpha tocoferol, phosphatidylethanolamine, sphingomyelin, phosphatidylserine, phosphatidylinositol, dimyristoylphosphatidylcholine, dioleoylphosphatidylcholine, dipalmitoylphosphatidylcholine, distearoylphosphatidylcholine, phosphatidylethanolamines phosphatidylglycerols, sphingolipids, prostaglandins, gangliosides, neobee, niosomes, derivatives thereof, and combinations thereof.

Embodiment 90 provides the method of any one of Embodiments 85-89, wherein the water-soluble second additive is chosen from cholesteryl-polyethylene glycol 600 sebacate, polyoxyethanyl α-tocopheryl sebacate, methylated polyethylene glycol cholesterol (mPEG cholesterol), polyethylene glycol cholesterol (PEG cholesterol), polyethylene glycol ester cholesterol (PEG cholesterol), polyethylene glycol ether cholesterol (PEG cholesterol), methylated polyethylene glycol-amide-cholesterol (mPEG cholesterol), polyethylene glycol-amide-cholesterol (PEG cholesterol), polyethylene glycol (PEG)-cholesteryl sebacate, polyethylene glycol cholesterol, PEG amide ester cholesterol, PEG amide ether cholesterol, mPEG amide ester cholesterol, DSPE-PEG-cholesterol, PEGylated phospholipid, methylated PEGylated phospholipid, PEG caprylic/capric diglycerides, PEG8 caprylic/capric glycerides, PEG caprylate, PEG caprate, PEG caproate, PEG-20 sorbitan monolaurate (Tween-20), PEG-20 sorbitan monopalmitate (Tween-40), PEG-20 sorbitan monostearate (Tween-60), PEG-20 sorbitan monooleate (Tween-80), PEG laurate, PEG oleate, PEG stearate, PEG glyceryl laurate, PEG-30 glyceryl oleate, polyglyceryl fatty acid esters, polyglyceryl oleate, polyglyceryl-2 dioleate, polyglyceryl-10 trioleate, polyglyceryl stearate, polyglyceryl laurate, polyglyceryl myristate, polyglyceryl palmitate, polyglyceryl linoleate, polyglyceryl-10 laurate, polyglyceryl-10 oleate, polyglyceryl-10 mono/dioleate, polyglyceryl-10 stearate, polyglyceryl-10 laurate, polyglyceryl-10 myristate, polyglyceryl-10 palmitate, polyglyceryl-10 linoleate, polyglyceryl-6 stearate, polyglyceryl-6 laurate, polyglyceryl-6 myristate, polyglyceryl-6 palmitate, polyglyceryl-6 linoleate, and combinations thereof.

Embodiment 91 provides a method for preparing a drug coating solution comprising:

mixing water, water-miscible solvent, therapeutic agent, and a water-soluble additive to form a premix;

processing the premix to reduce the particle size of the therapeutic agent;

mixing insoluble water additive, the water-soluble additive, water, and water-miscible solvent to form a second premix;

mixing the second premix with the first processed premix to form a coating solution;

wherein the therapeutic agent is chosen from paclitaxel, docetaxel, taxol, an mTOR inhibitor, rapamycin, sirolimus, zotarolimus, everolimus, tacrolimus, umirolimus, an analogue thereof, and combinations thereof;

wherein the therapeutic agent is crystalline, partially crystalline, or a combination thereof;

wherein the coating solution is an aqueous suspension of the therapeutic agent;

wherein the particle size of the therapeutic agent is in the range of 0.2 micron to 5 micron;

wherein the first additive, the second additive, or a combination thereof encapsulates the therapeutic agent, the additive-encapsulated therapeutic agent has a larger particle size than the therapeutic agent itself, and the particle size of the additive-encapsulated therapeutic agent in the coating is in the range of 0.3 micron to 10 micron;

wherein the processing is one of microfluidization, homogenization, rotator-stator milling, high or low energy bead milling, or high-power ultrasonic probe homogenization;

wherein the first additive comprises a water-insoluble or slightly or partially water-insoluble additive comprising at least one alkyl fatty group or cholesteryl group, the first additive having a molecular weight of 50 to 750;

wherein the first additive in the coating has a lower melting temperature than that of the first additive in its pure form;

wherein the first additive in the coating has a lower crystallinity than that of the first additive in its pure form; and wherein the second additive is more hydrophilic or more water-soluble than the first additive and that comprises polyethylene glycol (—$(CH_2CH_2O)$—) or a polyglycerol (—$(CH_2$—CHOH—$CH_2O)$—) unit, and the second additive has a molecular weight in the range of 750 to 100,000.

Embodiment 92 provides a method for coating a balloon catheter comprising: preparing an aqueous suspension coating solution comprising mixing water, water-miscible solvent, therapeutic agent, and a water-soluble additive to form a premix;

processing the premix to reduce the particle size of the therapeutic agent;

mixing insoluble water additive, the water-soluble additive, water, and water-miscible solvent to form a second premix;

mixing the second premix with the first processed premix to form a coating solution;

wherein the therapeutic agent is chosen from paclitaxel, docetaxel, taxol, an mTOR inhibitor, rapamycin, sirolimus, zotarolimus, everolimus, tacrolimus, umirolimus, an analogue thereof, and combinations thereof, wherein the therapeutic agent is crystalline, partial crystalline, amorphous, partially amorphous, or a combination thereof;

wherein the coating solution is an aqueous suspension of the therapeutic agent;

wherein the particle size of the therapeutic agent in the coating solution is in the range of 0.2 micron to 5 micron;

wherein the water-soluble additive, the water-insoluble additive, or a combination thereof, encapsulates the therapeutic agent, the additive-encapsulated therapeutic agent has a larger particle size than the therapeutic agent itself, and the particle size of the additive-encapsulated therapeutic agent in the coating is in the range of 0.3 micron to 10 micron;

wherein the first additive comprises a water-insoluble or slightly or partially water-insoluble additive comprising at least one alkyl fatty group or cholesteryl group, the first additive having a molecular weight of 50 to 750;

wherein the first additive in the coating has a lower melting temperature than that of the first additive in its pure form;

wherein the first additive in the coating has a lower crystallinity than that of the first additive in its pure form;

wherein the second additive is more hydrophilic or more water-soluble than the first additive and that comprises a polyethylene glycol (—$(CH_2CH_2O)$—) or a polyglycerol (—$(CH_2$—CHOH—$CH_2O)$—) unit, and the second additive has a molecular weight in the range of 750 to 100,000;

preparing a balloon catheter comprising inflating the balloon catheter;

cleaning the surface of the balloon; and fixturing the balloon so it can be mounted inside a coating machine horizontally and rotated at a fixed speed;

dispensing the coating solution onto the surface of the balloon while the nozzle is translating laterally across the balloon;

continuing to rotate the balloon to evaporate the solvent at room temperature or higher than room temperature;

pleating and folding the balloon catheter; and sterilizing the coated balloon catheter.

Embodiment 93 provides a method for treatment or prevention of a stenosed heart valve, the method comprising:

inserting the balloon or stent of any one of Embodiments 31 or 53 into a target site in the heart valve;

inflating the balloon at the target site to contact the coating layer of the balloon with the inner luminal wall and dilate the heart valve stenosis until the balloon achieves an inflated balloon diameter for an inflation period;

deflating the balloon after the inflation period; and withdrawing the balloon catheter from the body lumen.

Embodiment 94 provides the polymer-encapsulated polymer particles, drug-releasing coating, balloon catheter, or method of any one or any combination of Embodiments 1-93 optionally configured such that all elements or options recited are available to use or select from.

What is claimed is:

1. Polymer-encapsulated drug particles comprising:

a therapeutic agent;

one or more polymers that encapsulate the therapeutic agent; and a first ionic or zwitterionic additive in the polymer-encapsulated drug particles;

wherein the one or more polymers are less than or equal to 80 wt % of the polymer-encapsulated drug particles, the first ionic or zwitterionic additive is 0.5 wt % to 20 wt % of the polymer-encapsulated drug particles, and a total amount of lipids in the polymer-encapsulated drug particles is 0.5 wt % to 20 wt % of the polymer-encapsulated drug particles, the polymer-encapsulated drug particles have a weight ratio of the first ionic or zwitterionic additive to the one or more polymers of 1:3 to 1:60, and a weight ratio of the total amount of lipids in the polymer-encapsulated drug particles to the one or more polymers of 1:3 to 1:60, the first ionic or zwitterionic additive comprises a mismatched charged lipid and/or phospholipid, 1,2-dihexanoyl-sn-glycero-3-phosphocholine, 1,2-diheptanoyl-sn-glycero-3-phosphocholine, 1,2-dioctanoyl-sn-glycero-3-phosphocholine, 1,2-dilauroyl-sn-glycero-3-phosphocholine, 1,2-dimyristoyl-sn-glycero-3-phosphocholine, 1,2-dinonanoyl-sn-glycero-3-phosphocholine, 1,2-didecanoyl-sn-glycero-3-phosphocholine, 1,2-diundecanoyl-sn-glycero-3-phosphocholine, 1,2-dipalmitoyl-sn-glycero-3-phosphocholine, 1,2-distearoyl-sn-glycero-3-phosphocholine, 1,2-dioleoyl-sn-glycero-3-phosphocholine (DOPC), or a combination thereof, two acyl groups of the mismatched charged lipid or phospholipid comprise mis-matched acyl groups, wherein the mis-matched acyl groups differ by length, degree of saturation, substituents thereon, substitution patterns thereon, or a combination thereof, and wherein the polymer-encapsulated drug particles are on a balloon of a balloon catheter such that a concentration density of the therapeutic agent on the balloon catheter is 1 μg/mm$^2$ to 20 μg/mm$^2$ as measured with the balloon at nominal diameter.

2. The polymer-encapsulated drug particles of claim 1, wherein the first ionic or zwitterionic additive further comprises polylysine and/or a cationic or anionic molecule.

3. The polymer-encapsulated drug particles of claim 1, wherein the therapeutic agent is amorphous, partially amorphous, or a combination thereof.

4. The polymer-encapsulated drug particles of claim 1, wherein the therapeutic agent is crystalline or partially crystalline.

5. The polymer-encapsulated drug particles of claim 1, wherein the polymer is at least one polymer chosen from polylactic acid (PLA), polyglycolic acid (PGA), a polylactic acid/polyglycolic acid copolymer (PLGA), polydioxanone, polycaprolactone, polyphosphazene, collagen, gelatin, chitosan, glycosoaminoglycans, and copolymers thereof.

6. The polymer-encapsulated drug particles of claim 1, wherein the first ionic or zwitterionic additive comprises 1,2-dihexanoyl-sn-glycero-3-phosphocholine, 1,2-dibeptanoyl-sn-glycero-3-phosphocholine, 1,2-dioctanoyl-sn-glycero-3-phosphocholine, 1,2-dilauroyl-sn-glycero-3-phosphocholine, 1,2-dimyristoyl-sn-glycero-3-phosphocholine, 1,2-dinonanoyl-sn-glycero-3-phosphocholine, 1,2-decanoyl-sn-glycero-3-phosphocholine, 1,2-diundecanoyl-sn-glycero-3-phosphocholine, 1,2-dipalmitoyl-sn-glycero-3-phosphocholine, 1,2-distearoyl-sn-glycero-3-phosphocholine, 1,2-dioleoyl-sn-glycero-3-phosphocholine (DOPC), or a combination thereof.

7. The polymer-encapsulated drug particles of claim 1, wherein the mis-matched acyl groups have lengths of C6-C34.

8. The polymer-encapsulated drug particles of claim 1, wherein the mis-matched acyl groups differ by length.

9. The polymer-encapsulated drug particles of claim 1, wherein the first ionic or zwitterionic additive is chosen from 1-palmitoyl-2-stearoyl-sn-glycero-3-phosphocholine, 1-stearoyl-2-palmitoyl-sn-glycero-3-phosphocholine, 1-palmitoyl-2-lauroyl-sn-glycero-3-phosphocholine, 1-palmitoyl-2-oleoyl-glycero-3-phosphocholine (POPC), 1-stearoyl-2-hydroxy-sn-glycero-3-phosphocholine, 1-lauroyl-2-hydroxy-sn-glycero-3-phosphocholine, 1-myristoyl-2-hydroxy-sn-glycero-3-phosphocholine, 1-palmitoyl-2-hydroxy-sn-glycero-3-phosphocholine, and a combination thereof.

10. The polymer-encapsulated drug particles of claim 1, wherein the therapeutic agent is chosen from paclitaxel, docetaxel, taxol, an mTOR inhibitor, rapamycin, sirolimus, zotarolimus, everolimus, tacrolimus, umirolimus, daunorubicin, doxorubicin, an analogue thereof, and a combination thereof.

11. The polymer-encapsulated drug particles of claim 1, wherein the polymer-encapsulated drug particles have a diameter of 1 micron to 5 microns.

12. The polymer-encapsulated drug particles of claim 1, wherein:

the one or more polymers are less than or equal to 80 wt % of the polymer-encapsulated drug particles, the first ionic or zwitterionic additive is 2 wt % to 10 wt % of the polymer-encapsulated drug particles, and the total amount of lipids in the polymer-encapsulated drug particles is 2 wt % to 10 wt % of the polymer-encapsulated drug particles, and the polymer-encapsulated drug particles have a weight ratio of the first ionic or zwitterionic additive to the one or more polymers of 1:3 to 1:30, and a weight ratio of the total amount of lipids in the polymer-encapsulated drug particles to the one or more polymers is 1:3 to 1:30.

13. The polymer-encapsulated drug particles of claim 1, wherein the one or more polymers comprise PLGA having a weight ratio of lactic acid to glycolic acid of about 85:15 and/or PLGA having a weight ratio of lactic acid to glycolic acid of about 75:25.

14. The polymer-encapsulated drug particles of claim 1, wherein the therapeutic agent is sirolimus.

15. The polymer-encapsulated drug particles of claim 1, wherein the polymer-encapsulated drug particles comprise a largest dimension of equal to or greater than 0.2 microns and less than or equal to 30 microns, as determined using laser light refraction.

16. A drug-releasing coating comprising:

the polymer-encapsulated drug particles of claim 1; and a release matrix comprising a second ionic or zwitterionic additive, wherein the second ionic or zwitterionic additive comprises a cationic molecule, an anionic molecule, a mismatched charged lipid and/or phospholipid, 1,2-dihexanoyl-sn-glycero-3-phosphocholine, 1,2-diheptanoyl-sn-glycero-3-phosphocholine, 1,2-dioctanoyl-sn-glycero-3-phosphocholine, 1,2-dilauroyl-sn-glycero-3-phosphocholine, 1,2-dimyristoyl-sn-glycero-3-phosphocholine, 1,2-dinonanoyl-sn-glycero-3-phosphocholine, 1,2-didecanoyl-sn-glycero-3-phosphocholine, 1,2-diundecanoyl-sn-glycero-3-phosphocholine, 1,2-dipalmitoyl-sn-glycero-3-phosphocholine, 1,2-distearoyl-sn-glycero-3-phosphocholine, 1,2-dioleoyl-sn-glycero-3-phosphocholine (DOPC), or a combination thereof, wherein two acyl groups of the mismatched charged lipid or phospholipid comprise mis-matched acyl groups, and wherein the mis-matched acyl groups differ by length, degree of saturation, substituents thereon, substitution patterns thereon, or combinations thereof.

17. The drug-releasing coating of claim 16, wherein the polymer-encapsulated drug particles are 10 wt % to 80 wt % of the drug-releasing coating by dry measure.

18. The drug-releasing coating of claim 17, wherein the second ionic or zwitterionic additive is chosen from 1-palmitoyl-2-stearoyl-sn-glycero-3-phosphocholine, 1-stearoyl-2-palmitoyl-sn-glycero-3-phosphocholine, 1-palmitoyl-2-lauroyl-sn-glycero-3-phosphocholine, 1-palmitoyl-2-oleoyl-glycero-3-phosphocholine (POPC), 1-stearoyl-2-hydroxy-sn-glycero-3-phosphocholine, 1-lauroyl-2-hydroxy-sn-glycero-3-phosphocholine, 1-myristoyl-2-hydroxy-sn-glycero-3-phosphocholine, 1-palmitoyl-2-hydroxy-sn-glycero-3-phosphocholine, and a combination thereof.

19. The drug-releasing coating of claim 16, wherein the second ionic or zwitterionic additive has a different molecular structure from the first ionic or zwitterionic additive.

20. The drug-releasing coating of claim 16, wherein the second ionic or zwitterionic additive in the release matrix comprises 1,2-dihexanoyl-sn-glycero-3-phosphocholine, 1,2-diheptanoyl-sn-glycero-3-phosphocholine, 1,2-dioctanoyl-sn-glycero-3-phosphocholine, 1,2-dilauroyl-sn-glycero-3-phosphocholine, 1,2-dimyristoyl-sn-glycero-3-phosphocholine, 1,2-dinonanoyl-sn-glycero-3-phosphocholine, 1,2-decanoyl-sn-glycero-3-phosphocholine, 1,2-diundecanoyl-sn-glycero-3-phosphocholine, 1,2-dipalmitoyl-sn-glycero-3-phosphocholine, 1,2-distearoyl-sn-glycero-3-phosphocholine, 1,2-dioleoyl-sn-glycero-3-phosphocholine (DOPC), or a combination thereof.

21. The drug-releasing coating of claim 16, further comprising pentaerythritol ethoxylate.

22. The drug-releasing coating of claim 16, wherein the release matrix comprises particles of a second therapeutic agent that are free of encapsulation by the polymer, the second therapeutic agent is chosen from paclitaxel, docetaxel, taxol, an mTOR inhibitor, rapamycin, sirolimus, zotarolimus, everolimus, tacrolimus, umirolimus, daunorubicin, doxorubicin, an analogue thereof, and a combination thereof.

23. The drug-releasing coating of claim 16, wherein the release matrix comprises poly-L-lysine, polylysine, polyvinyl alcohol (PVA), 1,2-dioleoyl-sn-glycero-3-phosphocholine (DOPC), or a combination thereof.

24. A balloon catheter comprising:

an elongated balloon; and a coating layer overlying an exterior surface of the balloon, the coating layer comprising the drug-releasing coating of claim 16.

25. Polymer-encapsulated drug particles comprising:

a therapeutic agent;

one or more polymers that encapsulate the therapeutic agent; and a first ionic or zwitterionic additive in the polymer-encapsulated drug particles;

wherein the one or more polymers are less than or equal to 80 wt % of the polymer-encapsulated drug particles, the first ionic or zwitterionic additive is less than or equal to 20 wt % of the polymer-encapsulated drug particles, and a total amount of lipids in the polymer-encapsulated drug particles is less than or equal to 20 wt % of the polymer-encapsulated drug particles, the polymer-encapsulated drug particles have a weight ratio of the first ionic or zwitterionic additive to the one or more polymers of 1:3 to 1:60, and a weight ratio of the total amount of lipids in the polymer-encapsulated drug particles to the one or more polymers of 1:3 to 1:60, the first ionic or zwitterionic additive comprises a mismatched charged lipid and/or phospholipid, 1,2-dihexanoyl-sn-glycero-3-phosphocholine, 1,2-diheptanoyl-sn-glycero-3-phosphocholine, 1,2-dioctanoyl-sn-glycero-3-phosphocholine, 1,2-dilauroyl-sn-glycero-3-phosphocholine, 1,2-dimyristoyl-sn-glycero-3-phosphocholine, 1,2-dinonanoyl-sn-glycero-3-phosphocholine, 1,2-didecanoyl-sn-glycero-3-phosphocholine, 1,2-diundecanoyl-sn-glycero-3-phosphocholine, 1,2-dipalmitoyl-sn-glycero-3-phosphocholine, 1,2-distearoyl-sn-glycero-3-phosphocholine, 1,2-dioleoyl-sn-glycero-3-phosphocholine (DOPC), or a combination thereof, two acyl groups of the mismatched charged lipid or phospholipid comprise mis-matched acyl groups, wherein the mis-matched acyl groups differ by length, degree of saturation, substituents thereon, substitution patterns thereon, or a combination thereof, and wherein the polymer-encapsulated drug particles are on a balloon of a balloon catheter such that a concentration density of the therapeutic agent on the balloon catheter is 1 μg/mm$^2$ to 20 μg/mm$^2$ as measured with the balloon at nominal diameter.

26. A drug-releasing coating comprising:

the polymer-encapsulated drug particles of claim 25; and a release matrix comprising a second ionic or zwitterionic additive, wherein the second ionic or zwitterionic additive comprises a cationic molecule, an anionic molecule, a mismatched charged lipid and/or phospholipid, 1,2-dihexanoyl-sn-glycero-3-phosphocholine, 1,2-diheptanoyl-sn-glycero-3-phosphocholine, 1,2-dioctanoyl-sn-glycero-3-phosphocholine, 1,2-dilauroyl-sn-glycero-3-phosphocholine, 1,2-dimyristoyl-sn-glycero-3-phosphocholine, 1,2-dinonanoyl-sn-glycero-3-phosphocholine, 1,2-didecanoyl-sn-glycero-3-phosphocholine, 1,2-diundecanoyl-sn-glycero-3-phosphocholine, 1,2-dipalmitoyl-sn-glycero-3-phosphocholine, 1,2-distearoyl-sn-glycero-3-phosphocholine, 1,2-dioleoyl-sn-glycero-3-phosphocholine (DOPC), or a combination thereof, wherein two acyl groups of the mismatched charged lipid or phospholipid comprise mis-matched acyl groups, and wherein the mis-matched acyl groups differ by length, degree of saturation, substituents thereon, substitution patterns thereon, or combinations thereof.

27. A method for treating or preventing a nonvascular or vascular stricture or stenosis, the method comprising:

inserting the balloon catheter comprising the polymer-encapsulated drug particles of claim 1 into the body lumen;

expanding the balloon or stent to contact the coating layer with the stricture, stenosis, or area wherein the stricture or stenosis is to be prevented;

when a balloon is used, the method further comprises deflating the balloon; and when a balloon is used, the method further comprises removing the balloon from the body lumen.

28. A method for treatment or prevention of a stenosed heart valve, the method comprising:

inserting the balloon catheter comprising the polymer-encapsulated drug articles of claim 1 into a target site in the heart valve;

inflating the balloon at the target site to contact the coating layer of the balloon with the inner luninal wall and dilate the heart valve stenosis until the balloon achieves an inflated balloon diameter for an inflation period;

deflating the balloon after the inflation period; and withdrawing the balloon catheter from the body lumen.

29. A method of making a balloon catheter, the method comprising:

applying the drug-releasing coating of claim 16 to an exterior of a balloon of a balloon catheter.

30. A method for prevention or treatment of strictures in the digestive body lumen or the gastrointestinal tract, the method comprising:

inserting the balloon catheter of claim 24 into a target site in a body lumen comprising the non-vascular stricture;

inflating the balloon at the target site to contact the coating layer with walls of the body lumen at the location of the non-vascular stricture until the balloon achieves an inflated balloon diameter for an inflation period;

deflating the balloon after the inflation period; and withdrawing the balloon catheter from the body lumen.

31. A method for prevention or treatment of stenosis or stricture in a vascular body lumen, the method comprising:

inserting the balloon catheter of claim 24 into a target site in a body lumen comprising the vascular stenosis or stricture;

inflating the balloon at the target site to contact the coating layer with walls of the body lumen at the location of the stenosis or stricture until the balloon achieves an inflated balloon diameter for an inflation period;

deflating the balloon after the inflation period; and withdrawing the balloon catheter from the body lumen.

* * * * *